(12) United States Patent
Johnson

(10) Patent No.: US 6,312,934 B1
(45) Date of Patent: Nov. 6, 2001

(54) HUMAN MEKK PROTEINS, CORRESPONDING NUCLEIC ACID MOLECULES, AND USES THEREFOR

(75) Inventor: Gary L. Johnson, Boulder, CO (US)

(73) Assignee: National Jewish Center for Immunology and Respiratory Medicine, Denver, CO (US)

(*) Notice: Subject to any disclaimer, the term of this patent is extended or adjusted under 35 U.S.C. 154(b) by 0 days.

(21) Appl. No.: 09/423,890

(22) PCT Filed: Mar. 15, 1999

(86) PCT No.: PCT/US99/05556

§ 371 Date: Mar. 6, 2000

§ 102(e) Date: Mar. 6, 2000

(87) PCT Pub. No.: WO99/47686

PCT Pub. Date: Sep. 23, 1999

Related U.S. Application Data

(60) Provisional application No. 60/099,165, filed on Sep. 4, 1998, and provisional application No. 60/078,153, filed on Mar. 16, 1998.

(51) Int. Cl.[7] .............................. C12N 9/12; C12N 1/20; C12N 15/00; C12N 5/00; C07H 21/04
(52) U.S. Cl. ................... 435/194; 435/252.3; 435/320.1; 435/325; 435/6; 536/23.2
(58) Field of Search ................. 435/194, 252.3, 435/320.1, 325, 6; 536/23.2

(56) References Cited

U.S. PATENT DOCUMENTS

| | | | |
|---|---|---|---|
| 5,405,941 | 4/1995 | Johnson | 530/350 |
| 5,753,446 | 5/1998 | Johnson | 435/7.1 |
| 5,854,043 | 12/1998 | Johnson | 435/194 |
| 5,981,265 | 11/1999 | Johnson | 435/254.1 |

FOREIGN PATENT DOCUMENTS

| | | |
|---|---|---|
| WO 95/28421 | 10/1995 | (WO). |
| WO 97/35014 | 9/1997 | (WO). |

OTHER PUBLICATIONS

Blank, Jonathan L. et al., "Molecular Cloning of Mitogen–activated Protein/ERK Kinase Kinases (MEKK) 2 and 3," *The Journal of Biological Chemistry* 271(10):5361–5368 (1996).

Blumer, K. J. et al., "Mammalian mitogen–activated protein kinase kinase kinase (MEKK) can function in a yeast mitogen–activated protein kinase pathway downstream of protein kinase C." *Proc. Natl. Acad. Sci. USA* 91(11):4925–9 (1994).

Cardone, Michael H. et al., "The Regulation of Anoikis: MEKK–1 Activation Requires Cleavage by Caspases," *Cell* 90:315–323 (1997).

Ellinger–Ziegelbauer, H. et al., "Direct activation of the stress–activated protein kinase (SAPK) and extracellular signal–regulated protein kinase (ERK) pathways by an inducible mitogen–activated protein Kinase/ERK kinase kinase 3 (MEKK) derivative." *Journal of Biological Chemistry* 272(5):2668–74 (1997).

Fanger G. R. et al., "MEK kinases are regulated by EGF and selectively interact with Rac/Cdc42," *The EMBO Journal* 16:4961–4972 (1997).

Fanger, Gary R. et al., "MEKKs, GCKs, MLKs, PAKs, TAKs, and Tpls: upstream regulators of the c–Jun amino––terminal kinases?" *Current Opinion in Genetics & Development* 7:67–74 (1997).

Gardner, A. M. et al., "Fibroblast growth factor suppression of tumor necrosis factor α mediated apoptosis requires Ras and the activation of mitogen–activated protein kinase," *Journal of Biological Chemistry* 271:14560–14566 (1996).

Genbank Accession No. U23470: "Mus musculus Map kinase kinase kinase (MEKK1) mRNA," (Jan. 4, 1996).

Genbank Accession No. AAA85038: "MEKK1. (Mus musculus)" (Jan. 1, 1996).

Genbank Accession No. U48596: "Rattus norvegicus MAP kinase kinase kinase 1(MEKK1) mRNA," (Jun. 5, 1996).

Genbank Accession No. AAC52596: "MAP kinase kinase kinase 1. (Rattus norvegicus)," (Jun. 5, 1996).

Genbank Accession No. AB014614, "Mus musculus mRNA for MEKK1 N–terminal," (Oct. 29, 1999).

Genbank Accession No. BAA85878: "MEKK1 N–terminal (Mus musculus)," (Oct. 29, 1999).

Genbank Accession No. AF117340: "Mus musculus MAP kinase kinase kinase 1 (MEKK1) mRNA," (Apr. 14, 1999).

Genbank Accession No. AAD25049: "MAP kinase kinase kinase 1 (Mus musculus)," (Apr. 14, 1999).

(List continued on next page.)

Primary Examiner—Rebecca E. Prouty
Assistant Examiner—M. Monshipouri
(74) Attorney, Agent, or Firm—Lahive & Cockfield, LLP; Peter C. Lauro, Esq; Debra J. Milasincic, Esq

(57) ABSTRACT

Isolated nucleic acid molecules encoding human MEKK proteins, and isolated MEKK proteins, are provided. The invention further provides antisense nucleic acid molecules, recombinant expression vectors containing a nucleic acid molecule of the invention, host cells into which the expression vectors have been introduced and nonhuman transgenic animals carrying a human MEKK transgene. The invention further provides human MEKK fusion proteins and anti-human MEKK antibodies. Methods of using the human MEKK proteins and nucleic acid molecules of the invention are also disclosed, including methods for detecting human MEKK activity in a biological sample, methods of modulating human MEKK activity in a cell, and methods for identifying agents that modulate the activity of human MEKK.

29 Claims, 35 Drawing Sheets

OTHER PUBLICATIONS

Genbank Accession No. L13103: "Mus musculus MEK kinase mRNA." (Apr. 18, 1996).

Genbank Accession No. AAA97500: "MEK Kinase (Mus Musculus)," (Apr. 18, 1996).

Genbank Accession No. NM_002401: "Homo sapiens mitogen–activated protein kinase kinase kinase 3 (MAP3K3) mRNA," (Oct. 12, 1999).

Genbank Accession No. NP_002392: "MAP/ERK kinase kinase 3; MAP kinase kinase kinase 3; MAPKKK3. (Homo sapiens)," (Oct. 12, 1999).

Genbank Accession No. AF042838: "Homo sapiens MEK kinase 1 (MEKK1) mRNA," (Dec. 18, 1998).

Genbank Accession No. AAC97073: "MEK kinase 1. (Homo sapiens)" (Dec. 17, 1998).

Genbank Accession No. NP_006600: "Mitogen–activated protein kinase kinase kinase 2. (Homo sapiens)" (Sep. 16, 1999).

Genbank Accession No. NM_006609: "Homo sapiens mitogen–activated protein kinase kinase kinase 2 (MAP3K2), mRNA" (Sep. 16, 1999).

Genbank Accession No. AAB03536: "MEK kinase 2 (Mus musculus)" (Jul. 9, 1996).

Genbank Accession No. U43186: "Mus musculus MEK kinase 2, mRNA," (Jul. 9, 1996).

Genbank Accession No. U43187: "Mus musculus MEK kinase 3, mRNA," (Jul. 9, 1996).

Genbank Accession No. AAB03535: "MEK Kinase 3 (Mus musculus)" (Jul. 9, 1996).

Gerwins, Pär et al., "Cloning of a Novel Mitogen–activated Protein Kinase Kinase Kinase, MEKK4, That Selectively Regulates the c–Jun Amino Terminal Kinase Pathway," *The Journal of Biological Chemistry* 272(13):8288–8295 (1997).

Hu, M. C. et al., "Human HPK1, a novel human hematopoietic progenitor kinase that activated the JNK/SAPK kinase cascade," *Genes Dev.* 10:2251–2264 (1996).

Ito, M. et al., "JSAP1, a novel jun N–terminal protein kinase (JNK)–binding protein that functions as a Scaffold factor in the JNK signaling pathway." *Mol. Cell. Biol.* 19(11):7539–48 (1999).

Karin, M. et al., "JNK or IKK, AP–1 or NFκB, which are targets for MEK kinase 1 action?" *Proc. Natl. Sci. USA* 95:9067–9069 (1998).

Khokhlatchev, A. et al., "Reconstitution of mitogen–activated protein kinase phosphorylation cascades in bacteria. Efficient synthesis of active protein kinases." *Journal of Biological Chemistry* 272(17):11057–62 (1997).

Lange–Carter, Carol A. and Johnson, Gary L., "Ras–Dependent Growth Factor Regulation of MEK Kinase in PC12 Cells," *Science* 265:1458–1461 (1994).

Lange–Carter, Carol A. et al., "A Divergence in the MAP Kinase Regulatory Network Defined by MEK Kinase and Raf," *Science* 260(5106):315–319 (1993).

Lassignal–Johnson, N. et al., "Signal transduction pathways regulated by MEK kinase are involved in mediating apoptosis," *Journal of Biological Chemistry* 271:3229–3237 (1996).

Minden, Audrey et al., "Differential Activation of ERK and JNK Mitogen–Activated protein Kinases by Raf–1 and MEKK," *Science* 266:1719–1723 (1994).

Russell, M. et al., "Direct interaction between Ras and the kinase domain of mitogen–activated protein kinase kinase kinase (MEKK1)," *Journal of Biological Chemistry* 270:11757–11760 (1995).

Schlesinger, T. K. et al., "The Tao of MEKK," *Front. Biosci.* 3:D1181–6 (1988).

Seger, R. et al., "The MAPK signaling cascade," *FASEB J.* 9:726–735 (1995).

Widmann, C. et al., "Caspase–dependent cleavage of signaling proteins during apoptosis. A turn–off mechanism for anti–apoptotic signals." *Journal of Biological Chemistry* 273(12):7141–7 (1998).

Widmann, Christian et al., "MEK Kinase 1, a Substrate for DEVD–Dire directed Caspases, Is Involved in Genotoxin––Induced Apoptosis," *Molecular and Cellular Biology* 18(4):2416–2429 (1998).

Widmann, Christian et al., "Potentiation of apoptosis by low dose stress stimuli in cells expressing activated MEK kinase 1," *Oncogene* 15(20):2439–47 (1997).

Winston, B. W. et al., "Tumor necrosis factor alpha rapidly activates the mitogen–activated protein kinase (MAPK) cascade in a MAPK kinase kinase–dependent, c–Raf–1–independent fashion in mouse macrophages," *Proc. Natl. Acad. Sci. USA* 92:1614–1618 (1995).

Xia, Y. et al., "JNKK1 organizes a MAP kinase module through specific and sequential interactions with upstream and downstream components mediated by its amino–terminal extension," *Genes Dev.* 12(21):3369–81 (1998).

Xu, S. et al., "Cloning of rat MEK kinase 1 cDNA reveals an endogenous membrane–associated 195-kDa protein with a large regulatory domain." *Proc. Natl. Acad. Sci. USA* 93(11):5291–5.

Xu, S. et al., "MEKK1 binds directly to the c–Jun N–terminal kinases/stress–activated protein kinases." *Journal of Biological Chemistry* 272(51):32056–60 (1997).

Xu, S. et al., "MEKK1 phosphorylates MEK1 and MEK2 but does not cause activation of mitogen–activated protein kinase." *Proc. Natl. Acad. Sci USA* 92(15):6808–12 (1995).

Yan, M. et al., "Activation of stress–activated protein kinase by MEKK1 phosphorylation of its activator SEK1." *Nature* 372 (6508):798–800 (1994).

Yujiri, T. et al., "Role of MEKK1 in cell survival and activation of JNK and ERK pathways defined by targeted gene disruption," *Science* 282(5395):1911–4 (1998).

Figure 1A

```
   1 CGGCCTGGAA GCACGAGTGG TTGGAAAGGA GAAATAGGCG AGGGCCTGTG GTGGTAAAAC
  61 CAATCCCAGT TAAAGGAGAT GGATCTGAAA TGAATCACTT AGCAGCTGAG TCTCCAGGAG
 121 AGGTCCAGGC AAGTGCGGCT TCACCAGCTT CCAAAGGCCG ACGCAGTCCT TCTCCTGGCA
 181 ACTCCCCATC AGGTCGCACA GTGAAATCAG AATCTCCAGG AGTAAGGAGA AAAAGAGTTT
 241 CCCCAGTGCC TTTTCAGAGT GGCAGAATCA CACCACCCCG AAGAGCCCCT TCACCAGATG
 301 GCTTCTCACC ATATAGCCCT GAGGAAACAA ACCGCCGTGT TAACAAAGTG ATGCGGGCCA
 361 GACTGTACTT ACTGCAGCAG ATAGGGCCTA ACTCTTTCCT GATTGGAGGA GACAGCCCAG
 421 ACAATAAATA CCGGGTGTTT ATTGGGCCTC AGAACTGCAG CTGTGCACGT GGAACATTCT
 481 GTATTCATCT GCTATTTGTG ATGCTCCGGG TGTTTCAACT AGAACCTTCA GACCCAATGT
 541 TATGGAGAAA AACTTTAAAG AATTTTGAGG TTGAGAGTTT GTTCCAGAAA TATCACAGTA
 601 GGCGTAGCTC AAGGATCAAA GCTCCATCTC GTAACACCAT CCAGAAGTTT GTTTCACGCA
 661 TGTCAAATTC TCATACATTG TCATCATCTA GTACTTCTAC ATCTAGTTCA GTAAACAGCA
 721 TAAAGGATGA AGAGGAACAG ATGTGTCCTA TTTGCTTGTT GGGCATGCTT GATGAAGAAA
 781 GTCTTACAGT GTGTGAAGAC GGCTGCAGGA ACAAGCTGCA CCACCACTGC ATGTCAATTT
 841 GGGCAGAAGA GTGTAGAAGA AATAGAGAAC CTTTAATATG TCCCCTTTGT AGATCTAAGT
 901 GGAGATCTCA TGATTTCTAC AGCCACGAGT TGTCAAGTCC TGTGGATTCC CCTTCTTCCC
 961 TCAGAGCTGC ACAGCAGCAA ACCGTACAGC AGCAGCCTTT GGCTGGATCA CGAAGGAATC
1021 AAGAGAGCAA TTTTAACCTT ACTCATTATG GAACTCAGCA AATCCCTCCT GCTTACAAAG
1081 ATTTAGCTGA GCCATGGATT CAGGTGTTTG GAATGGAACT CGTTGGCTGC TTATTCTCTA
1141 GAAACTGGAA CGTAAGGGAA ATGGCCCTTA GGCGTCTTTC CCACGACGTT AGTGGGGCCC
1201 TGTTGTTGGC AAACGGGGAG AGCACTGGAA ACTCTGGAGG CGGCAGTGGG GGCAGCTTAA
1261 GCGCGGGAGC GGCCAGCGGG TCCTCCCAGC CCAGCATCTC AGGGGATGTG GTGGAGGCGT
1321 GCTGCAGTGT CCTGTCTATA GTCTGCGCTG ACCCTGTCTA CAAAGTGTAC GTTGCTGCTT
1381 TAAAAACATT GAGAGCCATG CTGGTATACA CTCCTTGCCA CAGTCTGGCA GAAAGAATCA
1441 AACTTCAGAG ACTCCTCCGG CCAGTTGTAG ACACTATCCT TGTCAAGTGT GCAGATGCCA
1501 ACAGCCGCAC GAGTCAGCTG TCCATATCTA CAGTGCTGGA ACTCTGCAAT GGCCAAGCAG
1561 GAAAGCTGGC GGTTGGGAGA GAAATACTTA AAGCTGGGTC CATCGGGGTT GGTGGTGTCG
1621 ATTACGTCTT AAGTTGTATC CTTGGAAACC AAGCTGAATC AAACAACTGG CAAGAACTGC
1681 TGGGTCGCCT CTGTCTTATA GACAGGTTGC TGTTGGAATT TCCTGCTGAA TTCTATCCTC
1741 ATATTGTCAG TACTGATGTC TCACAAGCTG AGCCTGTTGA AATCAGGTAC AAGAAGCTGC
1801 TCTCCCTCTT AACCTTTGCC TTGCAATCCA TTGACAATTC CCACTCGATG GTTGGCAAGC
1861 TCTCTCGGAG GATATATCTG AGCTCTGCCA GGATGGTGAC CGCAGTGCCC GCTGTGTTTT
1921 CCAAGCTGGT AACCATGCTT AATGCTTCTG GCTCCACCCA CTTCACCAGG ATGCGCCGGC
1981 GTCTGATGGC TATCGCGGAT GAGGTAGAAA TTGCCGAGGT CATCCAGCTG GGTGTGGAGG
2041 ACACTGTGGA TGGGCATCAG GACAGCTTAC AGGCGCTGGC CCCGCCAGC TGTCTAGAAA
2101 ACAGCTCCCT TGAGCACACA GTCCATAGAG AGAAAACTGG AAAAGGACTA AGTGCTACGA
2161 GACTGAGTGC CAGCTCGGAG GACATTCTG ACAGACTGGC CGGCGTCTCT GTAGGACTTC
2221 CCAGCTCAAC AACAACAGAA CAACCAAAGC CAGCGGTTCA ATCAAAAGGC AGACCCCACA
2281 GTCAGTGTTT GAACTCCTCC CCTTTGTCTC ATGCTCAATT AATGTTCCCA GCACCATCAG
2341 CCCCTTGTTC CTCTGCCCCG TCTGTCCCAG ATATTTCTAA GCACAGACCC CAGGCATTTG
2401 TTCCCTGCAA AATACCTTCC GCATCTCCTC AGACACAGCG CAAGTTCTCT CTACAATTCC
2461 AGAGGAACTG CTCTGAACAC CGAGACTCAG ACCAGCTCTC CCCAGTCTTC ACTCAGTCAA
2521 GACCCCCACC CTCCAGTAAC ATACACAGGC CAAAGCCATC CCGACCCGTT CCGGGCAGTA
2581 CAAGCAAACT AGGGGACGCC ACAAAAAGTA GCATGACACT TGATCTGGGC AGTGCTTCCA
2641 GGTGTGACGA CAGCTTTGGC GGCGGCGGCA ACAGTGGCAA CGCCGTCATA CCCAGCGACG
2701 AGACAGTGTT CACGCCGGTG GAGGACAAGT GCAGGTTAGA TGTGAACACC GAGCTCAACT
2761 CCAGCATCGA GGACCTTCTT GAAGCATCCA TGCCTTCAAG TGACACGACA GTCACTTTCA
2821 AGTCCGAAGT CGCCGTCCTC TCTCCGGAAA AGGCCGAAAA TGACGACACC TACAAGACG
2881 ACGTCAATCA TAATCAAAAG TGCAAAGAAA AGATGGAAGC TGAAGAGGAG GAGGCTTTAG
2941 CGATCGCCAT GGCGATGTCA GCGTCTCAGG ATGCCCTCCC CATCGTCCCT CAGCTGCAGG
3001 TGGAAAATGG AGAAGATATT ATCATCATTC AGCAGGACAC ACCAGAAACT CTTCCAGGAC
3061 ATACCAAAGC GAAACAGCCT TACAGAAGG ACGCTGAGTG GCTGAAAGCC AGCAGATAG
3121 GCCTCGGAGC ATTTTCTTCT TGTTATCAGG CTCAAGATGT GGGAACTGGA ACTTTAATGG
3181 CTGTTAAACA GGTGACTTAT GTCAGAAACA CATCTTCTGA GCAAGAAGAA GTAGTAGAAG
3241 CACTAAGAGA AGAGATAAGA ATGATGAGCC ATCTGAATCA TCCAAACATC ATTAGGATGT
3301 TGGGAGCCAC GTGTGAGAAG AGCAATTACA ATCTCTTCAT TGAATGGATG GCAGGGGGAT
```

Figure 1B

```
3361 CGGTGGCTCA TTTGCTGAGT AAATATGGAG CCTTCAAAGA ATCAGTAGTT ATTAACTACA
3421 CTGAACAGTT ACTCCGTGGC CTTTCGTATC TCCATGAGAA CCAGATCATT CACAGAGATG
3481 TCAAAGGTGC CAATTTGCTC ATTGACAGCA CCGGTCAGAG GCTGAGAATT GCAGACTTTG
3541 GAGCTGCAGC CAGGTTGGCA TCAAAAGGAA CTGGTGCAGG AGAGTTTCAG GGACAATTAC
3601 TGGGACAAT TGCATTCATG GCGCCTGAGG TCCTAAGAGG TCAGCAGTAT GGTAGGAGCT
3661 GTGATGTATG GAGTGTTGGC TGCGCCATTA TAGAAATGGC TTGTGCAAAA CCACCTTGGA
3721 ATGCAGAAAA ACACTCCAAT CATCTCGCCT TGATATTTAA GATTGCTAGC GCAACTACTG
3781 CACCGTCCAT CCCGTCACAC CTGTCCCCTG GTTACGAGA TGTGGCTCTT CGTTGTTTAG
3841 AACTTCAGCC TCAGGACCGG CCTCCGTCAA GAGAGCTGCT GAAACATCCG GTCTTCCGTA
3901 CCACGTGGTA G
```

Figure 2

```
   1  AWKHEWLERR  NRRGPVVVKP  IPVKGDGSEM  NHLAAESPGE  VQASAASPAS  KGRRSPSPGN
  61  SPSGRTVKSE  SPGVRRKRVS  PVPFQSGRIT  PPRRAPSPDG  FSPYSPEETN  RRVNKVMRAR
 121  LYLLQQIGPN  SFLIGGDSPD  NKYRVFIGPQ  NCSCARGTFC  IHLLFVMLRV  FQLEPSDPML
 181  WRKTLKNFEV  ESLFQKYHSR  RSSRIKAPSR  NTIQKFVSRM  SNSHTLSSSS  TSTSSSVNSI
 241  KDEEEQMCPI  CLLGMLDEES  LTVCEDGCRN  KLHHHCMSIW  AEECRRNREP  LICPLCRSKW
 301  RSHDFYSHEL  SSPVDSPSSL  RAAQQQTVQQ  QPLAGSRRNQ  ESNFNLTHYG  TQQIPPAYKD
 361  LAEPWIQVFG  MELVGCLFSR  NWNVREMALR  RLSHDVSGAL  LLANGESTGN  SGGGSGGSLS
 421  AGAASGSSQP  SISGDVVEAC  CSVLSIVCAD  PVYKVYVAAL  KTLRAMLVYT  PCHSLAERIK
 481  LQRLLRPVVD  TILVKCADAN  SRTSQLSIST  VLELCNGQAG  KLAVGREILK  AGSIGVGGVD
 541  YVLSCILGNQ  AESNNWQELL  GRLCLIDRLL  LEFPAEFYPH  IVSTDVSQAE  PVEIRYKKLL
 601  SLLTFALQSI  DNSHSMVGKL  SRRIYLSSAR  MVTAVPAVFS  KLVTMLNASG  STHFTRMRRR
 661  LMAIADEVEI  AEVIQLGVED  TVDGHQDSLQ  ALAPASCLEN  SSLEHTVHRE  KTGKGLSATR
 721  LSASSEDISD  RLAGVSVGLP  SSTTEQKPKP  AVQTKGRPHS  QCLNSSPLSH  AQLMFPAPSA
 781  PCSSAPSVPD  ISKHRPQAFV  PCKIPSASPQ  TQRKFSLQFQ  RNCSEHRDSD  QLSPVFTQSR
 841  PPPSSNIHRP  KPSRPVPGST  SKLGDATKSS  MTLDLGSASR  CDDSFGGGGN  SGNAVIPSDE
 901  TVFTPVEDKC  RLDVNTELNS  SIEDLLEASM  PSSDTTVTFK  SEVAVLSPEK  AENDDTYKDD
 961  VNHNQKCKEK  MEAEEEEALA  IAMAMSASQD  ALPIVPQLQV  ENGEDIIIQ   QDTPETLPGH
1021  TKAKQPYRED  AEWLKGQQIG  LGAFSSCYQA  QDVGTGTLMA  VKQVTYVRNT  SSEQEEVVEA
1081  LREEIRMMSH  LNHPNIIRML  GATCEKSNYN  LFIEWMAGGS  VAHLLSKYGA  FKESVVINYT
1141  EQLLRGLSYL  HENQIIHRDV  KGANLLIDST  GQRLRIADFG  AAARLASKGT  GAGEFQGQLL
1201  GTIAFMAPEV  LRGQQYGRSC  DVWSVGCAII  EMACAKPPWN  AEKHSNHLAL  IFKIASATTA
1261  PSIPSHLSPG  LRDVALRCLE  LQPQDRPPSR  ELLKHPVFRT  TW*
```

Figure 3A

```
>_ SEQ ID NO:7                                              5253 nt vs.
>_ SEQ ID NO:1                                              3911 nt
scoring matrix:  , gap penalties: -12/-2
70.3% identity;           Global alignment score: 11397

10        20        30        40        50        60
SEQNO7 GCCCGCGAGAGAAAATGGCGGCGGCGGCGGGCGATCGCGCCTCGTCGTCGGGATTCCCGG

SEQNO1 ------------------------------------------------------------

70        80        90       100 ·     110       120
SEQNO7 GCGCCGCGGCGGCGAGTCCCGAGGCGGGCGGCGGCGGCGGAGGAGGAGGAGCTCTCCAGG

SEQNO1 ------------------------------------------------------------

130       140       150       160       170       180
SEQNO7 GAAGCGGCGCGCCCGCAGCGGGCGCGGCGGGGCTGCTGCGGGAGCCTGGCAGCGCGGGCC

SEQNO1 ------------------------------------------------------------

190       200       210       220       230       240
SEQNO7 GCGAGCGCGCGGACTGGCGGCGGCGGCACGTGCGCAAAGTGCGGAGTGTGGAGCTGGACC

SEQNO1 ------------------------------------------------------------

250       260       270       280       290       300
SEQNO7 AGCTGCCGGAGCAGCCGCTCTTCCTCGCCGCCGCCTCGCCGCCCTGCCCATCTACTTCCC

SEQNO1 ------------------------------------------------------------

310       320       330       340       350       360
SEQNO7 CGTCGCCGGAGCCCGCGGACGCGGCTGCAGGAGCGAGTCGCTTCCAGCCCGCGGCGGGAC

SEQNO1 ------------------------------------------------------------

370       380       390       400       410       420
SEQNO7 CGCCACCCCCGGGAGCGGCGAGTCGCTGCGGCTCCCACTCTGCCGAGCTGGCGGCCGCGC

SEQNO1 ------------------------------------------------------------

430       440       450       460       470       480
SEQNO7 GGGACAGCGGCGCCCGGAGCCCCGCGGGGGCGGAGCCGCCCTCTGCAGCGGCCCCCTCCG

SEQNO1 ------------------------------------------------------------

490       500       510       520       530       540
SEQNO7 GTCGAGAGATGGAGAATAAAGAAACCCTCAAAGGACTGCACAAGATGGAGGATCGCCCGG

SEQNO1 ------------------------------------------------------------
```

Figure 3B

```
              550        560        570        580        590        600
SEQNO7 AGGAGAGAATGATCCGGGAGAAGCTCAAGGCGACCTGTATGCCGGCCTGGAAGCACGAGT
                                                    ::::::::::::::::::
SEQNO1 ----------------------------------------------CGGCCTGGAAGCACGAGT
                                                             10

610        620        630        640        650        660
SEQNO7 GGTTGGAGAGGAGGAACAGGAGAGGCCCTGTGGTGGTGAAGCCAATCCCTATTAAAGGAG
       ::::::: :::::  :: :::  ::::  ::::::::::: :: :::::::: ::::::::::
SEQNO1 GGTTGGAAAGGAGAAATAGGCGAGGGCCTGTGGTGGTAAAACCAATCCCAGTTAAAGGAG
          20         30         40         50         60         70

670        680        690        700        710        720
SEQNO7 ATGGATCTGAAGTGAATAACTTGGCAGCTGAGCCCCAGGGAGAGGGCCAGGCAGGTTCCG
       :::::::::::  ::::: ::::  ::::::::::: : :  :::::::::::::: :: :
SEQNO1 ATGGATCTGAAATGAATCACTTAGCAGCTGAGTCTCCAGGAGAGGTCCAGGCAAGTGCGG
          80         90        100        110        120        130

730        740        750        760        770        780
SEQNO7 CTGCACCAGCCCCCAAGGGCCGACGAAGCCCATCTCCTGGCAGCTCTCCGTCAGGGCGCT
       ::  :::::::  ::::  ::::::::::  :: :::::::::::::: :::  :: ::: :::
SEQNO1 CTTCACCAGCTTCCAAAGGCCGACGCAGTCCTTCTCCTGGCAACTCCCCATCAGGTCGCA
         140        150        160        170        180        190

790        800        810        820        830        840
SEQNO7 CGGTGAAGCCGGAATCCCCAGGAGTAAGACGGAAACGAGTGTCCCCGGTGCCTTTCCAGA
       : :::::  : :::::  ::::::::::::::: : :::  :::: :::: ::::::::::: ::::
SEQNO1 CAGTGAAATCAGAATCTCCAGGAGTAAGGAGAAAAAGAGTTTCCCCAGTGCCTTTTCAGA
         200        210        220        230        240        250

850        860        870        880        890        900
SEQNO7 GTGGCAGAATCACACCACCCCGAAGAGCCCCATCACCGGATGGCTTCTCCCCGTACAGCC
       :::::::::::::::::::::::::::::::::::  :::::::::::::::::  :: ::::
SEQNO1 GTGGCAGAATCACACCACCCCGAAGAGCCCCTTCACCAGATGGCTTCTCACCATATAGCC
         260        270        280        290        300        310

910        920        930        940        950        960
SEQNO7 CAGAGGAGACGAGCCGCCGCGTGAACAAAGTGATGAGAGCCAGGCTGTACCTGCTGCAGC
       :  :::::::  :  :::::::  :: :::::::::::: :  :::::   :::::::  ::::::::
SEQNO1 CTGAGGAAACAAACCGCCGTGTTAACAAAGTGATGCGGGCCAGACTGTACTTACTGCAGC
         320        330        340        350        360        370

970        980        990       1000       1010       1020
SEQNO7 AGATAGGACCCAACTCTTTCCTGATTGGAGGAGACAGTCCAGACAATAAATACCGGGTGT
       ::::::: ::  :::::::::::::::::::::::::::  :::::::::::::::::::::::::
SEQNO1 AGATAGGGCCTAACTCTTTCCTGATTGGAGGAGACAGCCCAGACAATAAATACCGGGTGT
         380        390        400        410        420        430

1030       1040       1050       1060       1070       1080
SEQNO7 TTATTGGGCCACAGAACTGCAGCTGTGGGCGTGGAGCATTCTGTATTCACCTCTTGTTTG
       :::::::::::: :::::::::::::::::  : :::  :::::::::::::: : ::::
SEQNO1 TTATTGGGCCTCAGAACTGCAGCTGTGCACGTGGAACATTCTGTATTCATCTGCTATTTG
         440        450        460        470        480        490
```

Figure 3C

```
           1090      1100      1110      1120      1130      1140
SEQNO7 TCATGCTCCGGGTGTTTCAGCTAGAACCCTCTGACCCCATGTTATGGAGAAAAACTTTAA
       : ::::::: ::::::::: ::::::::: :: ::::: ::::::::::::::::::::::
SEQNO1 TGATGCTCCGGGTGTTTCAACTAGAACCTTCAGACCCAATGTTATGGAGAAAAACTTTAA
        500       510       520       530       540       550

1150      1160      1170      1180      1190      1200
SEQNO7 AAAATTTCGAGGTTGAGAGTTTGTTCCAGAAATACCACAGTAGGCGTAGCTCGAGAATCA
       : :::::  ::::::::::::::::::::::::::: :::::::::::::::  : ::::
SEQNO1 AGAATTTTGAGGTTGAGAGTTTGTTCCAGAAATATCACAGTAGGCGTAGCTCAAGGATCA
        560       570       580       590       600       610

1210      1220      1230      1240      1250      1260
SEQNO7 AAGCTCCATCCCGGAACACCATCCAGAAGTTTGTGTCACGCATGTCAAATTCTCACACAC
       :::::::::: ::  :::::::::::::::::::: :::::::::::::::::::: : 
SEQNO1 AAGCTCCATCTCGTAACACCATCCAGAAGTTTGTTTCACGCATGTCAAATTCTCATACAT
        620       630       640       650       660       670

1270      1280      1290      1300      1310      1320
SEQNO7 TGTCATCGTCTAGCACATCCACATCTAGTTCAGAAAACAGCATCAAGGATGAAGAGGAGC
       ::::::: ::::: :: :: ::::::::::::::::: :::::: :::::::::::::: :
SEQNO1 TGTCATCATCTAGTACTTCTACATCTAGTTCAGTAAACAGCATAAAGGATGAAGAGGAAC
        680       690       700       710       720       730

1330      1340      1350      1360      1370      1380
SEQNO7 AGATGTGTCCCATCTGCTTGCTGGGCATGCTGGATGAGGAGAGCCTGACTGTGTGTGAAG
       :::::::::: :: ::::::: ::::::::: ::::::  ::: :: :: :: :::::::
SEQNO1 AGATGTGTCCTATTTGCTTGTTGGGCATGCTTGATGAAGAAAGTCTTACAGTGTGTGAAG
        740       750       760       770       780       790

1390      1400      1410      1420      1430      1440
SEQNO7 ATGGCTGCAGGAACAAGCTGCACCACCATTGCATGTCCATCTGGGCGGAAGAGTGTAGAA
       : :::::::::::::::::::::::::::: ::::: ::::: :::: ::::::::::::
SEQNO1 ACGGCTGCAGGAACAAGCTGCACCACCACTGCATGTCAATTTGGGCAGAAGAGTGTAGAA
        800       810       820       830       840       850

1450      1460      1470      1480      1490      1500
SEQNO7 GAAATAGAGAGCCTTTAATATGTCCCCTTTGTAGATCTAAGTGGAGATCCCATGACTTCT
       :::::::::::  :::::::::::::::::::::::::::::::::::: ::::: ::::
SEQNO1 GAAATAGAGAACCTTTAATATGTCCCCTTTGTAGATCTAAGTGGAGATCTCATGATTTCT
        860       870       880       890       900       910

1510      1520      1530      1540      1550      1560
SEQNO7 ACAGCCATGAGTTATCAAGCCCCGTGGAGTCCCCCGCCTCCCTGCGAGCTGTCCAGCAGC
       ::::::  ::::: :::::  ::::: ::::: ::  :::::  ::::::  ::::::::
SEQNO1 ACAGCCACGAGTTGTCAAGTCCTGTGGATTCCCCTTCTTCCCTCAGAGCTGCACAGCAGC
        920       930       940       950       960       970

1570      1580      1590      1600      1610      1620
SEQNO7 CATCCTCCCCGCAGCAGCCCGTGGCCGGATCACAGCGGAGGAATCAGGAGAGCAGTTTTA
       : ::   :  :::::::: ::::  :::::::     ::::::::::: ::::::  :::::
SEQNO1 AAACCGTACAGCAGCAGCCTTTGGCTGGATCAC---GAAGGAATCAAGAGAGCAATTTTA
        980       990      1000      1010      1020      1030

1630      1640      1650      1660      1670      1680
SEQNO7 ACCTTACTCATTTTGGAACCCAGCAGATTCCTTCCGCTTACAAAGATTTGGCCGAGCCAT
       :::::::::::: : ::::: ::::: :: ::: ::::::::::::::: :: ::::::
SEQNO1 ACCTTACTCATTATGGAACTCAGCAAATCCCTCCTGCTTACAAAGATTTAGCTGAGCCAT
       1040      1050      1060      1070      1080      1090
```

*Figure 3D*

```
         1690       1700       1710       1720       1730       1740
SEQNO7 GGATTCAGGTGTTTGGAATGGAACTCGTTGGCTGCTTATTCTCTAGAAACTGGAACGTAA
       ::::::::::::::::::::::::::::::::::::::::::::::::::::::::::::
SEQNO1 GGATTCAGGTGTTTGGAATGGAACTCGTTGGCTGCTTATTCTCTAGAAACTGGAACGTAA
         1100       1110       1120       1130       1140       1150

1750       1760       1770       1780       1790       1800
SEQNO7 GGGAAATGGCCCTTAGGCGTCTTTCCCACGACGTTAGTGGGGCCCTGTTGTTGGCAAACG
       ::::::::::::::::::::::::::::::::::::::::::::::::::::::::::::
SEQNO1 GGGAAATGGCCCTTAGGCGTCTTTCCCACGACGTTAGTGGGGCCCTGTTGTTGGCAAACG
         1160       1170       1180       1190       1200       1210

1810       1820       1830       1840       1850       1860
SEQNO7 GGGAGAGCACTGGAAACTCTGGAGGCGGCAGTGGGGGCAGCTTAAGCGCGGGAGCGGCCA
       ::::::::::::::::::::::::::::::::::::::::::::::::::::::::::::
SEQNO1 GGGAGAGCACTGGAAACTCTGGAGGCGGCAGTGGGGGCACCTTAAGCGCGGGAGCGGCCA
         1220       1230       1240       1250       1260       1270

1870       1880       1890       1900       1910       1920
SEQNO7 GCGGGTCCTCCCAGCCCAGCATCTCAGGGGATGTGGTGGAGGCGTGCTGCAGTGTCCTGT
       ::::::::::::::::::::::::::::::::::::::::::::::::::::::::::::
SEQNO1 GCGGGTCCTCCCAGCCCAGCATCTCAGGGGATGTGGTGGAGGCGTGCTGCAGTGTCCTGT
         1280       1290       1300       1310       1320       1330

1930       1940       1950       1960       1970       1980
SEQNO7 CTATAGTCTGCGCTGACCCTGTCTACAAAGTGTACGTTGCTGCTTTAAAAACATTGAGAG
       ::::::::::::::::::::::::::::::::::::::::::::::::::::::::::::
SEQNO1 CTATAGTCTGCGCTGACCCTGTCTACAAAGTGTACGTTGCTGCTTTAAAAACATTGAGAG
         1340       1350       1360       1370       1380       1390

1990       2000       2010       2020       2030       2040
SEQNO7 CCATGCTGGTATACACTCCTTGCCACAGTCTGGCAGAAAGAATCAAACTTCAGAGACTCC
       ::::::::::::::::::::::::::::::::::::::::::::::::::::::::::::
SEQNO1 CCATGCTGGTATACACTCCTTGCCACAGTCTGGCAGAAAGAATCAAACTTCAGAGACTCC
         1400       1410       1420       1430       1440       1450

2050       2060       2070       2080       2090       2100
SEQNO7 TCCGGCCAGTTGTAGACACTATCCTTGTCAAGTGTGCAGATGCCAACAGCCGCACGAGTC
       ::::::::::::::::::::::::::::::::::::::::::::::::::::::::::::
SEQNO1 TCCGGCCAGTTGTAGACACTATCCTTGTCAAGTGTGCAGATGCCAACAGCCGCACGAGTC
         1460       1470       1480       1490       1500       1510

2110       2120       2130       2140       2150       2160
SEQNO7 AGCTGTCCATATCTACAGTGCTGGAACTCTGCAAGGGCCAAGCAGGAGAGCTGGCGGTTG
       :::::::::::::::::::::::::::::::::::::           :::::::::::
SEQNO1 AGCTGTCCATATCTACAGTGCTGGAACTCTGCAATGGCCAAGCAGGAAAGCTGGCGGTTG
         1520       1530       1540       1550       1560       1570

2170       2180       2190       2200       2210       2220
SEQNO7 GGAGAGAAATACTTAAAGCTGGGTCCATCGGGGTTGGTGGTGTCGATTACGTCTTAAGTT
       ::::::::::::::::::::::::::::::::::::::::::::::::::::::::::::
SEQNO1 GGAGAGAAATACTTAAAGCTGGGTCCATCGGGGTTGGTGGTGTCGATTACGTCTTAAGTT
         1580       1590       1600       1610       1620       1630
```

Figure 3E

```
            2230      2240      2250      2260      2270      2280
SEQNO7 GTATCCTTGGAAACCAAGCTGAATCAAACAACTGGCAAGAACTGCTGGGTCGCCTCTGTC
       ::::::::::::::::::::::::::::::::::::::::::::::::::::::::::::
SEQNO1 GTATCCTTGGAAACCAAGCTGAATCAAACAACTGGCAAGAACTGCTGGGTCGCCTCTGTC
            1640      1650      1660      1670      1680      1690

2290      2300      2310      2320      2330      2340
SEQNO7 TTATAGACAGGTTGCTGTTGGAATTTCCTGCTGAATTCTATCCTCATATTGTCAGTACTG
       ::::::::::::::::::::::::::::::::::::::::::::::::::::::::::::
SEQNO1 TTATAGACAGGTTGCTGTTGGAATTTCCTGCTGAATTCTATCCTCATATTGTCAGTACTG
            1700      1710      1720      1730      1740      1750

2350      2360      2370      2380      2390      2400
SEQNO7 ATGTCTCACAAGCTGAGCCTGTTGAAATCAGGTACAAGAAGCTGCTCTCCCTCTTAACCT
       ::::::::::::::::::::::::::::::::::::::::::::::::::::::::::::
SEQNO1 ATGTCTCACAAGCTGAGCCTGTTGAAATCAGGTACAAGAAGCTGCTCTCCCTCTTAACCT
            1760      1770      1780      1790      1800      1810

2410      2420      2430      2440      2450      2460
SEQNO7 TTGCCTTGCAATCCATTGACAATTCCCACTCGATGGTTGGCAAGCTCTCTCGGAGGATAT
       ::::::::::::::::::::::::::::::::::::::::::::::::::::::::::::
SEQNO1 TTGCCTTGCAATCCATTGACAATTCCCACTCGATGGTTGGCAAGCTCTCTCGGAGGATAT
            1820      1830      1840      1850      1860      1870

2470      2480      2490      2500      2510      2520
SEQNO7 ATCTGAGCTCTGCCAGGATGGTGACCGCAGTGCCCGCTGTGTTTTCCAAGCTGGTAACCA
       ::::::::::::::::::::::::::::::::::::::::::::::::::::::::::::
SEQNO1 ATCTGAGCTCTGCCAGGATGGTGACCGCAGTGCCCGCTGTGTTTTCCAAGCTGGTAACCA
            1880      1890      1900      1910      1920      1930

2530      2540      2550      2560      2570      2580
SEQNO7 TGCTTAATGCTTCTGGCTCCACCCACTTCACCAGGATGCGCCGGCGTCTGATGGCTATCG
       ::::::::::::::::::::::::::::::::::::::::::::::::::::::::::::
SEQNO1 TGCTTAATGCTTCTGGCTCCACCCACTTCACCAGGATGCGCCGGCGTCTGATGGCTATCG
            1940      1950      1960      1970      1980      1990

2590      2600      2610      2620      2630      2640
SEQNO7 CGGATGAGGTAGAAATTGCCGAGGTCATCCAGCTGGGTGTGGAGGACACTGTGGATGGGC
       ::::::::::::::::::::::::::::::::::::::::::::::::::::::::::::
SEQNO1 CGGATGAGGTAGAAATTGCCGAGGTCATCCAGCTGGGTGTGGAGGACACTGTGGATGGGC
            2000      2010      2020      2030      2040      2050

2650      2660      2670      2680      2690      2700
SEQNO7 ATCAGGACAGCTTACAGGCCGTGGCCCCCACCAGCTGTCTAGAAAACAGCTCCCTTGAGC
       :::::::::::::::::: :::::::::::::::::::::::::::::::::::::::::
SEQNO1 ATCAGGACAGCTTACAGGCGCTGGCCCCCGCCAGCTGTCTAGAAAACAGCTCCCTTGAGC
            2060      2070      2080      2090      2100      2110

2710      2720      2730      2740      2750      2760
SEQNO7 ACACAGTCCATAGAGAGAAAACTGGAAAAGGACTAAGTGCTACGAGACTGAGTGCCAGCT
       ::::::::::::::::::::::::::::::::::::::::::::::::::::::::::::
SEQNO1 ACACAGTCCATAGAGAGAAAACTGGAAAAGGACTAAGTGCTACGAGACTGAGTGCCAGCT
            2120      2130      2140      2150      2160      2170

2770      2780      2790      2800      2810      2820
SEQNO7 CGGAGGACATTTCTGACAGACTGGCCGGCGTCTCTGTAGGACTTCCCAGCTCAACAACAA
       ::::::::::::::::::::::::::::::::::::::::::::::::::::::::::::
SEQNO1 CGGAGGACATTTCTGACAGACTGGCCGGCGTCTCTGTAGGACTTCCCAGCTCAACAACAA
            2180      2190      2200      2210      2220      2230
```

Figure 3F

```
             2830       2840       2850       2860       2870       2880
SEQNO7  CAGAACAACCAAAGCCAGCGGTTCAAACAAAAGGCAGACCCCACAGTCAGTGTTTGAACT
        ::::::::::::::::::::::::::::::::::::::::::::::::::::::::::::
SEQNO1  CAGAACAACCAAAGCCAGCGGTTCAAACAAAAGGCAGACCCCACAGTCAGTGTTTGAACT
          2240       2250       2260       2270       2280       2290

2890       2900       2910       2920       2930       2940
SEQNO7  CCTCCCCTTTGTCTCATGCTCAATTAATGTTCCCAGCACCATCAGCCCCTTGTTCCTCTG
        ::::::::::::::::::::::::::::::::::::::::::::::::::::::::::::
SEQNO1  CCTCCCCTTTGTCTCATGCTCAATTAATGTTCCCAGCACCATCAGCCCCTTGTTCCTCTG
          2300       2310       2320       2330       2340       2350

2950       2960       2970       2980       2990       3000
SEQNO7  CCCCGTCTGTCCCAGATATTTCTAAGCACAGACCCCAGGCATTTGTTCCCTGCAAAATAC
        ::::::::::::::::::::::::::::::::::::::::::::::::::::::::::::
SEQNO1  CCCCGTCTGTCCCAGATATTTCTAAGCACAGACCCCAGGCATTTGTTCCCTGCAAAATAC
          2360       2370       2380       2390       2400       2410

3010       3020       3030       3040       3050       3060
SEQNO7  CTTCCGCATCTCCTCAGACACAGCGCAAGTTCTCTCTACAATTCCAGAGGAACTGCTCTG
        ::::::::::::::::::::::::::::::::::::::::::::::::::::::::::::
SEQNO1  CTTCCGCATCTCCTCAGACACAGCGCAAGTTCTCTCTACAATTCCAGAGGAACTGCTCTG
          2420       2430       2440       2450       2460       2470

3070       3080       3090       3100       3110       3120
SEQNO7  AACACCGAGACTCAGACCAGCTCTCCCCAGTCTTCACTCAGTCAAGACCCCCACCCTCCA
        ::::::::::::::::::::::::::::::::::::::::::::::::::::::::::::
SEQNO1  AACACCGAGACTCAGACCAGCTCTCCCCAGTCTTCACTCAGTCAAGACCCCCACCCTCCA
          2480       2490       2500       2510       2520       2530

3130       3140       3150       3160       3170       3180
SEQNO7  GTAACATACACAGGCCAAAGCCATCCCGACCCGTTCCGGGCAGTACAAGCAAACTAGGGG
        ::::::::::::::::::::::::::::::::::::::::::::::::::::::::::::
SEQNO1  GTAACATACACAGGCCAAAGCCATCCCGACCCGTTCCGGGCAGTACAAGCAAACTAGGGG
          2540       2550       2560       2570       2580       2590

3190       3200       3210       3220       3230       3240
SEQNO7  ACGCCACAAAAAGTAGCATGACACTTGATCTGGGCAGTGCTTCCAGGTGTGACGACAGCT
        ::::::::::::::::::::::::::::::::::::::::::::::::::::::::::::
SEQNO1  ACGCCACAAAAAGTAGCATGACACTTGATCTGGGCAGTGCTTCCAGGTGTGACGACAGCT
          2600       2610       2620       2630       2640       2650

3250       3260       3270       3280       3290       3300
SEQNO7  TTGGCGGCGGCGGCAACAGTGGCAACGCCGTCATACCCAGCGACGAGACAGTGTTCACGC
        ::::::::::::::::::::::::::::::::::::::::::::::::::::::::::::
SEQNO1  TTGGCGGCGGCGGCAACAGTGGCAACGCCGTCATACCCAGCGACGAGACAGTGTTCACGC
          2660       2670       2680       2690       2700       2710

3310       3320       3330       3340       3350       3360
SEQNO7  CGGTGGAGGACAAGTGCAGGTTAGATGTGAACACCGAGCTCAACTCCAGCATCGAGGACC
        ::::::::::::::::::::::::::::::::::::::::::::::::::::::::::::
SEQNO1  CGGTGGAGGACAAGTGCAGGTTAGATGTGAACACCGAGCTCAACTCCAGCATCGAGGACC
          2720       2730       2740       2750       2760       2770
```

Figure 3G

```
              3370      3380      3390      3400      3410      3420
SEQNO7 TTCTTGAAGCATCCATGCCTTCAAGTGACACGACAGTCACTTTCAAGTCCGAAGTCGCCG
       ::::::::::::::::::::::::::::::::::::::::::::::::::::::::::::
SEQNO1 TTCTTGAAGCATCCATGCCTTCAAGTGACACGACAGTCACTTTCAAGTCCGAAGTCGCCG
          2780      2790      2800      2810      2820      2830

3430      3440      3450      3460      3470      3480
SEQNO7 TCCTCTCTCCGGAAAAGGCCGAAAATGACGACACCTACAAAGACGACGTCAATCATAATC
       ::::::::::::::::::::::::::::::::::::::::::::::::::::::::::::
SEQNO1 TCCTCTCTCCGGAAAAGGCCGAAAATGACGACACCTACAAAGACGACGTCAATCATAATC
          2840      2850      2860      2870      2880      2890

3490      3500      3510      3520      3530      3540
SEQNO7 AAAAGTGCAAAGAAAAGATGGAAGCTGAAGAGGAGGAGGCTTTAGCGATCGCCATGGCGA
       ::::::::::::::::::::::::::::::::::::::::::::::::::::::::::::
SEQNO1 AAAAGTGCAAAGAAAAGATGGAAGCTGAAGAGGAGGAGGCTTTAGCGATCGCCATGGCGA
          2900      2910      2920      2930      2940      2950

3550      3560      3570      3580      3590      3600
SEQNO7 TGTCAGCGTCTCAGGATGCCCTCCCCATCGTCCCTCAGCTGCAGGTGGAAAATGGAGAAG
       ::::::::::::::::::::::::::::::::::::::::::::::::::::::::::::
SEQNO1 TGTCAGCGTCTCAGGATGCCCTCCCCATCGTCCCTCAGCTGCAGGTGGAAAATGGAGAAG
          2960      2970      2980      2990      3000      3010

3610      3620      3630      3640      3650      3660
SEQNO7 ATATTATCATCATTCAGCAGGACACACCAGAAACTCTTCCAGGACATACCAAAGCGAAAC
       :::::::::::::::::::::::::::::::::::::::::::::::::::::::::::
SEQNO1 ATATTATCATCATTCAGCAGGACACACCAGAAACTCTTCCAGGACATACCAAAGCGAAAC
          3020      3030      3040      3050      3060      3070

3670      3680      3690      3700      3710      3720
SEQNO7 AGCCTTACAGAGAAGACGCTGAGTGGCTGAAAGGCCAGCAGATAGGCCTCGGAGCATTTT
       ::::::::::::::::::::::::::::::::::::::::::::::::::::::::::::
SEQNO1 AGCCTTACAGAGAAGACGCTGAGTGGCTGAAAGGCCAGCAGATAGGCCTCGGAGCATTTT
          3080      3090      3100      3110      3120      3130

3730      3740      3750      3760      3770      3780
SEQNO7 CTTCCTGTTACCAAGCACAGGATGTGGGGACTGGGACTTTAATGGCTGTGAAACAGGTGA
       ::::  :::::  ::  ::  ::  :::::::  :::::   ::::::::::  ::::::::::
SEQNO1 CTTCTTGTTATCAGGCTCAAGATGTGGGAACTGGAACTTTAATGGCTGTTAAACAGGTGA
          3140      3150      3160      3170      3180      3190

3790      3800      3810      3820      3830      3840
SEQNO7 CGTACGTCAGAAACACATCCTCCGAGCAGGAGGAGGTGGTGGAAGCGTTGAGGGAAGAGA
       :  ::  ::::::::::::::  ::  ::::::  ::  ::  ::  :::::  :  ::  :::::::
SEQNO1 CTTATGTCAGAAACACATCTTCTGAGCAAGAAGAAGTAGTAGAAGCACTAAGAGAAGAGA
          3200      3210      3220      3230      3240      3250

3850      3860      3870      3880      3890      3900
SEQNO7 TCCGGATGATGGGTCACCTCAACCATCCAAACATCATCCGGATGCTGGGGGCCACGTGCG
       :  :  ::::::  :  ::  ::  ::  ::::::::::::  :::::  ::::  ::::::::: :
SEQNO1 TAAGAATGATGAGCCATCTGAATCATCCAAACATCATTAGGATGTTGGGAGCCACGTGTG
          3260      3270      3280      3290      3300      3310

3910      3920      3930      3940      3950      3960
SEQNO7 AGAAGAGCAACTACAACCTCTTCATTGAGTGGATGGCGGGAGGATCTGTGGCTCACCTCT
       ::::::::::  ::::  :::::::::::::::::  ::  :::::  ::::::::  :
SEQNO1 AGAAGAGCAATTACAATCTCTTCATTGAATGGATGGCAGGGGATCGGTGGCTCATTTGC
          3320      3330      3340      3350      3360      3370
```

Figure 3H

```
           3970       3980       3990       4000       4010      4020
SEQNO7 TGAGTAAATACGGAGCTTTCAAGGAGTCAGTCGTCATTAACTACACTGAGCAGTTACTGC
       ::::::::::  :::::  :::::  ::  :::::  ::  ::::::::::::  :::::::: :
SEQNO1 TGAGTAAATATGGAGCCTTCAAAGAATCAGTAGTTATTAACTACACTGAACAGTTACTCC
           3380       3390       3400       3410       3420      3430

4030       4040       4050       4060       4070      4080
SEQNO7 GTGGCCTTTCCTATCTCCACGAGAACCAGATCATTCACAGAGACGTCAAAGGTGCCAACC
       ::::::::::  ::::: ::::::::::::::::::::::::::::::  ::::::::::::
SEQNO1 GTGGCCTTTCGTATCTCCATGAGAACCAGATCATTCACAGAGATGTCAAAGGTGCCAATT
           3440       3450       3460       3470       3480      3490

4090       4100       4110       4120       4130      4140
SEQNO7 TGCTCATTGACAGCACCGGTCAGAGGCTGAGAATTGCAGACTTTGGAGCTGCTGCCAGGT
       :::::::::::::::::::::::::::::::::::::::::::::::::::::  ::::::
SEQNO1 TGCTCATTGACAGCACCGGTCAGAGGCTGAGAATTGCAGACTTTGGAGCTGCAGCCAGGT
           3500       3510       3520       3530       3540      3550

4150       4160       4170       4180       4190      4200
SEQNO7 TGGCATCAAAAGGAACCGGTGCAGGAGAGTTCCAGGGACAGTTACTGGGGACAATTGCAT
       ::::::::::::::::  ::::::::::::::::::: :::::::  ::::::::::::::
SEQNO1 TGGCATCAAAAGGAACTGGTGCAGGAGAGTTTCAGGGACAATTACTGGGGACAATTGCAT
           3560       3570       3580       3590       3600      3610

4210       4220       4230       4240       4250      4260
SEQNO7 TCATGGCGCCTGAGGTCCTAAGAGGTCAGCAGTATGGTAGGAGCTGTGATGTATGGAGTG
       ::::::::::::::::::::::::::::::::::::::::::::::::::::::::::::
SEQNO1 TCATGGCGCCTGAGGTCCTAAGAGGTCAGCAGTATGGTAGGAGCTGTGATGTATGGAGTG
           3620       3630       3640       3650       3660      3670

4270       4280       4290       4300       4310      4320
SEQNO7 TTGGCTGCGCCATTATAGAAATGGCTTGTGCAAAACCACCTTGGAATGCAGAAAAACACT
       ::::::::::::::::::::::::::::::::::::::::::::::::::::::::::::
SEQNO1 TTGGCTGCGCCATTATAGAAATGGCTTGTGCAAAACCACCTTGGAATGCAGAAAAACACT
           3680       3690       3700       3710       3720      3730

4330       4340       4350       4360       4370      4380
SEQNO7 CCAATCATCTCGCCTTGATATTTAAGATTGCTAGCGCAACTACTGCACCGTCCATCCCGT
       ::::::::::::::::::::::::::::::::::::::::::::::::::::::::::::
SEQNO1 CCAATCATCTCGCCTTGATATTTAAGATTGCTAGCGCAACTACTGCACCGTCCATCCCGT
           3740       3750       3760       3770       3780      3790

4390       4400       4410       4420       4430      4440
SEQNO7 CACACCTGTCCCCGGGTCTGCGCGACGTGGCCGTGCGCTGCTTAGAACTTCAGCCTCAGG
       :::::::::::::  ::: : :: :: ::::: : :: :: :::::::::::::::::::
SEQNO1 CACACCTGTCCCCTGGTTTACGAGATGTGGCTCTTCGTTGTTTAGAACTTCAGCCTCAGG
           3800       3810       3820       3830       3840      3850

4450       4460       4470       4480       4490      4500
SEQNO7 ACCGGCCTCCGTCCAGAGAGCTGCTGAAACATCCGGTCTTCCGTACCACGTGGTAGTTAA
       :::::::::::::: :::::::::::::::::::::::::::::::::::::::::
SEQNO1 ACCGGCCTCCGTCAAGAGAGCTGCTGAAACATCCGGTCTTCCGTACCACGTGGTAG----
           3860       3870       3880       3890       3900      3910

4510       4520       4530       4540       4550      4560
SEQNO7 TTGTTCAGATCAGCTCTAATGGAGACAGGATATGCAACCGGGAGAGAGAAAAGAGAACTT

SEQNO1 ------------------------------------------------------------
```

*Figure 31*

```
            4570      4580      4590      4600      4610      4620
SEQNO7  GTGGGCGACCATGCCGCTAACCGCAGCCCTCACGCCACTGAACAGCCAGAAACGGGGCCA

SEQNO1  ------------------------------------------------------------

4630      4640      4650      4660      4670      4680
SEQNO7  GCGGGGAACCGTACCTAAGCATGTGATTGACAAATCATGACCTGTACCTAAGCTCGATAT

SEQNO1  ------------------------------------------------------------

4690      4700      4710      4720      4730      4740
SEQNO7  GCAGACATCTACAGCTCGTGCAGGAACTGCACACCGTGCCTTTCACAGGACTGGCTCTGG

SEQNO1  ------------------------------------------------------------

4750      4760      4770      4780      4790      4800
SEQNO7  GGGACCAGGAAGGCGATGGAGTTTGCATGACTAAAGAACAGAAGCATAAATTTATTTTTG

SEQNO1  ------------------------------------------------------------

4810      4820      4830      4840      4850      4860
SEQNO7  GAGCACTTTTTCAGCTAATCAGTATTACCATGTACATCAACATGCCCGCCACATTTCAAA

SEQNO1  ------------------------------------------------------------

4870      4880      4890      4900      4910      4920
SEQNO7  CTCAGACTGTCCCAGATGTCAAGATCCACTGTGTTTGAGTTTGTTTGCAGTTCCCTCAGC

SEQNO1  ------------------------------------------------------------

4930      4940      4950      4960      4970      4980
SEQNO7  TTGCTGGTAATTGTGGTGTTTTGTTTTCGATGCAAATGTGATGTAATATTCTTATTTTCT

SEQNO1  ------------------------------------------------------------

4990      5000      5010      5020      5030      5040
SEQNO7  TTGGATCAAAGCTGGACTGAAAATTGTACTGTGTAATTATTTTTGTGTTTTTAATGTTAT

SEQNO1  ------------------------------------------------------------

5050      5060      5070      5080      5090      5100
SEQNO7  TTGGTACTCGAATTGTAAATAACGTCTACTGCTGTTTATTCCAGTTTCTACTACCTCAGG

SEQNO1  ------------------------------------------------------------
```

Figure 3J

```
          5110      5120      5130      5140      5150      5160
SEQNO7 TGTCCTATAGATTTTTCTTCTACCAAAGTTCACTCTCCAGAATGAAATTCTACGTGTG

SEQNO1 ----------------------------------------------------------

5170      5180      5190      5200      5210      5220
SEQNO7 TGACTATGACTCCTAAGACTTCCAGGGCTTAAGGGCTAACTCCTATTAGCACCTTACTAT

SEQNO1 ----------------------------------------------------------

5230      5240      5250
SEQNO7 GTAAGCAAATGCTACAAAAAAAAAAAAAAAAA

SEQNO1 --------------------------------
```

Figure 4A

```
            1          10         20         30         40
mouse       MAAAAGDRAS SSGFPGAAAA SPEAGGGGGG GGALQGSGAP AAGAAGLLRE
human 50         60         70         80         90
mouse       PGSAGRERAD WRRRQLRKVR SVELDQLPEQ PLFLAAASPP CPSTSPSPEP
human 100        110        120        130        140
mouse       ADAAAGASRF QPAAGPPPPG AASRCGSHSA ELAAARDSGA RSPAGAEPPS
human 150        160        170        180        190
mouse       AAAPSGREME NKETLKGLHK MEDRPEERMI REKLKATCMP AWKHEWLERR
human                                                   AWKHEWLERR 200        210        220        230        240
mouse       NRRGPVVVKP IPIKGDGSEV NNLAAEPQGE GQAGSAAPAP KGRRSPSPGS
human       NRRGPVVVKP IPVKGDGSEM NHLAAESPGE VQASAASPAS KGRRSPSPGN 250        260        270        280        290
mouse       SPSGRSVKPE SPGVRRKRVS PVPFQSGRIT PPRRAPSPDG FSPYSPEETS
human       SPSGRTVKSE SPGVRRKRVS PVPFQSGRIT PPRRAPSPDG FSPYSPEETN 300        310        320        330        340
mouse       RRVNKVMRAR LYLLQQIGPN SFLIGGDSPD NKYRVFIGPQ NCSCGRGAFC
human       RRVNKVMRAR LYLLQQIGPN SFLIGGDSPD NKYRVFIGPQ NCSCARGTFC 350        360        370        380        390
mouse       IHLLFVMLRV FQLEPSDPML WRKTLKNFEV ESLFQKYHSR RSSRIKAPSR
human       IHLLFVMLRV FQLEPSDPML WRKTLKNFEV ESLFQKYHSR RSSRIKAPSR 400        410        420        430        440
mouse       NTIQKFVSRM SNSHTLSSSS TSTSSSENSI KDEEEQMCPI CLLGMLDEES
human       NTIQKFVSRM SNSHTLSSSS TSTSSSVNSI KDEEEQMCPI CLLGMLDEES 450        460        470        480        490
mouse       LTVCEDGCRN KLHHHCMSIW AEECRRNREP LICPLCRSKW RSHDFYSHEL
human       LTVCEDGCRN KLHHHCMSIW AEECRRNREP LICPLCRSKW RSHDFYSHEL 500        510        520        530        540
mouse       SSPVESPASL RAVQQPSSPQ QPVAGSQRRN QESSFNLTHF GTQQIPSAYK
human       SSPVDSPSSL RAAQQQTVQQ QPLAGS-RRN QESNFNLTHY GTQQIPPAYK 550        560        570        580        590
mouse       DLAEPWIQVF GMELVGCLFS RNWNVREMAL RRLSHDVSGA LLLANGESTG
human       DLAEPWIQVF GMELVGCLFS RNWNVREMAL RRLSHDVSGA LLLANGESTG 600        610        620        630        640
mouse       NSGGGSGGSL SAGAASGSSQ PSISGDVVEA CCSVLSIVCA DPVYKVYVAA
human       NSGGGSGGSL SAGAASGSSQ PSISGDVVEA CCSVLSIVCA DPVYKVYVAA
```

Figure 4B

```
               650        660        670        680        690
mouse          LKTLRAMLVY TPCHSLAERI KLQRLLRPVV DTILVKCADA NSRTSQLSIS
human          LKTLRAMLVY TPCHSLAERI KLQRLLRPVV DTILVKCADA NSRTSQLSIS 700        710        720        730        740
mouse          TVLELCKGQA GELAVGREIL KAGSIGVGGV DYVLSCILGN QAESNNWQEL
human          TVLELCNGQA GKLAVGREIL KAGSIGVGGV DYVLSCILGN QAESNNWQEL 750        760        770        780        790
mouse          LGRLCLIDRL LLEFPAEFYP HIVSTDVSQA EPVEIRYKKL LSLLTFALQS
human          LGRLCLIDRL LLEFPAEFYP HIVSTDVSQA EPVEIRYKKL LSLLTFALQS 800        810        820        830        840
mouse          IDNSHSMVGK LSRRIYLSSA RMVTAVPAVF SKLVTMLNAS GSTHFTRMRR
human          IDNSHSMVGK LSRRIYLSSA RMVTAVPAVF SKLVTMLNAS GSTHFTRMRR 850        860        870        880        890
mouse          RLMAIADEVE IAEVIQLGVE DTVDGHQDSL QAVAPTSCLE NSSLEHTVHR
human          RLMAIDAEVE IAEVIQLGVE DTVDGHQDSL QALAPASCLE NSSLEHTVHR 900        910        920        930        940
mouse          EKTGKGLSAT RLSASSEDIS DRLAGVSVGL PSSTTTEQPK PAVQTKGRPH
human          EKTGKGLSAT RLSASSEDIS DRLAGVSVGL PSSTTTEQPK PAVQTKGRPH 950        960        970        980        990
mouse          SQCLNSSPLS HAQLMFPAPS APCSSAPSVP DISKHRPQAF VPCKIPSASP
human          SQCLNSSPLS HAQLMFPAPS APCSSAPSVP DISKHRPQAF VPCKIPSASP 1000       1010       1020       1030       1040
mouse          QTQRKFSLQF QRNCSEHRDS DQLSPVFTQS RPPPSSNIHR PKPSRPVPGS
human          QTQRKFSLQF QRNCSEHRDS DQLSPVFTQS RPPPSSNIHR PKPSRPVPGS 1050       1060       1070       1080       1090
mouse          TSKLGDATKS SMTLDLGSAS RCDDSFGGGG NSGNAVIPSD ETVFTPVEDK
human          TSKLGDATKS SMTLDLGSAS RCDDSFGGGG NSGNAVIPSD ETVFTPVEDK 1100       1110       1120       1130       1140
mouse          CRLDVNTELN SSIEDLLEAS MPSSDTTVTF KSEVAVLSPE KAENDDTYKD
human          CRLDVNTELN SSIEDLLEAS MPSSDTTVTF KSEVAVLSPE KAENDDTYKD 1150       1160       1170       1180       1190
mouse          DVNHNQKCKE KMEAEEEEAL AIAMAMSASQ DALPIVPQLQ VENGEDIIII
human          DVNHNQKCKE KMEAEEEEAL AIAMAMSASQ DALPIVPQLQ VENGEDIIII 1200       1210       1220       1230       1240
mouse          QQDTPETLPG HTKAKQPYRE DAEWLKGQQI GLGAFSSCYQ AQDVGTGTLM
human          QQDTPETLPG HTKAKQPYRE DAEWLKGQQI GLGAFSSCYQ AQDVGTGTLM 1250       1260       1270       1280       1290
mouse          AVKQVTYVRN TSSEQEEVVE ALREEIRMMG HLNHPNIIRM LGATCEKSNY
human          AVKQVTYVRN TSSEQEEVVE ALREEIRMMS HLNHPNIIRM LGATCEKSNY
```

Figure 4C

```
              1300        1310        1320        1330        1340
mouse         NLFIEWMAGG  SVAHLLSKYG  AFKESVVINY  TEQLLRGLSY  LHENQIIHRD
human         NLFIEWMAGG  SVAHLLSKYG  AFKESVVINY  TEQLLRGLSY  LHENQIIHRD 1350        1360        1370        1380        1390
mouse         VKGANLLIDS  TGQRLRIADF  GAAARLASKG  TGAGEFQGQL  LGTIAFMAPE
human         VKGANLLIDS  TGQRLRIADF  GAAARLASKG  TGAGEFQGQL  LGTIAFMAPE 1400        1410        1420        1430        1440
mouse         VLRGQQYGRS  CDVWSVGCAI  IEMACAKPPW  NAEKHSNHLA  LIFKIASATT
human         VLRGQQYGRS  CDVWSVGCAI  IEMACAKPPW  NAEKHSNHLA  LIFKIASATT 1450        1460        1470        1480        1490
mouse         APSIPSHLSP  GLRDVAVRCL  ELQPQDRPPS  RELLKHPVFR  TIW*
human         APSIPSHLSP  GLRDVALRCL  ELQPQDRPPS  RELLKHPVFR  TIW*
```

*Figure 5*

```
   1  GGCCAGCTCG GTGGCCTCCT CTCGGCCCTC GGCTCCGCGA TCCCCGCCCA GCGGCCGGGC
  61  AATAAAGAAT GTTGATGGGA GAACCATTTT CCTAATTTTC AAATTATTGA GCTGGTCGCC
 121  ATAATGGATG ATCAGCAAGC TTTGAATTCA ATCATGCAAG ATTTGGCTGT CCTTCATAAG
 181  GCCAGTCGGC CAGCATTATC TTTACAAGAA ACCAGGAAAG CAAAACCTTC ATCACCAAAA
 241  AAACAGAATG ATGTTCGAGT CAAATTTGAA CATAGAGGAG AAAAAAGGAT CCTGCAGGTT
 301  ACTAGACCAG TTAAACTAGA AGACCTGAGA TCTAAGTCTA AGATCGCCTT TGGGCAGTCT
 361  ATGGATCTAC ACTATACCAA CAATGAGTTG GTAATTCCGT TAACTACCCA AGATGACTTG
 421  GACAAAGCTG TGGAACTGCT GGATCGCAGT ATTCACATGA AGAGTCTCAA GATATTACTT
 481  GTAGTAAATG GGAGTACACA GGCTACTAAT TTAGAACCAT CACCGTCACC AGAAGATTTG
 541  AATAATACAC CACTTGGTGC AGAGAGGAAA AAGCGGCTAT CTGTAGTAGG TCCCCCTAAT
 601  AGGGATAGAA GTTCCCCTCC TCCAGGATAC ATTCCAGACG AGCTACACCA GATTGCCCGG
 661  AATGGGTCAT TCACTAGCAT CAACAGTGAA GGAGAGTTCA TTCCAGAGAG CATGGACCAA
 721  ATGCTGGATC CATTGTCTTT AAGCAGCCCT GAAAATTCTG GCTCAGGAAG CTGTCCGTCA
 781  CTTGATAGTC CTTTGGATGG AGAAAGCTAC CCAAAATCAC GGATGCCTAG GGCACAGAGC
 841  TACCCAGATA ATCATCAGGA GTTTACAGAC TATGATAACC CCATTTTTGA GAAATTTGGA
 901  AAAGGAGGAA CATATCCAAG AAGGTACCAC GTTTCCTATC ATCACCAGGA GTATAATGAC
 961  GGTCGGAAGA CTTTTCCAAG AGCTAGAAGG ACCCAGGGCA CCAGTTTCCG GTCTCCTGTG
1021  AGCTTCAGTC CTACTGATCA CTCCTTAAGC AATAGTAGTG GAAGCAGTGT CTTTACCCCA
1081  GAGTATGACG ACAGTCGAAT GAGAAGACGG GGGAGTGACA TAGACAACCC TACTTTGACT
1141  GTCACAGACA TCAGCCCACC ATGCCGTTCA CCTCGAGCTC CGACCAACTG GAGACTGGGC
1201  AAGCTGCTTG GCCAAGGAGA TTTTGGTAGG GTCTACCTCT GCTATGATGT TGATACCGGA
1261  AGAGAGCTGG CTGTTAAGCA AGTTCAGTTT AACCCTGAGA GCCCAGAGAC CAGCAAGGAA
1321  GTAAATGCAC TTGAGTGTGA AATTCAGTTG TTGAAAAACT TGTTGCATGA GCGAATTGTT
1381  CAGTATTATG GCTGTTTGAG GGATCCTCAG GAGAAAACAC TTTCCATCTT TATGGAGTAT
1441  ATGCCAGGGG GTTCAATTAA GGACCAACTA AAAGCCTACG GAGCTCTTAC TGAGAACGTG
1501  ACGAGGAAGT ACACCCGTCA GATTCTGGAG GGGGTCCATT ATTTGCATAG TAATATGATT
1561  GTCCATAGAG ATATCAAAGG AGCAAATATC TTAAGGGATT CCACAGGCAA TATCAAGTTA
1621  GGAGACTTTG GGCTAGTAA ACGGCTTCAG ACCATCTGTC TCTCAGGCAC AGGAATGAAG
1681  TCTGTCACAG GCACGCCATA CTGGATGAGT CCTGAGGTCA TCAGTGGAGA AGGCTATGGA
1741  AGAAAAGCAG ACATCTGGAG TGTAGCATGT AGAGTGGTAG AAATGCTAAC TGAAAAGCCA
1801  CCTTGGGCTG AATTTGAAGC AATGGCTGCC ATCTTTAAGA TCGCCACTCA GCCAACGAAC
1861  CCAAAGCTGC CACCTCATGT CTCAGACTAT ACTCGGGACT TCCTCAAACG GATTTTTGTA
1921  GAGGCCAAAC TTCGACCTTC AGCGGAGGAG CTCTTGCGGC ACATGTTTGT GCATTATCAC
1981  TAGCATCGGC GGCTTCGGTC CTCCACCATC TCC
```

Figure 6

```
  1 MDDQQALNSI MQDLAVLHKA SRPALSLQET RKAKPSSPKK QNDVRVKFEH RGEKRILQVT
 61 RPVKLEDLRS KSKIAFGQSM DLHYTNNELV IPLTTQDDLD KAVELLDRSI HMKSLKILLV
121 VNGSTQATNL EPSPSPEDLN NTPLGAERKK RLSVVGPPNR DRSSPPPGYI PDELHQIARN
181 GSFTSINSEG EFIPESMDQM LDPLSLSSPE NSGSGSCPSL DSPLDGESYP KSRMPRAQSY
241 PDNHQEFTDY DNPIFEKFGK GGTYPRRYHV SYHHQEYNDG RKTFPRARRT QGTSFRSPVS
301 FSPTDHSLSN SSGSSVFTPE YDDSRMRRRG SDIDNPTLTV TDISPPCRSP RAPTNWRLGK
361 LLGQGDFGRV YLCYDVDTGR ELAVKQVQFN PESPETSKEV NALECEIQLL KNLLHERIVQ
421 YYGCLRDPQE KTLSIFMEYM PGGSIKDQLK AYGALTENVT RKYTRQILEG VHYLHSNMIV
481 HRDIKGANIL RDSTGNIKLG DFGASKRLQT ICLSGTGMKS VTGTPYWMSP EVISGEGYGR
541 KADIWSVACR VVEMLTEKPP WAEFEAMAAI FKIATQPTNP KLPPHVSDYT RDFLKRIFVE
601 AKLRPSAEEL LRHMFVHYH*
```

Figure 7A

```
>_ SEQ ID NO:9                                          2465 nt vs.
>_ SEQ ID NO:3                                          2013 nt
scoring matrix: , gap penalties: -12/-2
80.7% identity;          Global alignment score: 6932

10        20        30        40        50        60
SEQNO9 GAATTCGGCACGAGGGACGATCCAGCGGCAGAGTCGCCGCTTCCGCTTCGCTGCTTCTCC
       :
SEQNO3 G-----------------------------------------------------------

70        80        90       100       110       120
SEQNO9 GGTCACCGGCGACGCGGGCCCGGGGCTTCCTTTTCATCGGCCCAGCTTATTCCGCGGGCC

SEQNO3 ------------------------------------------------------------

130       140       150       160       170       180
SEQNO9 CCGGGGCTGCAGCTACCCAGAAGCGGCGAAGAGGCCCTGGGCTGCGCGCCCGCTGTCCCA

SEQNO3 ------------------------------------------------------------

190       200       210       220       230       240
SEQNO9 TGTGAAGCAGGTTGGGCCTGGTCCCCGGCCCGTGCCCGGTTGTCTGCGGCCCTTCAGGCC

SEQNO3 ------------------------------------------------------------

250       260       270       280       290       300
SEQNO9 TCAGGGACCCCCGCGAGGCGCTGCTCCTGGGGGGCGCGGTGACAGGCCGTGCGGGGGCGG

SEQNO3 ------------------------------------------------------------

310       320       330       340       350
SEQNO9 AGGGGCCAGCTCGGTGGCCTCCTCTCGGCCCTCGCGTCCGCGATCCC-GCCCAGCGGCCG
               ::::::::::::::::::::::::::::::::::  ::::::::::  ::::::::::::
SEQNO3 ----GCCAGCTCGGTGGCCTCCTCTCGGCCCTCGGCTCCGCGATCCCCGCCCAGCGGCCG
               10        20        30        40        50

360       370       380       390       400       410
SEQNO9 GGCAATAAAGAATGTTGATGGGAGAACCATTTTCCTAATTTTCAAATTATTGAGCTGGTC
       ::::::::::::::::::::::::::::::::::::::::::::::::::::::::::::
SEQNO3 GGCAATAAAGAATGTTGATGGGAGAACCATTTTCCTAATTTTCAAATTATTGAGCTGGTC
               60        70        80        90       100       110

420       430       440       450       460       470
SEQNO9 GCGCATAATGGATGATCAGCAAGCTTTGAATTCAATCATGCAAGATTTGGCTGTCCTTCA
       ::  ::::::::::::::::::::::::::::::::::::::::::::::::::::::::
SEQNO3 GC-CATAATGGATGATCAGCAAGCTTTGAATTCAATCATGCAAGATTTGGCTGTCCTTCA
              120       130       140       150       160       170
```

Figure 7B

```
        480       490       500       510       520       530
SEQNO9 TAAG-CCAGTCGGCCAGCATTATCTTTACAAGAAACCAGGAAAGCAAAACCTTCATCACC
       ::::  :::::::::::::::::::::::::::::::::::::::::::::::::::::
SEQNO3 TAAGGCCAGTCGGCCAGCATTATCTTTACAAGAAACCAGGAAAGCAAAACCTTCATCACC
        180       190       200       210       220       230

540       550       560       570       580       590
SEQNO9 AAAAAAACAGAATGATGTTCGAGTCAAATTTGAACATAGAGGAGGAAAAAAGGATCCTGC
       :::::::::::::::::::::::::::::::::::::::::::::  :::::::::::::
SEQNO3 AAAAAAACAGAATGATGTTCGAGTCAAATTTGAACATAGAGGAG-AAAAAAGGATCCTGC
        240       250       260       270       280       290

600       610       620       630       640       650
SEQNO9 AGGTTACTAGACCAGTTAAACTAGAAGACCTGAGATCTAAGTCTAAGATCGCCTTTGGGC
       ::::::::::::::::::::::::::::::::::::::::::::::::::::::::::::
SEQNO3 AGGTTACTAGACCAGTTAAACTAGAAGACCTGAGATCTAAGTCTAAGATCGCCTTTGGGC
        300       310       320       330       340       350

660       670       680       690       700       710
SEQNO9 AGTCTATGGATCTACACTATACCAACAATGAGTTGGTAATTCCGTTAACTACCCAAGATG
       ::::::::::::::::::::::::::::::::::::::::::::::::::::::::::::
SEQNO3 AGTCTATGGATCTACACTATACCAACAATGAGTTGGTAATTCCGTTAACTACCCAAGATG
        360       370       380       390       400       410

720       730       740       750       760       770
SEQNO9 ACTTGGACAAAGCTGTGGAACTGCTGGATCGCAGTATTCACATGAAGAGTCTCAAGATAT
       ::::::::::::::::::::::::::::::::::::::::::::::::::::::::::::
SEQNO3 ACTTGGACAAAGCTGTGGAACTGCTGGATCGCAGTATTCACATGAAGAGTCTCAAGATAT
        420       430       440       450       460       470

780       790       800       810       820       830
SEQNO9 TACTTGTAGTAAATGGGAGTACACAGGCTACTAATTTAGAACCATCACCGTCACCAGAAG
       ::::::::::::::::::::::::::::::::::::::::::::::::::::::::::::
SEQNO3 TACTTGTAGTAAATGGGAGTACACAGGCTACTAATTTAGAACCATCACCGTCACCAGAAG
        480       490       500       510       520       530

840       850       860       870       880       890
SEQNO9 ATTTGAATAATACACCACTTGGTGCAGAGAGGAAAAAGCGGCTATCTGTAGTAGGTCCCC
       ::::::::::::::::::::::::::::::::::::::::::::::::::::::::::::
SEQNO3 ATTTGAATAATACACCACTTGGTGCAGAGAGGAAAAAGCGGCTATCTGTAGTAGGTCCCC
        540       550       560       570       580       590

900       910       920       930       940       950
SEQNO9 CTAATAGGGATAGAAGTTCCCCTCCTCCAGGATACATTCCAGACATACTACACCAGATTG
       :::::::::::::::::::::::::::::::::::::::::::::::   :::::::::::
SEQNO3 CTAATAGGGATAGAAGTTCCCCTCCTCCAGGATACATTCCAGACGAGCTACACCAGATTG
        600       610       620       630       640       650

960       970       980       990      1000      1010
SEQNO9 CCCGGAATGGGTCATTCACTAGCATCAACAGTGAAGGAGAGTTCATTCCAGAGAGCATGG
       ::::::::::::::::::::::::::::::::::::::::::::::::::::::::::::
SEQNO3 CCCGGAATGGGTCATTCACTAGCATCAACAGTGAAGGAGAGTTCATTCCAGAGAGCATGG
        660       670       680       690       700       710
```

Figure 7C

```
              1020       1030       1040       1050       1060       1070
SEQNO9 ACCAAATGCTGGATCCATTGTCTTTAAGCAGCCCTGAAAATTCTGGCTCAGGAAGCTGTC
       ::::::::::::::::::::::::::::::::::::::::::::::::::::::::::::
SEQNO3 ACCAAATGCTGGATCCATTGTCTTTAAGCAGCCCTGAAAATTCTGGCTCAGGAAGCTGTC
               720        730        740        750        760        770

1080       1090       1100       1110       1120       1130
SEQNO9 CGTCACTTGATAGTCCTTTGGATGGAGAAAGCTACCCAAAATCACGGATGCCTAGGGCAC
       ::::::::::::::::::::::::::::::::::::::::::::::::::::::::::::
SEQNO3 CGTCACTTGATAGTCCTTTGGATGGAGAAAGCTACCCAAAATCACGGATGCCTAGGGCAC
               780        790        800        810        820        830

1140       1150       1160       1170       1180       1190
SEQNO9 AGAGCTACCCAGATAATCATCAGGAGTTTACAGACTATGATAACCCCATTTTTGAGAAAT
       ::::::::::::::::::::::::::::::::::::::::::::::::::::::::::::
SEQNO3 AGAGCTACCCAGATAATCATCAGGAGTTTACAGACTATGATAACCCCATTTTTGAGAAAT
               840        850        860        870        880        890

1200       1210       1220       1230       1240       1250
SEQNO9 TTGGAAAAGGAGGAACATATCCAAGAAGGTACCACGTTTCCTATCATCACCAGGAGTATA
       ::::::::::::::::::::::::::::::::::::::::::::::::::::::::::::
SEQNO3 TTGGAAAAGGAGGAACATATCCAAGAAGGTACCACGTTTCCTATCATCACCAGGAGTATA
               900        910        920        930        940        950

1260       1270       1280       1290       1300       1310
SEQNO9 ATGACGGTCGGAAGACTTTTCCAAGAGCTAGAAGGACCCAGGGCACCAGTTTCCGGTCTC
       ::::::::::::::::::::::::::::::::::::::::::::::::::::::::::::
SEQNO3 ATGACGGTCGGAAGACTTTTCCAAGAGCTAGAAGGACCCAGGGCACCAGTTTCCGGTCTC
               960        970        980        990       1000       1010

1320       1330       1340       1350       1360       1370
SEQNO9 CTGTGAGCTTCAGTCCTACTGATCACTCCTTAAGCACTAGTAGTGGAAGCAGTGTCTTTA
       :::::::::::::::::::::::::::::::::::::::  :::::::::::::::::::
SEQNO3 CTGTGAGCTTCAGTCCTACTGATCACTCCTTAAGCAATAGTAGTGGAAGCAGTGTCTTTA
              1020       1030       1040       1050       1060       1070

1380       1390       1400       1410       1420       1430
SEQNO9 CCCCAGAGTATGACGACAGTCGAATAAGAAGACGGGGGAGTGACATAGACAATCCTACTT
       :::::::::::::::::::::::::::::  ::::::::::::::::::::::  :::::
SEQNO3 CCCCAGAGTATGACGACAGTCGAATGAGAAGACGGGGGAGTGACATAGACAACCCTACTT
              1080       1090       1100       1110       1120       1130

1440       1450       1460       1470       1480       1490
SEQNO9 TGACTGTCACAGACATCAGCCCACCCAGCCGTTCACCTCGAGCTCCGACCAACTGGAGAC
       ::::::::::::::::::::::::::::::  ::::::::::::::::::::::::::::
SEQNO3 TGACTGTCACAGACATCAGCCCACCATGCCGTTCACCTCGAGCTCCGACCAACTGGAGAC
              1140       1150       1160       1170       1180       1190

1500       1510       1520       1530       1540       1550
SEQNO9 TGGGCAAGCTGCTTGGCCAAGGAGCTTTTGGTAGGGTCTACCTCTGCTATGATGTTGATA
       ::::::::::::::::::::::::::::: ::::::::::::::::::::::::::::::
SEQNO3 TGGGCAAGCTGCTTGGCCAAGGAGATTTTGGTAGGGTCTACCTCTGCTATGATGTTGATA
              1200       1210       1220       1230       1240       1250
```

*Figure 7D*

```
        1560      1570      1580      1590      1600      1610
SEQNO9  CCGGAAGAGAGCTGGCTGTTAAGCAAGTTCAGTTTAACCCTGAGAGCCCAGAGACCAGCA
        ::::::::::::::::::::::::::::::::::::::::::::::::::::::::::::
SEQNO3  CCGGAAGAGAGCTGGCTGTTAAGCAAGTTCAGTTTAACCCTGAGAGCCCAGAGACCAGCA
        1260      1270      1280      1290      1300      1310

1620      1630      1640      1650      1660      1670
SEQNO9  AGGAAGTAAATGCACTTGAGTGTGAAATTCAGTTGTTGAAAAACTTGTTGCATGAGCGAA
        ::::::::::::::::::::::::::::::::::::::::::::::::::::::::::::
SEQNO3  AGGAAGTAAATGCACTTGAGTGTGAAATTCAGTTGTTGAAAAACTTGTTGCATGAGCGAA
        1320      1330      1340      1350      1360      1370

1680      1690      1700      1710      1720      1730
SEQNO9  TTGTTCAGTATTATGGCTGTTTGAGGGATCCTCAGGAGAAAACACTTTCCATCTTTATGG
        ::::::::::::::::::::::::::::::::::::::::::::::::::::::::::::
SEQNO3  TTGTTCAGTATTATGGCTGTTTGAGGGATCCTCAGGAGAAAACACTTTCCATCTTTATGG
        1380      1390      1400      1410      1420      1430

1740      1750      1760      1770      1780      1790
SEQNO9  AGCTCTCGCCAGGGGGTTCAATTAAGGACCAACTAAAAGCCTACGGAGCTCTTACTGAGA
        ::        ::::::::::::::::::::::::::::::::::::::::::::::::::
SEQNO3  AGTATATGCCAGGGGGTTCAATTAAGGACCAACTAAAAGCCTACGGAGCTCTTACTGAGA
        1440      1450      1460      1470      1480      1490

1800      1810      1820      1830      1840      1850
SEQNO9  ACGTGACGAGGAAGTACACCCGTCAGATTCTGGAGGGGGTCCATTATTTGCATAGTAATA
        ::::::::::::::::::::::::::::::::::::::::::::::::::::::::::::
SEQNO3  ACGTGACGAGGAAGTACACCCGTCAGATTCTGGAGGGGGTCCATTATTTGCATAGTAATA
        1500      1510      1520      1530      1540      1550

1860      1870      1880      1890      1900      1910
SEQNO9  TGATTGTCCATAGAGATATCAAAGGAGCAAATATCTTAAGGGATTCCACAGGCAATATCA
        ::::::::::::::::::::::::::::::::::::::::::::::::::::::::::::
SEQNO3  TGATTGTCCATAGAGATATCAAAGGAGCAAATATCTTAAGGGATTCCACAGGCAATATCA
        1560      1570      1580      1590      1600      1610

1920      1930      1940      1950      1960      1970
SEQNO9  AGTTAGGAGACTTTGGGGCTAGTAAACGGCTTCAGACCATCTGTCTCTCAGGCACAGGAA
        ::::::::::::::::::::::::::::::::::::::::::::::::::::::::::::
SEQNO3  AGTTAGGAGACTTTGGGGCTAGTAAACGGCTTCAGACCATCTGTCTCTCAGGCACAGGAA
        1620      1630      1640      1650      1660      1670

1980      1990      2000      2010      2020      2030
SEQNO9  TGAAGTCTGTCACAGGCACGCCATACTGGATGAGTCCTGAGGTCATCAGTGGAGAAGGCT
        ::::::::::::::::::::::::::::::::::::::::::::::::::::::::::::
SEQNO3  TGAAGTCTGTCACAGGCACGCCATACTGGATGAGTCCTGAGGTCATCAGTGGAGAAGGCT
        1680      1690      1700      1710      1720      1730

2040      2050      2060      2070      2080      2090
SEQNO9  ATGGAAGAAAAGCAGACATCTGGAGTGTAGCATGTACTGTGGTAGAAATGCTAACTGAAA
        ::::::::::::::::::::::::::::::::::        ::::::::::::::::::
SEQNO3  ATGGAAGAAAAGCAGACATCTGGAGTGTAGCATGTAGAGTGGTAGAAATGCTAACTGAAA
        1740      1750      1760      1770      1780      1790
```

Figure 7E

```
          2100      2110      2120      2130      2140      2150
SEQNO9 AGCCACCTTGGGCTGAATTTGAAGCAATGGCTGCCATCTTTAAGATCGCCACTCAGCCAA
       ::::::::::::::::::::::::::::::::::::::::::::::::::::::::::::
SEQNO3 AGCCACCTTGGGCTGAATTTGAAGCAATGGCTGCCATCTTTAAGATCGCCACTCAGCCAA
          1800      1810      1820      1830      1840      1850

2160      2170      2180      2190      2200      2210
SEQNO9 CGAACCCAAAGCTGCCACCTCATGTCTCAGACTATACTCGGGACTTCCTCAAACGGATTT
       ::::::::::::::::::::::::::::::::::::::::::::::::::::::::::::
SEQNO3 CGAACCCAAAGCTGCCACCTCATGTCTCAGACTATACTCGGGACTTCCTCAAACGGATTT
          1860      1870      1880      1890      1900      1910

2220      2230      2240      2250      2260      2270
SEQNO9 TTGTAGAGGCCAAACTTCGACCTTCAGCGGAGGAGCTCTTGCGGCACATGTTTGTGCATT
       ::::::::::::::::::::::::::::::::::::::::::::::::::::::::::::
SEQNO3 TTGTAGAGGCCAAACTTCGACCTTCAGCGGAGGAGCTCTTGCGGCACATGTTTGTGCATT
          1920      1930      1940      1950      1960      1970

2280      2290      2300      2310      2320      2330
SEQNO9 ATCACTAGCAGCGGCGGCTTCGGTCCTCCACCAGCTCCATCCTCGCGGCCACCTTCTCTC
       :::::::::  :::::::::::::::::::::  ::::
SEQNO3 ATCACTAGCATCGGCGGCTTCGGTCCTCCACCATCTCC----------------------
          1980      1990      2000      2010

2340      2350      2360      2370      2380      2390
SEQNO9 TTACTGCACTTTCCTTTTTTATAAAAAAGAGAGATGGGGAGAAAAAGACAAGAGGGAAAA

SEQNO3 ------------------------------------------------------------

2400      2410      2420      2430      2440      2450
SEQNO9 TATTTCTCTTGATTCTTGGTTAAATTTGTTTAATAATAATAGTAAACTAAAAAAAAAAAA

SEQNO3 ------------------------------------------------------------

2460
SEQNO9 AAAAAAA

SEQNO3 -------
```

Figure 8

|       |       1          10         20         30         40  |
|-------|--------------------------------------------------------|
| mouse | MDDQQALNSI MQDLAVLHKA SRPALSLQET RKAKPSSPKK QNDVRVKFEH |
| human | MDDQQALNSI MQDLAVLHKA SRPALSLQET RKAKPSSPKK QNDVRVKFEH |

|       |      50         60         70         80         90   |
|-------|--------------------------------------------------------|
| mouse | RGEKRILQVT RPVKLEDLRS KSKIAFGQSM DLHYTNNELV IPLTTQDDLD |
| human | RGEKRILQVT RPVKLEDLRS KSKIAFGQSM DLHYTNNELV IPLTTQDDLD |

|       |     100        110        120        130        140   |
|-------|--------------------------------------------------------|
| mouse | KAVELLDRSI HMKSLKILLV VNGSTQATNL EPSPSPEDLN NTPLGAERKK |
| human | KAVELLDRSI HMKSLKILLV VNGSTQATNL EPSPSPEDLN NTPLGAERKK |

|       |     150        160        170        180        190   |
|-------|--------------------------------------------------------|
| mouse | RLSVVGPPNR DRSSPPPGYI PDELHQIARN GSFTSINSEG EFIPESMDQM |
| human | RLSVVGPPNR DRSSLPPGYI PDELHQIARN GSFTSINSEG EFIPESMDQM |

|       |     200        210        220        230        240   |
|-------|--------------------------------------------------------|
| mouse | LDPLSLSSPE NSGSGSCPSL DSPLDGESYP KSRMPRAQSY PDNHQEFTDY |
| human | LDPLSLSSPE NSGSGSCPSL DSPLDGESYP KSRMPRAQSY PDNHQEFTDY |

|       |     250        260        270        280        290   |
|-------|--------------------------------------------------------|
| mouse | DNPIFEKFGK GGTYPRRYHV SYHHQEYNDG RKTFPRARRT QGTSFRSPVS |
| human | DNPIFEKFGK GGTYPRRYHV SYHHQEYNDG RKTFPRARRT QGTSFRSPVS |

|       |     300        310        320        330        340   |
|-------|--------------------------------------------------------|
| mouse | FSPTDHSLST SSGSSVFTPE YDDSRIRRRG SDIDNPTLTV TDISPPSRSP |
| human | FSPTDHSLSN SSGSSVFTPE YDDSRMRRRG SDIDNPTLTV TDISPPCRSP |

|       |     350        360        370        380        390   |
|-------|--------------------------------------------------------|
| mouse | RAPTNWRLGK LLGQGAFGRV YLCYDVDTGR ELAVKQVQFN PESPETSKEV |
| human | RAPTNWRLGK LLGQGDFGRV YLCYDVDTGR ELAVKQVQFN PESPETSKEV |

|       |     400        410        420        430        440   |
|-------|--------------------------------------------------------|
| mouse | NALECEIQLL KNLLHERIVQ YYGCLRDPQE KTLSIFMEYM PGGSIKDQLK |
| human | NALECEIQLL KNLLHERIVQ YYGCLRDPQE KTLSIFMEYM PGGSIKDQLK |

|       |     450        460        470        480        490   |
|-------|--------------------------------------------------------|
| mouse | AYGALTENVT RKYTRQILEG VHYLHSNMIV HRDIKGANIL RDSTGNIKLG |
| human | AYGALTENVT RKYTRQILEG VHYLHSNMIV HRDIKGANIL RDSTGNIKLG |

|       |     500        510        520        530        540   |
|-------|--------------------------------------------------------|
| mouse | DFGASKRLQT ICLSGTGMKS VTGTPYWMSP EVISGEGYGR KADIWSVACT |
| human | DFGASKRLQT ICLSGTGMKS VTGTPYWMSP EVISGEGYGR KADIWSVACR |

|       |     550        560        570        580        590   |
|-------|--------------------------------------------------------|
| mouse | VVEMLTEKPP WAEFEAMAAI FKIATQPTNP KLPPHVSDYT RDFLKRIFVE |
| human | VVEMLTEKPP WAEFEAMAAI FKIATQPTNP KLPPHVSDYT RDFLKRIFVE |

|       |     600        610                                     |
|-------|--------------------------------------------------------|
| mouse | AKLRPSAEEL LRHMFVHYH*                                  |
| human | AKLRPSAEEL LRHMFVHYH*                                  |

Figure 9

```
   1 ACCGCCGCCT CCGCCATCGC CACCATGGAT CAACAAGAGG CATTAGACTC GATCATGAAG
  61 GACCTGGTGG CCCTCCAGAT GAGCCGACGA ACCCGGTTGT CTGGATATGA GACCATGAGG
 121 AATAAGGACA CAGGTCACCC AAACAGGCAG AGTGACGTCA GAATCAAGTT TGAACACAAT
 181 GGGGAGAGAC GAATTATAGC ATTCAGCCGG CCTGTGAGAT ACGAAGATGT GGAGCACAAG
 241 GTGACAACAG TCTTTGGGCA GTCTCTTGAT TTGCATTATA TGAATAATGA GCTCTCCATC
 301 CTGTTGAAAA ACCAAGATGA TCTCGATAAA GCCATTGACA TTTTGGATAG AAGCTCAAGT
 361 ATGAAAAGCC TTAGGATACT ACTGTTATCC CAAGACAGAT ACCATACTAG TTCCTCTCCC
 421 CACTCTGGAG TGTCCAGGCA GGTTCGGATC AAGCCTTCCC AGTCTGCAGG GGATATAAAT
 481 ACCATCTACC AAGCTCCTGA GCCCAGAAGC AGGCACCTGT CTGTCAGCTC CCAGAACCCT
 541 GGCCGAAGCT CACCTCCCCC GGGATATGTT CCTGAGCGGC AACAGCACAT TGCCCGGCAA
 601 GGATCCTACA CCAGCATCAA CAGTGAGGGG GAGTTCATCC AGAGACCAG CGAGCAGTGC
 661 ATGCTGGATC CCCTGAGCAG TGCAGAAAAT TCCTTGTCTG GAAGCTGCCA ATCCTTGGAC
 721 AGGTCAGCAG ACAGCCCATC CTTCCGGAAA TCACGAATGT CCCGTGCCCA GAGCTTCCCT
 781 GACAACAGAC AGGAATACTC AGATCGGGAA ACTCAGCTTT ATGACAAAGG GGTCAAAGGT
 841 GGAACCTACC CCCGGCGCTA CCACGTGTCT GTGCACCACA AGGACTACAG TGATGGCAGA
 901 AGAACATTTC CCCGAATACG GCGTCATCAA GGCAACTTGT TCACCCTGGT GCCCTCCAGC
 961 CGCTCCCTGA GCACAAATGG CGAGAACATG GGTCTGGCTG TGCAATACCT GGACCCCGT
1021 GGGCGCCTGC GGAGTGCGGA CAGCGAGAAT GCCCTCTCTG TGCAGGAGAG GAATGTGCCA
1081 ACCAAGTCTC CCAGTGCCCC CATCAACTGG CGCCGGGGAA AGCTCCTGGG CCAGGGTGCC
1141 TTCGGCAGGG TCTATTTGTG CTATGACGTG GACACGGGAC GTGAACTTGC TTCCAAGCAG
1201 GTCCAATTTG ATCCAGACAG TCCTGAGACA AGCAAGGAGG TGAGTGCTCT GGAGTGCGAG
1261 ATCCAGTTGC TAAAGAACTT GCAGCATGAG CGCACTGTGC AGTACTACGG CTGCCTGCGG
1321 GACCGTACTC AGAAGATCCT CACCATCTTT ATGGAGTATA TGCCAGGGGG CTCTGTAAAA
1381 GACCAGTTGA AGGCCTACGG AGCTCTGACA GAGAGTGTGA CCCGCAAGTA CACCCGGCAG
1441 ATTCTGGAGG GCATGTCATA CCTGCACAGC AACATGATTG TGCATCGGGA CATCAAGGGA
1501 GCCAATATCC TCCGAGACTC AGCTGGGAAT GTGAAGCTTG GGGATTTTGG GGCCAGCAAA
1561 CACCTACAGA CCATCTGCAT GTCAGGGACA GGCATTCGCT CTGTCACTGA CACACCCTAC
1621 TGGATGAGTC CTGAAGTCAT CAGTGGCGAG GGCTATGGAA GAAAGGCAGA CGTGTGGAGC
1681 CTGGGCTGTA CTGTGGTGGA TATGCTGACA GAGAAACCAC CTTGGGCAGA GTATGAAGCT
1741 ATGGCTGCCA TTTTCAAGAT TGCCACCCAG CCTACCAATC CTCAGCTGCC CTCTCACATC
1801 TCAGAACACG GCAGGGACTT CCTGAGGCGC ATATTTGTGG AAGCTCGTCA GAGACCCTCA
1861 GCCGAGGAAC TGCTCACACA CCACTTTACA CAGCTAGTGT ACTGAGCTCT CAAGGCTATC
1921 AGGCTGCCAG CTGCC
```

Figure 10

```
  1 MDQQEALDSI MKDLVALQMS RRTRLSGYET MRNKDTGHPN RQSDVRIKFE HNGERRIIAF
 61 SRPVRYEDVE HKVTTVFGQS LDLHYMNNEL SILLKNQDDL DKAIDILDRS SSMKSLRILL
121 LSQDRYHTSS SPHSGVSRQV RIKPSQSAGD INTIYQAPEP RSRHLSVSSQ NPGRSSPPPG
181 YVPERQQHIA RQGSYTSINS EGEFIPETSE QCMLDPLSSA ENSLSGSCQS LDRSADSPSF
241 RKSRMSRAQS FPDNRQEYSD RETQLYDKGV KGGTYPRRYH VSVHHKDYSD GRRTFPRIRR
301 HQGNLFTLVP SSRSLSTNGE NMGLAVQYLD PRGRLRSADS ENALSVQERN VPTKSPSAPI
361 NWRRGKLLGQ GAFGRVYLCY DVDTGRELAS KQVQFDPDSP ETSKEVSALE CEIQLLKNLQ
421 HERTVQYYGC LRDRTQKILT IFMEYMPGGS VKDQLKAYGA LTESVTRKYT RQILEGMSYL
481 HSNMIVHRDI KGANILRDSA GNVKLGDFGA SKHLQTICMS GTGIRSVTDT PYWMSPEVIS
541 GEGYGRKADV WSLGCTVVDM LTEKPPWAEY EAMAAIFKIA TQPTNPQLPS HISEHGRDFL
601 RRIFVEARQR PSAEELLTHH FTQLVY*    627
```

Figure 11A

```
>_ SEQ ID NO:11 (mouse MEKK3)                          3332 nt vs.
>_ SEQ ID NO:5  (human MEKK3)                          1935 nt
scoring matrix: , gap penalties: -12/-2
55.7% identity;         Global alignment score: 4373

10        20        30        40        50        60
SEQIDNO:11 GAATTCGGCACGAGGAACAGTGGCCGGTCGGAGCGTCTTCTGGACTTCAGGACTCGCAGG

SEQIDNO:5  ------------------------------------------------------------

70        80        90       100       110       120
SEQIDNO:11 CGGCCCGGTCGAGTGGCGCCGCCGAGGCCGGGTTGGGCCGAGCCTGGGAGCGCCGGGGAT

SEQIDNO:5  ------------------------------------------------------------

130       140       150       160       170       180
SEQIDNO:11 GTAGCGGGCCAACCTGCTCATGCCACAGCGCCCGGCCGCGGCCGGAGCCGGAGCCTGGGG

SEQIDNO:5  ------------------------------------------------------------

190       200       210       220       230       240
SEQIDNO:11 AGGCGGCGGGGGCCCCGAGCGCAGCCCACGGCCCCCGCGCGGAGCCAGGCCCGCTGCCGT

SEQIDNO:5  ------------------------------------------------------------

250       260       270       280       290       300
SEQIDNO:11 CCCCGCCGCCCGCTCCCCCGGCATGCAGCCCCGGCTGCGGAGGTGACACTTCTGGGCTGT

SEQIDNO:5  ------------------------------------------------------------

310       320       330       340       350       360
SEQIDNO:11 AGTCGCCACCGCCGCCTCCGCCATCGCCACCATGGATGAACAAGAGGCATTAGACTCGAT
                  ::::::::::::::::::::::::::::: :::::::::::::::::::::
SEQIDNO:5  -------ACCGCCGCCTCCGCCATCGCCACCATGGATCAACAAGAGGCATTAGACTCGAT
                         10        20        30        40        50

370       380       390       400       410       420
SEQIDNO:11 CATGAAGGACCTGGTGGCCCTCCAGATGAGCCGACGAACCCGGTTGTCTGGATATGAGAC
           ::::::::::::::::::::::::::::::::::::::::::::::::::::::::::::
SEQIDNO:5  CATGAAGGACCTGGTGGCCCTCCAGATGAGCCGACGAACCCGGTTGTCTGGATATGAGAC
                 60        70        80        90       100       110

430       440       450       460       470       480
SEQIDNO:11 CATGAAGAATAAGGACACAGGTCACCCAAACAGGCAGAGTGACGTCAGAATCAAGTTTGA
           :::::  :::::::::::::::::::::::::::::::::::::::::::::::::::::
SEQIDNO:5  CATGAGGAATAAGGACACAGGTCACCCAAACAGGCAGAGTGACGTCAGAATCAAGTTTGA
                120       130       140       150       160       170
```

Figure 11B

```
                          490        500        510        520        530        540
SEQIDNO:11   ACACAATGGGGAGAGACGAATTATAGCATTCAGCCGGCCTGTGAGATACGAAGATGTGGA
             ::::::::::::::::::::::::::::::::::::::::::::::::::::::::::::
SEQIDNO:5    ACACAATGGGGAGAGACGAATTATAGCATTCAGCCGGCCTGTGAGATACGAAGATGTGGA
              180       190        200        210        220        230

550        560        570        580        590        600
SEQIDNO:11   GCACAAGGTGACAACAGTCTTTGGGCAGCCTCTTGATTTGCATTATATGAATAATGAGCT
             :::::::::::::::::::::::::: :::::::::::::::::::::::::::::::::
SEQIDNO:5    GCACAAGGTGACAACAGTCTTTGGGCAGTCTCTTGATTTGCATTATATGAATAATGAGCT
              240       250        260        270        280        290

610        620        630        640        650        660
SEQIDNO:11   CTCCATCCTGTTGAAAAACCAAGATGATCTCGATAAAGCCATTGACATTTTGGATAGAAG
             ::::::::::::::::::::::::::::::::::::::::::::::::::::::::::::
SEQIDNO:5    CTCCATCCTGTTGAAAAACCAAGATGATCTCGATAAAGCCATTGACATTTTGGATAGAAG
              300       310        320        330        340        350

670        680        690        700        710        720
SEQIDNO:11   CTCAAGTATGAAAAGCCTTAGGATACTACTGTTATCCCAAGACAGAAACCATACTAGTTC
             :::::::::::::::::::::::::::::::::::::::::::: :::::::::::::::
             CTCAAGTATGAAAAGCCTTAGGATACTACTGTTATCCCAAGACAGATACCATACTAGTTC
              360       370        380        390        400        410

730        740        750        760        770        780
SEQIDNO:11   CTCTCCCCACTCTGGAGTGTCCAGGCAGGTTCGGATCAAGCCTTCCCAGTCTGCAGGGGA
             ::::::::::::::::::::::::::::::::::::::::::::::::::::::::::::
SEQIDNO:5    CTCTCCCCACTCTGGAGTGTCCAGGCAGGTTCGGATCAAGCCTTCCCAGTCTGCAGGGGA
              420       430        440        450        460        470

790        800        810        820        830        840
SEQIDNO:11   TATAAATACCATCTACCAAGCTCCTGAGCCCAGAAGCAGGCACCTGTCTGTCAGCTCCCA
             ::::::::::::::::::::::::::::::::::::::::::::::::::::::::::::
SEQIDNO:5    TATAAATACCATCTACCAAGCTCCTGAGCCCAGAAGCAGGCACCTGTCTGTCAGCTCCCA
              480       490        500        510        520        530

850        860        870        880        890        900
SEQIDNO:11   GAACCCTGGCCGAAGCTCTCCTCCCCCGGGATATGTACCTGAGCGACAACAGCACATTGC
             ::::::::::::::::::::: ::::::::::::::::: :::::::: ::::::::::::
SEQIDNO:5    GAACCCTGGCCGAAGCTCACCTCCCCCGGGATATGTTCCTGAGCGGCAACAGCACATTGC
              540       550        560        570        580        590

910        920        930        940        950        960
SEQIDNO:11   CCGGCAAGGATCCTATACGAGCATCAACAGCGAAGGTGAATTCATCCCAGAGACCAGCGA
             :::::::::::::::: :: :::::::::::: :: :: :: ::::::::::::::::::
SEQIDNO:5    CCGGCAAGGATCCTACACCAGCATCAACAGTGAGGGGGAGTTCATCCCAGAGACCAGCGA
              600       610        620        630        640        650

970        980        990       1000       1010       1020
SEQIDNO:11   ACAGTGTATGCTAGATCCCCTCAGCAGTGCCGAAAATTCCTTGTCAGGAAGCTGCCAATC
             ::::: ::::: ::::: :::::::::::::: :::::::::::::: :::::::::::
SEQIDNO:5    GCAGTGCATGCTGGATCCCCTCAGCAGTGCAGAAAATTCCTTGTCTGGAAGCTGCCAATC
              660       670        680        690        700        710
```

Figure 11C

```
              1030      1040      1050      1060      1070      1080
SEQIDNO:11 CTTGGACAGGTCAGCAGACAGCCCATCCTTCAGGAAATCACAAATGTCCCGAGCCCGGAG
           ::::::::::::::::::::::::::::::::::: :::::::::: ::::::::: :::: :::
SEQIDNO:5  CTTGGACAGGTCAGCAGACAGCCCATCCTTCCGGAAATCACGAATGTCCCGTGCCCAGAG
              720       730       740       750       760       770

1090      1100      1110      1120      1130      1140
SEQIDNO:11 CTTCCCAGACAACAGAAAGGAATGCTCAGATCGGGAGACCCAGCTCTATGATAAAGGTGT
           :::::: :::::::::: :::::: ::::::::::::: :: ::::: ::::: ::::: ::
SEQIDNO:5  CTTCCCTGACAACAGACAGGAATACTCAGATCGGGAAACTCAGCTTTATGACAAAGGGGT
              780       790       800       810       820       830

1150      1160      1170      1180      1190      1200
SEQIDNO:11 CAAAGGTGGAACCTATCCCAGGCGCTACCATGTGTCTGTGCATCACAAAGACTACAATGA
           ::::::::::::::::: ::: :::::::::::: :::::::::::: :::: ::::::::: :::
SEQIDNO:5  CAAAGGTGGAACCTACCCCCGGCGCTACCACGTGTCTGTGCACCACAAGGACTACAGTGA
              840       850       860       870       880       890

1210      1220      1230      1240      1250      1260
SEQIDNO:11 TGGCAGAAGAACATTTCCCCGAATACGACGGCATCAAGGCAACCTATTCACTCTGGTGCC
           ::::::::::::::::::::::::::::: :: ::::::::::::: : ::::: ::::::::::
SEQIDNO:5  TGGCAGAAGAACATTTCCCCGAATACGGCGTCATCAAGGCAACTTGTTCACCCTGGTGCC
              900       910       920       930       940       950

1270      1280      1290      1300      1310      1320
SEQIDNO:11 CTCAAGTCGCTCCTTGAGCACAAATGGCGAGAACATGGGTGTAGCTGTGCAATACCTGGA
           ::: :: :::::::::::::::::::::::::::::::::::::: : :::::::::::::::::::
SEQIDNO:5  CTCCAGCCGCTCCCTGAGCACAAATGGCGAGAACATGGGTCTGGCTGTGCAATACCTGGA
              960       970       980       990       1000      1010

1330      1340      1350      1360      1370      1380
SEQIDNO:11 CCCCCGTGGGCGCCTACGGAGTGCAGACAGTGAGAATGCCCTCACTGTGCAGGAAAGGAA
           ::::::::::::::::::: ::::::::: ::::::::::::::::: ::::::::: :::::
SEQIDNO:5  CCCCCGTGGGCGCCTGCGGAGTGCGGACAGCGAGAATGCCCTCTCTGTGCAGGAGAGGAA
              1020      1030      1040      1050      1060      1070

1390      1400      1410      1420      1430      1440
SEQIDNO:11 TGTGCCAACCAAATCTCCTAGTGCTCCCATCAATTGGCGTCGGGGGAAGCTCCTGGGTCA
           ::::::::::::: ::::: ::::: :::::::::: :::::::::: ::::::::::::: ::
SEQIDNO:5  TGTGCCAACCAAGTCTCCCAGTGCCCCCATCAACTGGCGCCGGGGAAAGCTCCTGGGCCA
              1080      1090      1100      1110      1120      1130

1450      1460      1470      1480      1490      1500
SEQIDNO:11 AGGTGCCTTCGGCAGGGTCTACTTGTGCTATGATGTGGACACAGGACGTGAACTTGCTTC
           :::::::::::::::::::::::: ::::::::::::: ::::::::: :::::::::::::::
SEQIDNO:5  GGGTGCCTTCGGCAGGGTCTATTTGTGCTATGACGTGGACACGGGACGTGAACTTGCTTC
              1140      1150      1160      1170      1180      1190

1510      1520      1530      1540      1550      1560
SEQIDNO:11 TAAGCAGGTCCAGTTTGACCCAGATAGTCCTGAGACAAGCAAGGAGGTGAGTGCTCTGGA
           :::::::::::: ::::: ::::: ::::::::::::::::::::::::::::::::::::
SEQIDNO:5  CAAGCAGGTCCAATTTGATCCAGACAGTCCTGAGACAAGCAAGGAGGTGAGTGCTCTGGA
              1200      1210      1220      1230      1240      1250
```

Figure 11D

```
              1570       1580       1590       1600       1610       1620
SEQIDNO:11 GTGTGAGATCCAGTTGCTGAAGAACCTGCAGCATGAGCGCATTGTGCAGTACTACGGCTG
           ::: ::::::::::::  ::::::  :::::::::::::::::  ::::::::::::::::
SEQIDNO:5  GTGCGAGATCCAGTTGCTAAAGAACTTGCAGCATGAGCGCACTGTGCAGTACTACGGCTG
              1260       1270       1280       1290       1300       1310

1630       1640       1650       1660       1670       1680
SEQIDNO:11 CCTGCGGGACCGTGCTGAGAAGATCCTCACCATCTTTATGGAGTATATGCCAGGGGGCTC
           ::::::::::::  :: :::::::::::::::::::::::::::::::::::::::::::
SEQIDNO:5  CCTGCGGGACCGTACTCAGAAGATCCTCACCATCTTTATGGAGTATATGCCAGGGGGCTC
              1320       1330       1340       1350       1360       1370

1690       1700       1710       1720       1730       1740
SEQIDNO:11 TGTAAAAGACCAGTTGAAGGCCTACGGAGCTCTGACAGAGAGTGTGACCCGCAAGTACAC
           ::::::::::::::::::::::::::::::::::::::::::::::::::::::::::::
SEQIDNO:5  TGTAAAAGACCAGTTGAAGGCCTACGGAGCTCTGACAGAGAGTGTGACCCGCAAGTACAC
              1380       1390       1400       1410       1420       1430

1750       1760       1770       1780       1790       1800
SEQIDNO:11 CCGGCAGATTCTGGAGGGCATGTCATACCTGCACAGCAACATGATTGTGCATCGGGACAT
           ::::::::::::::::::::::::::::::::::::::::::::::::::::::::::::
SEQIDNO:5  CCGGCAGATTCTGGAGGGCATGTCATACCTGCACAGCAACATGATTGTGCATCGGGACAT
              1440       1450       1460       1470       1480       1490

1810       1820       1830       1840       1850       1860
SEQIDNO:11 CAAGGGAGCCAATATCCTCCGAGACTCAGCTGGGAATGTGAAGCTTGGGGATTTTGGGGC
           ::::::::::::::::::::::::::::::::::::::::::::::::::::::::::::
SEQIDNO:5  CAAGGGAGCCAATATCCTCCGAGACTCAGCTGGGAATGTGAAGCTTGGGGATTTTGGGGC
              1500       1510       1520       1530       1540       1550

1870       1880       1890       1900       1910       1920
SEQIDNO:11 CAGCAAACGCCTACAGACCATCTGCATGTCAGGGACAGGCATTCGCTCTGTCACTGGCAC
           ::::::::  ::::::::::::::::::::::::::::::::::::::::::::::: :::
SEQIDNO:5  CAGCAAACACCTACAGACCATCTGCATGTCAGGGACAGGCATTCGCTCTGTCACTGACAC
              1560       1570       1580       1590       1600       1610

1930       1940       1950       1960       1970       1980
SEQIDNO:11 ACCCTACTGGATGAGTCCTGAAGTCATCAGTGGCGAGGGCTATGGAAGAAAGGCAGACGT
           ::::::::::::::::::::::::::::::::::::::::::::::::::::::::::::
SEQIDNO:5  ACCCTACTGGATGAGTCCTGAAGTCATCAGTGGCGAGGGCTATGGAAGAAAGGCAGACGT
              1620       1630       1640       1650       1660       1670

1990       2000       2010       2020       2030       2040
SEQIDNO:11 GTGGAGCCTGGGCTGTACTGTGGTGGAAATGCTGACAGAGAAACCACCTTGGGCAGAGTA
           ::::::::::::::::::::::::::::::  ::::::::::::::::::::::::::::
SEQIDNO:5  GTGGAGCCTGGGCTGTACTGTGGTGGATATGCTGACAGAGAAACCACCTTGGGCAGAGTA
              1680       1690       1700       1710       1720       1730

2050       2060       2070       2080       2090       2100
SEQIDNO:11 TGAAGCTATGGCTGCCATTTTCAAGATTGCCACCCAGCCTACCAATCCTCAGCTGCCCTC
           ::::::::::::::::::::::::::::::::::::::::::::::::::::::::::::
SEQIDNO:5  TGAAGCTATGGCTGCCATTTTCAAGATTGCCACCCAGCCTACCAATCCTCAGCTGCCCTC
              1740       1750       1760       1770       1780       1790
```

Figure 11E

```
                  2110      2120      2130      2140      2150      2160
SEQIDNO:11 TCACATCTCAGAACACGGCAGGGACTTCCTGAGGCGCATATTTGTGGAAGCTCGTCAGAG
           ::::::::::::::::::::::::::::::::::::::::::::::::::::::::::::
SEQIDNO:5  TCACATCTCAGAACACGGCAGGGACTTCCTGAGGCGCATATTTGTGGAAGCTCGTCAGAG
              1800      1810      1820      1830      1840      1850

2170      2180      2190      2200      2210      2220
SEQIDNO:11 ACCCTCAGCTGAGGAGCTGCTCACACACCACTTTGCACAGCTAGTGTACTGAGCTCTCAA
           ::::::::: :::::  ::::::::::::::::::: ::::::::::::::::::::::
SEQIDNO:5  ACCCTCAGCCGAGGAACTGCTCACACACCACTTTACACAGCTAGTGTACTGAGCTCTCAA
              1860      1870      1880      1890      1900      1910

2230      2240      2250      2260      2270      2280
SEQIDNO:11 GGCTATCAGGCTGCCAGCTGCCACCTGCTGAGCAGGCAAGGGGCTGCTGTCAGGCTCAGT
           :::::::::::::::::::::::
SEQIDNO:5  GGCTATCAGGCTGCCAGCTGCC-------------------------------------
              1920      1930

2290      2300      2310      2320      2330      2340
SEQIDNO:11 GAAGTTGCTGCTTCTTCCAGGCAAGGCTATGACCAGTGGAGCATCGGTCCAGCCATTGTT

SEQIDNO:5  ------------------------------------------------------------

2350      2360      2370      2380      2390      2400
SEQIDNO:11 TGTCTGTGCCCCATCTGCCACTGGGACTCAAAGCCAGGATGGGATAGCTCTGGCATCAAG

SEQIDNO:5  ------------------------------------------------------------

2410      2420      2430      2440      2450      2460
SEQIDNO:11 ACTGGGAGCTCCAGCCTGTAAGACCCAAGAGCTTTAGCACCTTAAGCTCAGTATGGCGGG

SEQIDNO:5  ------------------------------------------------------------

2470      2480      2490      2500      2510      2520
SEQIDNO:11 AAGGGCTGGAAACAGTATGCAAGACTGCCATGGGTCCTGCCTACCCTCAGATGTGTCCTA

SEQIDNO:5  ------------------------------------------------------------

2530      2540      2550      2560      2570      2580
SEQIDNO:11 ACACTGCAGACAGCACTGAAGTCAAGAGGGACTGGGGCACAGGAGGTCCTCAAGGGTATG

SEQIDNO:5  ------------------------------------------------------------

2590      2600      2610      2620      2630      2640
SEQIDNO:11 AATAGTGTTACTTCATTCAGAGTGTTACTTTGTTTCTCTCCCAATGTTTGGAGACCACCA

SEQIDNO:5  ------------------------------------------------------------
```

Figure 11F

```
                 2650      2660      2670      2680      2690      2700
SEQIDNO:11  GCCTGTCTCTGGGCTGCAAGCCTGAGGTAAAGCCCAGCATCCCCCAGCCAACAGAAGGTA

SEQIDNO:5   ------------------------------------------------------------

2710      2720      2730      2740      2750      2760
SEQIDNO:11  GAGGTTTGGGCTACCCCACTATAGCTTCCAGGTATTCGGTGTCAGTCCTGTCTTACCAAA

SEQIDNO:5   ------------------------------------------------------------

2770      2780      2790      2800      2810      2820
SEQIDNO:11  GATGAATGAAGCAAATGTTACACTGCCTTATTCTGGGAAGGAGGAGCTACTCGGATAAGC

SEQIDNO:5   ------------------------------------------------------------

2830      2840      2850      2860      2870      2880
SEQIDNO:11  AGGGCCTGAGAGATGGAGCTGCCTCCAGAAACTGGGGAGACCCAGTCTTGTCAATGCAAT

SEQIDNO:5   ------------------------------------------------------------

2890      2900      2910      2920      2930      2940
SEQIDNO:11  TGTCTCTGTTTTACAAGTTGGAGTCACTCTTATGCTGTTCCCAGTTTTAAAACTGGAGAC

SEQIDNO:5   ------------------------------------------------------------

2950      2960      2970      2980      2990      3000
SEQIDNO:11  TTTGCCCTCTGAGCTCTGGAGACCCATGTGGGCTTAGGCTTGGACTGGATGGAAGAGCTG

SEQIDNO:5   ------------------------------------------------------------

3010      3020      3030      3040      3050      3060
SEQIDNO:11  ATGGCCTCTGCCCCCTGGCCTGCCCTCTGTTCCCTCACTGGAGCAGAGAAAGTAGACAAC

SEQIDNO:5   ------------------------------------------------------------

3070      3080      3090      3100      3110      3120
SEQIDNO:11  ACAAGTCAGGGCACCTGGTTCTGGGCAGCTCAGCAGAGTGCAGGGGGTTGTCTCAGGCTG

SEQIDNO:5   ------------------------------------------------------------

3130      3140      3150      3160      3170      3180
SEQIDNO:11  TCTGCATCTCAAATCTGTCAGGCCTGAGCCCACTCCATGGGAAAGTCCTTGAGCTGCCAC

SEQIDNO:5   ------------------------------------------------------------
```

Figure 11G

```
              3190      3200      3210      3220      3230      3240
SEQIDNO:11  AACCGTGTCCAAAGCCACCAGCTGTGTTCCTCAGCCCGACCTGTCCACTTGTCATCAACC
SEQIDNO:5   ------------------------------------------------------------

3250      3260      3270      3280      3290      3300
SEQIDNO:11  TCATTCCCTTCTTGTTCCTCCCACAAAGGAGGATGCCAGTAGGGGCTAGGGAAAGAGTTA
SEQIDNO:5   ------------------------------------------------------------

3310      3320      3330
SEQIDNO:11  TCATTAAAGGAAAGGAAAAAAAAAAAAAAAA
SEQIDNO:5   -------------------------------
```

Figure 12

```
                        10          20          30          40          50
muMEKK3      MDEQEALDSI MKDLVALQMS RRTRLSGYET MRNKDTGHPN RQSDVRIKFE
huMEKK3      MDQQEALDSI MKDLVALQMS RRTRLSGYET MRNKDTGHPN RQSDVRIKFE 60          70          80          90         100
muMEKK3      HNGERRIIAF SRPVRYEDVE HKVTTVFGQP LDLHYMNNEL SILLKNQDDL
huMEKK3      HNGERRIIAF SRPVRYEDVE HKVTTVFGQS LDLHYMNNEL SILLKNQDDL 110         120         130         140         150
muMEKK3      DKAIDILDRS SSMKSLRILL LSQDRNHTSS SPHSGVSRQV RIKPSQSAGD
huMEKK3      DKAIDILDRS SSMKSLRILL LSQDRYHTSS SPHSGVSRQV RIKPSQSAGD 160         170         180         190         200
muMEKK3      INTIYQAPEP RSRHLSVSSQ NPGRSSPPPG YVPERQQHIA RQGSYTSINS
huMEKK3      INTIYQAPEP RSRHLSVSSQ NPGRSSPPPG YVPERQQHIA RQGSYTSINS 210         220         230         240         250
muMEKK3      EGEFIPETSE QCMLDPLSSA ENSLSGSCQS LDRSADSPSF RKSQMSRARS
huMEKK3      EGEFIPETSE QCMLDPLSSA ENSLSGSCQS LDRSADSPSF RKSRMSRAQS 260         270         280         290         300
muMEKK3      FPDNRKECSD RETQLYDKGV KGGTYPRRYH VSVHHKDYND GRRTFPRIRR
huMEKK3      FPDNRQEYSD RETQLYDKGV KGGTYPRRYH VSVHHKDYSD GRRTFPRIRR 310         320         330         340         350
muMEKK3      HQGNLFTLVP SSRSLSTNGE NMGVAVQYLD PRGRLRSADS ENALTVQERN
huMEKK3      HQGNLFTLVP SSRSLSTNGE NMGLAVQYLD PRGRLRSADS ENALSVQERN 360         370         380         390         400
muMEKK3      VPTKSPSAPI NWRRGKLLGQ GAFGRVYLCY DVDTGRELAS KQVQFDPDSP
huMEKK3      VPTKSPSAPI NWRRGKLLGQ GAFGRVYLCY DVDTGRELAS KQVQFDPDSP 410         420         430         440         450
muMEKK3      ETSKEVSALE CEIQLLKNLQ HERIVQYYGC LRDRAEKILT IFMEYMPGGS
huMEKK3      ETSKEVSALE CEIQLLKNLQ HERTVQYYGC LRDRTQKILT IFMEYMPGGS 460         470         480         490         500
muMEKK3      VKDQLKAYGA LTESVTRKYT RQILEGMSYL HSNMIVHRDI KGANILRDSA
huMEKK3      VKDQLKAYGA LTESVTRKYT RQILEGMSYL HSNMIVHRDI KGANILRDSA 510         520         530         540         550
muMEKK3      GNVKLGDFGA SKRLQTICMS GTGIRSVTGT PYWMSPEVIS GEGYGRKADV
huMEKK3      GNVKLGDFGA SKHLQTICMS GTGIRSVTDT PYWMSPEVIS GEGYGRKADV 560         570         580         590         600
muMEKK3      WSLGCTVVEM LTEKPPWAEY EAMAAIFKIA TQPTNPQLPS HISEHGRDFL
huMEKK3      WSLGCTVVDM LTEKPPWAEY EAMAAIFKIA TQPTNPQLPS HISEHGRDFL 610         620
muMEKK3      RRIFVEARQR PSAEELLTHH FAQLVY*
huMEKK3      RRIFVEARQR PSAEELLTHH FTQLVY*
```

Figure 13

```
                     I                      II                      III
mMEKK1    QIGLGAFSSCYQAQDVGTGT-LMAVKQVTYVRNT--SSEQEEVVEALREE-
mMEKK2    LLGQGAFGRVYLCYDVDTGREL-AVKQVQFNPESPETSKEVNALECEIQL-
mMEKK3    LLGQGAFGRVYLCYDVDTGREL-ASKQVQFDPESPETSKEVSALECEIQL-
mMEKK4    KIGEGQYGKVYTCISVDTG-ELMAMKEIRFQPNDHKTIKETAD-ELKIFEG
hMEKK1    QIGLGAFSSCYQAQDVGTGT-LMAVKQVTYVRNT--SSEQEEVVEALREE-
hMEKK2    LLGQGDFGRVYLCYDVDTGREL-AVKQVQFNPESPETSKEVNALECEIQL-
hMEKK3    LLGQGAFGRVYLCYDVDTGREL-ASKQVQFDPESPETSKEVSALECEIQL-

IV                    V
mMEKK1    IRMMGHLNHPNIIRM--LGATCEKSNYNLFIEWMA-GGSVAHL-LSKYGAF
mMEKK2    LK--NLLHERIVQYYGCLRDPQEKTLS-IFMELSP-GGSIKDQ-LKAYGAL
mMEKK3    LK--NLQHERIVQYYGCLRDRAEKILT-IFMEYMP-GGSVKDQ-LKAYGAL
mMEKK4    IKHPNLV--R--YFGVELH-REE--MY-IFMEYCDEGTLEEVSRLGLQEHV
hMEKK1    IRMMSHLNHPNIIRM--LGATCEKSNYNLFIEWMA-GGSVAHL-LSKYGAF
hMEKK2    LK--NLLHERIVQYYGCLRDPQEKTLS-IFMELSP-GGSIKDQ-LKAYGAL
hMEKK3    LK--NLQHERTVQYYGCLRDRTQKILT-IFMEYMP-GGSVKDQ-LKAYGAL

VI                      VII
mMEKK1    KE-SVVINYTEQLLRGLSYLHENQIIHRDVKGANLLIDSTGQRLRIADFGA
mMEKK2    TEN-VTRKYTRQILEGVHYLHSNMIVHRDIKGANILRDSTGN-IKLGDFGA
mMEKK3    TE-SVTRKYTRQILEGMSYLHSNMIVHRDIKGANILRDSAGN-VKLGDFGA
mMEKK4    IR--LYTK--QITV-AINVLHEHGIVHRDIKGANIFLTSSGL-IKLGDFGC
hMEKK1    KE-SVVINYTEQLLRGLSYLHENQIIHRDVKGANLLIDSTGQRLRIADFGA
hMEKK2    TEN-VTRKYTRQILEGVHYLHSNMIVHRDIKGANILRDSTGN-IKLGDFGA
hMEKK3    TE-SVTRKYTRQILEGMSYLHSNMIVHRDIKGANILRDSAGN-VKLGDFGA

VIII                      IX
mMEKK1    AARLASK---GTGAGEFQGQLLGTIAFMAPEVL---RGQQYGRSCDVWSVG
mMEKK2    SKRLQTICLSGTGMKSVT----GTPYWMSPEVIS---GEGYGRKADIWSVA
mMEKK3    SKRLQTICMSGTGIRSVT----GTPYWMSPEVIS---GEGYGRKADVWSLG
mMEKK4    SVKLKNNAQTMPGEVNST---LGTAAYMAPEVITRAKGEGHGRAADIWSLG
hMEKK1    AARLASK---GTGAGEFQGQLLGTIAFMAPEVL---RGQQYGRSCDVWSVG
hMEKK2    SKRLQTICLSGTGMKSVT----GTPYWMSPEVIS---GEGYGRKADIWSVA
hMEKK3    SKHLQTICMSGTGIRSVT----DTPYWMSPEVIS---GEGYGRKADVWSLG

X
mMEKK1    CAIIEMACAKPPW-NAEKHSNHLALIFKIASATTAPSIPSHLSPGLRDVAV
mMEKK2    CTVVEMLTEKPPWAEFEAMA---AI-FKIATQPTNPKLPPHVSDYTRDFLK
mMEKK3    CTVVEMLTEKPPWAEYEAMA---AI-FKIATQPTNPQLPSHISEHGRDFLR
mMEKK4    CVVIEMVTGKRPWHEYEHNFQ-I-M-YKVGMGHKPP-IPERLSPEGKAFLS
hMEKK1    CAIIEMACAKPPW-NAEKHSNHLALIFKIASATTAPSIPSHLSPGLRDVAV
hMEKK2    CRVVEMLTEKPPWAEFEAMA---AI-FKIATQPTNPKLPPHVSDYTRDFLK
hMEKK3    CTVVDMLTEKPPWAEYEAMA---AI-FKIATQPTNPQLPSHISEHGRDFLR

XI
mMEKK1    RC-LELQPQDRPPSP-ELLKHPVFRTT-W
mMEKK2    RIFVEAKLR---PSAEELLRHM-FVH--YH
mMEKK3    RIFVEARQR---PSAEELLTHH-FAQLVY
mMEKK4    HC-LESDPKIR-WTASQLLDHA-FVKVCTDEE
hMEKK1    RC-LELQPQDRPPSP-ELLKHPVFRTT-W
hMEKK2    RIFVEAKLR---PSAEELLRHM-FVH--YH
hMEKK3    RIFVEARQR---PSAEELLTHH-FTQLVY
```

SEQUENCE LISTING

```
<160> NUMBER OF SEQ ID NOS: 38

<210> SEQ ID NO 1
<211> LENGTH: 3911
<212> TYPE: DNA
<213> ORGANISM: Homo sapiens
<220> FEATURE:
<221> NAME/KEY: CDS
<222> LOCATION: (3)..(3908)

<400> SEQUENCE: 1 cg gcc tgg aag cac gag tgg ttg gaa agg aga aat agg cga ggg cct        47
   Ala Trp Lys His Glu Trp Leu Glu Arg Arg Asn Arg Arg Gly Pro
   1               5                   10                  15 gtg gtg gta aaa cca atc cca gtt aaa gga gat gga tct gaa atg aat       95
Val Val Val Lys Pro Ile Pro Val Lys Gly Asp Gly Ser Glu Met Asn
            20                  25                  30 cac tta gca gct gag tct cca gga gag gtc cag gca agt gcg gct tca      143
His Leu Ala Ala Glu Ser Pro Gly Glu Val Gln Ala Ser Ala Ala Ser
        35                  40                  45 cca gct tcc aaa ggc cga cgc agt cct tct cct ggc aac tcc cca tca      191
Pro Ala Ser Lys Gly Arg Arg Ser Pro Ser Pro Gly Asn Ser Pro Ser
    50                  55                  60 ggt cgc aca gtg aaa tca gaa tct cca gga gta agg aga aaa aga gtt      239
Gly Arg Thr Val Lys Ser Glu Ser Pro Gly Val Arg Arg Lys Arg Val
65                  70                  75 tcc cca gtg cct ttt cag agt ggc aga atc aca cca ccc cga aga gcc      287
Ser Pro Val Pro Phe Gln Ser Gly Arg Ile Thr Pro Pro Arg Arg Ala
80                  85                  90                  95
```

-continued

| | | | | | | | | | | | | |
|---|---|---|---|---|---|---|---|---|---|---|---|---|
| cct | tca | cca | gat | ggc | ttc | tca | cca | tat | agc | cct | gag | gaa aca aac cgc | 335 |
| Pro | Ser | Pro | Asp | Gly | Phe | Ser | Pro | Tyr | Ser | Pro | Glu | Glu Thr Asn Arg |
|  |  |  | 100 |  |  |  |  | 105 |  |  |  | 110 |

| cgt gtt aac aaa gtg atg cgg gcc aga ctg tac tta ctg cag cag ata | 383 |
| Arg Val Asn Lys Val Met Arg Ala Arg Leu Tyr Leu Leu Gln Gln Ile |  |
|         115                 120                 125              |  |

| ggg cct aac tct ttc ctg att gga gga gac agc cca gac aat aaa tac | 431 |
| Gly Pro Asn Ser Phe Leu Ile Gly Gly Asp Ser Pro Asp Asn Lys Tyr |  |
|             130                 135                 140          |  |

| cgg gtg ttt att ggg cct cag aac tgc agc tgt gca cgt gga aca ttc | 479 |
| Arg Val Phe Ile Gly Pro Gln Asn Cys Ser Cys Ala Arg Gly Thr Phe |  |
|         145                 150                 155              |  |

| tgt att cat ctg cta ttt gtg atg ctc cgg gtg ttt caa cta gaa cct | 527 |
| Cys Ile His Leu Leu Phe Val Met Leu Arg Val Phe Gln Leu Glu Pro |  |
| 160                 165                 170                 175  |  |

| tca gac cca atg tta tgg aga aaa act tta aag aat ttt gag gtt gag | 575 |
| Ser Asp Pro Met Leu Trp Arg Lys Thr Leu Lys Asn Phe Glu Val Glu |  |
|             180                 185                 190          |  |

| agt ttg ttc cag aaa tat cac agt agg cgt agc tca agg atc aaa gct | 623 |
| Ser Leu Phe Gln Lys Tyr His Ser Arg Arg Ser Ser Arg Ile Lys Ala |  |
|         195                 200                 205              |  |

| cca tct cgt aac acc atc cag aag ttt gtt tca cgc atg tca aat tct | 671 |
| Pro Ser Arg Asn Thr Ile Gln Lys Phe Val Ser Arg Met Ser Asn Ser |  |
|         210                 215                 220              |  |

| cat aca ttg tca tca tct agt act tct aca tct agt tca gta aac agc | 719 |
| His Thr Leu Ser Ser Ser Ser Thr Ser Thr Ser Ser Ser Val Asn Ser |  |
|     225                 230                 235                  |  |

| ata aag gat gaa gag gaa cag atg tgt cct att tgc ttg ttg ggc atg | 767 |
| Ile Lys Asp Glu Glu Glu Gln Met Cys Pro Ile Cys Leu Leu Gly Met |  |
| 240                 245                 250                 255  |  |

| ctt gat gaa gaa agt ctt aca gtg tgt gaa gac ggc tgc agg aac aag | 815 |
| Leu Asp Glu Glu Ser Leu Thr Val Cys Glu Asp Gly Cys Arg Asn Lys |  |
|             260                 265                 270          |  |

| ctg cac cac cac tgc atg tca att tgg gca gaa gag tgt aga aga aat | 863 |
| Leu His His His Cys Met Ser Ile Trp Ala Glu Glu Cys Arg Arg Asn |  |
|         275                 280                 285              |  |

| aga gaa cct tta ata tgt ccc ctt tgt aga tct aag tgg aga tct cat | 911 |
| Arg Glu Pro Leu Ile Cys Pro Leu Cys Arg Ser Lys Trp Arg Ser His |  |
|         290                 295                 300              |  |

| gat ttc tac agc cac gag ttg tca agt cct gtg gat tcc cct tct tcc | 959 |
| Asp Phe Tyr Ser His Glu Leu Ser Ser Pro Val Asp Ser Pro Ser Ser |  |
| 305                 310                 315                      |  |

| ctc aga gct gca cag cag caa acc gta cag cag cag cct ttg gct gga | 1007 |
| Leu Arg Ala Ala Gln Gln Gln Thr Val Gln Gln Gln Pro Leu Ala Gly |  |
| 320                 325                 330                 335  |  |

| tca cga agg aat caa gag agc aat ttt aac ctt act cat tat gga act | 1055 |
| Ser Arg Arg Asn Gln Glu Ser Asn Phe Asn Leu Thr His Tyr Gly Thr |  |
|             340                 345                 350          |  |

| cag caa atc cct cct gct tac aaa gat tta gct gag cca tgg att cag | 1103 |
| Gln Gln Ile Pro Pro Ala Tyr Lys Asp Leu Ala Glu Pro Trp Ile Gln |  |
|         355                 360                 365              |  |

| gtg ttt gga atg gaa ctc gtt ggc tgc tta ttc tct aga aac tgg aac | 1151 |
| Val Phe Gly Met Glu Leu Val Gly Cys Leu Phe Ser Arg Asn Trp Asn |  |
|     370                 375                 380                  |  |

| gta agg gaa atg gcc ctt agg cgt ctt tcc cac gac gtt agt ggg gcc | 1199 |
| Val Arg Glu Met Ala Leu Arg Arg Leu Ser His Asp Val Ser Gly Ala |  |
|     385                 390                 395                  |  |

| ctg ttg ttg gca aac ggg gag agc act gga aac tct gga ggc ggc agt | 1247 |
| Leu Leu Leu Ala Asn Gly Glu Ser Thr Gly Asn Ser Gly Gly Gly Ser |  |
| 400                 405                 410                 415  |  |

```
ggg ggc agc tta agc gcg gga gcg gcc agc ggg tcc tcc cag ccc agc    1295
Gly Gly Ser Leu Ser Ala Gly Ala Ala Ser Gly Ser Ser Gln Pro Ser
                420                 425                 430 atc tca ggg gat gtg gtg gag gcg tgc tgc agt gtc ctg tct ata gtc    1343
Ile Ser Gly Asp Val Val Glu Ala Cys Cys Ser Val Leu Ser Ile Val
                435                 440                 445 tgc gct gac cct gtc tac aaa gtg tac gtt gct gct tta aaa aca ttg    1391
Cys Ala Asp Pro Val Tyr Lys Val Tyr Val Ala Ala Leu Lys Thr Leu
                450                 455                 460 aga gcc atg ctg gta tac act cct tgc cac agt ctg gca gaa aga atc    1439
Arg Ala Met Leu Val Tyr Thr Pro Cys His Ser Leu Ala Glu Arg Ile
            465                 470                 475 aaa ctt cag aga ctc ctc cgg cca gtt gta gac act atc ctt gtc aag    1487
Lys Leu Gln Arg Leu Leu Arg Pro Val Val Asp Thr Ile Leu Val Lys
480                 485                 490                 495 tgt gca gat gcc aac agc cgc acg agt cag ctg tcc ata tct aca gtg    1535
Cys Ala Asp Ala Asn Ser Arg Thr Ser Gln Leu Ser Ile Ser Thr Val
                500                 505                 510 ctg gaa ctc tgc aat ggc caa gca gga aag ctg gcg gtt ggg aga gaa    1583
Leu Glu Leu Cys Asn Gly Gln Ala Gly Lys Leu Ala Val Gly Arg Glu
                515                 520                 525 ata ctt aaa gct ggg tcc atc ggg gtt ggt ggt gtc gat tac gtc tta    1631
Ile Leu Lys Ala Gly Ser Ile Gly Val Gly Gly Val Asp Tyr Val Leu
                530                 535                 540 agt tgt atc ctt gga aac caa gct gaa tca aac aac tgg caa gaa ctg    1679
Ser Cys Ile Leu Gly Asn Gln Ala Glu Ser Asn Asn Trp Gln Glu Leu
            545                 550                 555 ctg ggt cgc ctc tgt ctt ata gac agg ttg ctg ttg gaa ttt cct gct    1727
Leu Gly Arg Leu Cys Leu Ile Asp Arg Leu Leu Leu Glu Phe Pro Ala
560                 565                 570                 575 gaa ttc tat cct cat att gtc agt act gat gtc tca caa gct gag cct    1775
Glu Phe Tyr Pro His Ile Val Ser Thr Asp Val Ser Gln Ala Glu Pro
                580                 585                 590 gtt gaa atc agg tac aag aag ctg ctc tcc ctc tta acc ttt gcc ttg    1823
Val Glu Ile Arg Tyr Lys Lys Leu Leu Ser Leu Leu Thr Phe Ala Leu
                595                 600                 605 caa tcc att gac aat tcc cac tcg atg gtt ggc aag ctc tct cgg agg    1871
Gln Ser Ile Asp Asn Ser His Ser Met Val Gly Lys Leu Ser Arg Arg
                610                 615                 620 ata tat ctg agc tct gcc agg atg gtg acc gca gtg ccc gct gtg ttt    1919
Ile Tyr Leu Ser Ser Ala Arg Met Val Thr Ala Val Pro Ala Val Phe
            625                 630                 635 tcc aag ctg gta acc atg ctt aat gct tct ggc tcc acc cac ttc acc    1967
Ser Lys Leu Val Thr Met Leu Asn Ala Ser Gly Ser Thr His Phe Thr
640                 645                 650                 655 agg atg cgc cgg cgt ctg atg gct atc gcg gat gag gta gaa att gcc    2015
Arg Met Arg Arg Arg Leu Met Ala Ile Ala Asp Glu Val Glu Ile Ala
                660                 665                 670 gag gtc atc cag ctg ggt gtg gag gac act gtg gat ggg cat cag gac    2063
Glu Val Ile Gln Leu Gly Val Glu Asp Thr Val Asp Gly His Gln Asp
                675                 680                 685 agc tta cag gcg ctg gcc ccc gcc agc tgt cta gaa aac agc tcc ctt    2111
Ser Leu Gln Ala Leu Ala Pro Ala Ser Cys Leu Glu Asn Ser Ser Leu
            690                 695                 700 gag cac aca gtc cat aga gag aaa act gga aaa gga cta agt gct acg    2159
Glu His Thr Val His Arg Glu Lys Thr Gly Lys Gly Leu Ser Ala Thr
705                 710                 715 aga ctg agt gcc agc tcg gag gac att tct gac aga ctg gcc ggc gtc    2207
Arg Leu Ser Ala Ser Ser Glu Asp Ile Ser Asp Arg Leu Ala Gly Val
```

```
                720               725               730               735
tct gta gga ctt ccc agc tca aca aca aca gaa caa cca aag cca gcg         2255
Ser Val Gly Leu Pro Ser Ser Thr Thr Thr Glu Gln Pro Lys Pro Ala
                    740               745               750 gtt caa aca aaa ggc aga ccc cac agt cag tgt ttg aac tcc tcc cct         2303
Val Gln Thr Lys Gly Arg Pro His Ser Gln Cys Leu Asn Ser Ser Pro
                755               760               765 ttg tct cat gct caa tta atg ttc cca gca cca tca gcc cct tgt tcc         2351
Leu Ser His Ala Gln Leu Met Phe Pro Ala Pro Ser Ala Pro Cys Ser
            770               775               780 tct gcc ccg tct gtc cca gat att tct aag cac aga ccc cag gca ttt         2399
Ser Ala Pro Ser Val Pro Asp Ile Ser Lys His Arg Pro Gln Ala Phe
        785               790               795 gtt ccc tgc aaa ata cct tcc gca tct cct cag aca cag cgc aag ttc         2447
Val Pro Cys Lys Ile Pro Ser Ala Ser Pro Gln Thr Gln Arg Lys Phe
800               805               810               815 tct cta caa ttc cag agg aac tgc tct gaa cac cga gac tca gac cag         2495
Ser Leu Gln Phe Gln Arg Asn Cys Ser Glu His Arg Asp Ser Asp Gln
                820               825               830 ctc tcc cca gtc ttc act cag tca aga ccc cca ccc tcc agt aac ata         2543
Leu Ser Pro Val Phe Thr Gln Ser Arg Pro Pro Pro Ser Ser Asn Ile
                835               840               845 cac agg cca aag cca tcc cga ccc gtt ccg ggc agt aca agc aaa cta         2591
His Arg Pro Lys Pro Ser Arg Pro Val Pro Gly Ser Thr Ser Lys Leu
            850               855               860 ggg gac gcc aca aaa agt agc atg aca ctt gat ctg ggc agt gct tcc         2639
Gly Asp Ala Thr Lys Ser Ser Met Thr Leu Asp Leu Gly Ser Ala Ser
865               870               875 agg tgt gac gac agc ttt ggc ggc ggc ggc aac agt ggc aac gcc gtc         2687
Arg Cys Asp Asp Ser Phe Gly Gly Gly Gly Asn Ser Gly Asn Ala Val
880               885               890               895 ata ccc agc gac gag aca gtg ttc acg ccg gtg gag gac aag tgc agg         2735
Ile Pro Ser Asp Glu Thr Val Phe Thr Pro Val Glu Asp Lys Cys Arg
                900               905               910 tta gat gtg aac acc gag ctc aac tcc agc atc gag gac ctt ctt gaa         2783
Leu Asp Val Asn Thr Glu Leu Asn Ser Ser Ile Glu Asp Leu Leu Glu
                915               920               925 gca tcc atg cct tca agt gac acg aca gtc act ttc aag tcc gaa gtc         2831
Ala Ser Met Pro Ser Ser Asp Thr Thr Val Thr Phe Lys Ser Glu Val
            930               935               940 gcc gtc ctc tct ccg gaa aag gcc gaa aat gac gac acc tac aaa gac         2879
Ala Val Leu Ser Pro Glu Lys Ala Glu Asn Asp Asp Thr Tyr Lys Asp
        945               950               955 gac gtc aat cat aat caa aag tgc aaa gaa aag atg gaa gct gaa gag         2927
Asp Val Asn His Asn Gln Lys Cys Lys Glu Lys Met Glu Ala Glu Glu
960               965               970               975 gag gag gct tta gcg atc gcc atg gcg atg tca gcg tct cag gat gcc         2975
Glu Glu Ala Leu Ala Ile Ala Met Ala Met Ser Ala Ser Gln Asp Ala
                980               985               990 ctc ccc atc gtc cct cag ctg cag gtg gaa aat gga gaa gat att atc         3023
Leu Pro Ile Val Pro Gln Leu Gln Val Glu Asn Gly Glu Asp Ile Ile
                995               1000              1005 atc att cag cag gac aca cca gaa act ctt cca gga cat acc aaa gcg         3071
Ile Ile Gln Gln Asp Thr Pro Glu Thr Leu Pro Gly His Thr Lys Ala
            1010              1015              1020 aaa cag cct tac aga gaa gac gct gag tgg ctg aaa ggc cag cag ata         3119
Lys Gln Pro Tyr Arg Glu Asp Ala Glu Trp Leu Lys Gly Gln Gln Ile
        1025              1030              1035 ggc ctc gga gca ttt tct tct tgt tat cag gct caa gat gtg gga act         3167
```

| | | | | | | | | | | | | |
|---|---|---|---|---|---|---|---|---|---|---|---|---|
| Gly | Leu | Gly | Ala | Phe | Ser | Ser | Cys | Tyr | Gln | Ala | Gln | Asp | Val | Gly | Thr |
| 1040 | | | | | 1045 | | | | | 1050 | | | | | 1055 |

```
gga act tta atg gct gtt aaa cag gtg act tat gtc aga aac aca tct      3215
Gly Thr Leu Met Ala Val Lys Gln Val Thr Tyr Val Arg Asn Thr Ser
        1060                1065                1070 tct gag caa gaa gaa gta gta gaa gca cta aga gaa gag ata aga atg      3263
Ser Glu Gln Glu Glu Val Val Glu Ala Leu Arg Glu Glu Ile Arg Met
        1075                1080                1085 atg agc cat ctg aat cat cca aac atc att agg atg ttg gga gcc acg      3311
Met Ser His Leu Asn His Pro Asn Ile Ile Arg Met Leu Gly Ala Thr
        1090                1095                1100 tgt gag aag agc aat tac aat ctc ttc att gaa tgg atg gca ggg gga      3359
Cys Glu Lys Ser Asn Tyr Asn Leu Phe Ile Glu Trp Met Ala Gly Gly
        1105                1110                1115 tcg gtg gct cat ttg ctg agt aaa tat gga gcc ttc aaa gaa tca gta      3407
Ser Val Ala His Leu Leu Ser Lys Tyr Gly Ala Phe Lys Glu Ser Val
1120                1125                1130                1135 gtt att aac tac act gaa cag tta ctc cgt ggc ctt tcg tat ctc cat      3455
Val Ile Asn Tyr Thr Glu Gln Leu Leu Arg Gly Leu Ser Tyr Leu His
        1140                1145                1150 gag aac cag atc att cac aga gat gtc aaa ggt gcc aat ttg ctc att      3503
Glu Asn Gln Ile Ile His Arg Asp Val Lys Gly Ala Asn Leu Leu Ile
        1155                1160                1165 gac agc acc ggt cag agg ctg aga att gca gac ttt gga gct gca gcc      3551
Asp Ser Thr Gly Gln Arg Leu Arg Ile Ala Asp Phe Gly Ala Ala Ala
        1170                1175                1180 agg ttg gca tca aaa gga act ggt gca gga gag ttt cag gga caa tta      3599
Arg Leu Ala Ser Lys Gly Thr Gly Ala Gly Glu Phe Gln Gly Gln Leu
        1185                1190                1195 ctg ggg aca att gca ttc atg gcg cct gag gtc cta aga ggt cag cag      3647
Leu Gly Thr Ile Ala Phe Met Ala Pro Glu Val Leu Arg Gly Gln Gln
1200                1205                1210                1215 tat ggt agg agc tgt gat gta tgg agt gtt ggc tgc gcc att ata gaa      3695
Tyr Gly Arg Ser Cys Asp Val Trp Ser Val Gly Cys Ala Ile Ile Glu
        1220                1225                1230 atg gct tgt gca aaa cca cct tgg aat gca gaa aaa cac tcc aat cat      3743
Met Ala Cys Ala Lys Pro Pro Trp Asn Ala Glu Lys His Ser Asn His
        1235                1240                1245 ctc gcc ttg ata ttt aag att gct agc gca act act gca ccg tcc atc      3791
Leu Ala Leu Ile Phe Lys Ile Ala Ser Ala Thr Thr Ala Pro Ser Ile
        1250                1255                1260 ccg tca cac ctg tcc cct ggt tta cga gat gtg gct ctt cgt tgt tta      3839
Pro Ser His Leu Ser Pro Gly Leu Arg Asp Val Ala Leu Arg Cys Leu
        1265                1270                1275 gaa ctt cag cct cag gac cgg cct ccg tca aga gag ctg ctg aaa cat      3887
Glu Leu Gln Pro Gln Asp Arg Pro Pro Ser Arg Glu Leu Leu Lys His
1280                1285                1290                1295 ccg gtc ttc cgt acc acg tgg tag                                      3911
Pro Val Phe Arg Thr Thr Trp
        1300
```

<210> SEQ ID NO 2
<211> LENGTH: 1302
<212> TYPE: PRT
<213> ORGANISM: Homo sapiens

<400> SEQUENCE: 2

Ala Trp Lys His Glu Trp Leu Glu Arg Arg Asn Arg Arg Gly Pro Val
 1               5                  10                  15

Val Val Lys Pro Ile Pro Val Lys Gly Asp Gly Ser Glu Met Asn His

```
                  20                  25                  30
Leu Ala Ala Glu Ser Pro Gly Glu Val Gln Ala Ser Ala Ala Ser Pro
             35                  40                  45
Ala Ser Lys Gly Arg Arg Ser Pro Ser Pro Gly Asn Ser Pro Ser Gly
 50                  55                  60
Arg Thr Val Lys Ser Glu Ser Pro Gly Val Arg Arg Lys Arg Val Ser
 65                  70                  75                  80
Pro Val Pro Phe Gln Ser Gly Arg Ile Thr Pro Pro Arg Arg Ala Pro
                 85                  90                  95
Ser Pro Asp Gly Phe Ser Pro Tyr Ser Pro Glu Glu Thr Asn Arg Arg
            100                 105                 110
Val Asn Lys Val Met Arg Ala Arg Leu Tyr Leu Leu Gln Gln Ile Gly
            115                 120                 125
Pro Asn Ser Phe Leu Ile Gly Gly Asp Ser Pro Asp Asn Lys Tyr Arg
            130                 135                 140
Val Phe Ile Gly Pro Gln Asn Cys Ser Cys Ala Arg Gly Thr Phe Cys
145                 150                 155                 160
Ile His Leu Leu Phe Val Met Leu Arg Val Phe Gln Leu Glu Pro Ser
                165                 170                 175
Asp Pro Met Leu Trp Arg Lys Thr Leu Lys Asn Phe Glu Val Glu Ser
            180                 185                 190
Leu Phe Gln Lys Tyr His Ser Arg Arg Ser Ser Arg Ile Lys Ala Pro
            195                 200                 205
Ser Arg Asn Thr Ile Gln Lys Phe Val Ser Arg Met Ser Asn Ser His
    210                 215                 220
Thr Leu Ser Ser Ser Ser Thr Ser Thr Ser Ser Ser Val Asn Ser Ile
225                 230                 235                 240
Lys Asp Glu Glu Glu Gln Met Cys Pro Ile Cys Leu Leu Gly Met Leu
                245                 250                 255
Asp Glu Glu Ser Leu Thr Val Cys Glu Asp Gly Cys Arg Asn Lys Leu
            260                 265                 270
His His His Cys Met Ser Ile Trp Ala Glu Glu Cys Arg Arg Asn Arg
            275                 280                 285
Glu Pro Leu Ile Cys Pro Leu Cys Arg Ser Lys Trp Arg Ser His Asp
    290                 295                 300
Phe Tyr Ser His Glu Leu Ser Ser Pro Val Asp Ser Pro Ser Ser Leu
305                 310                 315                 320
Arg Ala Ala Gln Gln Gln Thr Val Gln Gln Gln Pro Leu Ala Gly Ser
                325                 330                 335
Arg Arg Asn Gln Glu Ser Asn Phe Asn Leu Thr His Tyr Gly Thr Gln
            340                 345                 350
Gln Ile Pro Pro Ala Tyr Lys Asp Leu Ala Glu Pro Trp Ile Gln Val
            355                 360                 365
Phe Gly Met Glu Leu Val Gly Cys Leu Phe Ser Arg Asn Trp Asn Val
    370                 375                 380
Arg Glu Met Ala Leu Arg Arg Leu Ser His Asp Val Ser Gly Ala Leu
385                 390                 395                 400
Leu Leu Ala Asn Gly Glu Ser Thr Gly Asn Ser Gly Gly Gly Ser Gly
                405                 410                 415
Gly Ser Leu Ser Ala Gly Ala Ala Ser Gly Ser Ser Gln Pro Ser Ile
            420                 425                 430
Ser Gly Asp Val Val Glu Ala Cys Cys Ser Val Leu Ser Ile Val Cys
            435                 440                 445
```

-continued

```
Ala Asp Pro Val Tyr Lys Val Tyr Val Ala Ala Leu Lys Thr Leu Arg
    450                 455                 460

Ala Met Leu Val Tyr Thr Pro Cys His Ser Leu Ala Glu Arg Ile Lys
465                 470                 475                 480

Leu Gln Arg Leu Leu Arg Pro Val Val Asp Thr Ile Leu Val Lys Cys
                485                 490                 495

Ala Asp Ala Asn Ser Arg Thr Ser Gln Leu Ser Ile Ser Thr Val Leu
            500                 505                 510

Glu Leu Cys Asn Gly Gln Ala Gly Lys Leu Ala Val Gly Arg Glu Ile
        515                 520                 525

Leu Lys Ala Gly Ser Ile Gly Val Gly Val Asp Tyr Val Leu Ser
    530                 535                 540

Cys Ile Leu Gly Asn Gln Ala Glu Ser Asn Asn Trp Gln Glu Leu Leu
545                 550                 555                 560

Gly Arg Leu Cys Leu Ile Asp Arg Leu Leu Glu Phe Pro Ala Glu
                565                 570                 575

Phe Tyr Pro His Ile Val Ser Thr Asp Val Ser Gln Ala Glu Pro Val
            580                 585                 590

Glu Ile Arg Tyr Lys Lys Leu Leu Ser Leu Leu Thr Phe Ala Leu Gln
    595                 600                 605

Ser Ile Asp Asn Ser His Ser Met Val Gly Lys Leu Ser Arg Arg Ile
    610                 615                 620

Tyr Leu Ser Ser Ala Arg Met Val Thr Ala Val Pro Ala Val Phe Ser
625                 630                 635                 640

Lys Leu Val Thr Met Leu Asn Ala Ser Gly Ser Thr His Phe Thr Arg
                645                 650                 655

Met Arg Arg Arg Leu Met Ala Ile Ala Asp Glu Val Glu Ile Ala Glu
                660                 665                 670

Val Ile Gln Leu Gly Val Glu Asp Thr Val Asp Gly His Gln Asp Ser
    675                 680                 685

Leu Gln Ala Leu Ala Pro Ala Ser Cys Leu Glu Asn Ser Ser Leu Glu
    690                 695                 700

His Thr Val His Arg Glu Lys Thr Gly Lys Gly Leu Ser Ala Thr Arg
705                 710                 715                 720

Leu Ser Ala Ser Ser Glu Asp Ile Ser Asp Arg Leu Ala Gly Val Ser
                725                 730                 735

Val Gly Leu Pro Ser Ser Thr Thr Glu Gln Pro Lys Pro Ala Val
            740                 745                 750

Gln Thr Lys Gly Arg Pro His Ser Gln Cys Leu Asn Ser Ser Pro Leu
            755                 760                 765

Ser His Ala Gln Leu Met Phe Pro Ala Pro Ser Ala Pro Cys Ser Ser
    770                 775                 780

Ala Pro Ser Val Pro Asp Ile Ser Lys His Arg Pro Gln Ala Phe Val
785                 790                 795                 800

Pro Cys Lys Ile Pro Ser Ala Ser Pro Gln Thr Gln Arg Lys Phe Ser
                805                 810                 815

Leu Gln Phe Gln Arg Asn Cys Ser Glu His Arg Asp Ser Asp Gln Leu
            820                 825                 830

Ser Pro Val Phe Thr Gln Ser Arg Pro Pro Ser Ser Asn Ile His
            835                 840                 845

Arg Pro Lys Pro Ser Arg Pro Val Pro Gly Ser Thr Ser Lys Leu Gly
    850                 855                 860
```

-continued

```
Asp Ala Thr Lys Ser Ser Met Thr Leu Asp Leu Gly Ser Ala Ser Arg
865                 870                 875                 880

Cys Asp Asp Ser Phe Gly Gly Gly Asn Ser Gly Asn Ala Val Ile
                885                 890                 895

Pro Ser Asp Glu Thr Val Phe Thr Pro Val Glu Asp Lys Cys Arg Leu
                900                 905                 910

Asp Val Asn Thr Glu Leu Asn Ser Ser Ile Glu Asp Leu Leu Glu Ala
                915                 920                 925

Ser Met Pro Ser Ser Asp Thr Thr Val Thr Phe Lys Ser Glu Val Ala
                930                 935                 940

Val Leu Ser Pro Glu Lys Ala Glu Asn Asp Asp Thr Tyr Lys Asp Asp
945                 950                 955                 960

Val Asn His Asn Gln Lys Cys Lys Glu Lys Met Glu Ala Glu Glu Glu
                965                 970                 975

Glu Ala Leu Ala Ile Ala Met Ala Met Ser Ala Ser Gln Asp Ala Leu
                980                 985                 990

Pro Ile Val Pro Gln Leu Gln Val Glu Asn Gly Glu Asp Ile Ile Ile
                995                 1000                1005

Ile Gln Gln Asp Thr Pro Glu Thr Leu Pro Gly His Thr Lys Ala Lys
        1010                1015                1020

Gln Pro Tyr Arg Glu Asp Ala Glu Trp Leu Lys Gly Gln Gln Ile Gly
1025                1030                1035                1040

Leu Gly Ala Phe Ser Ser Cys Tyr Gln Ala Gln Asp Val Gly Thr Gly
                1045                1050                1055

Thr Leu Met Ala Val Lys Gln Val Thr Tyr Val Arg Asn Thr Ser Ser
                1060                1065                1070

Glu Gln Glu Glu Val Val Glu Ala Leu Arg Glu Glu Ile Arg Met Met
        1075                1080                1085

Ser His Leu Asn His Pro Asn Ile Ile Arg Met Leu Gly Ala Thr Cys
        1090                1095                1100

Glu Lys Ser Asn Tyr Asn Leu Phe Ile Glu Trp Met Ala Gly Gly Ser
1105                1110                1115                1120

Val Ala His Leu Leu Ser Lys Tyr Gly Ala Phe Lys Glu Ser Val Val
                1125                1130                1135

Ile Asn Tyr Thr Glu Gln Leu Leu Arg Gly Leu Ser Tyr Leu His Glu
                1140                1145                1150

Asn Gln Ile Ile His Arg Asp Val Lys Gly Ala Asn Leu Leu Ile Asp
        1155                1160                1165

Ser Thr Gly Gln Arg Leu Arg Ile Ala Asp Phe Gly Ala Ala Ala Arg
        1170                1175                1180

Leu Ala Ser Lys Gly Thr Gly Ala Gly Glu Phe Gln Gly Gln Leu Leu
1185                1190                1195                1200

Gly Thr Ile Ala Phe Met Ala Pro Glu Val Leu Arg Gly Gln Gln Tyr
                1205                1210                1215

Gly Arg Ser Cys Asp Val Trp Ser Val Gly Cys Ala Ile Ile Glu Met
                1220                1225                1230

Ala Cys Ala Lys Pro Pro Trp Asn Ala Glu Lys His Ser Asn His Leu
        1235                1240                1245

Ala Leu Ile Phe Lys Ile Ala Ser Ala Thr Thr Ala Pro Ser Ile Pro
        1250                1255                1260

Ser His Leu Ser Pro Gly Leu Arg Asp Val Ala Leu Arg Cys Leu Glu
1265                1270                1275                1280

Leu Gln Pro Gln Asp Arg Pro Pro Ser Arg Glu Leu Leu Lys His Pro
```

-continued

```
                       1285              1290              1295
Val Phe Arg Thr Thr Trp
            1300

<210> SEQ ID NO 3
<211> LENGTH: 2013
<212> TYPE: DNA
<213> ORGANISM: Homo sapiens
<220> FEATURE:
<221> NAME/KEY: CDS
<222> LOCATION: (124)..(1980)

<400> SEQUENCE: 3
ggccagctcg gtggcctcct ctcggccctc ggctccgcga tccccgccca gcggccgggc      60
aataaagaat gttgatggga gaaccatttt cctaattttc aaattattga gctggtcgcc     120 ata atg gat gat cag caa gct ttg aat tca atc atg caa gat ttg gct      168
    Met Asp Asp Gln Gln Ala Leu Asn Ser Ile Met Gln Asp Leu Ala
     1               5                  10                  15 gtc ctt cat aag gcc agt cgg cca gca tta tct tta caa gaa acc agg      216
Val Leu His Lys Ala Ser Arg Pro Ala Leu Ser Leu Gln Glu Thr Arg
                 20                  25                  30 aaa gca aaa cct tca tca cca aaa aaa cag aat gat gtt cga gtc aaa      264
Lys Ala Lys Pro Ser Ser Pro Lys Lys Gln Asn Asp Val Arg Val Lys
             35                  40                  45 ttt gaa cat aga gga gaa aaa agg atc ctg cag gtt act aga cca gtt      312
Phe Glu His Arg Gly Glu Lys Arg Ile Leu Gln Val Thr Arg Pro Val
         50                  55                  60 aaa cta gaa gac ctg aga tct aag tct aag atc gcc ttt ggg cag tct      360
Lys Leu Glu Asp Leu Arg Ser Lys Ser Lys Ile Ala Phe Gly Gln Ser
     65                  70                  75 atg gat cta cac tat acc aac aat gag ttg gta att ccg tta act acc      408
Met Asp Leu His Tyr Thr Asn Asn Glu Leu Val Ile Pro Leu Thr Thr
 80                  85                  90                  95 caa gat gac ttg gac aaa gct gtg gaa ctg ctg gat cgc agt att cac      456
Gln Asp Asp Leu Asp Lys Ala Val Glu Leu Leu Asp Arg Ser Ile His
                100                 105                 110 atg aag agt ctc aag ata tta ctt gta gta aat ggg agt aca cag gct      504
Met Lys Ser Leu Lys Ile Leu Leu Val Val Asn Gly Ser Thr Gln Ala
            115                 120                 125 act aat tta gaa cca tca ccg tca cca gaa gat ttg aat aat aca cca      552
Thr Asn Leu Glu Pro Ser Pro Ser Pro Glu Asp Leu Asn Asn Thr Pro
        130                 135                 140 ctt ggt gca gag agg aaa aag cgg cta tct gta gta ggt ccc cct aat      600
Leu Gly Ala Glu Arg Lys Lys Arg Leu Ser Val Val Gly Pro Pro Asn
    145                 150                 155 agg gat aga agt tcc cct cct cca gga tac att cca gac gag cta cac      648
Arg Asp Arg Ser Ser Pro Pro Pro Gly Tyr Ile Pro Asp Glu Leu His
160                 165                 170                 175 cag att gcc cgg aat ggg tca ttc act agc atc aac agt gaa gga gag      696
Gln Ile Ala Arg Asn Gly Ser Phe Thr Ser Ile Asn Ser Glu Gly Glu
                180                 185                 190 ttc att cca gag agc atg gac caa atg ctg gat cca ttg tct tta agc      744
Phe Ile Pro Glu Ser Met Asp Gln Met Leu Asp Pro Leu Ser Leu Ser
            195                 200                 205 agc cct gaa aat tct ggc tca gga agc tgt ccg tca ctt gat agt cct      792
Ser Pro Glu Asn Ser Gly Ser Gly Ser Cys Pro Ser Leu Asp Ser Pro
        210                 215                 220 ttg gat gga gaa agc tac cca aaa tca cgg atg cct agg gca cag agc      840
Leu Asp Gly Glu Ser Tyr Pro Lys Ser Arg Met Pro Arg Ala Gln Ser
    225                 230                 235
```

```
tac cca gat aat cat cag gag ttt aca gac tat gat aac ccc att ttt    888
Tyr Pro Asp Asn His Gln Glu Phe Thr Asp Tyr Asp Asn Pro Ile Phe
240             245                 250                 255 gag aaa ttt gga aaa gga gga aca tat cca aga agg tac cac gtt tcc    936
Glu Lys Phe Gly Lys Gly Gly Thr Tyr Pro Arg Arg Tyr His Val Ser
                260                 265                 270 tat cat cac cag gag tat aat gac ggt cgg aag act ttt cca aga gct    984
Tyr His His Gln Glu Tyr Asn Asp Gly Arg Lys Thr Phe Pro Arg Ala
        275                 280                 285 aga agg acc cag ggc acc agt ttc cgg tct cct gtg agc ttc agt cct   1032
Arg Arg Thr Gln Gly Thr Ser Phe Arg Ser Pro Val Ser Phe Ser Pro
    290                 295                 300 act gat cac tcc tta agc aat agt agt gga agc agt gtc ttt acc cca   1080
Thr Asp His Ser Leu Ser Asn Ser Ser Gly Ser Ser Val Phe Thr Pro
305                 310                 315 gag tat gac gac agt cga atg aga aga cgg ggg agt gac ata gac aac   1128
Glu Tyr Asp Asp Ser Arg Met Arg Arg Arg Gly Ser Asp Ile Asp Asn
320                 325                 330                 335 cct act ttg act gtc aca gac atc agc cca cca tgc cgt tca cct cga   1176
Pro Thr Leu Thr Val Thr Asp Ile Ser Pro Pro Cys Arg Ser Pro Arg
                340                 345                 350 gct ccg acc aac tgg aga ctg ggc aag ctg ctt ggc caa gga gat ttt   1224
Ala Pro Thr Asn Trp Arg Leu Gly Lys Leu Leu Gly Gln Gly Asp Phe
        355                 360                 365 ggt agg gtc tac ctc tgc tat gat gtt gat acc gga aga gag ctg gct   1272
Gly Arg Val Tyr Leu Cys Tyr Asp Val Asp Thr Gly Arg Glu Leu Ala
    370                 375                 380 gtt aag caa gtt cag ttt aac cct gag agc cca gag acc agc aag gaa   1320
Val Lys Gln Val Gln Phe Asn Pro Glu Ser Pro Glu Thr Ser Lys Glu
385                 390                 395 gta aat gca ctt gag tgt gaa att cag ttg ttg aaa aac ttg ttg cat   1368
Val Asn Ala Leu Glu Cys Glu Ile Gln Leu Leu Lys Asn Leu Leu His
400                 405                 410                 415 gag cga att gtt cag tat tat ggc tgt ttg agg gat cct cag gag aaa   1416
Glu Arg Ile Val Gln Tyr Tyr Gly Cys Leu Arg Asp Pro Gln Glu Lys
                420                 425                 430 aca ctt tcc atc ttt atg gag tat atg cca ggg ggt tca att aag gac   1464
Thr Leu Ser Ile Phe Met Glu Tyr Met Pro Gly Gly Ser Ile Lys Asp
        435                 440                 445 caa cta aaa gcc tac gga gct ctt act gag aac gtg acg agg aag tac   1512
Gln Leu Lys Ala Tyr Gly Ala Leu Thr Glu Asn Val Thr Arg Lys Tyr
    450                 455                 460 acc cgt cag att ctg gag ggg gtc cat tat ttg cat agt aat atg att   1560
Thr Arg Gln Ile Leu Glu Gly Val His Tyr Leu His Ser Asn Met Ile
465                 470                 475 gtc cat aga gat atc aaa gga gca aat atc tta agg gat tcc aca ggc   1608
Val His Arg Asp Ile Lys Gly Ala Asn Ile Leu Arg Asp Ser Thr Gly
480                 485                 490                 495 aat atc aag tta gga gac ttt ggg gct agt aaa cgg ctt cag acc atc   1656
Asn Ile Lys Leu Gly Asp Phe Gly Ala Ser Lys Arg Leu Gln Thr Ile
                500                 505                 510 tgt ctc tca ggc aca gga atg aag tct gtc aca ggc acg cca tac tgg   1704
Cys Leu Ser Gly Thr Gly Met Lys Ser Val Thr Gly Thr Pro Tyr Trp
        515                 520                 525 atg agt cct gag gtc atc agt gga gaa ggc tat gga aga aaa gca gac   1752
Met Ser Pro Glu Val Ile Ser Gly Glu Gly Tyr Gly Arg Lys Ala Asp
    530                 535                 540 atc tgg agt gta gca tgt aga gtg gta gaa atg cta act gaa aag cca   1800
Ile Trp Ser Val Ala Cys Arg Val Val Glu Met Leu Thr Glu Lys Pro
```

-continued

```
           545                 550                 555
cct tgg gct gaa ttt gaa gca atg gct gcc atc ttt aag atc gcc act      1848
Pro Trp Ala Glu Phe Glu Ala Met Ala Ala Ile Phe Lys Ile Ala Thr
560                 565                 570                 575 cag cca acg aac cca aag ctg cca cct cat gtc tca gac tat act cgg      1896
Gln Pro Thr Asn Pro Lys Leu Pro Pro His Val Ser Asp Tyr Thr Arg
            580                 585                 590 gac ttc ctc aaa cgg att ttt gta gag gcc aaa ctt cga cct tca gcg      1944
Asp Phe Leu Lys Arg Ile Phe Val Glu Ala Lys Leu Arg Pro Ser Ala
        595                 600                 605 gag gag ctc ttg cgg cac atg ttt gtg cat tat cac tagcatcggc           1990
Glu Glu Leu Leu Arg His Met Phe Val His Tyr His
            610                 615 ggcttcggtc ctccaccatc tcc                                            2013

<210> SEQ ID NO 4
<211> LENGTH: 619
<212> TYPE: PRT
<213> ORGANISM: Homo sapiens

<400> SEQUENCE: 4

Met Asp Asp Gln Gln Ala Leu Asn Ser Ile Met Gln Asp Leu Ala Val
 1               5                  10                  15

Leu His Lys Ala Ser Arg Pro Ala Leu Ser Leu Gln Glu Thr Arg Lys
             20                  25                  30

Ala Lys Pro Ser Ser Pro Lys Lys Gln Asn Asp Val Arg Val Lys Phe
         35                  40                  45

Glu His Arg Gly Glu Lys Arg Ile Leu Gln Val Thr Arg Pro Val Lys
     50                  55                  60

Leu Glu Asp Leu Arg Ser Lys Ser Lys Ile Ala Phe Gly Gln Ser Met
 65                  70                  75                  80

Asp Leu His Tyr Thr Asn Asn Glu Leu Val Ile Pro Leu Thr Thr Gln
                 85                  90                  95

Asp Asp Leu Asp Lys Ala Val Glu Leu Leu Asp Arg Ser Ile His Met
            100                 105                 110

Lys Ser Leu Lys Ile Leu Leu Val Val Asn Gly Ser Thr Gln Ala Thr
        115                 120                 125

Asn Leu Glu Pro Ser Pro Ser Pro Glu Asp Leu Asn Asn Thr Pro Leu
    130                 135                 140

Gly Ala Glu Arg Lys Lys Arg Leu Ser Val Val Gly Pro Pro Asn Arg
145                 150                 155                 160

Asp Arg Ser Ser Pro Pro Pro Gly Tyr Ile Pro Asp Glu Leu His Gln
                165                 170                 175

Ile Ala Arg Asn Gly Ser Phe Thr Ser Ile Asn Ser Glu Gly Glu Phe
            180                 185                 190

Ile Pro Glu Ser Met Asp Gln Met Leu Asp Pro Leu Ser Leu Ser Ser
        195                 200                 205

Pro Glu Asn Ser Gly Ser Gly Ser Cys Pro Ser Leu Asp Ser Pro Leu
    210                 215                 220

Asp Gly Glu Ser Tyr Pro Lys Ser Arg Met Pro Arg Ala Gln Ser Tyr
225                 230                 235                 240

Pro Asp Asn His Gln Glu Phe Thr Asp Tyr Asp Asn Pro Ile Phe Glu
                245                 250                 255

Lys Phe Gly Lys Gly Gly Thr Tyr Pro Arg Arg Tyr His Val Ser Tyr
            260                 265                 270
```

```
His His Gln Glu Tyr Asn Asp Gly Arg Lys Thr Phe Pro Arg Ala Arg
            275                 280                 285

Arg Thr Gln Gly Thr Ser Phe Arg Ser Pro Val Ser Phe Ser Pro Thr
        290                 295                 300

Asp His Ser Leu Ser Asn Ser Ser Gly Ser Ser Val Phe Thr Pro Glu
305                 310                 315                 320

Tyr Asp Asp Ser Arg Met Arg Arg Gly Ser Asp Ile Asp Asn Pro
                325                 330                 335

Thr Leu Thr Val Thr Asp Ile Ser Pro Pro Cys Arg Ser Pro Arg Ala
            340                 345                 350

Pro Thr Asn Trp Arg Leu Gly Lys Leu Leu Gly Gln Gly Asp Phe Gly
            355                 360                 365

Arg Val Tyr Leu Cys Tyr Asp Val Asp Thr Gly Arg Glu Leu Ala Val
        370                 375                 380

Lys Gln Val Gln Phe Asn Pro Glu Ser Pro Glu Thr Ser Lys Glu Val
385                 390                 395                 400

Asn Ala Leu Glu Cys Glu Ile Gln Leu Leu Lys Asn Leu Leu His Glu
                405                 410                 415

Arg Ile Val Gln Tyr Tyr Gly Cys Leu Arg Asp Pro Gln Glu Lys Thr
            420                 425                 430

Leu Ser Ile Phe Met Glu Tyr Met Pro Gly Gly Ser Ile Lys Asp Gln
            435                 440                 445

Leu Lys Ala Tyr Gly Ala Leu Thr Glu Asn Val Thr Arg Lys Tyr Thr
        450                 455                 460

Arg Gln Ile Leu Glu Gly Val His Tyr Leu His Ser Asn Met Ile Val
465                 470                 475                 480

His Arg Asp Ile Lys Gly Ala Asn Ile Leu Arg Asp Ser Thr Gly Asn
                485                 490                 495

Ile Lys Leu Gly Asp Phe Gly Ala Ser Lys Arg Leu Gln Thr Ile Cys
            500                 505                 510

Leu Ser Gly Thr Gly Met Lys Ser Val Thr Gly Thr Pro Tyr Trp Met
            515                 520                 525

Ser Pro Glu Val Ile Ser Gly Glu Gly Tyr Gly Arg Lys Ala Asp Ile
        530                 535                 540

Trp Ser Val Ala Cys Arg Val Val Glu Met Leu Thr Glu Lys Pro Pro
545                 550                 555                 560

Trp Ala Glu Phe Glu Ala Met Ala Ala Ile Phe Lys Ile Ala Thr Gln
                565                 570                 575

Pro Thr Asn Pro Lys Leu Pro Pro His Val Ser Asp Tyr Thr Arg Asp
            580                 585                 590

Phe Leu Lys Arg Ile Phe Val Glu Ala Lys Leu Arg Pro Ser Ala Glu
            595                 600                 605

Glu Leu Leu Arg His Met Phe Val His Tyr His
        610                 615

<210> SEQ ID NO 5
<211> LENGTH: 1935
<212> TYPE: DNA
<213> ORGANISM: Homo sapiens
<220> FEATURE:
<221> NAME/KEY: CDS
<222> LOCATION: (25)..(1902)

<400> SEQUENCE: 5
accgccgcct ccgccatcgc cacc atg gat caa caa gag gca tta gac tcg          51
                           Met Asp Gln Gln Glu Ala Leu Asp Ser
```

```
                        1                    5
atc atg aag gac ctg gtg gcc ctc cag atg agc cga cga acc cgg ttg        99
Ile Met Lys Asp Leu Val Ala Leu Gln Met Ser Arg Arg Thr Arg Leu
 10              15                  20                  25 tct gga tat gag acc atg agg aat aag gac aca ggt cac cca aac agg       147
Ser Gly Tyr Glu Thr Met Arg Asn Lys Asp Thr Gly His Pro Asn Arg
                 30                  35                  40 cag agt gac gtc aga atc aag ttt gaa cac aat ggg gag aga cga att       195
Gln Ser Asp Val Arg Ile Lys Phe Glu His Asn Gly Glu Arg Arg Ile
                 45                  50                  55 ata gca ttc agc cgg cct gtg aga tac gaa gat gtg gag cac aag gtg       243
Ile Ala Phe Ser Arg Pro Val Arg Tyr Glu Asp Val Glu His Lys Val
             60                  65                  70 aca aca gtc ttt ggg cag tct ctt gat ttg cat tat atg aat aat gag       291
Thr Thr Val Phe Gly Gln Ser Leu Asp Leu His Tyr Met Asn Asn Glu
         75                  80                  85 ctc tcc atc ctg ttg aaa aac caa gat gat ctc gat aaa gcc att gac       339
Leu Ser Ile Leu Leu Lys Asn Gln Asp Asp Leu Asp Lys Ala Ile Asp
 90              95                 100                 105 att ttg gat aga agc tca agt atg aaa agc ctt agg ata cta ctg tta       387
Ile Leu Asp Arg Ser Ser Ser Met Lys Ser Leu Arg Ile Leu Leu Leu
                110                 115                 120 tcc caa gac aga tac cat act agt tcc tct ccc cac tct gga gtg tcc       435
Ser Gln Asp Arg Tyr His Thr Ser Ser Ser Pro His Ser Gly Val Ser
                125                 130                 135 agg cag gtt cgg atc aag cct tcc cag tct gca ggg gat ata aat acc       483
Arg Gln Val Arg Ile Lys Pro Ser Gln Ser Ala Gly Asp Ile Asn Thr
            140                 145                 150 atc tac caa gct cct gag ccc aga agc agg cac ctg tct gtc agc tcc       531
Ile Tyr Gln Ala Pro Glu Pro Arg Ser Arg His Leu Ser Val Ser Ser
        155                 160                 165 cag aac cct ggc cga agc tca cct ccc ccg gga tat gtt cct gag cgg       579
Gln Asn Pro Gly Arg Ser Ser Pro Pro Pro Gly Tyr Val Pro Glu Arg
170                 175                 180                 185 caa cag cac att gcc cgg caa gga tcc tac acc agc atc aac agt gag       627
Gln Gln His Ile Ala Arg Gln Gly Ser Tyr Thr Ser Ile Asn Ser Glu
                190                 195                 200 ggg gag ttc atc cca gag acc agc gag cag tgc atg ctg gat ccc ctg       675
Gly Glu Phe Ile Pro Glu Thr Ser Glu Gln Cys Met Leu Asp Pro Leu
                205                 210                 215 agc agt gca gaa aat tcc ttg tct gga agc tgc caa tcc ttg gac agg       723
Ser Ser Ala Glu Asn Ser Leu Ser Gly Ser Cys Gln Ser Leu Asp Arg
            220                 225                 230 tca gca gac agc cca tcc ttc cgg aaa tca cga atg tcc cgt gcc cag       771
Ser Ala Asp Ser Pro Ser Phe Arg Lys Ser Arg Met Ser Arg Ala Gln
        235                 240                 245 agc ttc cct gac aac aga cag gaa tac tca gat cgg gaa act cag ctt       819
Ser Phe Pro Asp Asn Arg Gln Glu Tyr Ser Asp Arg Glu Thr Gln Leu
250                 255                 260                 265 tat gac aaa ggg gtc aaa ggt gga acc tac ccc cgg cgc tac cac gtg       867
Tyr Asp Lys Gly Val Lys Gly Gly Thr Tyr Pro Arg Arg Tyr His Val
                270                 275                 280 tct gtg cac cac aag gac tac agt gat ggc aga aga aca ttt ccc cga       915
Ser Val His His Lys Asp Tyr Ser Asp Gly Arg Arg Thr Phe Pro Arg
            285                 290                 295 ata cgg cgt cat caa ggc aac ttg ttc acc ctg gtg ccc tcc agc cgc       963
Ile Arg Arg His Gln Gly Asn Leu Phe Thr Leu Val Pro Ser Ser Arg
        300                 305                 310 tcc ctg agc aca aat ggc gag aac atg ggt ctg gct gtg caa tac ctg      1011
```

```
                        -continued

Ser Leu Ser Thr Asn Gly Glu Asn Met Gly Leu Ala Val Gln Tyr Leu
    315                 320                 325 gac ccc cgt ggg cgc ctg cgg agt gcg gac agc gag aat gcc ctc tct      1059
Asp Pro Arg Gly Arg Leu Arg Ser Ala Asp Ser Glu Asn Ala Leu Ser
330                 335                 340                 345 gtg cag gag agg aat gtg cca acc aag tct ccc agt gcc ccc atc aac      1107
Val Gln Glu Arg Asn Val Pro Thr Lys Ser Pro Ser Ala Pro Ile Asn
                350                 355                 360 tgg cgc cgg gga aag ctc ctg ggc cag ggt gcc ttc ggc agg gtc tat      1155
Trp Arg Arg Gly Lys Leu Leu Gly Gln Gly Ala Phe Gly Arg Val Tyr
            365                 370                 375 ttg tgc tat gac gtg gac acg gga cgt gaa ctt gct tcc aag cag gtc      1203
Leu Cys Tyr Asp Val Asp Thr Gly Arg Glu Leu Ala Ser Lys Gln Val
        380                 385                 390 caa ttt gat cca gac agt cct gag aca agc aag gag gtg agt gct ctg      1251
Gln Phe Asp Pro Asp Ser Pro Glu Thr Ser Lys Glu Val Ser Ala Leu
    395                 400                 405 gag tgc gag atc cag ttg cta aag aac ttg cag cat gag cgc act gtg      1299
Glu Cys Glu Ile Gln Leu Leu Lys Asn Leu Gln His Glu Arg Thr Val
410                 415                 420                 425 cag tac tac ggc tgc ctg cgg gac cgt act cag aag atc ctc acc atc      1347
Gln Tyr Tyr Gly Cys Leu Arg Asp Arg Thr Gln Lys Ile Leu Thr Ile
                430                 435                 440 ttt atg gag tat atg cca ggg ggc tct gta aaa gac cag ttg aag gcc      1395
Phe Met Glu Tyr Met Pro Gly Gly Ser Val Lys Asp Gln Leu Lys Ala
            445                 450                 455 tac gga gct ctg aca gag agt gtg acc cgc aag tac acc cgg cag att      1443
Tyr Gly Ala Leu Thr Glu Ser Val Thr Arg Lys Tyr Thr Arg Gln Ile
        460                 465                 470 ctg gag ggc atg tca tac ctg cac agc aac atg att gtg cat cgg gac      1491
Leu Glu Gly Met Ser Tyr Leu His Ser Asn Met Ile Val His Arg Asp
    475                 480                 485 atc aag gga gcc aat atc ctc cga gac tca gct ggg aat gtg aag ctt      1539
Ile Lys Gly Ala Asn Ile Leu Arg Asp Ser Ala Gly Asn Val Lys Leu
490                 495                 500                 505 ggg gat ttt ggg gcc agc aaa cac cta cag acc atc tgc atg tca ggg      1587
Gly Asp Phe Gly Ala Ser Lys His Leu Gln Thr Ile Cys Met Ser Gly
                510                 515                 520 aca ggc att cgc tct gtc act gac aca ccc tac tgg atg agt cct gaa      1635
Thr Gly Ile Arg Ser Val Thr Asp Thr Pro Tyr Trp Met Ser Pro Glu
            525                 530                 535 gtc atc agt ggc gag ggc tat gga aga aag gca gac gtg tgg agc ctg      1683
Val Ile Ser Gly Glu Gly Tyr Gly Arg Lys Ala Asp Val Trp Ser Leu
        540                 545                 550 ggc tgt act gtg gtg gat atg ctg aca gag aaa cca cct tgg gca gag      1731
Gly Cys Thr Val Val Asp Met Leu Thr Glu Lys Pro Pro Trp Ala Glu
    555                 560                 565 tat gaa gct atg gct gcc att ttc aag att gcc acc cag cct acc aat      1779
Tyr Glu Ala Met Ala Ala Ile Phe Lys Ile Ala Thr Gln Pro Thr Asn
570                 575                 580                 585 cct cag ctg ccc tct cac atc tca gaa cac ggc agg gac ttc ctg agg      1827
Pro Gln Leu Pro Ser His Ile Ser Glu His Gly Arg Asp Phe Leu Arg
                590                 595                 600 cgc ata ttt gtg gaa gct cgt cag aga ccc tca gcc gag gaa ctg ctc      1875
Arg Ile Phe Val Glu Ala Arg Gln Arg Pro Ser Ala Glu Glu Leu Leu
            605                 610                 615 aca cac cac ttt aca cag cta gtg tac tgagctctca aggctatcag            1922
Thr His His Phe Thr Gln Leu Val Tyr
        620                 625
```
gctgccagct gcc							1935

<210> SEQ ID NO 6
<211> LENGTH: 626
<212> TYPE: PRT
<213> ORGANISM: Homo sapiens

<400> SEQUENCE: 6

```
Met Asp Gln Gln Glu Ala Leu Asp Ser Ile Met Lys Asp Leu Val Ala
 1               5                  10                  15

Leu Gln Met Ser Arg Arg Thr Arg Leu Ser Gly Tyr Glu Thr Met Arg
            20                  25                  30

Asn Lys Asp Thr Gly His Pro Asn Arg Gln Ser Asp Val Arg Ile Lys
        35                  40                  45

Phe Glu His Asn Gly Glu Arg Arg Ile Ile Ala Phe Ser Arg Pro Val
    50                  55                  60

Arg Tyr Glu Asp Val Glu His Lys Val Thr Thr Val Phe Gly Gln Ser
65                  70                  75                  80

Leu Asp Leu His Tyr Met Asn Asn Glu Leu Ser Ile Leu Leu Lys Asn
                85                  90                  95

Gln Asp Asp Leu Asp Lys Ala Ile Asp Ile Leu Asp Arg Ser Ser Ser
            100                 105                 110

Met Lys Ser Leu Arg Ile Leu Leu Leu Ser Gln Asp Arg Tyr His Thr
        115                 120                 125

Ser Ser Ser Pro His Ser Gly Val Ser Arg Gln Val Arg Ile Lys Pro
    130                 135                 140

Ser Gln Ser Ala Gly Asp Ile Asn Thr Ile Tyr Gln Ala Pro Glu Pro
145                 150                 155                 160

Arg Ser Arg His Leu Ser Val Ser Ser Gln Asn Pro Gly Arg Ser Ser
                165                 170                 175

Pro Pro Pro Gly Tyr Val Pro Glu Arg Gln Gln His Ile Ala Arg Gln
            180                 185                 190

Gly Ser Tyr Thr Ser Ile Asn Ser Glu Gly Glu Phe Ile Pro Glu Thr
        195                 200                 205

Ser Glu Gln Cys Met Leu Asp Pro Leu Ser Ser Ala Glu Asn Ser Leu
    210                 215                 220

Ser Gly Ser Cys Gln Ser Leu Asp Arg Ser Ala Asp Ser Pro Ser Phe
225                 230                 235                 240

Arg Lys Ser Arg Met Ser Arg Ala Gln Ser Phe Pro Asp Asn Arg Gln
                245                 250                 255

Glu Tyr Ser Asp Arg Glu Thr Gln Leu Tyr Asp Lys Gly Val Lys Gly
            260                 265                 270

Gly Thr Tyr Pro Arg Arg Tyr His Val Ser Val His His Lys Asp Tyr
        275                 280                 285

Ser Asp Gly Arg Arg Thr Phe Pro Arg Ile Arg Arg His Gln Gly Asn
    290                 295                 300

Leu Phe Thr Leu Val Pro Ser Arg Ser Leu Ser Thr Asn Gly Glu
305                 310                 315                 320

Asn Met Gly Leu Ala Val Gln Tyr Leu Asp Pro Arg Gly Arg Leu Arg
                325                 330                 335

Ser Ala Asp Ser Glu Asn Ala Leu Ser Val Gln Glu Arg Asn Val Pro
            340                 345                 350

Thr Lys Ser Pro Ser Ala Pro Ile Asn Trp Arg Arg Gly Lys Leu Leu
        355                 360                 365
```

-continued

```
Gly Gln Gly Ala Phe Gly Arg Val Tyr Leu Cys Tyr Asp Val Asp Thr
    370                 375                 380
Gly Arg Glu Leu Ala Ser Lys Gln Val Gln Phe Asp Pro Asp Ser Pro
385                 390                 395                 400
Glu Thr Ser Lys Glu Val Ser Ala Leu Glu Cys Glu Ile Gln Leu Leu
                405                 410                 415
Lys Asn Leu Gln His Glu Arg Thr Val Gln Tyr Tyr Gly Cys Leu Arg
            420                 425                 430
Asp Arg Thr Gln Lys Ile Leu Thr Ile Phe Met Glu Tyr Met Pro Gly
        435                 440                 445
Gly Ser Val Lys Asp Gln Leu Lys Ala Tyr Gly Ala Leu Thr Glu Ser
    450                 455                 460
Val Thr Arg Lys Tyr Thr Arg Gln Ile Leu Glu Gly Met Ser Tyr Leu
465                 470                 475                 480
His Ser Asn Met Ile Val His Arg Asp Ile Lys Gly Ala Asn Ile Leu
                485                 490                 495
Arg Asp Ser Ala Gly Asn Val Lys Leu Gly Asp Phe Gly Ala Ser Lys
            500                 505                 510
His Leu Gln Thr Ile Cys Met Ser Gly Thr Gly Ile Arg Ser Val Thr
        515                 520                 525
Asp Thr Pro Tyr Trp Met Ser Pro Glu Val Ile Ser Gly Glu Gly Tyr
    530                 535                 540
Gly Arg Lys Ala Asp Val Trp Ser Leu Gly Cys Thr Val Val Asp Met
545                 550                 555                 560
Leu Thr Glu Lys Pro Pro Trp Ala Glu Tyr Glu Ala Met Ala Ala Ile
                565                 570                 575
Phe Lys Ile Ala Thr Gln Pro Thr Asn Pro Gln Leu Pro Ser His Ile
            580                 585                 590
Ser Glu His Gly Arg Asp Phe Leu Arg Arg Ile Phe Val Glu Ala Arg
        595                 600                 605
Gln Arg Pro Ser Ala Glu Glu Leu Leu Thr His His Phe Thr Gln Leu
    610                 615                 620
Val Tyr
625

<210> SEQ ID NO 7
<211> LENGTH: 5253
<212> TYPE: DNA
<213> ORGANISM: Mus musculus
<220> FEATURE:
<221> NAME/KEY: CDS
<222> LOCATION: (15)..(4493)

<400> SEQUENCE: 7
gcccgcgaga gaaa atg gcg gcg gcg gcg ggc gat cgc gcc tcg tcg tcg     50
             Met Ala Ala Ala Ala Gly Asp Arg Ala Ser Ser Ser
             1               5                   10 gga ttc ccg ggc gcc gcg gcg agt ccc gag gcg ggc ggc ggc            98
Gly Phe Pro Gly Ala Ala Ala Ser Pro Glu Ala Gly Gly Gly
    15                  20                  25 gga gga gga gga gct ctc cag gga agc ggc gcg ccc gca gcg ggc gcg    146
Gly Gly Gly Gly Ala Leu Gln Gly Ser Gly Ala Pro Ala Ala Gly Ala
    30                  35                  40 gcg ggg ctg ctg cgg gag cct ggc agc gcg ggc cgc gag cgc gcg gac    194
Ala Gly Leu Leu Arg Glu Pro Gly Ser Ala Gly Arg Glu Arg Ala Asp
45                  50                  55                  60 tgg cgg cgg cgg cac gtg cgc aaa gtg cgg agt gtg gag ctg gac cag    242
```

```
                                                          -continued

Trp Arg Arg Arg His Val Arg Lys Val Arg Ser Val Glu Leu Asp Gln
                 65                  70                  75 ctg ccg gag cag ccg ctc ttc ctc gcc gcc gcc tcg ccg ccc tgc cca         290
Leu Pro Glu Gln Pro Leu Phe Leu Ala Ala Ala Ser Pro Pro Cys Pro
                 80                  85                  90 tct act tcc ccg tcg ccg gag ccc gcg gac gcg gct gca gga gcg agt         338
Ser Thr Ser Pro Ser Pro Glu Pro Ala Asp Ala Ala Ala Gly Ala Ser
             95                     100                 105 cgc ttc cag ccc gcg gcg gga ccg cca ccc ccg gga gcg gcg agt cgc         386
Arg Phe Gln Pro Ala Ala Gly Pro Pro Pro Pro Gly Ala Ala Ser Arg
            110                 115                     120 tgc ggc tcc cac tct gcc gag ctg gcg gcc gcg cgg gac agc ggc gcc         434
Cys Gly Ser His Ser Ala Glu Leu Ala Ala Ala Arg Asp Ser Gly Ala
125                 130                 135                 140 cgg agc ccc gcg ggg gcg gag ccg ccc tct gca gcg gcc ccc tcc ggt         482
Arg Ser Pro Ala Gly Ala Glu Pro Pro Ser Ala Ala Ala Pro Ser Gly
                145                 150                 155 cga gag atg gag aat aaa gaa acc ctc aaa gga ctg cac aag atg gag         530
Arg Glu Met Glu Asn Lys Glu Thr Leu Lys Gly Leu His Lys Met Glu
                    160                 165                 170 gat cgc ccg gag gag aga atg atc cgg gag aag ctc aag gcg acc tgt         578
Asp Arg Pro Glu Glu Arg Met Ile Arg Glu Lys Leu Lys Ala Thr Cys
                175                 180                 185 atg ccg gcc tgg aag cac gag tgg ttg gag agg agg aac agg aga ggc         626
Met Pro Ala Trp Lys His Glu Trp Leu Glu Arg Arg Asn Arg Arg Gly
            190                 195                 200 cct gtg gtg gtg aag cca atc cct att aaa gga gat gga tct gaa gtg         674
Pro Val Val Val Lys Pro Ile Pro Ile Lys Gly Asp Gly Ser Glu Val
205                 210                 215                 220 aat aac ttg gca gct gag ccc cag gga gag ggc cag gca ggt tcc gct         722
Asn Asn Leu Ala Ala Glu Pro Gln Gly Glu Gly Gln Ala Gly Ser Ala
                225                 230                 235 gca cca gcc ccc aag ggc cga cga agc cca tct cct ggc agc tct ccg         770
Ala Pro Ala Pro Lys Gly Arg Arg Ser Pro Ser Pro Gly Ser Ser Pro
                240                 245                 250 tca ggg cgc tcg gtg aag ccg gaa tcc cca gga gta aga cgg aaa cga         818
Ser Gly Arg Ser Val Lys Pro Glu Ser Pro Gly Val Arg Arg Lys Arg
            255                 260                 265 gtg tcc ccg gtg cct ttc cag agt ggc aga atc aca cca ccc cga aga         866
Val Ser Pro Val Pro Phe Gln Ser Gly Arg Ile Thr Pro Pro Arg Arg
270                 275                 280 gcc cca tca ccg gat ggc ttc tcc ccg tac agc cca gag gag acg agc         914
Ala Pro Ser Pro Asp Gly Phe Ser Pro Tyr Ser Pro Glu Glu Thr Ser
                290                 295                 300
285 cgc cgc gtg aac aaa gtg atg aga gcc agg ctg tac ctg ctg cag cag         962
Arg Arg Val Asn Lys Val Met Arg Ala Arg Leu Tyr Leu Leu Gln Gln
                305                 310                 315 ata gga ccc aac tct ttc ctg att gga gga gac agt cca gac aat aaa         1010
Ile Gly Pro Asn Ser Phe Leu Ile Gly Gly Asp Ser Pro Asp Asn Lys
                320                 325                 330 tac cgg gtg ttt att ggg cca cag aac tgc agc tgt ggg cgt gga gca         1058
Tyr Arg Val Phe Ile Gly Pro Gln Asn Cys Ser Cys Gly Arg Gly Ala
            335                 340                 345 ttc tgt att cac ctc ttg ttt gtc atg ctc cgg gtg ttt cag cta gaa         1106
Phe Cys Ile His Leu Leu Phe Val Met Leu Arg Val Phe Gln Leu Glu
        350                 355                 360 ccc tct gac ccc atg tta tgg aga aaa act tta aaa aat ttc gag gtt         1154
Pro Ser Asp Pro Met Leu Trp Arg Lys Thr Leu Lys Asn Phe Glu Val
365                 370                 375                 380
```

-continued

| | |
|---|---|
| gag agt ttg ttc cag aaa tac cac agt agg cgt agc tcg aga atc aaa<br>Glu Ser Leu Phe Gln Lys Tyr His Ser Arg Arg Ser Ser Arg Ile Lys<br>                      385                              390                        395 | 1202 |
| gct cca tcc cgg aac acc atc cag aag ttt gtg tca cgc atg tca aat<br>Ala Pro Ser Arg Asn Thr Ile Gln Lys Phe Val Ser Arg Met Ser Asn<br>              400                            405                        410 | 1250 |
| tct cac aca ctg tca tcg tct agc aca tcc aca tct agt tca gaa aac<br>Ser His Thr Leu Ser Ser Ser Ser Thr Ser Thr Ser Ser Ser Glu Asn<br>              415                          420                        425 | 1298 |
| agc atc aag gat gaa gag gag cag atg tgt ccc atc tgc ttg ctg ggc<br>Ser Ile Lys Asp Glu Glu Glu Gln Met Cys Pro Ile Cys Leu Leu Gly<br>      430                            435                        440 | 1346 |
| atg ctg gat gag gag agc ctg act gtg tgt gaa gat ggc tgc agg aac<br>Met Leu Asp Glu Glu Ser Leu Thr Val Cys Glu Asp Gly Cys Arg Asn<br>445                        450                        455                        460 | 1394 |
| aag ctg cac cac cat tgc atg tcc atc tgg gcg gaa gag tgt aga aga<br>Lys Leu His His His Cys Met Ser Ile Trp Ala Glu Glu Cys Arg Arg<br>                      465                            470                        475 | 1442 |
| aat aga gag cct tta ata tgt ccc ctt tgt aga tct aag tgg aga tcc<br>Asn Arg Glu Pro Leu Ile Cys Pro Leu Cys Arg Ser Lys Trp Arg Ser<br>              480                            485                        490 | 1490 |
| cat gac ttc tac agc cat gag tta tca agc ccc gtg gag tcc ccc gcc<br>His Asp Phe Tyr Ser His Glu Leu Ser Ser Pro Val Glu Ser Pro Ala<br>                      495                            500                        505 | 1538 |
| tcc ctg cga gct gtc cag cag cca tcc tcc ccg cag cag ccc gtg gcc<br>Ser Leu Arg Ala Val Gln Gln Pro Ser Ser Pro Gln Gln Pro Val Ala<br>      510                            515                        520 | 1586 |
| gga tca cag cgg agg aat cag gag agc agt ttt aac ctt act cat ttt<br>Gly Ser Gln Arg Arg Asn Gln Glu Ser Ser Phe Asn Leu Thr His Phe<br>525                        530                        535                        540 | 1634 |
| gga acc cag cag att cct tcc gct tac aaa gat ttg gcc gag cca tgg<br>Gly Thr Gln Gln Ile Pro Ser Ala Tyr Lys Asp Leu Ala Glu Pro Trp<br>                      545                            550                        555 | 1682 |
| att cag gtg ttt gga atg gaa ctc gtt ggc tgc tta ttc tct aga aac<br>Ile Gln Val Phe Gly Met Glu Leu Val Gly Cys Leu Phe Ser Arg Asn<br>              560                            565                        570 | 1730 |
| tgg aac gta agg gaa atg gcc ctt agg cgt ctt tcc cac gac gtt agt<br>Trp Asn Val Arg Glu Met Ala Leu Arg Arg Leu Ser His Asp Val Ser<br>                      575                            580                        585 | 1778 |
| ggg gcc ctg ttg ttg gca aac ggg gag agc act gga aac tct gga ggc<br>Gly Ala Leu Leu Leu Ala Asn Gly Glu Ser Thr Gly Asn Ser Gly Gly<br>      590                            595                        600 | 1826 |
| ggc agt ggg ggc agc tta agc gcg gga gcg gcc agc ggg tcc tcc cag<br>Gly Ser Gly Gly Ser Leu Ser Ala Gly Ala Ala Ser Gly Ser Ser Gln<br>605                        610                        615                        620 | 1874 |
| ccc agc atc tca ggg gat gtg gtg gag gcg tgc tgt agt gtc ctg tct<br>Pro Ser Ile Ser Gly Asp Val Val Glu Ala Cys Cys Ser Val Leu Ser<br>              625                            630                        635 | 1922 |
| ata gtc tgc gct gac cct gtc tac aaa gtg tac gtt gct gct tta aaa<br>Ile Val Cys Ala Asp Pro Val Tyr Lys Val Tyr Val Ala Ala Leu Lys<br>                      640                            645                        650 | 1970 |
| aca ttg aga gcc atg ctg gta tac act cct tgc cac agt ctg gca gaa<br>Thr Leu Arg Ala Met Leu Val Tyr Thr Pro Cys His Ser Leu Ala Glu<br>      655                            660                        665 | 2018 |
| aga atc aaa ctt cag aga ctc ctc cgg cca gtt gta gac act atc ctt<br>Arg Ile Lys Leu Gln Arg Leu Leu Arg Pro Val Val Asp Thr Ile Leu<br>670                        675                        680 | 2066 |
| gtc aag tgt gca gat gcc aac agc cgc acg agt cag ctg tcc ata tct<br>Val Lys Cys Ala Asp Ala Asn Ser Arg Thr Ser Gln Leu Ser Ile Ser<br>685                        690                        695                        700 | 2114 |

```
aca gtg ctg gaa ctc tgc aag ggc caa gca gga gag ctg gcg gtt ggg    2162
Thr Val Leu Glu Leu Cys Lys Gly Gln Ala Gly Glu Leu Ala Val Gly
            705                 710                 715 aga gaa ata ctt aaa gct ggg tcc atc ggg gtt ggt ggt gtc gat tac    2210
Arg Glu Ile Leu Lys Ala Gly Ser Ile Gly Val Gly Gly Val Asp Tyr
            720                 725                 730 gtc tta agt tgt atc ctt gga aac caa gct gaa tca aac aac tgg caa    2258
Val Leu Ser Cys Ile Leu Gly Asn Gln Ala Glu Ser Asn Asn Trp Gln
            735                 740                 745 gaa ctg ctg ggt cgc ctc tgt ctt ata gac agg ttg ctg tta gaa ttt    2306
Glu Leu Leu Gly Arg Leu Cys Leu Ile Asp Arg Leu Leu Leu Glu Phe
            750                 755                 760 cct gct gaa ttc tat cct cat att gtc agt act gat gtc tca caa gct    2354
Pro Ala Glu Phe Tyr Pro His Ile Val Ser Thr Asp Val Ser Gln Ala
765                 770                 775                 780 gag cct gtt gaa atc agg tac aag aag ctg ctc tcc ctc tta acc ttt    2402
Glu Pro Val Glu Ile Arg Tyr Lys Lys Leu Leu Ser Leu Leu Thr Phe
                785                 790                 795 gcc ttg caa tcc att gac aat tcc cac tcg atg gtt ggc aag ctc tct    2450
Ala Leu Gln Ser Ile Asp Asn Ser His Ser Met Val Gly Lys Leu Ser
            800                 805                 810 cgg agg ata tat ctg agc tct gcc agg atg gtg acc gca gtg ccc gct    2498
Arg Arg Ile Tyr Leu Ser Ser Ala Arg Met Val Thr Ala Val Pro Ala
            815                 820                 825 gtg ttt tcc aag ctg gta acc atg ctt aat gct tct ggc tcc acc cac    2546
Val Phe Ser Lys Leu Val Thr Met Leu Asn Ala Ser Gly Ser Thr His
            830                 835                 840 ttc acc agg atg cgc cgg cgt ctg atg gct atc gcg gat gag gta gaa    2594
Phe Thr Arg Met Arg Arg Arg Leu Met Ala Ile Ala Asp Glu Val Glu
845                 850                 855                 860 att gcc gag gtc atc cag ctg ggt gtg gag gac act gtg gat ggg cat    2642
Ile Ala Glu Val Ile Gln Leu Gly Val Glu Asp Thr Val Asp Gly His
                865                 870                 875 cag gac agc tta cag gcc gtg gcc ccc acc agc tgt cta gaa aac agc    2690
Gln Asp Ser Leu Gln Ala Val Ala Pro Thr Ser Cys Leu Glu Asn Ser
            880                 885                 890 tcc ctt gag cac aca gtc cat aga gag aaa act gga aaa gga cta agt    2738
Ser Leu Glu His Thr Val His Arg Glu Lys Thr Gly Lys Gly Leu Ser
            895                 900                 905 gct acg aga ctg agt gcc agc tcg gag gac att tct gac aga ctg gcc    2786
Ala Thr Arg Leu Ser Ala Ser Ser Glu Asp Ile Ser Asp Arg Leu Ala
910                 915                 920 ggc gtc tct gta gga ctt ccc agc tca aca aca aca gaa caa cca aag    2834
Gly Val Ser Val Gly Leu Pro Ser Ser Thr Thr Thr Glu Gln Pro Lys
925                 930                 935                 940 cca gcg gtt caa aca aaa ggc aga ccc cac agt cag tgt ttg aac tcc    2882
Pro Ala Val Gln Thr Lys Gly Arg Pro His Ser Gln Cys Leu Asn Ser
            945                 950                 955 tcc cct ttg tct cat gct caa tta atg ttc cca gca cca tca gcc cct    2930
Ser Pro Leu Ser His Ala Gln Leu Met Phe Pro Ala Pro Ser Ala Pro
            960                 965                 970 tgt tcc tct gcc ccg tct gtc cca gat att tct aag cac aga ccc cag    2978
Cys Ser Ser Ala Pro Ser Val Pro Asp Ile Ser Lys His Arg Pro Gln
            975                 980                 985 gca ttt gtt ccc tgc aaa ata cct tcc gca tct cct cag aca cag cgc    3026
Ala Phe Val Pro Cys Lys Ile Pro Ser Ala Ser Pro Gln Thr Gln Arg
            990                 995                 1000 aag ttc tct cta caa ttc cag agg aac tgc tct gaa cac cga gac tca    3074
Lys Phe Ser Leu Gln Phe Gln Arg Asn Cys Ser Glu His Arg Asp Ser
```

-continued

```
       1005                1010                1015                1020
gac cag ctc tcc cca gtc ttc act cag tca aga ccc cca ccc tcc agt         3122
Asp Gln Leu Ser Pro Val Phe Thr Gln Ser Arg Pro Pro Pro Ser Ser
                    1025                1030                1035 aac ata cac agg cca aag cca tcc cga ccc gtt ccg ggc agt aca agc         3170
Asn Ile His Arg Pro Lys Pro Ser Arg Pro Val Pro Gly Ser Thr Ser
                1040                1045                1050 aaa cta ggg gac gcc aca aaa agt agc atg aca ctt gat ctg ggc agt         3218
Lys Leu Gly Asp Ala Thr Lys Ser Ser Met Thr Leu Asp Leu Gly Ser
            1055                1060                1065 gct tcc agg tgt gac gac agc ttt ggc ggc ggc ggc aac agt ggc aac         3266
Ala Ser Arg Cys Asp Asp Ser Phe Gly Gly Gly Gly Asn Ser Gly Asn
        1070                1075                1080 gcc gtc ata ccc agc gac gag aca gtg ttc acg ccg gtg gag gac aag         3314
Ala Val Ile Pro Ser Asp Glu Thr Val Phe Thr Pro Val Glu Asp Lys
1085                1090                1095                1100 tgc agg tta gat gtg aac acc gag ctc aac tcc agc atc gag gac ctt         3362
Cys Arg Leu Asp Val Asn Thr Glu Leu Asn Ser Ser Ile Glu Asp Leu
                    1105                1110                1115 ctt gaa gca tcc atg cct tca agt gac acg aca gtc act ttc aag tcc         3410
Leu Glu Ala Ser Met Pro Ser Ser Asp Thr Thr Val Thr Phe Lys Ser
                1120                1125                1130 gaa gtc gcc gtc ctc tct ccg gaa aag gcc gaa aat gac gac acc tac         3458
Glu Val Ala Val Leu Ser Pro Glu Lys Ala Glu Asn Asp Asp Thr Tyr
            1135                1140                1145 aaa gac gac gtc aat cat aat caa aag tgc aaa gaa aag atg gaa gct         3506
Lys Asp Asp Val Asn His Asn Gln Lys Cys Lys Glu Lys Met Glu Ala
        1150                1155                1160 gaa gag gag gag gct tta gcg atc gcc atg gcg atg tca gcg tct cag         3554
Glu Glu Glu Glu Ala Leu Ala Ile Ala Met Ala Met Ser Ala Ser Gln
1165                1170                1175                1180 gat gcc ctc ccc atc gtc cct cag ctg cag gtg gaa aat gga gaa gat         3602
Asp Ala Leu Pro Ile Val Pro Gln Leu Gln Val Glu Asn Gly Glu Asp
                    1185                1190                1195 att atc atc att cag cag gac aca cca gaa act ctt cca gga cat acc         3650
Ile Ile Ile Ile Gln Gln Asp Thr Pro Glu Thr Leu Pro Gly His Thr
                1200                1205                1210 aaa gcg aaa cag cct tac aga gaa gac gct gag tgg ctg aaa ggc cag         3698
Lys Ala Lys Gln Pro Tyr Arg Glu Asp Ala Glu Trp Leu Lys Gly Gln
            1215                1220                1225 cag ata ggc ctc gga gca ttt tct tcc tgt tac caa gca cag gat gtg         3746
Gln Ile Gly Leu Gly Ala Phe Ser Ser Cys Tyr Gln Ala Gln Asp Val
        1230                1235                1240 ggg act ggg act tta atg gct gtg aaa cag gtg acg tac gtc aga aac         3794
Gly Thr Gly Thr Leu Met Ala Val Lys Gln Val Thr Tyr Val Arg Asn
1245                1250                1255                1260 aca tcc tcc gag cag gag gag gtg gtg gaa gcg ttg agg gaa gag atc         3842
Thr Ser Ser Glu Gln Glu Glu Val Val Glu Ala Leu Arg Glu Glu Ile
                    1265                1270                1275 cgg atg atg ggt cac ctc aac cat cca aac atc atc cgg atg ctg ggg         3890
Arg Met Met Gly His Leu Asn His Pro Asn Ile Ile Arg Met Leu Gly
                1280                1285                1290 gcc acg tgc gag aag agc aac tac aac ctc ttc att gag tgg atg gcg         3938
Ala Thr Cys Glu Lys Ser Asn Tyr Asn Leu Phe Ile Glu Trp Met Ala
            1295                1300                1305 gga gga tct gtg gct cac ctc ttg agt aaa tac gga gct ttc aag gag         3986
Gly Gly Ser Val Ala His Leu Leu Ser Lys Tyr Gly Ala Phe Lys Glu
        1310                1315                1320 tca gtc gtc att aac tac act gag cag tta ctg cgt ggc ctt tcc tat         4034
```

-continued

| | | |
|---|---|---|
| Ser Val Val Ile Asn Tyr Thr Glu Gln Leu Leu Arg Gly Leu Ser Tyr<br>1325             1330               1335            1340 | | |
| ctc cac gag aac cag atc att cac aga gac gtc aaa ggt gcc aac ctg<br>Leu His Glu Asn Gln Ile Ile His Arg Asp Val Lys Gly Ala Asn Leu<br>             1345               1350            1355 | 4082 |
| ctc att gac agc acc ggt cag agg ctg aga att gca gac ttt gga gct<br>Leu Ile Asp Ser Thr Gly Gln Arg Leu Arg Ile Ala Asp Phe Gly Ala<br>        1360               1365               1370 | 4130 |
| gct gcc agg ttg gca tca aaa gga acc ggt gca gga gag ttc cag gga<br>Ala Ala Arg Leu Ala Ser Lys Gly Thr Gly Ala Gly Glu Phe Gln Gly<br>1375               1380              1385 | 4178 |
| cag tta ctg ggg aca att gca ttc atg gcg cct gag gtc cta aga ggt<br>Gln Leu Leu Gly Thr Ile Ala Phe Met Ala Pro Glu Val Leu Arg Gly<br>     1390             1395             1400 | 4226 |
| cag cag tat ggt agg agc tgt gat gta tgg agt gtt ggc tgc gcc att<br>Gln Gln Tyr Gly Arg Ser Cys Asp Val Trp Ser Val Gly Cys Ala Ile<br>1405             1410               1415           1420 | 4274 |
| ata gaa atg gct tgt gca aaa cca cct tgg aat gca gaa aaa cac tcc<br>Ile Glu Met Ala Cys Ala Lys Pro Pro Trp Asn Ala Glu Lys His Ser<br>                  1425            1430           1435 | 4322 |
| aat cat ctc gcc ttg ata ttt aag att gct agc gca act act gca ccg<br>Asn His Leu Ala Leu Ile Phe Lys Ile Ala Ser Ala Thr Thr Ala Pro<br>         1440             1445              1450 | 4370 |
| tcc atc ccg tca cac ctg tcc ccg ggt ctg cgc gac gtg gcc gtg cgc<br>Ser Ile Pro Ser His Leu Ser Pro Gly Leu Arg Asp Val Ala Val Arg<br>             1455               1460           1465 | 4418 |
| tgc tta gaa ctt cag cct cag gac cgg cct ccg tcc aga gag ctg ctg<br>Cys Leu Glu Leu Gln Pro Gln Asp Arg Pro Pro Ser Arg Glu Leu Leu<br>1470             1475               1480 | 4466 |
| aaa cat ccg gtc ttc cgt acc acg tgg tagttaattg ttcagatcag<br>Lys His Pro Val Phe Arg Thr Thr Trp<br>1485            1490 | 4513 |
| ctctaatgga gacaggatat gcaaccggga gagagaaaag agaacttgtg ggcgaccatg | 4573 |
| ccgctaaccg cagccctcac gccactgaac agccagaaac ggggccagcg gggaaccgta | 4633 |
| cctaagcatg tgattgacaa atcatgacct gtacctaagc tcgatatgca gacatctaca | 4693 |
| gctcgtgcag gaactgcaca ccgtgccttt cacaggactg gctctggggg accaggaagg | 4753 |
| cgatggagtt tgcatgacta agaacagaa gcataaattt attttggag cacttttca | 4813 |
| gctaatcagt attaccatgt acatcaacat gcccgccaca tttcaaactc agactgtccc | 4873 |
| agatgtcaag atccactgtg tttgagtttg tttgcagttc cctcagcttg ctggtaattg | 4933 |
| tggtgttttg ttttcgatgc aaatgtgatg taatattctt attttctttg gatcaaagct | 4993 |
| ggactgaaaa ttgtactgtg taattatttt tgtgttttta atgttatttg gtactcgaat | 5053 |
| tgtaaataac gtctactgct gtttattcca gtttctacta cctcaggtgt cctatagatt | 5113 |
| tttcttctac caaagttcac tctcagaatg aaattctacg tgctgtgtga ctatgactcc | 5173 |
| taagacttcc agggcttaag ggctaactcc tattagcacc ttactatgta agcaaatgct | 5233 |
| acaaaaaaaa aaaaaaaaaa | 5253 |

<210> SEQ ID NO 8
<211> LENGTH: 1493
<212> TYPE: PRT
<213> ORGANISM: Mus musculus

<400> SEQUENCE: 8

Met Ala Ala Ala Ala Gly Asp Arg Ala Ser Ser Ser Gly Phe Pro Gly
1               5                 10              15

-continued

```
Ala Ala Ala Ala Ser Pro Glu Ala Gly Gly Gly Gly Gly Gly
             20                  25                  30

Ala Leu Gln Gly Ser Gly Ala Pro Ala Gly Ala Ala Gly Leu Leu
             35                  40                  45

Arg Glu Pro Gly Ser Ala Gly Arg Glu Arg Ala Asp Trp Arg Arg Arg
     50                  55                  60

His Val Arg Lys Val Arg Ser Val Glu Leu Asp Gln Leu Pro Glu Gln
 65                  70                  75                  80

Pro Leu Phe Leu Ala Ala Ser Pro Pro Cys Pro Ser Thr Ser Pro
                 85                  90                  95

Ser Pro Glu Pro Ala Asp Ala Ala Gly Ala Ser Arg Phe Gln Pro
                100                 105                 110

Ala Ala Gly Pro Pro Pro Gly Ala Ala Ser Arg Cys Gly Ser His
                115                 120                 125

Ser Ala Glu Leu Ala Ala Ala Arg Asp Ser Gly Ala Arg Ser Pro Ala
    130                 135                 140

Gly Ala Glu Pro Pro Ser Ala Ala Pro Ser Gly Arg Glu Met Glu
145                 150                 155                 160

Asn Lys Glu Thr Leu Lys Gly Leu His Lys Met Glu Asp Arg Pro Glu
                165                 170                 175

Glu Arg Met Ile Arg Glu Lys Leu Lys Ala Thr Cys Met Pro Ala Trp
                180                 185                 190

Lys His Glu Trp Leu Glu Arg Arg Asn Arg Arg Gly Pro Val Val Val
                195                 200                 205

Lys Pro Ile Pro Ile Lys Gly Asp Gly Ser Glu Val Asn Asn Leu Ala
    210                 215                 220

Ala Glu Pro Gln Gly Glu Gly Gln Ala Gly Ser Ala Ala Pro Ala Pro
225                 230                 235                 240

Lys Gly Arg Arg Ser Pro Ser Pro Gly Ser Ser Pro Ser Gly Arg Ser
                245                 250                 255

Val Lys Pro Glu Ser Pro Gly Val Arg Arg Lys Arg Val Ser Pro Val
                260                 265                 270

Pro Phe Gln Ser Gly Arg Ile Thr Pro Pro Arg Arg Ala Pro Ser Pro
    275                 280                 285

Asp Gly Phe Ser Pro Tyr Ser Pro Glu Glu Thr Ser Arg Arg Val Asn
290                 295                 300

Lys Val Met Arg Ala Arg Leu Tyr Leu Leu Gln Gln Ile Gly Pro Asn
305                 310                 315                 320

Ser Phe Leu Ile Gly Gly Asp Ser Pro Asp Asn Lys Tyr Arg Val Phe
                325                 330                 335

Ile Gly Pro Gln Asn Cys Ser Cys Gly Arg Gly Ala Phe Cys Ile His
                340                 345                 350

Leu Leu Phe Val Met Leu Arg Val Phe Gln Leu Glu Pro Ser Asp Pro
    355                 360                 365

Met Leu Trp Arg Lys Thr Leu Lys Asn Phe Glu Val Glu Ser Leu Phe
370                 375                 380

Gln Lys Tyr His Ser Arg Arg Ser Ser Arg Ile Lys Ala Pro Ser Arg
385                 390                 395                 400

Asn Thr Ile Gln Lys Phe Val Ser Arg Met Ser Asn Ser His Thr Leu
                405                 410                 415

Ser Ser Ser Ser Thr Ser Ser Ser Glu Asn Ser Ile Lys Asp
                420                 425                 430
```

-continued

```
Glu Glu Glu Gln Met Cys Pro Ile Cys Leu Leu Gly Met Leu Asp Glu
            435                 440                 445

Glu Ser Leu Thr Val Cys Glu Asp Gly Cys Arg Asn Lys Leu His His
        450                 455                 460

His Cys Met Ser Ile Trp Ala Glu Glu Cys Arg Arg Asn Arg Glu Pro
465                 470                 475                 480

Leu Ile Cys Pro Leu Cys Arg Ser Lys Trp Arg Ser His Asp Phe Tyr
                485                 490                 495

Ser His Glu Leu Ser Ser Pro Val Glu Ser Pro Ala Ser Leu Arg Ala
            500                 505                 510

Val Gln Gln Pro Ser Ser Pro Gln Gln Pro Val Ala Gly Ser Gln Arg
        515                 520                 525

Arg Asn Gln Glu Ser Ser Phe Asn Leu Thr His Phe Gly Thr Gln Gln
        530                 535                 540

Ile Pro Ser Ala Tyr Lys Asp Leu Ala Glu Pro Trp Ile Gln Val Phe
545                 550                 555                 560

Gly Met Glu Leu Val Gly Cys Leu Phe Ser Arg Asn Trp Asn Val Arg
                565                 570                 575

Glu Met Ala Leu Arg Arg Leu Ser His Asp Val Ser Gly Ala Leu Leu
            580                 585                 590

Leu Ala Asn Gly Glu Ser Thr Gly Asn Ser Gly Gly Ser Gly Gly
        595                 600                 605

Ser Leu Ser Ala Gly Ala Ala Ser Gly Ser Ser Gln Pro Ser Ile Ser
        610                 615                 620

Gly Asp Val Val Glu Ala Cys Cys Ser Val Leu Ser Ile Val Cys Ala
625                 630                 635                 640

Asp Pro Val Tyr Lys Val Tyr Val Ala Ala Leu Lys Thr Leu Arg Ala
                645                 650                 655

Met Leu Val Tyr Thr Pro Cys His Ser Leu Ala Glu Arg Ile Lys Leu
            660                 665                 670

Gln Arg Leu Leu Arg Pro Val Val Asp Thr Ile Leu Val Lys Cys Ala
        675                 680                 685

Asp Ala Asn Ser Arg Thr Ser Gln Leu Ser Ile Ser Thr Val Leu Glu
690                 695                 700

Leu Cys Lys Gly Gln Ala Gly Glu Leu Ala Val Gly Arg Glu Ile Leu
705                 710                 715                 720

Lys Ala Gly Ser Ile Gly Val Gly Gly Val Asp Tyr Val Leu Ser Cys
                725                 730                 735

Ile Leu Gly Asn Gln Ala Glu Ser Asn Asn Trp Gln Glu Leu Leu Gly
            740                 745                 750

Arg Leu Cys Leu Ile Asp Arg Leu Leu Leu Glu Phe Pro Ala Glu Phe
        755                 760                 765

Tyr Pro His Ile Val Ser Thr Asp Val Ser Gln Ala Glu Pro Val Glu
        770                 775                 780

Ile Arg Tyr Lys Lys Leu Leu Ser Leu Leu Thr Phe Ala Leu Gln Ser
785                 790                 795                 800

Ile Asp Asn Ser His Ser Met Val Gly Lys Leu Ser Arg Arg Ile Tyr
                805                 810                 815

Leu Ser Ser Ala Arg Met Val Thr Ala Val Pro Ala Val Phe Ser Lys
            820                 825                 830

Leu Val Thr Met Leu Asn Ala Ser Gly Ser Thr His Phe Thr Arg Met
        835                 840                 845

Arg Arg Arg Leu Met Ala Ile Ala Asp Glu Val Glu Ile Ala Glu Val
```

-continued

```
        850                 855                 860
Ile Gln Leu Gly Val Glu Asp Thr Val Asp Gly His Gln Asp Ser Leu
865                 870                 875                 880

Gln Ala Val Ala Pro Thr Ser Cys Leu Glu Asn Ser Ser Leu Glu His
                885                 890                 895

Thr Val His Arg Glu Lys Thr Gly Lys Gly Leu Ser Ala Thr Arg Leu
                900                 905                 910

Ser Ala Ser Ser Glu Asp Ile Ser Asp Arg Leu Ala Gly Val Ser Val
                915                 920                 925

Gly Leu Pro Ser Ser Thr Thr Thr Glu Gln Pro Lys Pro Ala Val Gln
                930                 935                 940

Thr Lys Gly Arg Pro His Ser Gln Cys Leu Asn Ser Ser Pro Leu Ser
945                 950                 955                 960

His Ala Gln Leu Met Phe Pro Ala Pro Ser Ala Pro Cys Ser Ser Ala
                965                 970                 975

Pro Ser Val Pro Asp Ile Ser Lys His Arg Pro Gln Ala Phe Val Pro
                980                 985                 990

Cys Lys Ile Pro Ser Ala Ser Pro Gln Thr Gln Arg Lys Phe Ser Leu
                995                 1000                1005

Gln Phe Gln Arg Asn Cys Ser Glu His Arg Asp Ser Asp Gln Leu Ser
                1010                1015                1020

Pro Val Phe Thr Gln Ser Arg Pro Pro Ser Ser Asn Ile His Arg
1025                1030                1035                1040

Pro Lys Pro Ser Arg Pro Val Pro Gly Ser Thr Ser Lys Leu Gly Asp
                1045                1050                1055

Ala Thr Lys Ser Ser Met Thr Leu Asp Leu Gly Ser Ala Ser Arg Cys
                1060                1065                1070

Asp Asp Ser Phe Gly Gly Gly Gly Asn Ser Gly Asn Ala Val Ile Pro
                1075                1080                1085

Ser Asp Glu Thr Val Phe Thr Pro Val Glu Asp Lys Cys Arg Leu Asp
                1090                1095                1100

Val Asn Thr Glu Leu Asn Ser Ser Ile Glu Asp Leu Leu Glu Ala Ser
1105                1110                1115                1120

Met Pro Ser Ser Asp Thr Thr Val Thr Phe Lys Ser Glu Val Ala Val
                1125                1130                1135

Leu Ser Pro Glu Lys Ala Glu Asn Asp Asp Thr Tyr Lys Asp Asp Val
                1140                1145                1150

Asn His Asn Gln Lys Cys Lys Glu Lys Met Glu Ala Glu Glu Glu
                1155                1160                1165

Ala Leu Ala Ile Ala Met Ala Met Ser Ala Ser Gln Asp Ala Leu Pro
                1170                1175                1180

Ile Val Pro Gln Leu Gln Val Glu Asn Gly Glu Asp Ile Ile Ile Ile
1185                1190                1195                1200

Gln Gln Asp Thr Pro Glu Thr Leu Pro Gly His Thr Lys Ala Lys Gln
                1205                1210                1215

Pro Tyr Arg Glu Asp Ala Glu Trp Leu Lys Gly Gln Gln Ile Gly Leu
                1220                1225                1230

Gly Ala Phe Ser Ser Cys Tyr Gln Ala Gln Asp Val Gly Thr Gly Thr
                1235                1240                1245

Leu Met Ala Val Lys Gln Val Thr Tyr Val Arg Asn Thr Ser Ser Glu
                1250                1255                1260

Gln Glu Glu Val Val Glu Ala Leu Arg Glu Glu Ile Arg Met Met Gly
1265                1270                1275                1280
```

```
His Leu Asn His Pro Asn Ile Ile Arg Met Leu Gly Ala Thr Cys Glu
            1285                1290                1295

Lys Ser Asn Tyr Asn Leu Phe Ile Glu Trp Met Ala Gly Gly Ser Val
        1300                1305                1310

Ala His Leu Leu Ser Lys Tyr Gly Ala Phe Lys Glu Ser Val Val Ile
            1315                1320                1325

Asn Tyr Thr Glu Gln Leu Leu Arg Gly Leu Ser Tyr Leu His Glu Asn
        1330                1335                1340

Gln Ile Ile His Arg Asp Val Lys Gly Ala Asn Leu Leu Ile Asp Ser
1345                1350                1355                1360

Thr Gly Gln Arg Leu Arg Ile Ala Asp Phe Gly Ala Ala Ala Arg Leu
            1365                1370                1375

Ala Ser Lys Gly Thr Gly Ala Gly Glu Phe Gln Gly Gln Leu Leu Gly
            1380                1385                1390

Thr Ile Ala Phe Met Ala Pro Glu Val Leu Arg Gly Gln Gln Tyr Gly
            1395                1400                1405

Arg Ser Cys Asp Val Trp Ser Val Gly Cys Ala Ile Ile Glu Met Ala
        1410                1415                1420

Cys Ala Lys Pro Pro Trp Asn Ala Glu Lys His Ser Asn His Leu Ala
1425                1430                1435                1440

Leu Ile Phe Lys Ile Ala Ser Ala Thr Thr Ala Pro Ser Ile Pro Ser
                1445                1450                1455

His Leu Ser Pro Gly Leu Arg Asp Val Ala Val Arg Cys Leu Glu Leu
            1460                1465                1470

Gln Pro Gln Asp Arg Pro Pro Ser Arg Glu Leu Leu Lys His Pro Val
            1475                1480                1485

Phe Arg Thr Thr Trp
        1490

<210> SEQ ID NO 9
<211> LENGTH: 2465
<212> TYPE: DNA
<213> ORGANISM: Mus musculus
<220> FEATURE:
<221> NAME/KEY: CDS
<222> LOCATION: (427)..(2283)

<400> SEQUENCE: 9
gaattcggca cgagggacga tccagcggca gagtcgccgc ttccgcttcg ctgcttctcc      60
ggtcaccggc gacgcgggcc cggggcttcc ttttcatcgg cccagcttat tccgcgggcc     120
ccggggctgc agctacccag aagcggcgaa gaggccctgg gctgcgcgcc cgctgtccca     180
tgtgaagcag gttgggcctg gtccccggcc cgtgcccggt tgtctgcggc ccttcaggcc     240
tcagggaccc ccgcgaggcg ctgctcctgg gggcgcggt gacaggccgt gcggggcgg      300 agggccagc tcggtggcct cctctcggcc ctcgcgtccg cgatcccgcc cagcggccgg      360
gcaataaaga atgttgatgg agaaccatt ttcctaattt tcaaattatt gagctggtcg      420 cgcata atg gat gat cag caa gct ttg aat tca atc atg caa gat ttg       468
       Met Asp Asp Gln Gln Ala Leu Asn Ser Ile Met Gln Asp Leu
        1                5                  10 gct gtc ctt cat aag cca gtc ggc cag cat tat ctt tac aag aaa cca      516
Ala Val Leu His Lys Pro Val Gly Gln His Tyr Leu Tyr Lys Lys Pro
 15                 20                 25                 30 gga aag caa aac ctt cat cac caa aaa aac aga atg atg ttc gag tca      564
Gly Lys Gln Asn Leu His His Gln Lys Asn Arg Met Met Phe Glu Ser
             35                 40                 45
```

| | | |
|---|---|---|
| aat ttg aac ata gag gag gaa aaa agg atc ctg cag gtt act aga cca<br>Asn Leu Asn Ile Glu Glu Glu Lys Arg Ile Leu Gln Val Thr Arg Pro<br>50 55 60 | | 612 |
| gtt aaa cta gaa gac ctg aga tct aag tct aag atc gcc ttt ggg cag<br>Val Lys Leu Glu Asp Leu Arg Ser Lys Ser Lys Ile Ala Phe Gly Gln<br>65 70 75 | | 660 |
| tct atg gat cta cac tat acc aac aat gag ttg gta att ccg tta act<br>Ser Met Asp Leu His Tyr Thr Asn Asn Glu Leu Val Ile Pro Leu Thr<br>80 85 90 | | 708 |
| acc caa gat gac ttg gac aaa gct gtg gaa ctg ctg gat cgc agt att<br>Thr Gln Asp Asp Leu Asp Lys Ala Val Glu Leu Leu Asp Arg Ser Ile<br>95 100 105 110 | | 756 |
| cac atg aag agt ctc aag ata tta ctt gta gta aat ggg agt aca cag<br>His Met Lys Ser Leu Lys Ile Leu Leu Val Val Asn Gly Ser Thr Gln<br>115 120 125 | | 804 |
| gct act aat tta gaa cca tca ccg tca cca gaa gat ttg aat aat aca<br>Ala Thr Asn Leu Glu Pro Ser Pro Ser Pro Glu Asp Leu Asn Asn Thr<br>130 135 140 | | 852 |
| cca ctt ggt gca gag agg aaa aag cgg cta tct gta gta ggt ccc cct<br>Pro Leu Gly Ala Glu Arg Lys Lys Arg Leu Ser Val Val Gly Pro Pro<br>145 150 155 | | 900 |
| aat agg gat aga agt tcc cct cct cca gga tac att cca gac ata cta<br>Asn Arg Asp Arg Ser Ser Pro Pro Pro Gly Tyr Ile Pro Asp Ile Leu<br>160 165 170 | | 948 |
| cac cag att gcc cgg aat ggg tca ttc act agc atc aac agt gaa gga<br>His Gln Ile Ala Arg Asn Gly Ser Phe Thr Ser Ile Asn Ser Glu Gly<br>175 180 185 190 | | 996 |
| gag ttc att cca gag agc atg gac caa atg ctg gat cca ttg tct tta<br>Glu Phe Ile Pro Glu Ser Met Asp Gln Met Leu Asp Pro Leu Ser Leu<br>195 200 205 | | 1044 |
| agc agc cct gaa aat tct ggc tca gga agc tgt ccg tca ctt gat agt<br>Ser Ser Pro Glu Asn Ser Gly Ser Gly Ser Cys Pro Ser Leu Asp Ser<br>210 215 220 | | 1092 |
| cct ttg gat gga gaa agc tac cca aaa tca cgg atg cct agg gca cag<br>Pro Leu Asp Gly Glu Ser Tyr Pro Lys Ser Arg Met Pro Arg Ala Gln<br>225 230 235 | | 1140 |
| agc tac cca gat aat cat cag gag ttt aca gac tat gat aac ccc att<br>Ser Tyr Pro Asp Asn His Gln Glu Phe Thr Asp Tyr Asp Asn Pro Ile<br>240 245 250 | | 1188 |
| ttt gag aaa ttt gga aaa gga gga aca tat cca aga agg tac cac gtt<br>Phe Glu Lys Phe Gly Lys Gly Gly Thr Tyr Pro Arg Arg Tyr His Val<br>255 260 265 270 | | 1236 |
| tcc tat cat cac cag gag tat aat gac ggt cgg aag act ttt cca aga<br>Ser Tyr His His Gln Glu Tyr Asn Asp Gly Arg Lys Thr Phe Pro Arg<br>275 280 285 | | 1284 |
| gct aga agg acc cag ggc acc agt ttc cgg tct cct gtg agc ttc agt<br>Ala Arg Arg Thr Gln Gly Thr Ser Phe Arg Ser Pro Val Ser Phe Ser<br>290 295 300 | | 1332 |
| cct act gat cac tcc tta agc act agt agt gga agc agt gtc ttt acc<br>Pro Thr Asp His Ser Leu Ser Thr Ser Ser Gly Ser Ser Val Phe Thr<br>305 310 315 | | 1380 |
| cca gag tat gac gac agt cga ata aga aga cgg ggg agt gac ata gac<br>Pro Glu Tyr Asp Asp Ser Arg Ile Arg Arg Arg Gly Ser Asp Ile Asp<br>320 325 330 | | 1428 |
| aat cct act ttg act gtc aca gac atc agc cca ccc agc cgt tca cct<br>Asn Pro Thr Leu Thr Val Thr Asp Ile Ser Pro Pro Ser Arg Ser Pro<br>335 340 345 350 | | 1476 |
| cga gct ccg acc aac tgg aga ctg ggc aag ctg ctt ggc caa gga gct<br>Arg Ala Pro Thr Asn Trp Arg Leu Gly Lys Leu Leu Gly Gln Gly Ala | | 1524 |

```
                      355                 360                 365
ttt ggt agg gtc tac ctc tgc tat gat gtt gat acc gga aga gag ctg    1572
Phe Gly Arg Val Tyr Leu Cys Tyr Asp Val Asp Thr Gly Arg Glu Leu
            370                 375                 380 gct gtt aag caa gtt cag ttt aac cct gag agc cca gag acc agc aag    1620
Ala Val Lys Gln Val Gln Phe Asn Pro Glu Ser Pro Glu Thr Ser Lys
        385                 390                 395 gaa gta aat gca ctt gag tgt gaa att cag ttg ttg aaa aac ttg ttg    1668
Glu Val Asn Ala Leu Glu Cys Glu Ile Gln Leu Leu Lys Asn Leu Leu
    400                 405                 410 cat gag cga att gtt cag tat tat ggc tgt ttg agg gat cct cag gag    1716
His Glu Arg Ile Val Gln Tyr Tyr Gly Cys Leu Arg Asp Pro Gln Glu
415                 420                 425                 430 aaa aca ctt tcc atc ttt atg gag ctc tcg cca ggg ggt tca att aag    1764
Lys Thr Leu Ser Ile Phe Met Glu Leu Ser Pro Gly Gly Ser Ile Lys
                435                 440                 445 gac caa cta aaa gcc tac gga gct ctt act gag aac gtg acg agg aag    1812
Asp Gln Leu Lys Ala Tyr Gly Ala Leu Thr Glu Asn Val Thr Arg Lys
            450                 455                 460 tac acc cgt cag att ctg gag ggg gtc cat tat ttg cat agt aat atg    1860
Tyr Thr Arg Gln Ile Leu Glu Gly Val His Tyr Leu His Ser Asn Met
        465                 470                 475 att gtc cat aga gat atc aaa gga gca aat atc tta agg gat tcc aca    1908
Ile Val His Arg Asp Ile Lys Gly Ala Asn Ile Leu Arg Asp Ser Thr
    480                 485                 490 ggc aat atc aag tta gga gac ttt ggg gct agt aaa cgg ctt cag acc    1956
Gly Asn Ile Lys Leu Gly Asp Phe Gly Ala Ser Lys Arg Leu Gln Thr
495                 500                 505                 510 atc tgt ctc tca ggc aca gga atg aag tct gtc aca ggc acg cca tac    2004
Ile Cys Leu Ser Gly Thr Gly Met Lys Ser Val Thr Gly Thr Pro Tyr
                515                 520                 525 tgg atg agt cct gag gtc atc agt gga gaa ggc tat gga aga aaa gca    2052
Trp Met Ser Pro Glu Val Ile Ser Gly Glu Gly Tyr Gly Arg Lys Ala
            530                 535                 540 gac atc tgg agt gta gca tgt act gtg gta gaa atg cta act gaa aag    2100
Asp Ile Trp Ser Val Ala Cys Thr Val Val Glu Met Leu Thr Glu Lys
        545                 550                 555 cca cct tgg gct gaa ttt gaa gca atg gct gcc atc ttt aag atc gcc    2148
Pro Pro Trp Ala Glu Phe Glu Ala Met Ala Ala Ile Phe Lys Ile Ala
    560                 565                 570 act cag cca acg aac cca aag ctg cca cct cat gtc tca gac tat act    2196
Thr Gln Pro Thr Asn Pro Lys Leu Pro Pro His Val Ser Asp Tyr Thr
575                 580                 585                 590 cgg gac ttc ctc aaa cgg att ttt gta gag gcc aaa ctt cga cct tca    2244
Arg Asp Phe Leu Lys Arg Ile Phe Val Glu Ala Lys Leu Arg Pro Ser
                595                 600                 605 gcg gag gag ctc ttg cgg cac atg ttt gtg cat tat cac tagcagcggc    2293
Ala Glu Glu Leu Leu Arg His Met Phe Val His Tyr His
            610                 615 ggcttcggtc ctccaccagc tccatcctcg cggccacctt ctctcttact gcactttcct    2353
tttttataaa aagagagat ggggagaaaa agacaagagg gaaaatattt ctcttgattc     2413
ttggttaaat tgtttaata ataatagtaa actaaaaaaa aaaaaaaaaa aa             2465
```

<210> SEQ ID NO 10
<211> LENGTH: 619
<212> TYPE: PRT
<213> ORGANISM: Mus musculus

<400> SEQUENCE: 10

-continued

```
Met Asp Asp Gln Gln Ala Leu Asn Ser Ile Met Gln Asp Leu Ala Val
 1               5                  10                  15

Leu His Lys Pro Val Gly Gln His Tyr Leu Tyr Lys Lys Pro Gly Lys
            20                  25                  30

Gln Asn Leu His His Gln Lys Asn Arg Met Met Phe Glu Ser Asn Leu
        35                  40                  45

Asn Ile Glu Glu Glu Lys Arg Ile Leu Gln Val Thr Arg Pro Val Lys
    50                  55                  60

Leu Glu Asp Leu Arg Ser Lys Ser Lys Ile Ala Phe Gly Gln Ser Met
 65              70                  75                  80

Asp Leu His Tyr Thr Asn Asn Glu Leu Val Ile Pro Leu Thr Thr Gln
                85                  90                  95

Asp Asp Leu Asp Lys Ala Val Glu Leu Leu Asp Arg Ser Ile His Met
            100                 105                 110

Lys Ser Leu Lys Ile Leu Leu Val Val Asn Gly Ser Thr Gln Ala Thr
            115                 120                 125

Asn Leu Glu Pro Ser Pro Ser Pro Glu Asp Leu Asn Asn Thr Pro Leu
        130                 135                 140

Gly Ala Glu Arg Lys Lys Arg Leu Ser Val Val Gly Pro Pro Asn Arg
145                 150                 155                 160

Asp Arg Ser Ser Pro Pro Pro Gly Tyr Ile Pro Asp Ile Leu His Gln
                165                 170                 175

Ile Ala Arg Asn Gly Ser Phe Thr Ser Ile Asn Ser Glu Gly Glu Phe
                180                 185                 190

Ile Pro Glu Ser Met Asp Gln Met Leu Asp Pro Leu Ser Leu Ser Ser
            195                 200                 205

Pro Glu Asn Ser Gly Ser Gly Ser Cys Pro Ser Leu Asp Ser Pro Leu
        210                 215                 220

Asp Gly Glu Ser Tyr Pro Lys Ser Arg Met Pro Arg Ala Gln Ser Tyr
225                 230                 235                 240

Pro Asp Asn His Gln Glu Phe Thr Asp Tyr Asp Asn Pro Ile Phe Glu
                245                 250                 255

Lys Phe Gly Lys Gly Thr Tyr Pro Arg Arg Tyr His Val Ser Tyr
            260                 265                 270

His His Gln Glu Tyr Asn Asp Gly Arg Lys Thr Phe Pro Arg Ala Arg
        275                 280                 285

Arg Thr Gln Gly Thr Ser Phe Arg Ser Pro Val Ser Phe Ser Pro Thr
        290                 295                 300

Asp His Ser Leu Ser Thr Ser Ser Gly Ser Ser Val Phe Thr Pro Glu
305                 310                 315                 320

Tyr Asp Asp Ser Arg Ile Arg Arg Gly Ser Asp Ile Asp Asn Pro
                325                 330                 335

Thr Leu Thr Val Thr Asp Ile Ser Pro Pro Ser Arg Ser Pro Arg Ala
            340                 345                 350

Pro Thr Asn Trp Arg Leu Gly Lys Leu Leu Gly Gln Gly Ala Phe Gly
            355                 360                 365

Arg Val Tyr Leu Cys Tyr Asp Val Asp Thr Gly Arg Glu Leu Ala Val
        370                 375                 380

Lys Gln Val Gln Phe Asn Pro Glu Ser Pro Glu Thr Ser Lys Glu Val
385                 390                 395                 400

Asn Ala Leu Glu Cys Glu Ile Gln Leu Leu Lys Asn Leu Leu His Glu
            405                 410                 415
```

-continued

```
Arg Ile Val Gln Tyr Tyr Gly Cys Leu Arg Asp Pro Gln Glu Lys Thr
            420                 425                 430

Leu Ser Ile Phe Met Glu Leu Ser Pro Gly Gly Ser Ile Lys Asp Gln
            435                 440                 445

Leu Lys Ala Tyr Gly Ala Leu Thr Glu Asn Val Thr Arg Lys Tyr Thr
            450                 455                 460

Arg Gln Ile Leu Glu Gly Val His Tyr Leu His Ser Asn Met Ile Val
465                 470                 475                 480

His Arg Asp Ile Lys Gly Ala Asn Ile Leu Arg Asp Ser Thr Gly Asn
                    485                 490                 495

Ile Lys Leu Gly Asp Phe Gly Ala Ser Lys Arg Leu Gln Thr Ile Cys
            500                 505                 510

Leu Ser Gly Thr Gly Met Lys Ser Val Thr Gly Thr Pro Tyr Trp Met
            515                 520                 525

Ser Pro Glu Val Ile Ser Gly Glu Gly Tyr Gly Arg Lys Ala Asp Ile
            530                 535                 540

Trp Ser Val Ala Cys Thr Val Val Glu Met Leu Thr Glu Lys Pro Pro
545                 550                 555                 560

Trp Ala Glu Phe Glu Ala Met Ala Ala Ile Phe Lys Ile Ala Thr Gln
                    565                 570                 575

Pro Thr Asn Pro Lys Leu Pro Pro His Val Ser Asp Tyr Thr Arg Asp
            580                 585                 590

Phe Leu Lys Arg Ile Phe Val Glu Ala Lys Leu Arg Pro Ser Ala Glu
            595                 600                 605

Glu Leu Leu Arg His Met Phe Val His Tyr His
        610                 615
```

```
<210> SEQ ID NO 11
<211> LENGTH: 3332
<212> TYPE: DNA
<213> ORGANISM: Mus musculus
<220> FEATURE:
<221> NAME/KEY: CDS
<222> LOCATION: (332)..(2209)

<400> SEQUENCE: 11
gaattcggca cgaggaacag tggccggtcg gagcgtcttc tggacttcag gactcgcagg      60
cggcccggtc gagtggcgcc gccgaggccg ggttgggccg agcctgggag cgccggggat     120
gtagcgggcc aacctgctca tgccacagcg cccggccgcg gccggagccg agcctgggg      180 aggcggcggg ggccccgagc gcagcccacg gccccgcgc ggagccaggc ccgctgccgt      240
ccccgccgcc cgctcccccg gcatgcagcc ccggctgcgg aggtgacact tctgggctgt     300
agtcgccacc gccgcctccg ccatcgccac c atg gat gaa caa gag gca tta       352
                                   Met Asp Glu Gln Glu Ala Leu
                                     1               5 gac tcg atc atg aag gac ctg gtg gcc ctc cag atg agc cga cga acc      400
Asp Ser Ile Met Lys Asp Leu Val Ala Leu Gln Met Ser Arg Arg Thr
         10                  15                  20 cgg ttg tct gga tat gag acc atg aag aat aag gac aca ggt cac cca      448
Arg Leu Ser Gly Tyr Glu Thr Met Lys Asn Lys Asp Thr Gly His Pro
     25                  30                  35 aac agg cag agt gac gtc aga atc aag ttt gaa cac aat ggg gag aga      496
Asn Arg Gln Ser Asp Val Arg Ile Lys Phe Glu His Asn Gly Glu Arg
 40                  45                  50                  55 cga att ata gca ttc agc cgg cct gtg aga tac gaa gat gtg gag cac      544
Arg Ile Ile Ala Phe Ser Arg Pro Val Arg Tyr Glu Asp Val Glu His
                 60                  65                  70
```

```
aag gtg aca aca gtc ttt ggg cag cct ctt gat ttg cat tat atg aat        592
Lys Val Thr Thr Val Phe Gly Gln Pro Leu Asp Leu His Tyr Met Asn
             75                  80                  85 aat gag ctc tcc atc ctg ttg aaa aac caa gat gat ctc gat aaa gcc        640
Asn Glu Leu Ser Ile Leu Leu Lys Asn Gln Asp Asp Leu Asp Lys Ala
         90                  95                 100 att gac att ttg gat aga agc tca agt atg aaa agc ctt agg ata cta        688
Ile Asp Ile Leu Asp Arg Ser Ser Ser Met Lys Ser Leu Arg Ile Leu
        105                 110                 115 ctg tta tcc caa gac aga aac cat act agt tcc tct ccc cac tct gga        736
Leu Leu Ser Gln Asp Arg Asn His Thr Ser Ser Pro His Ser Gly
120                 125                 130                 135 gtg tcc agg cag gtt cgg atc aag cct tcc cag tct gca ggg gat ata        784
Val Ser Arg Gln Val Arg Ile Lys Pro Ser Gln Ser Ala Gly Asp Ile
                140                 145                 150 aat acc atc tac caa gct cct gag ccc aga agc agg cac ctg tct gtc        832
Asn Thr Ile Tyr Gln Ala Pro Glu Pro Arg Ser Arg His Leu Ser Val
            155                 160                 165 agc tcc cag aac cct ggc cga agc tct cct ccc ccg gga tat gta cct        880
Ser Ser Gln Asn Pro Gly Arg Ser Ser Pro Pro Pro Gly Tyr Val Pro
        170                 175                 180 gag cga caa cag cac att gcc cgg caa gga tcc tat acg agc atc aac        928
Glu Arg Gln Gln His Ile Ala Arg Gln Gly Ser Tyr Thr Ser Ile Asn
    185                 190                 195 agc gaa ggt gaa ttc atc cca gag acc agc gaa cag tgt atg cta gat        976
Ser Glu Gly Glu Phe Ile Pro Glu Thr Ser Glu Gln Cys Met Leu Asp
200                 205                 210                 215 ccc ctc agc agt gcc gaa aat tcc ttg tca gga agc tgc caa tcc ttg       1024
Pro Leu Ser Ser Ala Glu Asn Ser Leu Ser Gly Ser Cys Gln Ser Leu
                220                 225                 230 gac agg tca gca gac agc cca tcc ttc agg aaa tca caa atg tcc cga       1072
Asp Arg Ser Ala Asp Ser Pro Ser Phe Arg Lys Ser Gln Met Ser Arg
            235                 240                 245 gcc cgg agc ttc cca gac aac aga aag gaa tgc tca gat cgg gag acc       1120
Ala Arg Ser Phe Pro Asp Asn Arg Lys Glu Cys Ser Asp Arg Glu Thr
        250                 255                 260 cag ctc tat gat aaa ggt gtc aaa ggt gga acc tat ccc agg cgc tac       1168
Gln Leu Tyr Asp Lys Gly Val Lys Gly Gly Thr Tyr Pro Arg Arg Tyr
    265                 270                 275 cat gtg tct gtg cat cac aaa gac tac aat gat ggc aga aga aca ttt       1216
His Val Ser Val His His Lys Asp Tyr Asn Asp Gly Arg Arg Thr Phe
280                 285                 290                 295 ccc cga ata cga cgg cat caa ggc aac cta ttc act ctg gtg ccc tca       1264
Pro Arg Ile Arg Arg His Gln Gly Asn Leu Phe Thr Leu Val Pro Ser
                300                 305                 310 agt cgc tcc ttg agc aca aat ggc gag aac atg ggt gta gct gtg caa       1312
Ser Arg Ser Leu Ser Thr Asn Gly Glu Asn Met Gly Val Ala Val Gln
            315                 320                 325 tac ctg gac ccc cgt ggg cgc cta cgg agt gca gac agt gag aat gcc       1360
Tyr Leu Asp Pro Arg Gly Arg Leu Arg Ser Ala Asp Ser Glu Asn Ala
        330                 335                 340 ctc act gtg cag gaa agg aat gtg cca acc aaa tct cct agt gct ccc       1408
Leu Thr Val Gln Glu Arg Asn Val Pro Thr Lys Ser Pro Ser Ala Pro
    345                 350                 355 atc aat tgg cgt cgg ggg aag ctc ctg ggt caa ggt gcc ttc ggc agg       1456
Ile Asn Trp Arg Arg Gly Lys Leu Leu Gly Gln Gly Ala Phe Gly Arg
360                 365                 370                 375 gtc tac ttg tgc tat gat gtg gac aca gga cgt gaa ctt gct tct aag       1504
Val Tyr Leu Cys Tyr Asp Val Asp Thr Gly Arg Glu Leu Ala Ser Lys
```

-continued

|  |  |  | 380 |  |  |  |  | 385 |  |  |  |  | 390 |  |  |  |
|---|---|---|---|---|---|---|---|---|---|---|---|---|---|---|---|---|
| cag | gtc | cag | ttt | gac | cca | gat | agt | cct | gag | aca | agc | aag | gag | gtg | agt | 1552 |
| Gln | Val | Gln | Phe | Asp | Pro | Asp | Ser | Pro | Glu | Thr | Ser | Lys | Glu | Val | Ser |  |
|  |  |  | 395 |  |  |  |  | 400 |  |  |  |  | 405 |  |  |  |
| gct | ctg | gag | tgt | gag | atc | cag | ttg | ctg | aag | aac | ctg | cag | cat | gag | cgc | 1600 |
| Ala | Leu | Glu | Cys | Glu | Ile | Gln | Leu | Leu | Lys | Asn | Leu | Gln | His | Glu | Arg |  |
|  |  | 410 |  |  |  |  | 415 |  |  |  |  | 420 |  |  |  |  |
| att | gtg | cag | tac | tac | ggc | tgc | ctg | cgg | gac | cgt | gct | gag | aag | atc | ctc | 1648 |
| Ile | Val | Gln | Tyr | Tyr | Gly | Cys | Leu | Arg | Asp | Arg | Ala | Glu | Lys | Ile | Leu |  |
|  | 425 |  |  |  |  | 430 |  |  |  |  | 435 |  |  |  |  |  |
| acc | atc | ttt | atg | gag | tat | atg | cca | ggg | ggc | tct | gta | aaa | gac | cag | ttg | 1696 |
| Thr | Ile | Phe | Met | Glu | Tyr | Met | Pro | Gly | Gly | Ser | Val | Lys | Asp | Gln | Leu |  |
| 440 |  |  |  |  | 445 |  |  |  |  | 450 |  |  |  |  | 455 |  |
| aag | gcc | tac | gga | gct | ctg | aca | gag | agt | gtg | acc | cgc | aag | tac | acc | cgg | 1744 |
| Lys | Ala | Tyr | Gly | Ala | Leu | Thr | Glu | Ser | Val | Thr | Arg | Lys | Tyr | Thr | Arg |  |
|  |  |  | 460 |  |  |  |  | 465 |  |  |  |  | 470 |  |  |  |
| cag | att | ctg | gag | ggc | atg | tca | tac | ctg | cac | agc | aac | atg | att | gtg | cat | 1792 |
| Gln | Ile | Leu | Glu | Gly | Met | Ser | Tyr | Leu | His | Ser | Asn | Met | Ile | Val | His |  |
|  |  | 475 |  |  |  |  | 480 |  |  |  |  | 485 |  |  |  |  |
| cgg | gac | atc | aag | gga | gcc | aat | atc | ctc | cga | gac | tca | gct | ggg | aat | gtg | 1840 |
| Arg | Asp | Ile | Lys | Gly | Ala | Asn | Ile | Leu | Arg | Asp | Ser | Ala | Gly | Asn | Val |  |
|  | 490 |  |  |  |  | 495 |  |  |  |  | 500 |  |  |  |  |  |
| aag | ctt | ggg | gat | ttt | ggg | gcc | agc | aaa | cgc | cta | cag | acc | atc | tgc | atg | 1888 |
| Lys | Leu | Gly | Asp | Phe | Gly | Ala | Ser | Lys | Arg | Leu | Gln | Thr | Ile | Cys | Met |  |
| 505 |  |  |  |  | 510 |  |  |  |  | 515 |  |  |  |  |  |  |
| tca | ggg | aca | ggc | att | cgc | tct | gtc | act | ggc | aca | ccc | tac | tgg | atg | agt | 1936 |
| Ser | Gly | Thr | Gly | Ile | Arg | Ser | Val | Thr | Gly | Thr | Pro | Tyr | Trp | Met | Ser |  |
| 520 |  |  |  |  | 525 |  |  |  |  | 530 |  |  |  |  | 535 |  |
| cct | gaa | gtc | atc | agt | ggc | gag | ggc | tat | gga | aga | aag | gca | gac | gtg | tgg | 1984 |
| Pro | Glu | Val | Ile | Ser | Gly | Glu | Gly | Tyr | Gly | Arg | Lys | Ala | Asp | Val | Trp |  |
|  |  |  | 540 |  |  |  |  | 545 |  |  |  |  | 550 |  |  |  |
| agc | ctg | ggc | tgt | act | gtg | gtg | gaa | atg | ctg | aca | gag | aaa | cca | cct | tgg | 2032 |
| Ser | Leu | Gly | Cys | Thr | Val | Val | Glu | Met | Leu | Thr | Glu | Lys | Pro | Pro | Trp |  |
|  |  | 555 |  |  |  |  | 560 |  |  |  |  | 565 |  |  |  |  |
| gca | gag | tat | gaa | gct | atg | gct | gcc | att | ttc | aag | att | gcc | acc | cag | cct | 2080 |
| Ala | Glu | Tyr | Glu | Ala | Met | Ala | Ala | Ile | Phe | Lys | Ile | Ala | Thr | Gln | Pro |  |
|  | 570 |  |  |  |  | 575 |  |  |  |  | 580 |  |  |  |  |  |
| acc | aat | cct | cag | ctg | ccc | tct | cac | atc | tca | gaa | cac | ggc | agg | gac | ttc | 2128 |
| Thr | Asn | Pro | Gln | Leu | Pro | Ser | His | Ile | Ser | Glu | His | Gly | Arg | Asp | Phe |  |
| 585 |  |  |  |  | 590 |  |  |  |  | 595 |  |  |  |  |  |  |
| ctg | agg | cgc | ata | ttt | gtg | gaa | gct | cgt | cag | aga | ccc | tca | gct | gag | gag | 2176 |
| Leu | Arg | Arg | Ile | Phe | Val | Glu | Ala | Arg | Gln | Arg | Pro | Ser | Ala | Glu | Glu |  |
| 600 |  |  |  |  | 605 |  |  |  |  | 610 |  |  |  |  | 615 |  |
| ctc | ctc | aca | cac | cac | ttt | gca | cag | cta | gtg | tac | tgagctctca aggctatcag |  |  |  | 2229 |
| Leu | Leu | Thr | His | His | Phe | Ala | Gln | Leu | Val | Tyr |  |  |  |  |  |  |
|  |  |  | 620 |  |  |  |  | 625 |  |  |  |  |  |  |  |  | gctgccagct gccacctgct gagcaggcaa ggggctgctg tcaggctcag tgaagttgct 2289 gcttcttcca ggcaaggcta tgaccagtgg agcatcggtc cagccattgt ttgtctgtgc 2349 cccatctgcc actgggactc aaagccagga tgggatagct ctggcatcaa gactgggagc 2409 tccagcctgt aagacccaag agctttagca ccttaagctc agtatggcgg aagggctgg 2469 aaacagtatg caagactgcc atgggtcctg cctaccctca gatgtgtcct aacactgcag 2529 acagcactga agtcaagagg gactgggca caggaggtcc tcaagggtat gaatagtgtt 2589 acttcattca gagtgttact ttgtttctct cccaatgttt ggagaccacc agcctgtctc 2649 tgggctgcaa gcctgaggta aagcccagca tcccccagcc aacagaaggt agaggtttgg 2709 gctaccccac tatagcttcc aggtattcgg tgtcagtcct gtcttaccaa agatgaatga 2769

-continued

```
agcaaatgtt acactgcctt attctgggaa ggaggagcta ctcggataag cagggcctga    2829
gagatggagc tgcctccaga aactggggag acccagtctt gtcaatgcaa ttgtctctgt    2889
tttacaagtt ggagtcactc ttatgctgtt cccagtttta aaactggaga ctttgccctc    2949
tgagctctgg agaccatgt gggcttaggc ttggactgga tggaagagct gatggcctct     3009 gcccctggc ctgccctctg ttccctcact ggagcagaga agtagacaa cacaagtcag      3069 ggcacctggt tctgggcagc tcagcagagt gcaggggtt gtctcaggct gtctgcatct     3129
caaatctgtc aggcctgagc ccactccatg ggaaagtcct tgagctgcca caaccgtgtc    3189
caaagccacc agctgtgttc ctcagcccga cctgtccact tgtcatcaac ctcattccct    3249
tcttgttcct cccacaaagg aggatgccag tagggctag ggaaagagtt atcattaaag     3309
gaaaggaaaa aaaaaaaaaa aaa                                            3332
```

<210> SEQ ID NO 12
<211> LENGTH: 626
<212> TYPE: PRT
<213> ORGANISM: Mus musculus

<400> SEQUENCE: 12

```
Met Asp Glu Gln Glu Ala Leu Asp Ser Ile Met Lys Asp Leu Val Ala
  1               5                  10                  15

Leu Gln Met Ser Arg Arg Thr Arg Leu Ser Gly Tyr Glu Thr Met Lys
                 20                  25                  30

Asn Lys Asp Thr Gly His Pro Asn Arg Gln Ser Asp Val Arg Ile Lys
             35                  40                  45

Phe Glu His Asn Gly Glu Arg Arg Ile Ile Ala Phe Ser Arg Pro Val
         50                  55                  60

Arg Tyr Glu Asp Val Glu His Lys Val Thr Thr Val Phe Gly Gln Pro
     65                  70                  75                  80

Leu Asp Leu His Tyr Met Asn Asn Glu Leu Ser Ile Leu Leu Lys Asn
                 85                  90                  95

Gln Asp Asp Leu Asp Lys Ala Ile Asp Ile Leu Asp Arg Ser Ser Ser
                100                 105                 110

Met Lys Ser Leu Arg Ile Leu Leu Leu Ser Gln Asp Arg Asn His Thr
            115                 120                 125

Ser Ser Ser Pro His Ser Gly Val Ser Arg Gln Val Arg Ile Lys Pro
        130                 135                 140

Ser Gln Ser Ala Gly Asp Ile Asn Thr Ile Tyr Gln Ala Pro Glu Pro
145                 150                 155                 160

Arg Ser Arg His Leu Ser Val Ser Gln Asn Pro Gly Arg Ser Ser
                165                 170                 175

Pro Pro Pro Gly Tyr Val Pro Glu Arg Gln Gln His Ile Ala Arg Gln
            180                 185                 190

Gly Ser Tyr Thr Ser Ile Asn Ser Glu Gly Glu Phe Ile Pro Glu Thr
        195                 200                 205

Ser Glu Gln Cys Met Leu Asp Pro Leu Ser Ser Ala Glu Asn Ser Leu
    210                 215                 220

Ser Gly Ser Cys Gln Ser Leu Asp Arg Ser Ala Asp Ser Pro Ser Phe
225                 230                 235                 240

Arg Lys Ser Gln Met Ser Arg Ala Arg Ser Phe Pro Asp Asn Arg Lys
                245                 250                 255

Glu Cys Ser Asp Arg Glu Thr Gln Leu Tyr Asp Lys Gly Val Lys Gly
            260                 265                 270
```

Gly Thr Tyr Pro Arg Arg Tyr His Val Ser Val His His Lys Asp Tyr
            275                 280                 285
Asn Asp Gly Arg Arg Thr Phe Pro Arg Ile Arg Arg His Gln Gly Asn
    290                 295                 300
Leu Phe Thr Leu Val Pro Ser Ser Arg Ser Leu Ser Thr Asn Gly Glu
305                 310                 315                 320
Asn Met Gly Val Ala Val Gln Tyr Leu Asp Pro Arg Gly Arg Leu Arg
                325                 330                 335
Ser Ala Asp Ser Glu Asn Ala Leu Thr Val Gln Glu Arg Asn Val Pro
            340                 345                 350
Thr Lys Ser Pro Ser Ala Pro Ile Asn Trp Arg Arg Gly Lys Leu Leu
            355                 360                 365
Gly Gln Gly Ala Phe Gly Arg Val Tyr Leu Cys Tyr Asp Val Asp Thr
    370                 375                 380
Gly Arg Glu Leu Ala Ser Lys Gln Val Gln Phe Asp Pro Asp Ser Pro
385                 390                 395                 400
Glu Thr Ser Lys Glu Val Ser Ala Leu Glu Cys Glu Ile Gln Leu Leu
                405                 410                 415
Lys Asn Leu Gln His Glu Arg Ile Val Gln Tyr Tyr Gly Cys Leu Arg
            420                 425                 430
Asp Arg Ala Glu Lys Ile Leu Thr Ile Phe Met Glu Tyr Met Pro Gly
            435                 440                 445
Gly Ser Val Lys Asp Gln Leu Lys Ala Tyr Gly Ala Leu Thr Glu Ser
    450                 455                 460
Val Thr Arg Lys Tyr Thr Arg Gln Ile Leu Glu Gly Met Ser Tyr Leu
465                 470                 475                 480
His Ser Asn Met Ile Val His Arg Asp Ile Lys Gly Ala Asn Ile Leu
                485                 490                 495
Arg Asp Ser Ala Gly Asn Val Lys Leu Gly Asp Phe Gly Ala Ser Lys
            500                 505                 510
Arg Leu Gln Thr Ile Cys Met Ser Gly Thr Gly Ile Arg Ser Val Thr
            515                 520                 525
Gly Thr Pro Tyr Trp Met Ser Pro Glu Val Ile Ser Gly Glu Gly Tyr
    530                 535                 540
Gly Arg Lys Ala Asp Val Trp Ser Leu Gly Cys Thr Val Val Glu Met
545                 550                 555                 560
Leu Thr Glu Lys Pro Pro Trp Ala Glu Tyr Glu Ala Met Ala Ala Ile
                565                 570                 575
Phe Lys Ile Ala Thr Gln Pro Thr Asn Pro Gln Leu Pro Ser His Ile
            580                 585                 590
Ser Glu His Gly Arg Asp Phe Leu Arg Arg Ile Phe Val Glu Ala Arg
            595                 600                 605
Gln Arg Pro Ser Ala Glu Glu Leu Leu Thr His His Phe Ala Gln Leu
    610                 615                 620
Val Tyr
625

<210> SEQ ID NO 13
<211> LENGTH: 1597
<212> TYPE: PRT
<213> ORGANISM: Mus musculus

<400> SEQUENCE: 13

Met Arg Asp Ala Ile Ala Glu Pro Val Pro Pro Ala Leu Ala Asp

-continued

```
  1               5                   10                  15
Thr Pro Ala Ala Ala Met Glu Glu Leu Arg Pro Ala Pro Pro Gln
             20                  25                  30
Pro Glu Pro Asp Pro Glu Cys Cys Pro Ala Ala Arg Gln Glu Cys Met
             35                  40                  45
Leu Gly Glu Ser Ala Arg Lys Ser Met Glu Ser Asp Pro Glu Asp Phe
 50                  55                  60
Ser Asp Glu Thr Asn Thr Glu Thr Leu Tyr Gly Thr Ser Pro Pro Ser
 65                  70                  75                  80
Thr Pro Arg Gln Met Lys Arg Leu Ser Ala Lys His Gln Arg Asn Ser
                 85                  90                  95
Ala Gly Arg Pro Ala Ser Arg Ser Asn Leu Lys Glu Lys Met Asn Thr
                100                 105                 110
Pro Ser Gln Ser Pro His Lys Asp Leu Gly Lys Gly Val Glu Thr Val
                115                 120                 125
Glu Glu Tyr Ser Tyr Lys Gln Glu Lys Lys Ile Arg Ala Thr Leu Arg
                130                 135                 140
Thr Thr Glu Arg Asp His Lys Lys Asn Ala Gln Cys Ser Phe Met Leu
145                 150                 155                 160
Asp Ser Val Ala Gly Ser Leu Pro Lys Lys Ser Ile Pro Asp Val Asp
                165                 170                 175
Leu Asn Lys Pro Tyr Leu Ser Leu Gly Cys Ser Asn Ala Lys Leu Pro
                180                 185                 190
Val Ser Met Pro Met Pro Ile Ala Arg Thr Ala Arg Gln Thr Ser Arg
                195                 200                 205
Thr Asp Cys Pro Ala Asp Arg Leu Lys Phe Phe Glu Thr Leu Arg Leu
                210                 215                 220
Leu Leu Lys Leu Thr Ser Val Ser Lys Lys Asp Arg Glu Gln Arg
225                 230                 235                 240
Gly Gln Glu Asn Thr Ala Ala Phe Trp Phe Asn Arg Ser Asn Glu Leu
                245                 250                 255
Ile Trp Leu Glu Leu Gln Ala Trp His Ala Gly Arg Thr Ile Asn Asp
                260                 265                 270
Gln Asp Leu Phe Leu Tyr Thr Ala Arg Gln Ala Ile Pro Asp Ile Ile
                275                 280                 285
Asn Glu Ile Leu Thr Phe Lys Val Asn Tyr Gly Ser Ile Ala Phe Ser
                290                 295                 300
Ser Asn Gly Ala Gly Phe Asn Gly Pro Leu Val Glu Gly Gln Cys Arg
305                 310                 315                 320
Thr Pro Gln Glu Thr Asn Arg Val Gly Cys Ser Ser Tyr His Glu His
                325                 330                 335
Leu Gln Arg Gln Arg Val Ser Phe Glu Gln Val Lys Arg Ile Met Glu
                340                 345                 350
Leu Leu Glu Tyr Met Glu Ala Leu Tyr Pro Ser Leu Gln Ala Leu Gln
                355                 360                 365
Lys Asp Tyr Glu Arg Tyr Ala Ala Lys Asp Phe Glu Asp Arg Val Gln
                370                 375                 380
Ala Leu Cys Leu Trp Leu Asn Ile Thr Lys Asp Leu Asn Gln Lys Leu
385                 390                 395                 400
Arg Ile Met Gly Thr Val Leu Gly Ile Lys Asn Leu Ser Asp Ile Gly
                405                 410                 415
Trp Pro Val Phe Glu Ile Pro Ser Pro Arg Pro Ser Lys Gly Tyr Glu
                420                 425                 430
```

```
Pro Glu Asp Glu Val Glu Asp Thr Glu Val Leu Arg Glu Leu Glu
            435                 440                 445

Ser Gly Thr Glu Glu Ser Asp Glu Glu Pro Thr Pro Ser Pro Arg Val
        450                 455                 460

Pro Glu Leu Arg Leu Ser Thr Asp Thr Ile Leu Asp Ser Arg Ser Gln
465                 470                 475                 480

Gly Cys Val Ser Arg Lys Leu Glu Arg Leu Glu Ser Glu Glu Asp Ser
                485                 490                 495

Ile Gly Trp Gly Thr Ala Asp Cys Gly Pro Glu Ala Ser Arg His Cys
            500                 505                 510

Leu Thr Ser Ile Tyr Arg Pro Phe Val Asp Lys Ala Leu Lys Gln Met
        515                 520                 525

Gly Leu Arg Lys Leu Ile Leu Arg Leu His Lys Leu Met Asn Gly Ser
    530                 535                 540

Leu Gln Arg Ala Arg Val Ala Leu Val Lys Asp Asp Arg Pro Val Glu
545                 550                 555                 560

Phe Ser Asp Phe Pro Gly Pro Met Trp Gly Ser Asp Tyr Val Gln Leu
                565                 570                 575

Ser Gly Thr Pro Pro Ser Ser Glu Gln Lys Cys Ser Ala Val Ser Trp
            580                 585                 590

Glu Glu Leu Arg Ala Met Asp Leu Pro Ser Phe Glu Pro Ala Phe Leu
        595                 600                 605

Val Leu Cys Arg Val Leu Leu Asn Val Ile His Glu Cys Leu Lys Leu
    610                 615                 620

Arg Leu Glu Gln Arg Pro Ala Gly Glu Pro Ser Leu Leu Ser Ile Lys
625                 630                 635                 640

Gln Leu Val Arg Glu Cys Lys Glu Val Leu Lys Gly Gly Leu Leu Met
                645                 650                 655

Lys Gln Tyr Tyr Gln Phe Met Leu Gln Glu Val Leu Gly Gly Leu Glu
            660                 665                 670

Lys Thr Asp Cys Asn Met Asp Ala Phe Glu Glu Asp Leu Gln Lys Met
        675                 680                 685

Leu Met Val Tyr Phe Asp Tyr Met Arg Ser Trp Ile Gln Met Leu Gln
    690                 695                 700

Gln Leu Pro Gln Ala Ser His Ser Leu Lys Asn Leu Leu Glu Glu Glu
705                 710                 715                 720

Trp Asn Phe Thr Lys Glu Ile Thr His Tyr Ile Arg Gly Gly Glu Ala
                725                 730                 735

Gln Ala Gly Lys Leu Phe Cys Asp Ile Ala Gly Met Leu Leu Lys Ser
            740                 745                 750

Thr Gly Ser Phe Leu Glu Ser Gly Leu Gln Glu Ser Cys Ala Glu Leu
        755                 760                 765

Trp Thr Ser Ala Asp Asp Asn Gly Ala Ala Asp Glu Leu Arg Arg Ser
    770                 775                 780

Val Ile Glu Ile Ser Arg Ala Leu Lys Glu Leu Phe His Glu Ala Arg
785                 790                 795                 800

Glu Arg Ala Ser Lys Ala Leu Gly Phe Ala Lys Met Leu Arg Lys Asp
                805                 810                 815

Leu Glu Ile Ala Ala Glu Phe Val Leu Ser Ala Ser Ala Arg Glu Leu
            820                 825                 830

Leu Asp Ala Leu Lys Ala Lys Gln Tyr Val Lys Val Gln Ile Pro Gly
        835                 840                 845
```

-continued

```
Leu Glu Asn Leu His Val Phe Val Pro Asp Ser Leu Ala Glu Lys
    850                 855                 860
Lys Ile Ile Leu Gln Leu Leu Asn Ala Ala Thr Gly Lys Asp Cys Ser
865                 870                 875                 880
Lys Asp Pro Asp Asp Val Phe Met Asp Ala Phe Leu Leu Leu Thr Lys
                885                 890                 895
His Gly Asp Arg Ala Arg Asp Ser Glu Asp Gly Trp Gly Thr Trp Glu
            900                 905                 910
Ala Arg Ala Val Lys Ile Val Pro Gln Val Glu Thr Val Asp Thr Leu
        915                 920                 925
Arg Ser Met Gln Val Asp Asn Leu Leu Val Val Met Glu Ser Ala
    930                 935                 940
His Leu Val Leu Gln Arg Lys Ala Phe Gln Gln Ser Ile Glu Gly Leu
945                 950                 955                 960
Met Thr Val Arg His Glu Gln Thr Ser Ser Gln Pro Ile Ile Ala Lys
                965                 970                 975
Gly Leu Gln Gln Leu Lys Asn Asp Ala Leu Glu Leu Cys Asn Arg Ile
            980                 985                 990
Ser Asp Ala Ile Asp Arg Val Asp His Met Phe Thr Leu Glu Phe Asp
        995                 1000                1005
Ala Glu Val Glu Glu Ser Glu Ser Ala Thr Leu Gln Gln Tyr Tyr Arg
    1010                1015                1020
Glu Ala Met Ile Gln Gly Tyr Asn Phe Gly Phe Glu Tyr His Lys Glu
1025                1030                1035                1040
Val Val Arg Leu Met Ser Gly Glu Phe Arg Gln Lys Ile Gly Asp Lys
                1045                1050                1055
Tyr Ile Ser Phe Ala Gln Lys Trp Met Asn Tyr Val Leu Thr Lys Cys
            1060                1065                1070
Glu Ser Gly Arg Gly Thr Arg Pro Arg Trp Ala Thr Gln Gly Phe Asp
        1075                1080                1085
Phe Leu Gln Ala Ile Glu Pro Ala Phe Ile Ser Ala Leu Pro Glu Asp
    1090                1095                1100
Asp Phe Leu Ser Leu Gln Ala Leu Met Asn Glu Cys Ile Gly His Val
1105                1110                1115                1120
Ile Gly Lys Pro His Ser Pro Val Thr Ala Ile His Arg Asn Ser Pro
                1125                1130                1135
Arg Pro Val Lys Val Pro Arg Cys His Ser Asp Pro Asn Pro His
            1140                1145                1150
Leu Ile Ile Pro Thr Pro Glu Gly Phe Ser Thr Arg Ser Val Pro Ser
        1155                1160                1165
Asp Ala Arg Thr His Gly Asn Ser Val Ala Ala Ala Ala Val Arg
    1170                1175                1180
Ala Ala Ala Thr Thr Ala Ala Gly Arg Pro Gly Pro Gly Gly Asp
1185                1190                1195                1200
Ser Val Pro Ala Lys Pro Val Asn Thr Ala Pro Asp Thr Arg Gly Ser
                1205                1210                1215
Ser Val Pro Glu Asn Asp Arg Leu Ala Ser Ile Ala Ala Glu Leu Gln
            1220                1225                1230
Phe Arg Ser Leu Ser Arg His Ser Ser Pro Thr Glu Glu Arg Asp Glu
        1235                1240                1245
Pro Ala Tyr Pro Arg Ser Asp Ser Ser Gly Ser Thr Arg Arg Ser Trp
    1250                1255                1260
Glu Leu Arg Thr Leu Ile Ser Gln Thr Lys Asp Ser Ala Ser Lys Gln
```

```
1265                1270                1275                1280

Gly Pro Ile Glu Ala Ile Gln Lys Ser Val Arg Leu Phe Glu Glu Arg
                1285                1290                1295

Arg Tyr Arg Glu Met Arg Lys Asn Ile Ile Gly Gln Val Cys Asp
        1300                1305                1310

Thr Pro Lys Ser Tyr Asp Asn Val Met His Val Gly Leu Arg Lys Val
                1315                1320                1325

Thr Phe Lys Trp Gln Arg Gly Asn Lys Ile Gly Glu Gly Gln Tyr Gly
    1330                1335                1340

Lys Val Tyr Thr Cys Ile Ser Val Asp Thr Gly Glu Leu Met Ala Met
1345                1350                1355                1360

Lys Glu Ile Arg Phe Gln Pro Asn Asp His Lys Thr Ile Lys Glu Thr
                1365                1370                1375

Ala Asp Glu Leu Lys Ile Phe Glu Gly Ile Lys His Pro Asn Leu Val
                1380                1385                1390

Arg Tyr Phe Gly Val Glu Leu His Arg Glu Glu Met Tyr Ile Phe Met
                1395                1400                1405

Glu Tyr Cys Asp Glu Gly Thr Leu Glu Glu Val Ser Arg Leu Gly Leu
    1410                1415                1420

Gln Glu His Val Ile Arg Leu Tyr Thr Lys Gln Ile Thr Val Ala Ile
1425                1430                1435                1440

Asn Val Leu His Glu His Gly Ile Val His Arg Asp Ile Lys Gly Ala
                1445                1450                1455

Asn Ile Phe Leu Thr Ser Ser Gly Leu Ile Lys Leu Gly Asp Phe Gly
                1460                1465                1470

Cys Ser Val Lys Leu Lys Asn Asn Ala Gln Thr Met Pro Gly Glu Val
                1475                1480                1485

Asn Ser Thr Leu Gly Thr Ala Ala Tyr Met Ala Pro Glu Val Ile Thr
    1490                1495                1500

Arg Ala Lys Gly Glu Gly His Gly Arg Ala Ala Asp Ile Trp Ser Leu
1505                1510                1515                1520

Gly Cys Val Val Ile Glu Met Val Thr Gly Lys Arg Pro Trp His Glu
                1525                1530                1535

Tyr Glu His Asn Phe Gln Ile Met Tyr Lys Val Gly Met Gly His Lys
                1540                1545                1550

Pro Pro Ile Pro Glu Arg Leu Ser Pro Glu Gly Lys Ala Phe Leu Ser
                1555                1560                1565

His Cys Leu Glu Ser Asp Pro Lys Ile Arg Trp Thr Ala Ser Gln Leu
    1570                1575                1580

Leu Asp His Ala Phe Val Lys Val Cys Thr Asp Glu Glu
1585                1590                1595

<210> SEQ ID NO 14
<211> LENGTH: 20
<212> TYPE: DNA
<213> ORGANISM: Artificial Sequence
<220> FEATURE:
<223> OTHER INFORMATION: synthetic construct

<400> SEQUENCE: 14
gaacaccatc cagaagtttg                                              20

<210> SEQ ID NO 15
<211> LENGTH: 21
<212> TYPE: DNA
<213> ORGANISM: Artificial Sequence
```

```
<220> FEATURE:
<223> OTHER INFORMATION: synthetic construct

<400> SEQUENCE: 15
cactttgtag acagggtcag c                                              21

<210> SEQ ID NO 16
<211> LENGTH: 25
<212> TYPE: DNA
<213> ORGANISM: Artificial Sequence
<220> FEATURE:
<223> OTHER INFORMATION: synthetic construct

<400> SEQUENCE: 16
tgggtcgcct ctgtcttata gacag                                          25

<210> SEQ ID NO 17
<211> LENGTH: 20
<212> TYPE: DNA
<213> ORGANISM: Artificial Sequence
<220> FEATURE:
<223> OTHER INFORMATION: synthetic construct

<400> SEQUENCE: 17
cacatcctgt gcttggtaac                                                20

<210> SEQ ID NO 18
<211> LENGTH: 21
<212> TYPE: DNA
<213> ORGANISM: Artificial Sequence
<220> FEATURE:
<223> OTHER INFORMATION: synthetic construct

<400> SEQUENCE: 18
aggacaagtg caggttagat g                                              21

<210> SEQ ID NO 19
<211> LENGTH: 21
<212> TYPE: DNA
<213> ORGANISM: synthetic construct

<400> SEQUENCE: 19
gctgtccata tctacagtgc t                                              21

<210> SEQ ID NO 20
<211> LENGTH: 21
<212> TYPE: DNA
<213> ORGANISM: Artificial Sequence
<220> FEATURE:
<223> OTHER INFORMATION: synthetic construct

<400> SEQUENCE: 20
cggcctggaa gcacgagtgg t                                              21

<210> SEQ ID NO 21
<211> LENGTH: 21
<212> TYPE: DNA
<213> ORGANISM: Artificial Sequence
<220> FEATURE:
<223> OTHER INFORMATION: synthetic construct

<400> SEQUENCE: 21
ttcatccttg atgctgtttt c                                              21

<210> SEQ ID NO 22
```

```
<211> LENGTH: 17
<212> TYPE: DNA
<213> ORGANISM: Artificial Sequence
<220> FEATURE:
<223> OTHER INFORMATION: synthetic construct

<400> SEQUENCE: 22
ggccagctcg gtggcct                                                   17

<210> SEQ ID NO 23
<211> LENGTH: 17
<212> TYPE: DNA
<213> ORGANISM: Artificial Sequence
<220> FEATURE:
<223> OTHER INFORMATION: synthetic construct

<400> SEQUENCE: 23
tctggaatgt atcctgg                                                   17

<210> SEQ ID NO 24
<211> LENGTH: 17
<212> TYPE: DNA
<213> ORGANISM: Artificial Sequence
<220> FEATURE:
<223> OTHER INFORMATION: synthetic construct

<400> SEQUENCE: 24
agagaggaaa aagcggc                                                   17

<210> SEQ ID NO 25
<211> LENGTH: 17
<212> TYPE: DNA
<213> ORGANISM: Artificial Sequence
<220> FEATURE:
<223> OTHER INFORMATION: synthetic construct

<400> SEQUENCE: 25
cagccagctc tcttccg                                                   17

<210> SEQ ID NO 26
<211> LENGTH: 17
<212> TYPE: DNA
<213> ORGANISM: Artificial Sequence
<220> FEATURE:
<223> OTHER INFORMATION: synthetic construct

<400> SEQUENCE: 26
ggaaaagtct tccgacc                                                   17

<210> SEQ ID NO 27
<211> LENGTH: 21
<212> TYPE: DNA
<213> ORGANISM: Artificial Sequence
<220> FEATURE:
<223> OTHER INFORMATION: synthetic construct

<400> SEQUENCE: 27
ggccaaggag cttttggtag g                                              21

<210> SEQ ID NO 28
<211> LENGTH: 21
<212> TYPE: DNA
<213> ORGANISM: Artificial Sequence
<220> FEATURE:
<223> OTHER INFORMATION: synthetic construct

<400> SEQUENCE: 28
```

-continued

```
ggagctggtg gaggaccgaa g                                      21

<210> SEQ ID NO 29
<211> LENGTH: 21
<212> TYPE: DNA
<213> ORGANISM: Artificial Sequence
<220> FEATURE:
<223> OTHER INFORMATION: synthetic construct

<400> SEQUENCE: 29
cccagaaccc tggccgaagc t                                      21

<210> SEQ ID NO 30
<211> LENGTH: 21
<212> TYPE: DNA
<213> ORGANISM: Artificial Sequence
<220> FEATURE:
<223> OTHER INFORMATION: synthetic construct

<400> SEQUENCE: 30
agcacggtcc cgcaggcagc c                                      21

<210> SEQ ID NO 31
<211> LENGTH: 21
<212> TYPE: DNA
<213> ORGANISM: Artificial Sequence
<220> FEATURE:
<223> OTHER INFORMATION: synthetic construct

<400> SEQUENCE: 31
gtagtcgcca ccgccgcctc c                                      21

<210> SEQ ID NO 32
<211> LENGTH: 21
<212> TYPE: DNA
<213> ORGANISM: Artificial Sequence
<220> FEATURE:
<223> OTHER INFORMATION: synthetic construct

<400> SEQUENCE: 32
ctgacaagga attttcggca c                                      21

<210> SEQ ID NO 33
<211> LENGTH: 21
<212> TYPE: DNA
<213> ORGANISM: Artificial Sequence
<220> FEATURE:
<223> OTHER INFORMATION: synthetic construct

<400> SEQUENCE: 33
accgccgcct ccgccatcgc c                                      21

<210> SEQ ID NO 34
<211> LENGTH: 21
<212> TYPE: DNA
<213> ORGANISM: Artificial Sequence
<220> FEATURE:
<223> OTHER INFORMATION: synthetic construct

<400> SEQUENCE: 34
cactgttcgc tggtctctgg g                                      21

<210> SEQ ID NO 35
<211> LENGTH: 21
<212> TYPE: DNA
```

```
<213> ORGANISM: Artificial Sequence
<220> FEATURE:
<223> OTHER INFORMATION: synthetic construct

<400> SEQUENCE: 35
agacaagcaa ggaggtgagt g                                              21

<210> SEQ ID NO 36
<211> LENGTH: 21
<212> TYPE: DNA
<213> ORGANISM: Artificial Sequence
<220> FEATURE:
<223> OTHER INFORMATION: synthetic construct

<400> SEQUENCE: 36
gcctgacagc agccccttgc c                                              21

<210> SEQ ID NO 37
<211> LENGTH: 21
<212> TYPE: DNA
<213> ORGANISM: Artificial Sequence
<220> FEATURE:
<223> OTHER INFORMATION: synthetic construct

<400> SEQUENCE: 37
tccagttgct aaagaacttg c                                              21

<210> SEQ ID NO 38
<211> LENGTH: 21
<212> TYPE: DNA
<213> ORGANISM: Artificial Sequence
<220> FEATURE:
<223> OTHER INFORMATION: synthetic construct

<400> SEQUENCE: 38
tggcagctgg cagcctgata g                                              21
```

US 6,312,934 B1

HUMAN MEKK PROTEINS, CORRESPONDING NUCLEIC ACID MOLECULES, AND USES THEREFOR

CROSS-REFERENCE TO RELATED APPLICATIONS

The present application claims the benefit of prior-filed provisional application U.S. patent application Ser. No. 60/078,153 entitled "Human MEKK2 Nucleic Acid and Protein Molecules and Uses Therefor", filed Mar. 16, 1998 and of prior-filed provisional application U.S. patent application Ser. No. 60/099,165 entitled "Human MEKK3 Protein and Nucleic Acid Molecules and Uses Therefor" filed Sep. 4, 1998. The present application is also related to PCT patent application Ser. No. PCT/US99/02974, entitled "MEKK1 Proteins and Fragments Thereof for Use in Regulating Apoptosis", filed Feb. 12, 1999, which claims priority to U.S. application Ser. No. 09/023,130 entitled "Method And Product For Regulating Apoptosis", filed Feb. 13, 1998. The contents of the above-referenced patent applications are incorporated herein by this reference in its entirety.

FIELD OF THE INVENTION

This invention relates to isolated nucleic acid molecules encoding MEKK proteins, substantially pure MEKK proteins, and products and methods for regulating signal transduction in a cell.

BACKGROUND OF THE INVENTION

Mitogen-activated protein kinase (MAPKs) (also called extracellular signal-regulated kinases or ERKs) are rapidly activated in response to ligand binding by both growth factor receptors that are tyrosine kinases (such as the epidermal growth factor (EGF) receptor) and receptors that are coupled to heterotrimeric guanine nucleotide binding proteins (G proteins) such as the thrombin receptor. In addition, receptors like the T cell receptor (TCR) and B cell receptor (BCR) are non-covalently associated with src family tyrosine kinases which activate MAPK pathways. Specific cytokines such as tumor necrosis factor (TNFα) can also regulate MAPK pathways. The MAPKs appear to integrate multiple intracellular signals transmitted by various second messengers. MAPKs phosphorylate and regulate the activity of enzymes and transcription factors including the EGF receptor, Rsk 90, phospholipase $A_2$, c-Myc, c-Jun and Elk-1/TCF. Although the rapid activation of MAPKs by receptors that are tyrosine kinases is dependent on Ras, G protein-mediated activation of MAPK appears to occur through pathways dependent and independent of Ras.

The MAPKs are activated by phosphorylation on both a threonine and tyrosine by dual specificity kinases, MAPK/ERK kinases (MEKs) which are, in turn, activated by serine/threonine phosphorylation MAPK kinase kinases (MKKKs or MEKKs). At present, at least four MEKKs have been identified. The four MEKK proteins range from 69.5–185 kDa in size, having their kinase domains in the carboxy-terminal end of the protein and their catalytic domains in the amino-terminal end of the protein. Murine MEKK1 was cloned initially on the basis of its homology with the STE11 and Byr2 kinases from yeast (Lange-Carter et al. (1993) Science 260:315–319; Xu et al. (1996) Proc. Natl. Acad. Sci. USA 93:5291–5295; and Blank et al. (1996) J. Biol. Chem. 271:5361–5368). Murine MEKK2 and MEKK3 were subsequently cloned and found to have 94% homology in their kinase domains as well as 65% homology within their catalytic domains. Blank et al., supra. The cloning of murine MEKK4 revealed approximately 55% homology to the kinase domains of MEKKs 1, 2, and 3 whereas the amino-terminal region of MEKK4 has little sequence homology to the other MEKK family members. Gerwin et al. (1997) J. Biol. Chem. 272:8288–8295. MEKK1 and MEKK4, but not MEKK2 and MEKK3, bind to the low molecular weight GTP-binding proteins Cdc42 and Rac. Furthermore, MEKK1 also binds to Ras in a GTP-dependent manner (Russell et al. (1996) J. Biol. Chem. 11757–11760) and Ras activity is required for EGF-mediated stimulation of MEKK1 activity (Lange-Carter and Johnson (1994) Science 265:1458–1461). In addition to growth factor receptor tyrosine kinases (i.e. EGF receptor), the TNF receptor, the FcεR1 in mast cells Ishizuka et al. et al. (1996) J. Biol. Chem. 271:12762–12766) and the N-formyl methionyl leucine peptide receptor in neutrophils have been shown to activate MEKK1. EGF and TNF also activate MEKK3 and it also appears that the other MEKK proteins are regulated by tyrosine kinase receptors but the intermediate components and effector molecules leading to their activation are poorly understood.

The cellular effects of MEKK1 are quite diverse and can be classified as being either JNK-dependent or JNK-independent. For example, MEKK1 can mediate activation of ERKI and ERK2 and, by a yet undefined mechanism, activation of the c-Myc transcription factor independent of JNK activity (Lassignal-Johnson et al. (1996) J. Biol. Chem. 271:3229–3237 and Lange-Carter et al. (1993) Science 260:315–319). Alternatively, MEKK1 may or may not require JNK activity for activation of IKB kinase which leads to NKκB activation (Liu et al. (1996) Cell 87:565–576 and Meyer et al. (1996) J. Biol. Chem. 271 :8971–8976). Furthermore, depending upon the cell type, MEKK1, but not MEKK2, 3 or 4, has been shown to mediate apoptosis by both JNK-dependent and JNK-independent mechanisms (Xia et al. (1995) Science 270:1326–1331 and Lassignal-Johnson et al. (1996) J. Biol. Chem. 271:3229–3237).

Given the important role of members of the MAPK signal transduction cascade, in particular the MEKK signal transduction molecules, in regulating mammalian cellular processes ranging from cellular proliferation and differation to cellular apoptosis, there exists a need for identifying human MEKK nucleic acid and protein molecules as well as for modulators of such molecules for use in regulating a variety of human cellular responses.

SUMMARY OF THE INVENTION

This invention provides human MEKK compositions. In particular, this invention provides isolated nucleic acid molecules encoding human MEKK1, human MEKK2, and human MEKK3. The invention further provides isolated human MEKK1, human MEKK2, and human MEKK3 proteins. Because the MEKK compositions of the invention are human-derived, they function optimally in human cells (compared with non-human MEKK compositions) and do not stimulate an immune response in humans.

One aspect of the invention pertains to an isolated nucleic acid molecule having a nucleotide sequence which encodes a human MEKK protein. In a preferred embodiment, the nucleic acid molecule has the nucleotide sequence of SEQ ID NO:1, SEQ ID NO:3, or SEQ ID NO:5. In other embodiments, the nucleic acid molecule has at least 90–91% nucleotide identity, more preferably 92–93% nucleotide identity, more preferably 94–95% nucleotide identity, more preferably 96–97% nucleotide identity, more preferably 98–99% nucleotide identity, and even more preferably 99.5% nucleotide identity with the nucleotide sequence SEQ ID NO:1, SEQ ID NO:3, or SEQ ID NO:5.

The isolated nucleic acid molecules of the invention encoding human MEKK proteins can be incorporated into a vector, such as an expression vector, and this vector can be introduced into a host cell. The invention also provides a method for producing a human MEKK protein by culturing a host cell of the invention (carrying a huMEKK1, huMEKK2, or huMEKK3 expression vector) in a suitable medium until a human MEKK protein is produced. The method can further involve isolating the human MEKK protein from the medium or the host cell.

Another aspect of the invention pertains to an isolated human MEKK proteins. Preferably, the human MEKK protein has the amino acid sequence of SEQ ID NO:2, SEQ ID NO:4, or SEQ ID NO:6. In other embodiments, the protein has at least 90–91% amino acid identity, more preferably 92–93% amino identity, more preferably 94–95% amino identity, more preferably 96–97% amino identity, more preferably 98–99% amino identity, and even more preferably 99.5% amino acid identity with the amino acid sequence of SEQ ID NO:2, SEQ ID NO:4, or SEQ ID NO:6.

Fusion proteins, including a human MEKK protein operatively linked to a polypeptide other than human MEKK, are also encompassed by the invention, as well as antibodies that specifically bind a human MEKK protein. The antibodies can be, for example, polyclonal antibodies or monoclonal antibodies. In one embodiment, the antibodies are coupled to a detectable substance.

Another aspect of the invention pertains to a nonhuman transgenic animal that contains cells carrying a transgene encoding a human MEKK protein.

Yet another aspect of the invention pertains to a method for detecting the presence of human MEKK in a biological sample. The method involves contacting the biological sample with an agent capable of detecting an indicator of human MEKK activity such that the presence of human MEKK is detected in the biological sample. The invention also provides a method for modulating human MEKK activity in a cell which involves contacting the cell with an agent that modulates human MEKK activity such that human MEKK activity in the cell is modulated.

Still another aspect of the invention pertains to methods for identifying a compound that modulates the activity of a human MEKK protein. These methods generally involve: providing an indicator composition that comprises a human MEKK protein; contacting the indicator composition with a test compound; and determining the effect of the test compound on the activity of the human MEKK protein in the indicator composition to thereby identify a compound that modulates the activity of a human MEKK protein.

BRIEF DESCRIPTION OF THE DRAWINGS

FIGS. 1A–1B depicts the cDNA sequence of human MEKK1. The nucleic acid sequence corresponds to nucleotides 1 to 3911 of SEQ ID NO:1.

FIG. 2 depicts the amino acid sequence of human MEKK1. The amino acid sequence corresponds to amino acids 1 to 1302 of SEQ ID NO:2.

FIGS. 3A–3J show a global alignment of the nucleic acid sequence of human MEKK (SEQ ID NO:1) with the nucleic acid sequence of mouse MEKK1 SEQ ID NO:7).

FIGS. 4A–4C show an alignment of the amino acid sequence of human MEKK1 (SEQ ID NO:2) with that of murine MEKK1 (SEQ ID NO:8). Amino acid differences between the two sequences are underlined and bolded.

FIG. 5 depicts the cDNA sequence of human MEKK2. The nucleic acid sequence corresponds to nucleotides 1 to 2013 of SEQ ID NO:3.

FIG. 6 depicts the amino acid sequence of human MEKK2. The amino acid sequence corresponds to amino acids 1 to 619 of SEQ ID NO:4.

FIGS. 7A–7E shows a global alignment of the nucleic acid sequences of human MEKK2 (SEQ ID NO:3) and murine MEKK2 (SEQ ID NO:9).

FIG. 8 shows an alignment of the amino acid sequences of human MEKK2 (SEQ ID NO:4) and murine MEKK2 (SEQ ID NO:10).

FIG. 9 depicts the cDNA sequence of human MEKK3. The nucleic acid sequence corresponds to nucleotides 1 to 1935 of SEQ ID NO:5.

FIG. 10 depicts the amino acid sequence of human MEKK3. The amino acid sequence corresponds to amino acids 1 to 626 of SEQ ID NO:6.

FIGS. 11A–11G show a global alignment of the nucleic acid sequences of human MEKK3 (SEQ ID NO:5) and murine MEKK3 (SEQ ID NO:11).

FIG. 12 shows an alignment of the amino acid sequences of human MEKK3 (SEQ ID NO:6) and murine MEKK3 (SEQ ID NO:12).

FIG. 13 shows an alignment of the amino acid sequences of the kinase catalytic domains of murine MEKK1 (corresponding to amino acids 1229–1493 of SEQ ID NO:8), murine MEKK2 (corresponding to amino acids 361–619 of SEQ ID NO:10), murine MEKK3 (corresponding to amino acids 367–626 of SEQ ID NO:12), murine MEKK4 (corresponding to amino acids 1337–1597 of SEQ ID NO:13), human MEKK1 (corresponding to amino acids 1038–1302 of SEQ ID NO:2), human MEKK2 (corresponding to amino acids 361–619 of SEQ ID NO:4), and human MEKK 3 (corresponding to amino acids 367–626 of SEQ ID NO:6). The consensus kinase domains are indicated by the roman numerals I through XI. The most highly conserved residues are underlined.

DETAILED DESCRIPTION OF THE INVENTION

This invention pertains to human MEKK compositions, such as isolated nucleic acid molecules encoding human MEKK1, human MEKK2, and human MEKK3. The invention also pertains to isolated human MEKK proteins (e.g., human MEKK1, human MEKK2, and human MEKK3), as well as methods of use therefor. The human compositions of the invention have the advantages that they function optimally in human cells (compared with non-human MEKK compositions) and do not stimulate an immune response in humans.

So that the invention may be more readily understood, certain terms are first defined.

As used herein, the term "human MEKK protein" is intended to encompass proteins that share the distinguishing structural and functional features (described further herein) of the human MEKK protein having the amino acid sequences of SEQ ID NO:2, SEQ ID NO:4, and SEQ ID NO:6, including the amino acid residues unique to human MEKK proteins (as compared to mouse MEKK proteins), which are underlined and bolded in FIG. 4, FIG. 8, and FIG. 12.

As used herein, the term "nucleic acid molecule" is intended to include DNA molecules (e.g., cDNA or genomic DNA) and RNA molecules (e.g., mRNA). The nucleic acid molecule may be single-stranded or double-stranded, but preferably is double-stranded DNA.

An used herein, an "isolated nucleic acid molecule" refers to a nucleic acid molecule that is free of gene sequences which naturally flank the nucleic acid in the genomic DNA of the organism from which the nucleic acid is derived (i.e., genetic sequences that are located adjacent to the gene for the isolated nucleic molecule in the genomic DNA of the organism from which the nucleic acid is derived). For example, in various embodiments, an isolated human MEKK nucleic acid molecule typically contains less than about 10 kb of nucleotide sequences which naturally flank the nucleic acid molecule in genomic DNA of the cell from which the nucleic acid is derived, and more preferably contains less than about 5 kb, 4 kb, 3 kb, 2 kb, 1 kb, 0.5 kb or 0.1 kb of naturally flanking nucleotide sequences. An "isolated" human MEKK nucleic acid molecule may, however, be linked to other nucleotide sequences that do not normally flank the human MEKK sequences in genomic DNA (e.g., the human MEKK nucleotide sequences may be linked to vector sequences). In certain preferred embodiments, an "isolated" nucleic acid molecule, such as a cDNA molecule, also may be free of other cellular material. However, it is not necessary for the human MEKK nucleic acid molecule to be free of other cellular material to be considered "isolated" (e.g., a human MEKK DNA molecule separated from other mammalian DNA and inserted into a bacterial cell would still be considered to be "isolated").

As used herein, the term "hybridizes under high stringency conditions" is intended to describe conditions for hybridization and washing under which nucleotide sequences having substantial homology to each other remain stably hybridized to each other. Preferably, the conditions are such that sequences at least about 70%, more preferably at least about 80%, even more preferably at least about 85% or 90% homologous to each other typically remain hybridized to each other. A preferred, non-limiting example of high stringency conditions are hybridization in a hybridization buffer that contains 6×sodium chloride/sodium citrate (SSC) at a temperature of about 45° C. for several hours to overnight, followed by one or more washes in a washing buffer containing 0.2×SSC, 0.1% SDS at a temperature of about 50–65° C.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the entire length of the reference sequence (e.g., when aligning a second sequence to the MEKK amino acid sequence of SEQ ID NO:6 having 626 amino acid residues, at least 188, preferably at least 250, more preferably at least 313, even more preferably at least 376, and even more preferably at least 438, 501 or 563 amino acid residues are aligned). In a more preferred embodiment, the aligned amino acid residues are consecutive (eg., homologous or identical over 188, 250, 313, 376, 438, 501, or 563 consecutive amino acid residues.) After aligning, the amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100).

The comparison of sequences and determination of percent homology between two sequences can be accomplished using a mathematical algorithim. A preferred, non-limiting example of a mathematical algorithim utilized for the comparison of sequences is the algorithm of Karlin and Altschul (1990) *Proc. Natl. Acad Sci. USA* 87:2264–68, modified as in Karlin and Altschul (1993) *Proc. Natl. Acad. Sci. USA* 90:5873–77. Such an algorithm is incorporated into the NBLAST and XBLAST programs (version 2.0) of Altschul, et al (1990) *J. Mol. Biol*. 215:403–10. BLAST nucleotide searches can be performed with the NBLAST program, score=100, word length=12 to obtain nucleotide sequences homologous to MEKK nucleic acid molecules of the invention. BLAST protein searches can be performed with the XBLAST program, score=50, word length=3 to obtain amino acid sequences homologous to MEKK protein molecules of the invention. To obtain gapped alignments for comparison purposes, Gapped BLAST can be utilized as described in Altschul et al., (1997) *Nucleic Acids Res*. 25(17):3389–3402. When utilizing BLAST and Gapped BLAST programs, the default parameters of the respective programs (e.g., XBLAST and NBLAST) can be used. See http://www.ncbi.nlm.nih.gov.

Another preferred, non-limiting example of a mathematical algorithim utilized for the comparison of sequences is the algorithm of Myers and Miller (1989) *CABIOS*. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Another preferred, non-limiting example of a mathematical algorithim utilized for the alignment of protein sequences is the Lipman-Pearson algorithm (Lipman and Pearson (1985) *Science* 227:1435–1441). When using the Lipman-Pearson algorithm, a PAM250 weight residue table, a gap length penalty of 12, a gap penalty of 4, and a Ktuple of 2 can be used. A preferred, non-limiting example of a mathematical algorithim utilized for the alignment of nucleic acid sequences is the Wilbur-Lipman algorithm (Wilbur and Lipman (1983) *Proc. Natl. Acad. Sci. USA* 80:726–730). When using the Wilbur-Lipman algorithm, a window of 20, gap penalty of 3, Ktuple of 3 can be used. Both the Lipman-Pearson algorithm and the Wilbur-Lipman algorithm are incorporated, for example, into the MEGALIGN program (e.g., version 3.1.7) which is part of the DNASTAR sequence analysis software package.

As used herein, a "naturally-occurring" nucleic acid molecule refers to an RNA or DNA molecule having a nucleotide sequence that occurs in nature (e.g., encodes a natural protein).

As used herein, an "antisense" nucleic acid comprises a nucleotide sequence which is complementary to a "sense" nucleic acid encoding a protein (e.g., complementary to the coding strand of a double-stranded cDNA molecule, complementary to an mRNA sequence or complementary to the coding strand of a gene. Accordingly, an antisense nucleic acid can hydrogen bond to a sense nucleic acid).

As used herein, the term "coding region" refers to regions of a nucleotide sequence comprising codons which are translated into amino acid residues, whereas the term "non-coding region" refers to regions of a nucleotide sequence that are not translated into amino acids (e.g., 5' and 3' untranslated regions).

As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As used herein, the term "host cell" is intended to refer to a cell into which a nucleic acid of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, a "transgenic animal" refers to a non-human animal, preferably a mammal, more preferably a mouse, in which one or more of the cells of the animal includes a "transgene". The term "transgene" refers to exogenous DNA which is integrated into the genome of a cell from which a transgenic animal develops and which remains in the genome of the mature animal, for example directing the expression of an encoded gene product in one or more cell types or tissues of the transgenic animal.

As used herein, a "homologous recombinant animal" refers to a type of transgenic non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

As used herein, an "isolated protein" refers to a protein that is substantially free of other proteins, cellular material and culture medium when isolated from cells or produced by recombinant DNA techniques, or chemical precursors or other chemicals when chemically synthesized.

In one embodiment, a MEKK protein is identified based on the presence of at least a "catalytic domain" in the protein or corresponding nucleic acid molecule. As used herein, the term "catalytic domain" refers to a protein domain consisting of at least about 150–400, preferably about 200–350, more preferably about 220–300, even more preferably at least about 240–280, and even more preferably about 260 amino acid residues in length. In one embodiment, a MEKK catalytic domain contains at least about 9–13, preferably about 10–12, and more preferably about 11 consensus kinase domains which are conserved among MEKK protein family members. Such consensus kinase domains are indicated by roman numerals in FIG. 13. Particularly conserved residues within the consensus kinase domains are underlined. A consensus kinase domain is further defined in Hanks et al. (1988) *Science* 241:42–52. In another embodiment, a MEKK catalytic domain is identified based in its ability to retain a functional activity of a MEKK protein, particularly a MEKK protein (e.g., retains the ability to phosphorylate a MEKK substrate) even in the absence of a MEKK regulatory domain, defined herein.

In another embodiment, a MEKK protein is identified based on the presence of at least a "regulatory domain" in the protein or corresponding nucleic acid molecule. As used herein, the term "regulatory domain" refers to a protein domain consisting of at least about 250–500, preferably about 300–450, more preferably about 320–400, even more preferably at least about 340–380, and even more preferably about 360 amino acid residues in length, of which at least 10%, preferably about 15%, and more preferably about 20% of the amino acid residues are serine and/or threonone residues. In another embodiment, a MEKK regulatory domain is identified based on its ability to regulate the activity of a MEKK catalytic domain. In one exemplary embodiment, a MEKK regulatory domain is capable of binding a MEKK binding partner such that the activity of a MEKK protein is modulated.

As used interchangeably herein, a "MEKK activity", "functional activity of MEKK", or "biological activity of MEKK", refers to an activity exerted by a MEKK protein, polypeptide or nucleic acid molecule as determined in vivo, or in vitro, according to standard techniques. In one embodiment, a MEKK activity is a direct activity, such as an association with a MEKK-target molecule. As used herein, a "target molecule" is a molecule with which a MEKK protein binds or interacts in nature, such that MEKK-mediated function is achieved. A MEKK target molecule can be a MEKK protein or polypeptide of the present invention or a non-MEKK molecule. For example, a MEKK target molecule can be a non-MEKK protein molecule (e.g., a MEKK binding partner such as a Ras protein, or a MEKK substrate such as a MEK protein). As used herein, a "MEKK" substrate is a molecule with which a MEKK protein interacts in vivo or in vitro such that the MEKK substrate is phosphorylated by the enzymatic activity of the MEKK protein. Also as used herein, a MEKK "binding partner" is a molecule with which a MEKK protein interacts in vivo or in vitro such that the enzymatic activity of the MEKK protein is effected. Alternatively, a MEKK activity is an indirect activity, such as an activity mediated by interaction of the MEKK protein with a MEKK target molecule such that the target molecule modulates a downstream cellular activity (e.g., MAPK activity).

In a preferred embodiment, a MEKK activity is at least one or more of the following activities: (i) interaction of a MEKK protein with a MEKK target molecule, wherein the target molecule effects the activity of the MEKK molecule;

(ii) interaction of a MEKK protein with a MEKK target molecule, wherein the MEKK molecule effects the activity of the target molecule; (iii) phosphorylation of a MEKK target molecule (e.g., MEK or JNK kinase); (iv) activation of a MEKK target molecule (e.g., MEK or JNK kinase); (v) mediation of activation of MAPK signal transduction molecules (e.g., c-Jun kinase (JNK) or p42/p44$^{MAPK}$); (vi) autophosphorylation of MEKK; (vii) autoactivation of MEKK 3; and (viii) modulation of the activity of a nuclear transcription factor (e.g., ATF 2).

Accordingly, another embodiment of the invention features isolated MEKK proteins and polypeptides having a MEKK activity. Preferred proteins are MEKK proteins having at least a MEKK catalytic domain and, preferably, a MEKK activity. Additional preferred proteins are MEKK proteins having at least a MEKK regulatory domain and, preferably, a MEKK activity. In another preferred embodiment, the isolated protein is a MEKK protein having a MEKK catalytic domain, a MEKK regulatory domain, and a MEKK activity.

As used herein, the term "antibody" is intended to include immunoglobulin molecules and immunologically active portions of immunoglobulin molecules, i.e., molecules that contain an antigen binding site which specifically binds (immunoreacts with) an antigen, such as Fab and F(ab')$_2$ fragments. The terms "monoclonal antibodies" and "monoclonal antibody composition", as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody compositions thus typically display a single binding affinity for a particular antigen with which it immunoreacts.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid molecule and the amino acid sequence encoded by that nucleic acid molecule, as defined by the genetic code.

GENETIC CODE

| | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |

-continued

GENETIC CODE

| | |
|---|---|
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA molecule coding for a human MEKK protein of the invention (or any portion thereof) can be used to derive the human MEKK amino acid sequence, using the genetic code to translate the DNA or RNA molecule into an amino acid sequence. Likewise, for any human MEKK-amino acid sequence, corresponding nucleotide sequences that can encode the human MEKK protein can be deduced from the genetic code (which, because of its redundancy, will produce multiple nucleic acid sequences for any given amino acid sequence). Thus, description and/or disclosure herein of a human MEKK nucleotide sequence should be considered to also include description and/or disclosure of the amino acid sequence encoded by the nucleotide sequence. Similarly, description and/or disclosure of a human MEKK amino acid sequence herein should be considered to also include description and/or disclosure of all possible nucleotide sequences that can encode the amino acid sequence.

The human MEKK1 cDNA, which is approximately 3911 nucleotides in length, encodes a protein which is approximately 1302 amino acid residues in length. The coding region is from nucleotide 3 to 3908 of SEQ ID NO:1. The human MEKK1 protein has at least a catalytic domain. A catalytic domain includes, for example, about amino acids 1038–1302 of SEQ ID NO:2 (e.gcatalytic domain having 259 or 260–265 amino acid residues). Catalytic domains having 100, 150, 200, or 250 consecutive amino acids from about amino acids 1038–1302 of SEQ ID NO:2 are also intended to be within the scope of the invention. The human MEKK1 protein further has at least a regulatory domain. A regulatory domain includes, for example, about amino acids xx-xxx of SEQ ID NO:2. Regulatory domains having 200, 250, 300, or 350 consecutive amino acids from about amino acids xx-xxx of SEQ ID NO:2 are also intended to be within the scope of the invention. Also intended to be within the scope of the invention are modified catalytic and regulatory domains having about 1, 2, 3, 4, 5, 6, 7, 8, 9, 10, 11, 12, 13, 14, 15, 16, 17, 18, 19, 20,25, 30, 35,40,45, 50, 55, 60, 65,70,75. 80, 85, 90, 95, 100, 105, 110, 115, 116, 117, 118, 119, 120, 121, 122, 123, 145, 125 amino acid substitutions, insertions, and/or deletions when compared to the amino acid sequence of SEQ ID NO:2, wherein the modified catalytic or regulatory domain retains the function of a MEKK catalytic or reguatlory domain of SEQ ID NO:2.

The human MEKK2 cDNA, which is approximately 2013 nucleotides in length, encodes a protein which is approximately 619 amino acid residues in length. The coding region is from nucleotide 124 to 1980 of SEQ ID NO:3. The human MEKK2 protein has at least a catalytic domain. A catalytic domain includes, for example, about amino acids 361–619 of SEQ ID NO:4. Catalytic domains having 100, 150, 200, or 250 consecutive amino acids from about amino acids 361–619 of SEQ ID NO:4 are also intended to be within the scope of the invention. The human MEKK2 protein further has at least a regulatory domain. A regulatory domain includes, for example, about amino acids 1–360 of SEQ ID NO:4. Regulatory domains having 200, 250, 300 or 350 consecutive amino acids from about amino acids 1–360 of SEQ ID NO:4 are also intended to be within the scope of the invention. Also intended to be within the scope of the invention are modified catalytic and regulatory domains having about 1, 2, 3, 4, 5, 6, 7, 8, 9, 10, 11, 12, 13, 14, 15, 16, 17, 18, 19, 20, 25, 30, 35, 40, 45, 50, 55, 60, 61, or 62 amino acid substitutions, insertions, and/or deletions when compared to the amino acid sequence of SEQ ID NO:4, wherein the modified catalytic or regulatory domain retains the function of a MEKK catalytic or regualtory domain of SEQ ID NO:4.

The human MEKK3 cDNA, which is approximately 1935 nucleotides in length, encodes a protein which is approximately 626 amino acid residues in length. The coding region is from nucleotide 25 to 1902 of SEQ ID NO:5. The human MEKK3 protein has at least a catalytic domain. A catalytic domain includes, for example, about amino acids 367–626 of SEQ ID NO:6. Catalytic domains having 100, 150, 200, or 250 consecutive amino acids from about amino acids 367–626 of SEQ ID NO:6 are also intended to be within the scope of the invention. The human MEKK3 protein further has at least a regulatory domain. A regulatory domain includes, for example, about amino acids 1–366 of SEQ ID NO:6. Regulatory domains having 200, 250, 300, or 350 consecutive amino acids from about amino acids 1–366 of SEQ ID NO:6 are also intended to be within the scope of the invention. Also intended to be within the scope of the invention are modified catalytic and regulatory domains having about 1, 2, 3, 4, 5, 6, 7, 8, 9, 10, 11, 12, 13, 14, 15, 16, 17, 18, 19, 20, 25, 30, 35, or 40 amino acid substitutions, insertions, and/or deletions when compared to the amino acid sequence of SEQ ID NO:6, wherein the modified catalytic or regulatory domain retains the function of a MEKK catalytic or regualtory domain of SEQ ID NO:6.

Various aspects of the invention are described in further detail in the following subsections:

I. Isolated Nucleic Acid Molecules

One aspect of the invention pertains to isolated nucleic acid molecules that encode human MEKK proteins. The nucleotide sequence of human MEKK1, and corresponding predicted amino acid sequence, are shown in SEQ ID NODS:1 and 2, respectively. The nucleotide sequence of human MEKK2, and corresponding predicted amino acid sequence, are shown in SEQ ID NODS:3 and 4, respectively. The nucleotide sequence of human MEKK3, and corresponding predicted amino acid sequence, are shown in SEQ ID NODS:5 and 6, respectively. In a preferred embodiment, the nucleic acid molecule comprises the nucleotide sequence of SEQ ID NO:1, SEQ ID NO:3, or SEQ ID NO:5. In other embodiments, the nucleic acid molecule has at least 90–91% nucleotide identity, more preferably 92–93% nucleotide identity, more preferably 94–95% nucleotide identity, more preferably 96–97% nucleotide identity, more preferably 98–99% nucleotide identity, and even more preferably 99.5% nucleotide identity with the nucleotide sequence of SEQ ID NO:1, SEQ ID NO:3, or SEQ ID NO:5.

Nucleic acid molecules that differ from SEQ ID NO:1, SEQ ID NO:3, or SEQ ID NO:5 due to degeneracy of the genetic code, and thus encode the same human MEKK protein as that encoded by SEQ ID NO:1, SEQ ID NO:3, or SEQ ID NO:5, are encompassed by the invention. Accordingly, in another embodiment, an isolated nucleic acid molecule of the invention has a nucleotide sequence encoding a protein having an amino acid sequence shown in SEQ ID NO:2, SEQ ID NO:4, or SEQ ID NO:6.

A nucleic acid molecule having the nucleotide sequence of human MEKK1, human MEKK2, or human MEKK3 can be isolated using standard molecular biology techniques and the sequence information provided herein. For example, a human MEKK DNA can be isolated from a human genomic DNA library using all or portion of SEQ ID NO: 1, SEQ ID NO:3, or SEQ ID NO:5 as a hybridization probe and standard hybridization techniques (e.g., as described in Sambrook, J., et al. *Molecular Cloning: A Laboratory Manual*. 2nd, ed., Cold Spring Harbor Laboratory, Cold Spring Harbor, N.Y., 1989). Moreover, a nucleic acid molecule encompassing all or a portion of SEQ ID NO:1, SEQ ID NO:3, or SEQ ID NO:5 can be isolated by the polymerase chain reaction using oligonucleotide primers designed based upon the sequence of SEQ ID NO 1, SEQ ID NO:3, or SEQ ID NO:5. For example, mRNA can be isolated from cells (e.g., by the guanidinium-thiocyanate extraction procedure of Chirgwin et al. (1979) Biochemistry 18: 5294–5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NO:1, SEQ ID NO:3, or SEQ ID NO:5. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a human MEKK nucleotide sequence can be prepared by standard synthetic techniques, e.g., using an automated DNA synthesizer.

In addition to the human MEKK nucleotide sequence shown in SEQ ID NO:1, SEQ ID NO:3, or SEQ ID NO:5, it will be appreciated by those skilled in the art that DNA sequence polymorphisms that lead to minor changes in the nucleotide or amino acid sequences of human MEKK may exist within a population. Such genetic polymorphism in the human MEKK gene may exist among individuals within a population due to natural allelic variation. Such natural allelic variations can typically result in 1–2% variance in the nucleotide sequence of the a gene. Any and all such nucleotide variations and resulting amino acid polymorphisms in human MEKK that are the result of natural allelic variation and that do not alter the functional activity of human MEKK are intended to be within the scope of the invention.

Nucleic acid molecules corresponding to natural allelic variants of the human MEKK DNAs of the invention can be isolated based on their homology to the human MEKK nucleic acid molecules disclosed herein using the human DNA, or a portion thereof, as a hybridization probe according to standard hybridization techniques under high stringency hybridization conditions. Accordingly, in another embodiment, an isolated nucleic acid molecule of the invention hybridizes under high stringency conditions to a second nucleic acid molecule comprising the nucleotide sequence of SEQ ID NO:1, SEQ ID NO:3, or SEQ ID NO:5. In certain embodiment, the isolated nucleic acid molecule comprises at least 30, 50, 100, 200, 300, 400, 500, 600, 700, 800, 900, 1000, 2000 or 3000 contiguous nucleotides of SEQ ID NO:1, SEQ ID NO:3, or SEQ ID NO:5. Preferably, an isolated nucleic acid molecule of the invention that hybridizes under high stringency conditions to the sequence of SEQ ID NO:1, SEQ ID NO:3, or SEQ ID NO:5 corresponds to a naturally-occurring allelic variant of a human MEKK nucleic acid molecule.

In addition to naturally-occurring allelic variants of the human MEKK sequence that may exist in the population, the skilled artisan will further appreciate that minor changes may be introduced by mutation into the nucleotide sequence of SEQ ID NO:1, SEQ ID NO:3, or SEQ ID NO:5, thereby leading to changes in the amino acid sequence of the encoded protein, without altering the functional activity of the human MEKK protein. For example, nucleotide substitutions leading to amino acid substitutions at "non-essential" amino acid residues may be made in the sequence of SEQ ID NO:1, SEQ ID NO:3, or SEQ ID NO:5. A "non-essential" amino acid residue is a residue that can be altered from the wild-type sequence of human MEKK (e.g., the sequence of SEQ ID NO:2, SEQ ID NQ:4, or SEQ ID NO:6) without altering the functional activity of MEKK, whereas an "essential" amino acid residue is required for functional activity.

Accordingly, another aspect of the invention pertains to nucleic acid molecules encoding human MEKK proteins that contain changes in amino acid residues that are not essential for human MEKK activity. Such human MEKK proteins differ in amino acid sequence from SEQ ID NO:2, SEQ ID NO:4, or SEQ ID NO:6 yet retain human MEKK activity. These non-natural variants of human MEKK also differ from non-human MEKK proteins (e.g., mouse or rat MEKK) in that they encode at least one amino acid residue that is unique to human MEKK (i.e., at least one residue that is not present in mouse or rat MEKK). Preferably, these non-natural variants of human MEKK encode at least 2, 3, 4, 5, 6, 7, 8, 9 or 10 amino acid residues that are unique to human MEKK (i.e., that are not present in mouse or rat MEKK).

An isolated nucleic acid molecule encoding a non-natural variant of a human MEKK protein can be created by introducing one or more nucleotide substitutions, additions or deletions into the nucleotide sequence of SEQ ID NO:1, SEQ ID NO:3, or SEQ ID NO:5 (or plasmid pHu-MEKK) such that one or more amino acid substitutions, additions or deletions are introduced into the encoded protein. Mutations can be introduced into SEQ ID NO:1, SEQ ID NO:3, or SEQ ID NO:5 by standard techniques, such as site-directed mutagenesis and PCR-mediated mutagenesis. Preferably, conservative amino acid substitutions are made at one or more non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in human MEKK is preferably replaced with another amino acid residue from the same side chain family. Alternatively, in another embodiment, mutations can be introduced randomly along all or part of the human MEKK coding sequence, such as by saturation mutagenesis, and the resultant mutants can be screened for their ability to bind to DNA and/or activate transcription, to identify mutants that retain functional activity. Following mutagenesis, the encoded human MEKK mutant protein can be expressed recombinantly in a host cell and the functional activity of the mutant protein can be determined using assays available in the art for assessing MEKK activity (e.g., assays such as those described in detail in PCT Publication WO 97/39721 and/or asays described in Blank et al. (1996) *J. Biol. Chem.* 271:5361–5368.

Another aspect of the invention pertains to isolated nucleic acid molecules that are antisense to the coding strand of a human MEKK MRNA or gene. An antisense nucleic acid of the invention can be complementary to an entire human MEKK coding strand, or to only a portion thereof. In one embodiment, an antisense nucleic acid molecule is antisense to a coding region of the coding strand of a nucleotide sequence encoding human MEKK that is unique to human MEKK (as compared to non-human MEKKs, such as mouse or rat MEKK). In another embodiment, the antisense nucleic acid molecule is antisense to a noncoding region of the coding strand of a nucleotide sequence encoding human MEKK that is unique to human MEKK (as compared to non-human MEKKs, such as mouse or rat MEKK). In preferred embodiments, an antisense of the invention comprises at least contiguous nucleotides of the noncoding strand of SEQ ID NO:1, SEQ ID NO:3, or SEQ ID NO:5, more preferably at least 50, 100, 200, 300, 400, 500, 600, 700, 800, 900 or 1000 contiguous nucleotides of the noncoding strand of SEQ ID NO:1, SEQ ID NO:3, or SEQ ID NO:5.

Given the coding strand sequences encoding human MEKK disclosed herein (e.g., nucleotides 3 to 3908 of SEQ ID NO:1, nucleotides 124–1980 of SEQ ID NO:3, or nucleotides 25–1902 of SEQ ID NO:5), antisense nucleic acids of the invention can be designed according to the rules of Watson and Crick base pairing. The antisense nucleic acid molecule may be complementary to the entire coding region of human MEKK mRNA, or alternatively can be an oligonucleotide which is antisense to only a portion of the coding or noncoding region of human MEKK mRNA. For example, the antisense oligonucleotide may be complementary to the region surrounding the translation start site of human MEKK mRNA. An antisense oligonucleotide can be, for example, about 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. A ribozyme having specificity for a human MEKK-encoding nucleic acid can be designed based upon the nucleotide sequence of a human MEKK gene disclosed herein. For example, a derivative of a Tetrahymena L-19 IVS RNA can be constructed in which the base sequence of the active site is complementary to the base sequence to be cleaved in a human MEKK-encoding mRNA. See for example Cech et al. U.S. Pat. No. 4,987,071; and Cech et al. U.S. Pat. No. 5,116,742. Alternatively, human MEKK mRNA can be used to select a catalytic RNA having a specific ribonuclease activity from a pool of RNA molecules. See for example Bartel, D, and Szostak, J. W. (1993) *Science* 261: 1411–1418.

Yet another aspect of the invention pertains to isolated nucleic acid molecules encoding human MEKK fusion proteins. Such nucleic acid molecules, comprising at least a first nucleotide sequence encoding a human MEKK protein, polypeptide or peptide operatively linked to a second nucleotide sequence encoding a non-human MEKK protein, polypeptide or peptide, can be prepared by standard recombinant DNA techniques. Human MEKK fusion proteins are described in further detail below in subsection III.

II. Recombinant Expression Vectors and Host Cells

Another aspect of the invention pertains to vectors, preferably recombinant expression vectors, containing a nucleic acid encoding human MEKK (or a portion thereof). The expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology. Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector may depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., human MEKK proteins, mutant forms of human MEKK proteins, human MEKK fusion proteins and the like).

The recombinant expression vectors of the invention can be designed for expression of human MEKK protein in prokaryotic or eukaryotic cells. For example, human MEKK can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector may be transcribed and translated in vitro, for example using T7 promoter regulatory sequences and T7 polymerase.

Expression of proteins in prokaryotes is most often carried out in *E. coli* with vectors containing constitutive or inducible promotors directing the expression of either fusion or non-fusion proteins. Fusion vectors add a number of amino acids to a protein encoded therein, usually to the amino terminus of the recombinant protein. Such fusion vectors can serve one or more purposes: 1) to increase expression of recombinant protein; 2) to increase the solubility of the recombinant protein; 3) to aid in the purification of the recombinant protein by acting as a ligand in affinity purification; 4) to provide an epitope tag to aid in detection and/or purification of the protein; and/or 5) to provide a marker to aid in detection of the protein (e.g., a color marker using β-galactosidase fusions). Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc.; Smith, D. B, and Johnson, K. S. (1988) *Gene* 67:3140), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Recombinant proteins also can be expressed in eukaryotic cells as fusion proteins for the same purposes discussed above.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada e1 al., (1992) *Nuc. Acids Res.* 20:2111–2118). Such alteration of nucleic acid sequences of the invention can be carried out by standard DNA synthesis techniques.

In another embodiment, the human MEKK expression vector is a yeast expression vector. Examples of vectors for expression in yeast *S. cerivisae* include pYepSec1 (Baldari. et al., (1987) *EMBO J.* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.).

Alternatively, human MEKK can be expressed in insect cells using baculovirus expression vectors. Baculovirus vectors available for expression of proteins in cultured insect cells (e.g., Sf 9 cells) include the pAc series (Smith et al., (1983) *Mol. Cell Biol.* 3:2156–2165) and the pVL series (Lucklow, V. A., and Summers, M. D., (1989) *Virology* 170:31–39).

In yet another embodiment, a nucleic acid of the invention is expressed in mammalian cells using a mammalian expression vector. Examples of mammalian expression vectors include pMex-NeoI, pCDM8 (Seed, B., (1987) *Nature* 329:840) and pMT2PC (Kaufman et al. (1987), *EMBO J.* 6:187–195). When used in mammalian cells, the expression vector's control functions are often provided by viral regulatory elements.

For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), the albumin promoter (liver-specific; Pinkert et al (1987) *Genes Dev.* 1:268–277), neuron-specific promoters (e.g., the neurofilament promoter; Byrne and Ruddle (1989) *Proc. Natl. Acad Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

Moreover, inducible regulatory systems for use in mammalian cells are known in the art, for example systems in which gene expression is regulated by heavy metal ions (see e.g., Mayo et al. (1982) *Cell* 29:99–108; Brinster et al. (1982) *Nature* 296:39–42; Searle et al. (1985) *Mol. Cell. Biol.* 5:1480–1489), heat shock (see e.g., Nouer et al. (1991) in *Heat Shock Response*, e.d. Nouer, L., CRC, Boca Raton, Fla., pp167–220), hormones (see e.g., Lee et al. (1981) *Nature* 294:228–232; Hynes et al. (1981) *Proc. Natl. Acad. Sci. USA* 78:2038–2042; Klock et al. (1987) *Nature* 329:734–736; Israel & Kaufman (1989) *Nucl. Acids Res.* 17:2589–2604; and PCT Publication No. WO 93/23431), FK506-related molecules (see e.g., PCT Publication No. WO 94/18317) or tetracyclines (Gossen, M, and Bujard, H. (1992) *Proc. Natl. Acad Sci. USA* 89:5547–5551; Gossen, M. et al. (1995) *Science* 268:1766–1769; PCT Publication No. WO 94/29442; and PCT Publication No. WO 96/01313). Accordingly, in another embodiment, the invention provides a recombinant expression vector in which human MEKK DNA is operatively linked to an inducible eukaryotic promoter, thereby allowing for inducible expression of human MEKK protein in eukaryotic cells.

The invention further provides a recombinant expression vector comprising a DNA molecule of the invention cloned into the expression vector in an antisense orientation. That is, the DNA molecule is operatively linked to a regulatory sequence in a marner which allows for expression (by transcription of the DNA molecule) of an RNA molecule which is antisense to human MEKK mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to recombinant host cells into which a vector, preferably a recombinant expression vector, of the invention has been introduced. A host cell may be any prokaryotic or eukaryotic cell. For example. human MEKK protein may be expressed in bacterial cells such as *E. coli*, insect cells, yeast or mammalian cells (such as Chinese hamster ovary cells (CHO) or COS cells). Other suitable host cells are known to those skilled in the art. Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual*, 2nd Edition, Cold Spring Harbor Laboratory press (1989)), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker may be introduced into a host cell on the same vector as that encoding human MEKK or may be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) human MEKK protein. Accordingly, the invention firther provides methods for producing human MEKK protein using the host cells of the invention. In one embodiment, the method comprises culturing the host cell of invention (into which a recombinant expression vector encoding human MEKK has been introduced) in a suitable medium until human MEKK is produced. In another embodiment, the method further comprises isolating human MEKK from the medium or the host cell. In its native form the human MEKK protein is an intracellular protein and, accordingly, recombinant human MEKK protein can be expressed intracellularly in a recombinant host cell and then isolated from the host cell, e.g., by lysing the host cell and recovering the recombinant human MEKK protein from the lysate. Alternatively, recombinant human MEKK protein can be prepared as a extracellular protein by operatively linking a heterologous signal sequence to the amino-terminus of the protein such that the protein is secreted from the host cells. In this case, recombinant human MEKK protein can be recovered from the culture medium in which the cells are cultured.

Certain host cells of the invention can also be used to produce nonhuman transgenic animals. For example, in one embodiment, a host cell of the invention is a fertilized oocyte or an embryonic stem cell into which human MEKK-coding sequences have been introduced. Such host cells can then be used to create non-human transgenic animals in which exogenous human MEKK sequences have been introduced into their genome or homologous recombinant animals in which endogenous MEKK sequences have been altered. Such animals are useful for studying the function and/or activity of human MEKK and for identifying and/or evaluating modulators of human MEKK activity. Accordingly, another aspect of the invention pertains to nonhuman transgenic animals which contain cells carrying a transgene encoding a human MEKK protein or a portion of a human MEKK protein. In a subembodiment, of the transgenic animals of the invention, the transgene alters an endogenous gene encoding an endogenous MEKK protein (e.g., homologous recombinant animals in which the endogenous MEKK gene has been functionally disrupted or "knocked out", or the nucleotide sequence of the endogenous MEKK gene has been mutated or the transcriptional regulatory region of the endogenous MEKK gene has been altered).

A transgenic animal of the invention can be created by introducing human MEKK-encoding nucleic acid into the male pronuclei of a fertilized oocyte, e.g., by microinjection, and allowing the oocyte to develop in a pseudopregnant female foster animal. The human MEKK nucleotide sequence of SEQ ID NO:1 (and plasmid pHu-MEKK) can be introduced as a transgene into the genome of a non-human animal.

Intronic sequences and polyadenylation signals can also be included in the transgene to increase the efficiency of expression of the transgene. A tissue-specific regulatory sequence(s) can be operably linked to the human MEKK transgene to direct expression of human MEKK protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al, and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the human MEKK transgene in its genome and/or expression of human MEKK mRNA in tissues or cells of the animals. A transgenic founder animal can then be used to breed additional animals carrying the transgene. Moreover, transgenic animals carrying a transgene encoding human MEKK can further be bred to other transgenic animals carrying other transgenes.

To create a homologous recombinant animal, a vector is prepared which contains at least a portion of a human MEKK gene into which a deletion, addition or substitution has been introduced to thereby alter, e.g., functionally disrupt, the endogenous MEKK gene. In one embodiment, a homologous recombination vector is designed such that, upon homologous recombination, the endogenous MEKK gene is functionally disrupted (i.e., no longer encodes a functional protein; also referred to as a "knock out" vector). Alternatively, the vector can be designed such that, upon homologous recombination, the endogenous MEKK gene replaced by the human MEKK gene. In the homologous recombination vector, the altered portion of theMEKK gene is flanked at its 5' and 3' ends by additional nucleic acid of the MEKK gene to allow for homologous recombination to occur between the exogenous human MEKK gene carried by the vector and an endogenous MEKK gene in an embryonic stem cell. The additional flanking MEKK nucleic acid is of sufficient length for successful homologous recombination with the endogenous gene. Typically, several kilobases of flanking DNA (both at the 5' and 3' ends) are included in the vector (see e.g., Thomas, K. R, and Capecchi, M. R. (1987) *Cell* 51:503 for a description of homologous recombination vectors). The vector is introduced into an embryonic stem cell line (e.g., by electroporation) and cells in which the introduced human MEKK gene has homologously recombined with the endogenous MEKK gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described flirther in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In addition to the foregoing, the skilled artisan will appreciate that other approaches known in the art for homologous recombination can be applied to the instant invention. Enzyme-assisted site-specific integration systems are known in the art and can be applied to integrate a DNA molecule at a predetermined location in a second target DNA molecule. Examples of such enzyme-assisted integration systems include the Cre recombinase-lox target system (e.g., as described in Baubonis, W, and Sauer, B. (1993) *Nucl. Acids Res.* 21:2025–2029; and Fukushige, S, and Sauer, B. (1992) *Proc. Natl. Acad. Sci. USA* 89:7905–7909) and the FLP recombinase-FRT target system (e.g., as described in Dang, D. T, and Perrimon, N. (1992) *Dev. Genet.* 13:367–375; and Fiering, S. et al. (1993) *Proc. Natl. Acad. Sci. USA* 90:8469–8473). Tetracycline-regulated inducible homologous recombination systems, such as described in PCT Publication No. WO 94/29442 and PCT Publication No. WO 96/01313, also can be used.

III. Isolated Human MEKK Proteins and Anti-Human MEKK Antibodies

Another aspect of the invention pertains to isolated human MEKK proteins. Preferably, the human MEKK protein comprises the amino acid sequence of SEQ ID NO: 2. In other embodiments, the protein has at least 90–91% amino acid identity, more preferably 92–93% amino identity, more preferably 94–95% amino identity, more preferably 96–97% amino identity, more preferably 98–99% amino identity, and even more preferably 99.5% amino acid identity with the amino acid sequence of SEQ ID NO:2, SEQ ID NO:4, or SEQ ID NO:6.

In other embodiments, the invention provides isolated portions of the human MEKK protein. For example, the invention further encompasses an amino-terninal portion of human MEKK that includes a regulatory domain. This portion encompasses, for example, about amino acids l-xxx of SEQ ID NO:2, about amino aicds 1–360 of SEQ ID NO:4, or about amino acids 1–366 of SEQ ID NO:6. Another isolated portion of human MEKK provided by the invention is a carboxy-terminal catalytic domain. This portion encompasses, for example, about amino acids 1038–1302 of SEQ ID NO:2, about amino acids 361–619 of SEQ ID NO:4, or about amino acids 367–626 of SEQ ID NO:6. In yet other embodiments, the invention provides biologically active portions of the human MEKK protein.

As used interchangeably herein, a "MEKK activity", "biological activity of MEKK" or "functional activity of MEKK", refers to an activity exerted by a MEKK protein, polypeptide or portion thereof as determined in vivo, or in vitro, according to standard techniques.

In one embodiment, a MEKK activity is a direct activity, such as an association with a MEKK-target molecule. As used herein, a "target molecule" is a molecule with which a MEKK protein binds or interacts in nature, such that MEKK-mediated function is acheived. A MEKK target molecule can be a non-MEKK molecule or a MEKK protein or polypeptide of the present invention (e.g., an autoactivity). In an exemplary embodiment, a MEKK target molecule is a MEKK substrate (e.g., MEK or JNKK). Alternatively, an STMST activity is an indirect activity, such as a cellular signaling activity mediated by interaction of the MEKK protein with a MEKK ligand.

In a preferred embodiment, a MEKK activity is at least one or more of the following activities: (i) interaction of a MEKK protein with soluble MEKK ligand (e.g., MEK or JNKK); (ii) modulation of the activity of a MEKK substrate; (iii) activation of a MEKK substrate; (iv) indirect modulation of a downstream signaling molecule (e.g., MAPK, for example $p^{42}/p^{44MAPK}$ or (JNK).

In yet another preferred embodiment, a MEKK activity is at least one or more of the following activities: (1) modulation of cellular signal transduction, either in vitro or in vivo; (2) regulation of gene transcription in a cell expressing a MEKK protein; (3) regulation of gene transcription in a cell expressing a MEKK protein, wherein said cell is involved inflammation; (4) regulation of cellular proliferation; (5) regulation of cellular differentiation; (6) regulation of develpoment; (7) regulation of cell death; or (8) regulation of regulation of inflammation.

Human MEKK proteins of the invention are preferably produced by recombinant DNA techniques. For example, a nucleic acid molecule encoding the protein is cloned into an expression vector (as described above), the expression vector is introduced into a host cell (as described above) and the human MEKK protein is expressed in the host cell. The human MEKK protein can then be isolated from the cells by an appropriate purification scheme using standard protein purification techniques. Alternative to recombinant expression, a human MEKK polypeptide can be synthesized chemically using standard peptide synthesis techniques. Moreover, native human MEKK protein can be isolated from cells (e.g., from T cells), for example by immunoprecipitation using an anti-human MEKK antibody.

The invention also provides human MEKK fusion proteins. As used herein, a human MEKK "fusion protein" comprises a human MEKK polypeptide operatively linked to a polypeptide other than human MEKK. A "human MEKK polypeptide" refers to a polypeptide having an amino acid sequence corresponding to human MEKK protein, or a peptide fragment thereof which is unique to human MEKK protein (as compared to non-human MEKK proteins, such as mouse or chicken MEKK", whereas a "polypeptide other than human MEKK" refers to a polypeptide having an amino acid sequence corresponding to another protein. Within the fusion protein, the term "operatively linked" is intended to indicate that the human MEKK polypeptide and the other polypeptide are fused in-frame to each other. The other polypeptide may be filed to the N-tenninus or C-terminus of the human MEKK polypeptide. For example, in one embodiment, the fusion protein is a GST-human MEKK fusion protein in which the human MEKK sequences are fused to the C-terminus of the GST sequences. In another embodiment, the fusion protein is a human MEKK-HA fusion protein in which the human MEKK nucleotide sequence is inserted in a vector such as pCEP4-HA vector (Herrscher, R. F. et al. (1995) *Genes Dev.* 9:3067–3082) such that the human MEKK sequences are fused in frame to an influenza hemagglutinin epitope tag. Such fusion proteins can facilitate the purification of recombinant human MEKK.

Preferably, a human MEKK fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide or an HA epitope tag). A human MEKK-encoding nucleic acid can be cloned into such an expression vector such that the fusion moiety is linked in-frame to the human MEKK protein.

An isolated human MEKK protein, or fragment thereof, can be used as an immunogen to generate antibodies that bind specifically to human MEKK using standard techniques for polyclonal and monoclonal antibody preparation. The human MEKK protein can be used to generate antibodies or, alternatively, an antigenic peptide fragment of human MEKK can be used as the immunogen. An antigenic peptide fragment of human MEKK typically comprises at least 8 amino acid residues of the amino acid sequence shown in SEQ ID NO:2, SEQ ID NO:4, or SEQ ID NO:6 and encompasses an epitope of human MEKK such that an antibody raised against the peptide forms a specific immune complex with human MEKK. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of human MEKK that are located on the surface of the protein, e.g., hydrophilic regions, and that are unique to human MEKK, as compared to MEKK proteins from other species, such as chicken or mouse (ie., an antigenic peptide that spans a region of human MEKK that is not conserved across species is used as immunogen; such non-conserved regions/residues are underlined and bolded in FIG. 4, FIG. 8, or FIG. 12). A standard hydrophobicity analysis of the human MEKK protein can be performed to identify hydrophilic regions.

A human MEKK immunogen typically is used to prepare antibodies by immunizing a suitable subject, (e.g., rabbit, goat, mouse or other mammal) with the immunogen. An appropriate immunogenic preparation can contain, for examples, recombinantly expressed human MEKK protein or a chemically synthesized human MEKK peptide. The preparation can further include an adjuvant, such as Freund's complete or incomplete adjuvant, or similar immunostimulatory agent. Immunization of a suitable subject with an immunogenic human MEKK preparation induces a polyclonal anti-human MEKK antibody response.

Accordingly, another aspect of the invention pertains to anti-human MEKK antibodies. Polyclonal anti-human MEKK antibodies can be prepared as described above by immunizing a suitable subject with a human MEKK immunogen. The anti-human MEKK antibody titer in the immunized subject can be monitored over time by standard techniques, such as with an enzyme linked immunosorbent assay (ELISA) using immobilized human MEKK. If desired, the antibody molecules directed against human MEKK can be isolated from the mammal (e.g., from the blood) and further purified by well known techniques, such as protein A chromatography to obtain the IgG fraction. At an appropriate time after immunization, e.g., when the anti-human MEKK antibody titers are highest, antibody-producing cells can be obtained from the subject and used to prepare monoclonal antibodies by standard techniques, such as the hybridoma technique originally described by Kohler and Milstein (1975, *Nature* 256:495–497) (see also, Brown et al. (1981) *J. Immunol* 127:539–46; Brown et al. (1980) *J Biol Chem* 255:4980–83; Yeh et al. (1976) *PNAS* 76:2927–31; and Yeh et al. (1982) *Int. J Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387402; M. L. Gefter et al. (1977) *Somatic Cell Genet.*, 3:231–36). Briefly, an immortal cell line (typically a myeloma) is fused to lymphocytes (typically splenocytes) from a mammal immunized with a human MEKK immunogen as described above, and the culture supernatants of the resulting hybridoma cells are screened to identify a hybridoma producing a monoclonal antibody that binds specifically to human MEKK.

Any of the many well known protocols used for fusing lymphocytes and immortalized cell lines can be applied for the purpose of generating an anti-human MEKK monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind human MEKK, e.g., using a standard ELISA assay.

Alternative to preparing monoclonal antibody-secreting hybridomas, a monoclonal anti-human MEKK antibody can be identified and isolated by screening a recombinant combinatorial immunoglobulin library (e.g., an antibody phage display library) with human MEKK to thereby isolate immunoglobulin library members that bind human MEKK. Kits for generating and screening phage display libraries are commercially available (e.g., the Pharmacia *Recombinant Phage Antibody System*, Catalog No. 27-9400-01; and the Stratagene SurfZAP™ *Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffiths et al. (1993) *EMBO J* 12:725–734; Hawkins et al. (1992) *J Mol Biol* 226:889–896; Clarkson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; Barbas et al. (1991) *PNAS* 88:7978–7982; and McCafferty et al. *Nature* (1990) 348:552–554.

Additionally, recombinant anti-human MEKK antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira, et al. European Patent Application 184,187; Taniguchi, M., European Patent Application 171,496; Morrison et al. European Patent Application 173,494; Neuberger et al. PCT Application WO 86/01533;

Cabilly et al. U.S. Pat. No. 4,816,567; Cabilly et al. European Patent Application 125,023; Better et al. (1988) *Science* 240:1041–1043; Liu et al. (1987) *PNAS* 84:3439–3443; Liu et al. (1987) *J Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1988) *J. Natl Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-human MEKK antibody (e.g., monoclonal antibody) can be used to isolate human MEKK by standard techniques, such as affinity chromatography or immunoprecipitation. An anti-human MEKK antibody can facilitate the purification of natural human MEKK from cells and of recombinantly produced human MEKK expressed in host cells. Moreover, an anti-human MEKK antibody can be used to detect human MEKK protein (e.g., in a cellular lysate or cell supernatant). Detection may be facilitated by coupling (i.e., physically linking) the antibody to a detectable substance. Accordingly, in one embodiment, an anti-human MEKK antibody of the invention is labeled with a detectable substance. Examples of detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}I$, $^{131}I$, $^{35}S$ or $^{3}H$.

Yet another aspect of the invention pertains to anti-human MEKK antibodies that are obtainable by a process comprising:

(a) immunizing an animal with an immunogenic human MEKK protein, or an immunogenic portion thereof unique to human MEKK protein; and (b) isolating from the animal antibodies that specifically bind to a human MEKK protein.

Methods for immunization and recovery of the specific anti-human MEKK antibodies are described further above.

IV. Pharmaceutical Compositions

Human MEKK modulators of the invention (e.g., human MEKK inhibitory or stimulatory agents, including human MEKK proteins and antibodies) can be incorporated into pharmaceutical compositions suitable for administration. Such compositions typically comprise the modulatory agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible ith its intended route of administration. For example, solutions or suspensions used for arenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811.

V. Methods of the Invention

A. Detection Assays

Another aspect of the invention pertains to methods of using the various human MEKK compositions of the invention. For example, the invention provides a method for detecting the presence of human MEKK activity in a biological sample. The method involves contacting the biological sample with an agent capable of detecting human MEKK activity, such as human MEKK protein or human MEKK mRNA, such that the presence of human MEKK activity is detected in the biological sample.

A preferred agent for detecting human MEKK mRNA is a labeled nucleic acid probe capable of specifically hybridizing to human MEKK mRNA. The nucleic acid probe can be, for example, the human MEKK DNA of SEQ ID NO:1, SEQ ID NO:3, or SEQ ID NO:5 (or plasmid pHu-MEKK1, plasmid pHu-MEKK2, or plasmid pHu-MEKK3), or a portion thereof unique to human MEKK (as compared to MEKK from other species, such as chicken or mouse), such as an oligonucleotide of at least 15, 30, 50, 100, 200, 300, 400, 500, 600, 700, 800, 900 or 1000 nucleotides in length and sufficient to specifically hybridize under stringent conditions to human MEKK mRNA.

A preferred agent for detecting human MEKK protein is a labeled antibody capable of binding to human MEKK protein. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (ie., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids. For example, techniques for detection of human MEKK mRNA include Northern hybridizations and in situ hybridizations. Techniques for detection of human MEKK protein include enzyme linked immunosorbent assays (ELISAs), Western blots, immunoprecipitations and immunofluorescence.

B. Screening Assays

The invention provides a method (also referred to herein as a "screening assay") for identifying modulators, ie., candidate or test compounds or agents (e.g., peptides, peptidomimetics, small molecules or other drugs) which bind to MEKK proteins, have a stimulatory or inhibitory effect on, for example, MEKK expression or MEKK activity, or have a stimulatory or inhibitory effect on, for example, the activity of an MEKK target molecule.

In one embodiment, the invention provides assays for screening candidate or test compounds which bind to or interact with a MEKK protein or polypeptide or biologically active portion thereof. In another embodiment, the invention provides assays for screening candidate or test compounds which bind to or modulate the activity of a MEKK protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223, 409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-free assay for identifying compounds which bind to or interact with a MEKK protein of the present invention. For example, the invention provides a method for identifying a compound that binds to or interacts with a human MEKK protein, comprising providing an indicator composition that comprises a human MEKK protein, or biologically active portion thereof;

contacting the indicator composition with a test compound; and determining the ability of the test compound to bind to or interact with the human MEKK protein or biologically active portion thereof in the indicator composition to thereby identify a compound that binds to or interacts with a human MEKK protein.

Determining the ability of the test compound to bind to or interact with the MEKK protein or biologically active potion thereof can be accomplished, for example, by coupling either the test compound or the MEKK protein or biologically active portion thereof with a radioisotope or enzymatic label such that binding can be determined by detecting the labeled test compound or MEKK protein or biologically active portion thereof in a complex. For example, compounds (e.g., MEKK protein or biologically active portion thereof) can be labeled with $^{125}$I, $^{35}$S, $^{14}$C, or $^{3}$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

Determining the ability of the test compound to bind to a MEKK protein or biologically active portion thereof can also be accomplished using a technology such as real-time Biomolecular Interaction Analysis (BIA). Sjolander, S, and Urbaniczky, C. (1991) *Anal. Chem.* 63:2338–2345 and Szabo et al. (1995) *Curr. Opin. Struct Biol.* 5;699–705, As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In another embodiment, an assay of the present invention the invention provides a method for identifying a compound that modulates the activity of a human MEKK protein, comprising providing an indicator composition that comprises a human MEKK protein, or biologically active portion thereof;

contacting the indicator composition with a test compound; and determining the effect of the test compound on the activity of the human MEKK protein or biologically active portion thereof, in the indicator composition to thereby identify a compound that modulates the activity of a human MEKK protein.

Determining the effect of the test compound on the activity of the human MEKK protein can be accomplished directly by detecting a biological activity of the MEKK protein or portion thereof. Alternatively, determining the effect of the test compound on the activity of the human MEKK protein can be accomplished by detecting activity of a downstream target of MEKK, e.g., induction of a cellular second messenger of the target (i.e. intracellular $Ca^{2+}$, diacylglycerol, $IP_3$, etc.), catalytic/enzymatic activity of the target an appropriate substrate, detecting the induction of a reporter gene (comprising a target-responsive regulatory element operatively linked to a nucleic acid encoding a detectable marker, e.g., luciferase), or detecting a target-regulated cellular response, for example, DNA:protein or protein:protein interactions.

In another embodiment, a screening assay of the invention is a cell based assay. For example, the indicator composition can comprise an indicator cell (e.g., a marnmalain cell or a yeast cell), wherein said indicator cell comprises: (i) the a human MEKK protein or biologically active portion thereof. Preferably, the indicator cell contains:

i) a recombinant expression vector encoding the human MEKK; and said method comprises:
        a) contacting the indicator cell with a test compound;
        b) determining the effect of the test compound on the activity of the MEKK protein or biologically active portion thereof to thereby identify a compound that modulates the activity of human MEKK.

In another embodiment, the assay further comprises the step of c) comparing the activity of the MEKK protein or biologically active portion thereof in the indicator cell in the presence of the test compound with the activity of the MEKK protein or biologically active portion thereof in the indicator cell in the absence of the test compound to thereby identify a compound that modulates the activity of human MEKK.

In another example, the indicator composition can comprise an indicator cell, wherein said indicator cell comprises: (i) the a human MEKK protein or biologically active portion thereof and (ii) a reporter gene responsive to the human MEKK protein. Preferably, the indicator cell contains:

i) a recombinant expression vector encoding the human MEKK; and
    ii) a vector comprising regulatory sequences of a gene responsive to MEKK signal transduction (e,g, a gene containing regulatory sequences responsive to the transcription factor, ATF 2) operatively linked to a reporter gene; and said method comprises:
        a) contacting the indicator cell with a test compound;
        b) determining the level of expression of the reporter gene in the indicator cell in the presence of the test compound to thereby identify a compound that modulates the activity of human MEKK.

In another embodiment, the assay further comprises the step of c) comparing the level of expression of the reporter gene in the indicator cell in the presence of the test compound with the level of expression of the reporter gene in the indicator cell in the absence of the test compound to thereby identify a compound that modulates the activity of human MEKK.

In another preferred embodiment, the indicator composition comprises a preparation of: (i) a human MEKK protein and (ii) a DNA molecule to which an ATF 2 transcription factor binds, and said method comprises:
        a) contacting the indicator composition with a test compound;
        b) determining the degree of interaction of an ATF 2 transcription factor and the DNA molecule in the presence of the test compound; and
        c) comparing the degree of interaction of ATF 2 transcription factor and the DNA molecule in the presence of the test compound with the degree of interaction of the ATF 2 transcription factor and the DNA molecule in the absence of the test compound to thereby identify a compound that modulates the activity of human MEKK.

In another preferred embodiment, the method identifies proteins that interact with human MEKK. In this embodiment, the indicator composition is an indicator cell, which indicator cell comprises:
        i) a reporter gene operably linked to a transcriptional regulatory sequence; and
        ii) a first chimeric gene which encodes a first fusion protein, said first fusion protein including human MEKK;
    the test compound comprises a library of second chimeric genes, which library encodes second fusion proteins;
    expression of the reporter gene being sensitive to interactions between the first fusion protein, the second fusion protein and the transcriptional regulatory sequence; and
    wherein the effect of the test compound on human MEKK in the indicator composition is determined by detecting the level of expression of the reporter gene in the indicator cell to thereby identify a test compound comprising a protein that interacts with human MEKK.

Furthermore, the present invention provides assays comprising the step of contacting an indicator composition with a compound which is known to interact with, bind to, or modulate the activity of a MEKK protein or biologically active portion thereof and determining the ability of a test compound to effect the ability of the known compound to bind to, interact with, or modulate the activity of the MEKK protein or biologically active portion thereof.

Recombinant expression vectors that can be used for expression of human MEKK in the indicator cell are known in the art (see discussions above). In one embodiment, within the expression vector the human MEKK-coding sequences are operatively linked to regulatory sequences that allow for constitutive expression of human MEKK in the indicator cell (e.g., viral regulatory sequences, such as a cytomegalovirus promoter/enhancer, can be used). Use of a recombinant expression vector that allows for constitutive expression of human MEKK in the indicator cell is preferred for identification of compounds that enhance or inhibit the activity of human MEKK. In an alternative embodiment, within the expression vector the human MEKK-coding sequences are operatively linked to regulatory sequences of the endogenous human MEKK gene (i.e., the promoter regulatory region derived from the endogenous human MEKK gene). Use of a recombinant expression vector in which human MEKK expression is controlled by the endogenous regulatory sequences is preferred for identification of compounds that enhance or inhibit the transcriptional expression of human MEKK.

A variety of reporter genes are known in the art and are suitable for use in the screening assays of the invention. Examples of suitable reporter genes include those which encode chloramphenicol acetyltransferase, beta-galactosidase, alkaline phosphatase or luciferase. Standard methods for measuring the activity of these gene products are known in the art. Likewise, a variety of cell types are suitable for use as an indicator cell in the screening assay. Preferably a cell line is used which does not normally express human MEKK. Mammalian cell lines as well as yeast cells can be used as indicator cells.

In one embodiment, the level of expression of the reporter gene in the indicator cell in the presence of the test compound is higher than the level of expression of the reporter gene in the indicator cell in the absence of the test compound and the test compound is identified as a compound that stimulates the expression or activity of human MEKK. In another embodiment, the level of expression of the reporter gene in the indicator cell in the presence of the test compound is lower than the level of expression of the reporter gene in the indicator cell in the absence of the test compound and the test compound is identified as a compound that inhibits the expression or activity of human MEKK.

Alternative to the use of a reporter gene construct, compounds that modulate the expression or activity of human MEKK can be identified by using other "read-outs." For example, an indicator cell can be transfected with a human MEKK expression vector. incubated in the presence and in the absence of a test compound, and MEKK activity be assessed by detecting the mRNA of an ATF 2-responsive gene product. Standard methods for detecting mRNA, such as reverse transcription-polymerase chain reaction (RT-PCR) are known in the art. Alternatively, MEKK activity can be assesed by detecting ATF2 mRNA levels.

As described above, the invention provides a screening assay for identifying proteins that interact with human MEKK. These assays can be designed based on the two-hybrid assay system (also referred to as an interaction trap assay) known in the art (see e.g., Field U.S. Pat. No. 5,283,173; Zervos et al. (1993) Cell 72:223–232; Madura et al. (1993) J. Biol. Chem. 268:12046–12054; Bartel et al. (1993) Biotechniques 14:920–924; and Iwabuchi et al. (1993) Oncogene 8:1693–1696). The two-hybrid assay is generally used for identifying proteins that interact with a particular target protein. The assay employs gene fusions to identify proteins capable of interacting to reconstitute a functional transcriptional activator. The transcriptional activator consists of a DNA-binding domain and a transcriptional activation domain, wherein both domains are required to activate transcription of genes downstream from a target sequence (such as an upstream activator sequence (UAS) for GAL4). DNA sequences encoding a target "bait" protein are fused to either of these domains and a library of DNA sequences is fused to the other domain. "Fish" fusion proteins (generated from the fusion library) capable of binding to the target-fusion protein (e.g., a target GAL4-fusion "bait") will generally bring the two domains (DNA-binding domain and transcriptional activation domain) into close enough proximity to activate the transcription of a reporter gene inserted downstream from the target sequence. Thus, the "fish" proteins can be identified by their ability to reconstitute a functional transcriptional activator (e.g., a functional GAL4 transactivator).

This general two-hybrid system can be applied to the identification of proteins in cells that interact with human MEKK by construction of a target human MEKK fusion protein (e.g., a human MEKK/GAL4 binding domain fusion as the "bait") and a cDNA library of "fish" fusion proteins (e.g., a cDNA/GAL4 activation domain library), wherein the cDNA library is prepared from mRNA of a cell type of interest, and introducing these constructs into a host cell that also contains a reporter gene construct linked to a regulatory sequence responsive to human MEKK. cDNAs encoding proteins that interact with human MEKK can be identified based upon transactivation of the reporter gene construct.

Alternatively, a "single-hybrid" assay, such as that described in Sieweke, M. H. et al. (1996) Cell 85:49–60, can be used to identify proteins that interact with human MEKK. This assay is a modification of the two-hybrid system discussed above. In this system, the "bait" is a transcription factor from which the transactivation domain has been removed (e.g., human MEKK from which the amino-terminal transactivation domain has been removed) and the "fish" is a non-fusion cDNA library (e.g., a cDNA library prepared from Th2 cells). These constructs are introduced into host cells (e.g., yeast cells) that also contains a reporter gene construct linked to a regulatory sequence responsive to human MEKK. cDNAs encoding proteins that interact with human MEKK can be identified based upon transactivation of the reporter gene construct.

As described above, the invention provides a screening assay for identifying compounds that modulate the activity of human MEKK by assessing the interaction between ATF 2 and a regulatory element of an ATF 2-responsive gene. Assays are known in the art that detect the interaction of a DNA binding protein with a target DNA sequence (e.g., electrophoretic mobility shift assays, DNAse I footprinting assays and the like). By performing such assays in the presence and absence of test compounds, these assays can be used to identify compounds that modulate (e.g., inhibit or enhance) the interaction of the DNA binding protein with its target DNA sequence.

In one embodiment, the amount of binding of ATF 2 to the DNA fragment in the presence of the test compound is greater than the amount of binding of ATF 2 to the DNA fragment in the absence of the test compound, in which case the test compound is identified as a compound that enhances activity of human MEKK. In another embodiment, the amount of binding of ATF 2 to the DNA fragment in the presence of the test compound is less than the amount of binding of ATF 2 to the DNA fragment in the absence of the test compound, in which case the test compound is identified as a compound that inhibits activity of human MEKK.

Yet another aspect of the invention pertains to methods of modulating human MEKK activity in a cell. The modulatory methods of the invention involve contacting the cell with an agent that modulates human MEKK activity such that human MEKK activity in the cell is modulated. The agent may act by modulating the activity of human MEKK protein in the cell or by modulating transcription of the human MEKK gene or translation of the human MEKK mRNA. As used herein, the term "modulating" is intended to include inhibiting or decreasing human MEKK activity and stimulating or increasing human MEKK activity. Accordingly, in one embodiment, the agent inhibits human MEKK activity. In another embodiment, the agent stimulates human MEKK activity.

C. Inhibitory Agents

According to a modulatory method of the invention, human MEKK activity is inhibited in a cell by contacting the cell with an inhibitory agent. Inhibitory agents of the invention can be, for example, intracellular binding molecules that act to inhibit the expression or activity of human MEKK. As used herein, the term "intracellular binding molecule" is intended to include molecules that act intracellularly to inhibit the expression or activity of a protein by binding to the protein itself, to a nucleic acid (e.g., an MRNA molecule) that encodes the protein or to a target with which the protein indirectly interacts (e.g, to a DNA target sequence to which ATF 2 binds). Examples of intracellular binding molecules, described in further detail below, include antisense human MEKK nucleic acid molecules (e.g., to inhibit translation of human MEKK mRNA), intracellular anti-human MEKK antibodies (e.g., to inhibit the activity of human MEKK protein) and dominant negative mutants of the human MEKK protein.

In one embodiment, an inhibitory agent of the invention is an antisense nucleic acid molecule that is complementary to a gene encoding human MEKK or to a portion of said gene, or a recombinant expression vector encoding said antisense nucleic acid molecule. The use of antisense nucleic acids to downregulate the expression of a particular protein in a cell is well known in the art (see e.g., Weintraub, H. et al, Antisense RNA as a molecular tool for genetic analysis, *Reviews—Trends in Genetics*, Vol. 1(1) 1986; Askari, F. K, and McDonnell, W. M. (1996) *N. Eng. J. Med.* 334:316–318; Bennett, M. R, and Schwartz, S. M. (1995) *Circulation* 92:1981–1993; Mercola, D. and Cohen, J. S. (1995) *Cancer Gene Ther.* 2:47–59; Rossi, J. J. (1995) *Br. Med. Bull.* 51:217–225; Wagner, R. W. (1994) *Nature* 372:333–335). An antisense nucleic acid molecule comprises a nucleotide sequence that is complementary to the coding strand of another nucleic acid molecule (e.g., an mRNA sequence) and accordingly is capable of hydrogen bonding to the coding strand of the other nucleic acid molecule. Antisense sequences complementary to a sequence of an mRNA can be complementary to a sequence found in the coding region of the mRNA, the 5' or 3' untranslated region of the mRNA or a region bridging the coding region and an untranslated region (e.g., at the junction of the 5' untranslated region and the coding region). Furthermore, an antisense nucleic acid can be complementary in sequence to a regulatory region of the gene encoding the mRNA, for instance a transcription initiation sequence or regulatory element. Preferably, an antisense nucleic acid is designed so as to be complementary to a region preceding or spanning the initiation codon on the coding strand or in the 3'untranslated region of an mRNA. An antisense nucleic acid for inhibiting the expression of human MEKK protein in a cell can be designed based upon the nucleotide sequence encoding the human MEKK protein (e.g., SEQ ID NO:1), constructed according to the rules of Watson and Crick base pairing.

An antisense nucleic acid can exist in a variety of different forms. For example, the antisense nucleic acid can be an oligonucleotide that is complementary to only a portion of a human MEKK gene. An antisense oligonucleotides can be constructed using chemical synthesis procedures known in the art. An antisense oligonucleotide can be chemically synthesized using naturally occurring nucleotides or variously modified nucleotides designed to increase the biological stability of the molecules or to increase the physical stability of the duplex formed between the antisense and sense nucleic acids, e.g. phosphorothioate derivatives and acridine substituted nucleotides can be used. To inhibit human MEKK expression in cells in culture, one or more antisense oligonucleotides can be added to cells in culture media, typically at about 200 µg oligonucleotide/ml.

Alternatively, an antisense nucleic acid can be produced biologically using an expression vector into which a nucleic acid has been subcloned in an antisense orientation (i.e., nucleic acid transcribed from the inserted nucleic acid will be of an antisense orientation to a target nucleic acid of interest). Regulatory sequences operatively linked to a nucleic acid cloned in the antisense orientation can be chosen which direct the expression of the antisense RNA molecule in a cell of interest, for instance promoters and/or enhancers or other regulatory sequences can be chosen which direct constitutive, tissue specific or inducible expression of antisense RNA. For example, for inducible expression of antisense RNA, an inducible eukaryotic regulatory system, such as the Tet system (e.g., as described in Gossen, M, and Bujard, H. (1992) *Proc. Natl. Acad. Sci. USA* 89:5547–5551; Gossen, M. et al. (1995) *Science* 268:1766–1769; PCT Publication No. WO 94/29442; and PCT Publication No. WO 96/01313) can be used. The antisense expression vector is prepared as described above for recombinant expression vectors, except that the cDNA (or portion thereof) is cloned into the vector in the antisense orientation. The antisense expression vector can be in the form of, for example, a recombinant plasmid, phagemid or attenuated virus. The antisense expression vector is introduced into cells using a standard transfection technique, as described above for recombinant expression vectors.

In another embodiment, an antisense nucleic acid for use as an inhibitory agent is a ribozvme. Ribozymes are catalytic RNA molecules with ribonuclease activity which are capable of cleaving a single-stranded nucleic acid, such as an mRNA, to which they have a complementary region (for reviews on ribozymes see e.g., Ohkawa, J. et al. (1995) *J. Biochem*. 118:251–258; Sigurdsson, S. T, and Eckstein, F. (1995) *Trends Biotechnol*. 13:286–289; Rossi, J. J. (1995) *Trends Biotechnol*. 13:301–306; Kiehntopf, M. et al. (1995) *J. Mol. Med*. 73:65–71). A ribozyme having specificity for human MEKK mRNA can be designed based upon the nucleotide sequence of the human MEKK cDNA. For example, a derivative of a Tetrahymena L-19 IVS RNA can be constructed in which the base sequence of the active site is complementary to the base sequence to be cleaved in a human MEKK mRNA. See for example U.S. Pat. Nos. 4,987,071 and 5,116,742, both by Cech et al. Alternatively, human MEKK mRNA can be used to select a catalytic RNA having a specific ribonuclease activity from a pool of RNA molecules. See for example Bartel, D. and Szostak, J. W. (1993) *Science* 261: 1411–1418.

Another type of inhibitory agent that can be used to inhibit the expression and/or activity of human MEKK in a cell is an intracellular antibody specific for the human MEKK protein. The use of intracellular antibodies to inhibit protein function in a cell is known in the art (see e.g., Carlson, J. R. (1988) *Mol. Cell. Biol.* 8:2638–2646; Biocca, S. et al. (1990) *EMBO J.* 9:101–108; Werge, T. M. et al. (1990) *FEBS Letters* 274:193–198; Carlson, J. R. (1993) *Proc. Natl. Acad. Sci. USA* 90:7427–7428; Marasco, W. A. et al. (1993) *Proc. Natl. Acad. Sci. USA* 90:7889–7893; Biocca, S. et al. (1994) *Bio/Technology* 12:396–399; Chen, S-Y. et al (1994) *Human Gene Therapy* 5:595–601; Duan, L et al. (1994) *Proc. Natl. Acad. Sci. USA* 91:5075–5079; Chen, S-Y. et al. (1994) *Proc. Natl. Acad Sci. USA* 91:5932–5936; Beerli, R. R. et al. (1994) *J. Biol. Chem.* 269:23931–23936; Beerli, R. R. et al. (1994) *Biochem. Biophys. Res. Commun.* 204:666–672; Mhashilkar, A. M. et al. (1995) *EMBO J.* 14:1542–1551; Richardson, J. H. et al. (1995) *Proc. Natl. Acad. Sci. USA* 92:3137–3141; PCT Publication No. WO 94/02610 by Marasco et al.; and PCT Publication No. WO 95/03832 by Duan et al.).

To inhibit protein activity using an intracellular antibody, a recombinant expression vector is prepared which encodes the antibody chains in a form such that, upon introduction of the vector into a cell, the antibody chains are expressed as a functional antibody in an intracellular compartment of the cell. For inhibition of human MEKK activity according to the inhibitory methods of the invention, an intracellular antibody that specifically binds the human MEKK protein is expressed in the cytoplasm of the cell. To prepare an intracellular antibody expression vector, antibody light and heavy chain cDNAs encoding antibody chains specific for the target protein of interest, e.g., human MEKK, are isolated, typically from a hybridoma that secretes a monoclonal antibody specific for the human MEKK protein. Hybridomas secreting anti-human MEKK monoclonal antibodies, or recombinant anti-human MEKK monoclonal antibodies, can be prepared as described above. Once a monoclonal antibody specific for human MEKK protein has been identified (e.g., either a hybridoma-derived monoclonal antibody or a recombinant antibody from a combinatorial library), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, CDNA encoding the light and heavy chains can be recovered from the display package (e.g., phage) isolated during the library screening process. Nucleotide sequences of antibody light and heavy chain genes from which PCR primers or CDNA library probes can be prepared are known in the art. For example, many such sequences are disclosed in Kabat, E. A., et al. (1991) *Sequences of Proteins of Immunological Interest, Fifth Edition*, U.S. Department of Health and Human Services, NIH Publication No. 91-3242 and in the "Vbase" human germline sequence database.

Once obtained, the antibody light and heavy chain sequences are cloned into a recombinant expression vector using standard methods. To allow for cytoplasmic expression of the light and heavy chains, the nucleotide sequences encoding the hydrophobic leaders of the light and heavy chains are removed. An intracellular antibody expression vector can encode an intracellular antibody in one of several different forms. For example, in one embodiment, the vector encodes full-length antibody light and heavy chains such that a full-length antibody is expressed intracellularly. in another embodiment, the vector encodes a full-length light chain but only the VH/CH1 region of the heavy chain such that a Fab fragment is expressed intracellularly. in the most preferred embodiment, the vector encodes a single chain antibody (scFv) wherein the variable regions of the light and heavy chains are linked by a flexible peptide linker (e.g., $(Gly_4Ser)_3$) and expressed as a single chain molecule. To inhibit human MEKK activity in a cell, the expression vector encoding the anti-human MEKK intracellular antibody is introduced into the cell by standard transfection methods, as discussed hereinbefore.

Yet another form of an inhibitory agent of the invention is an inhibitory form of human MEKK, also referred to herein as a dominant negative inhibitor. The MEKK proteins are known to modulate the activity of MEKK target molecules, particularly by modulating the phosphorylation state of the MEKK target molecule. One means to inhibit the activity of molecule that has an enzymatic activity is through the use of a dominant negative inhibitor that has the ability to interact with the target molecule but that lacks enzymatic activity. By interacting with the target molecule, such dominant negative inhibitors can inhibit the activation of the target molecule. This process may occur naturally as a means to regulate enzymatic activity of a cellular signal transduction molecule.

Accordingly, an inhibitory agent of the invention can be a form of a human MEKK protein that has the ability to interact with other proteins but that lacks enzymatic activity. This dominant negative form of a human MEKK protein may be, for example, a mutated form of human MEKK in which a kinase consensus sequence has been altered. Such dominant negative human MEKK proteins can be expressed in cells using a recombinant expression vector encoding the human MEKK protein, which is introduced into the cell by standard transfection methods. The mutated DNA is inserted into a recombinant expression vector, which is then introduced into a cell to allow for expression of the mutated human MEKK, lacking enzymatic activity.

Other inhibitory agents that can be used to inhibit the activity of a human MEKK protein are chemical compounds that directly inhibit human MEKK activity or inhibit the interaction between human MEKK and target molecules. Such compounds can be identified using screening assays that select for such compounds, as described in detail above.

D. Stimulatory Agents

According to a modulatory method of the invention, human MEKK activity is stimulated in a cell by contacting the cell with a stimulatory agent. Examples of such stimulatory agents include active human MEKK protein and nucleic acid molecules encoding human MEKK that are introduced into the cell to increase human MEKK activity in the cell. A preferred stimulatory agent is a nucleic acid molecule encoding a human MEKK protein, wherein the nucleic acid molecule is introduced into the cell in a form suitable for expression of the active human MEKK protein in the cell. To express a human MEKK protein in a cell, typically a human MEKK-encoding DNA is first introduced into a recombinant expression vector using standard molecular biology techniques, as described herein. A human MEKK-encoding DNA can be obtained, for example, by amplification using the polymerase chain reaction (PCR), using primers based on the human MEKK nucleotide sequence. Following isolation or amplification of human MEKK-encoding DNA, the DNA fragment is introduced into an expression vector and transfected into target cells by standard methods, as described herein.

Other stimulatory agents that can be used to stimulate the activity of a human MEKK protein are chemical compounds that stimulate human MEKK activity in cells, such as compounds that directly stimulate human MEKK protein and compounds that promote the interaction between human MEKK and target molecules. Such compounds can be identified using screening assays that select for such compounds, as described in detail above.

The modulatory methods of the invention can be performed in vitro (e.g., by culturing the cell with the agent or by introducing the agent into cells in culture) or, alternatively, in vivo (e.g., by administering the agent to a subject or by introducing the agent into cells of a subject, such as by gene therapy). For practicing the modulatory method in vitro, cells can be obtained from a subject by standard methods (i.e., cultured) and incubated (i.e., cultured) in vitro with a modulatory agent of the invention to modulate human MEKK activity in the cells. For example, peripheral blood mononuclear cells (PBMCs) can be obtained from a subject and isolated by density gradient centrifugation, e.g., with Ficoll/Hypaque. Specific cell populations can be depleted or enriched using standard methods. For example, monocytes/macrophages can be isolated by adherence on plastic. B cells can be enriched for example, by positive selection using antibodies to B cell surface markers, for example by incubating cells with a specific primary monoclonal antibody (mAb), followed by isolation of cells that bind the mAb using magnetic beads coated with a secondary antibody that binds the primary mAb. Specific cell populations can also be isolated by fluorescence activated cell sorting according to standard methods. If desired, cells treated in vitro with a modulatory agent of the invention can be readministered to the subject. For administration to a subject, it may be preferable to first remove residual agents in the culture from the cells before administering them to the subject. This can be done for example by a Ficoll/Hypaque gradient centrifugation of the cells. For further discussion of ex vivo genetic modification of cells followed by readministration to a subject, see also U.S. Pat. No. 5,399,346 by W. F. Anderson et al.

For practicing the modulatory method in vivo in a subject, the modulatory agent can be administered to the subject such that human MEKK activity in cells of the subject is modulated. The term "subject" is intended to include living organisms in which a MEKK-dependent cellular response can be elicited. Preferred subjects are mammals. Examples of subjects include humans, monkeys, dogs, cats, mice, rats, cows, horses, goats and sheep. For stimulatory or inhibitory agents that comprise nucleic acids (including recombinant expression vectors encoding human MEKK protein, antisense RNA, intracellular antibodies or dominant negative inhibitors), the agents can be introduced into cells of the subject using methods known in the art for introducing nucleic acid (e.g., DNA) into cells in vivo. Examples of such methods encompass both non-viral and 20. viral methods, including:

Direct Injection: Naked DNA can be introduced into cells in vivo by directly injecting the DNA into the cells (see e.g., Acsadi et al. (1991) *Nature* 332:815–818; Wolff et al. (1990) *Science* 247:1465–1468). For example, a delivery apparatus (e.g., a "gene gun") for injecting DNA into cells in vivo can be used. Such an apparatus is commercially available (e.g., from BioRad).

Cationic Lipids: Naked DNA can be introduced into cells in vivo by complexing the DNA with cationic lipids or encapsulating the DNA in cationic liposomes. Examples of suitable cationic lipid formulations include N-[-1-(2,3-dioleoyloxy)propyl]N,N,N-triethylammonium chloride (DOTMA) and a 1:1 molar ratio of 1,2-dimyristyloxy-propyl-3-dimethylhydroxyethylammonium bromide (DMRIE) and dioleoyl phosphatidylethanolamine (DOPE) (see e.g., Logan, J. J. et al. (1995) *Gene Therapy* 2:38–49; San, H. et al. (1993) *Human Gene Therapy* 4:781–788).

Receptor-Mediated DNA Uptake: Naked DNA can also be introduced into cells in vivo by complexing the DNA to a cation, such as polylysine, which is coupled to a ligand for a cell-surface receptor (see for example Wu, G, and Wu, C. H. (1988) *J. Biol. Chem.* 263:14621; Wilson et al. (1992) *J. Biol. Chem.* 267:963–967; and U.S. Pat. No. 5,166,320). Binding of the DNA-ligand complex to the receptor facilitates uptake of the DNA by receptor-mediated endocytosis. A DNA-ligand complex linked to adenovirus capsids which naturally disrupt endosomes, thereby releasing material into the cytoplasm can be used to avoid degradation of the complex by intracellular lysosomes (see for example Curiel et al. (1991) *Proc. Nati. Acad. Sci USA* 88:8850; Cristiano et al. (1993) *Proc. Natl. Acad. Sci. USA* 90:2122–2126).

Retroviruses: Defective retroviruses are well characterized for use in gene transfer for gene therapy purposes (for a review see Miller, A. D. (1990) *Blood* 76:271). A recombinant retrovirus can be constructed having a nucleotide sequences of interest incorporated into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals.

Examples of suitable retroviruses include pLJ, pZIP, pWE and pEM which are well known to those skilled in the art. Examples of suitable packaging virus lines include ψCrip, ψCre, ψ2 and ψAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

Adenoviruses: The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89:6482–6486), hepatocytes (Herz and Gerard (1993) *Proc. Natl. Acad. Sci. USA* 90:2812–2816) and muscle cells (Quantin et al. (1992) *Proc. Nati. Acad. Sci. USA* 89:2581–2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use are deleted for all or parts of the viral E1 and E3 genes but retain as much as 80% of the adenoviral genetic material.

Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics in Micro, and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al (1988) *Mol. Endocrinol.* 2:32–39; Tratschin et al. (1984) *J. Virol.* 51:611–619; and Flotte et al. (1993) *J. Biol. Chem.* 268:3781–3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product.

In a preferred embodiment, a retroviral expression vector encoding human MEKK is used to express human MEKK protein in cells in vivo, to thereby stimulate MEKK protein activity in vivo. Such retroviral vectors can be prepared according to standard methods known in the art (discussed further above).

A modulatory agent, such as a chemical compound, can be administered to a subject as a pharmaceutical composition. Such compositions typically comprise the modulatory agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described above in subsection IV.

This invention is further illustrated by the following example, which should not be construed as limiting. The contents of all references, patents and published patent applications cited throughout this application are hereby incorporated by reference.

Additionally, all nucleotide and amino acid sequences deposited in public databases referred to herein are also hereby incorporated by reference.

EXAMPLE 1

Isolation and Characterization of a Human MEKK1 Nucleic Acid

The following strategy was used to identify the nucleic acid sequence encoding human MEKK1.

cDNA Preparation—Total MRNA was extracted and isolated from T47D cells using $1\times10^7$ cells per purification in the QuickPrep Micro mRNA Purification Kit (Pharmacia). First strand cDNA was produced using 33 microliters of the purified mRNA per reaction in the Ready-to-Go T-Primed First-Strand Kit (Pharmacia).

PCR Amplification—The sense strand primer 5'-GAACACCATCCAGAAGTTTG-3' (SEQ ID NO:14), which was designed from the mouse MEKK1 (mMEKK1) cDNA sequence, was used in conjunction with the antisense primer 5'-CACTTTGTAGACAGGGTCAGC-3' (SEQ ID NO:15) in a polymerase chain reaction (PCR) using the first strand cDNA described above as a template (RT-PCR) to amplify the region from bases 1211–1950. Taq DNA Polymerase (Boehringer Mannheim) was used in a RT-PCR of 30 cycles (1 min. 94° C.; 1 min. 50° C.; 3 min., 72° C.), followed by a 10 min. incubation at 72° C. A band of approximately 800 bp was isolated by purification from a 1% agarose gel and ligated overnight at 14° C. into pGEM-T coli by heat shock at 42° C., and plated on Luria Broth (LB) plates containing ampicillin and X-gal. Colonies were screened by blue/white color selection, grown up in 5 ml of LB containing ampicillin, and the plasmid DNA was isolated using the Wizard Mini-pre Kit (Promega). Isolates were then screened for insert size by digesting with PstI and AatII (Promega), and running on a 1% agarose gel. Appropriately sized inserts were sequenced from both ends using T7 and SP6 vector primers. The resulting sequence was aligned to the known mMEKK1 sequence, and determined to be hMEKK1 by homology. In order to amplify the region from bases 2263–3743, the sense primer 5'-TGGGTCGCCTCTGTCTTATAGACAG-3' (SEQ ID NO:16) was used in conjunction with the antisense primer 5'-CACATCCTGTGCTTGGTAAC-3' (SEQ ID NO:17) in a RT-PCR of 30 cycles (1 min. 94° C.; 1 min., 50° C.; 2 min., 72° C.), followed by a 10 min. incubation at 72° C. A band of approximately 1.5 kb was isolated by purification from a 1% agarose gel, ligated, cloned, and sequenced as stated above. In order to amplify the 3' region of hMEKK1 from bases 3304–4493, the sense primer 5'-AGGACAAGTGCAGGTTAGATG-3' (SEQ ID NO:18) was used in a RT-PCR of 30 cycles (1 min., 94° C.; 1 min., 50° C.; 2 min., 72° C.), followed by a 10 min. incubation at 72° C. A band of approximately 1.3 kb was isolated by purification from a 1% agarose gel, ligated, cloned, and sequenced as stated above. Sequence was also confirmed for this clone using the internal sequencing primer 5'-GCTGTCCATATCTACAGTGCT-3' (SEQ ID NO:19). In order to amplify the region from bases 580–1310, the sense primer 5'-CGGCCTGGAAGCACGAGTGGT-3' (SEQ ID NO:20) was used in conjunction with the antisense primer 5'-TTCATCCTTGATGCTGTTTTC-3' (SEQ ID NO:21) in a RT-PCR of 30 cycles (1 min., 94° C.; 1 min., 50° C.; 2 min., 72° C.), followed by a 10 min A band of approximately 700 bp was isolated by purification from a 1% agarose gel, ligated, cloned, and sequenced as stated above. The overlapping sequence data was compiled into a single contig using Sequencer 2.0 (Gene Codes), and aligned to the mMEKK1 sequence (FIG. 3). The nucleotide and predicted amino acid sequences of human MEKK3 are shown in FIGS. 1 and 2, respectively. FIG. 4 depicts an alignment of the amino acid sequences of hMEKK1 and mMEKK1. Amino acid differences between the two proteins are indicated by bold underlining.

A BLASTN search using the nucleotide sequence of human MEKK1 as described in this example reveals the following nucleic acid sequences having homology to that set forth in SEQ ID NO:1: GenBank Accession Nos. L13103, U23470, AF042838, and U48596, having 96%, 96%, 95%, and 89% identity to SEQ ID NO:1, respectively.

A BLASTP search using the amino acid sequence of human MEKK1 as described in this example reveals the following amino acid sequences having homology to that set forth in SEQ ID NO:2: Swiss-Prot Accession No. Q62925, having 82% identity to SEQ ID NO :2; GenBank Accession No. AF042838, having 81% identity to SEQ ID NO:2; and GenBank Accession No. P53349, GenBank Accession No. U23470, PIR Accession No. A46212, and GenBank Accession No. L13103, each having 91% identity to SEQ ID NO:2; having 91% identity to SEQ ID NO:2.

EXAMPLE 2

Isolation and Characterization of a Human MEKK2 Nucleic Acid

The following strategy was used to identify the nucleic acid sequence encoding human MEKK2.

CDNA Preparation—Total mRNA was extracted and isolated from T47D cells using 1×10⁷ cells per purification in the QuickPrep Micro mRNA Purification Kit (Pharmacia). First strand cDNA was produced using 33 microlitres of the purified mRNA per reaction in the Ready-To-Go T-Primed First-Strand Kit (Pharmacia).

PCR Amplification—The sense strand primer 5'-GGCCAGCTCGGTGGCCT-3' (SEQ ID NO:22), which annealed to the 5' untranslated region of human MEKK2 (hMEKK2), was designed from the mouse MEKK2 (mMEKK2) cDNA sequence, and used in conjunction with the antisense primer 5'-TCTGGAATGTATCCTGG-3' (SEQ ID NO:23) in a polymerase chain reaction (PCR) using the first strand cDNA described above as a template (RT-PCR). Taq DNA Polymerase (Boehringer Mannheim) was used in a RT-PCR of 30 cycles (1 min, 94° C.; 1 min, 50° C.; 3 min, 68° C.), followed by a 10-min incubation at 72° C. One microlitre of the resulting reaction mixture was used as a template for a second PCR under the same conditions, and one microlitre of the secondary reaction mixture was used as a template again in a third PCR under the same conditions. A band of approximately 600 bp was isolated by purification from a 1% agarose gel and ligated overnight at 14° C. into pCR2.1 using the Original T/A Cloning Kit (Invitrogen). The ligation mixture was transformed by heat shock of the *E. Coli* strain TOP10F' at 42° C., and plated on Luria Broth (LB) plates containing ampicillin and X-gal. Colonies were screened by blue/white color selection, grown up in 5 ml of LB containing ampicillin, and the plasmid DNA was isolated using Mini-Prep Spin Columns (Qiagen). Isolates were then screened for insert size by digesting with EcoRI (Gibco/BRL), and running on a 1% agarose gel. Appropriately sized inserts were sequenced from both ends using M13 Forward and Reverse vector primers. The resulting sequence was aligned to the known mMEKK2 sequence, and determined to be hMEKK2 by homology. After sequencing the 5' portion of hMEKK2, the sense primer 5'-AGAGAGGAAAAAGCGGC-3' (SEQ ID NO:24), which annealed to a region that overlapped the previously sequenced portion of hMEKK2, was used in conjunction with the two antisense primers 5'-CAGCCAGCTCTCTTCCG-3' (SEQ ID NO:25) and 5'-GGAAAAGTCTTCCGACC-3' (SEQ ID NO:26) in two separate RT-PCR of 30 cycles (1 min, 94° C.; 1 min, 50° C.; 2 min, 68° C.), followed by a 10-min incubation at 72° C. One microlitre of the resulting reaction mixtures was used as a template for two separate second PCR under the same conditions. Two bands of approximately 700 bp and 400 bp respectively were isolated by purification from a 1% agarose gel, ligated, cloned, and sequenced as stated above. In order to sequence the 3' portion of hMEKK2, the sense primer 5'-GGCCAAGGAGCTTTTGGTAGG-3' (SEQ ID NO:27), which annealed to a region that overlapped the previously sequenced region of hMEKK2, was used in conjunction with the antisense primer 5'-GGAGCTGGTGGAGGACCGAAG-3' (SEQ ID NO:28), which annealed to the 3' untranslated region of hMEKK2, in a RT-PCR of 30 cycles (1 min, 94° C.; 1 min, 50° C.; 2 min, 68° C.), followed by a 10-min incubation at 72° C. One microlitre of the resulting reaction mixture was used as a template for a second PCR under the same conditions. A band of approximately 750 bp was isolated by purification from a 1% agarose gel, ligated, cloned, and sequenced as stated above. The overlapping sequence data was compiled into a single contig using Sequencher 2.0 (Gene Codes), and aligned to the mMEKK2 sequence (FIG. 7). The nucleotide and predicted amino acid sequences of human MEKK3 are shown in FIGS. 5 and 6, respectively. FIG. 8 depicts an alignment of the amino acid sequences of hMEKK2 and mMEKK2. Amino acid differences between the two proteins are indicated by bold underlining.

A BLASTN search using the nucleotide sequence of human MEKK2 as described in this example reveals that a nucleic acid molecule having GenBank Accession No. U43186 has 98% identity to the human MEKK2 nucleic acid sequence set forth as SEQ ID NO:3. A BLASTP search using the human MEKK2 amino acid sequence set forth in SEQ ID NO:4 reveals the following proteins having homology to human MEKK2: Swiss Prot Accession Nos. Q61083, Q61084, and Q99759 having 90%, 63% and 63% identity, respectively.

EXAMPLE 3
Isolation and Characterization of a Human MEKK3 Nucleic Acid

To isolate a nucleic acid molecule encoding human MEKK3, the sense primer 5'-CCCAGAACCCTGGCCGAAGCT-3' (SEQ ID NO:29), which annealed to a region in the middle of human MEKK3 (hMEKK3), was designed from the mouse MEKK3 (mMEKK3) cDNA sequence and used in conjunction with the antisense primer 5'-AGCACGGTCCCGCAGGCAGCC-3) (SEQ ID NO:30). Taq DNA Polymerase (Boehringer Mannheim) was used in a RT-PCR of 30 cycles (1 min, 94° C.; 1 min, 50° C.; 3 min, 72° C.), followed by a 10-min incubation at 72° C. using Marathon ReadyT™ human bone marrow, placental, and testis cDNA (Clontech) as templates. A band of approximately 800 bp was isolated from testis and placental template reactions by purification from a 1% agarose gel and ligated overnight at 14° C. into pCR2.1 using the Original T/A Cloning Kit (Invitrogen). The ligation mixture was transformed by heat shock of the E. coli strain TOP10F' at 42° C., and plated on Luria Broth (LB) plates containing ampicillin, IPTG and X-gal. Colonies were screened by blue/white color selection, grown up in 5ml of LB containing ampicillin, and the plasmid DNA was isolated using Mini-Prep™ Spin Columns (Qiagen). Isolates were then screened for insert size by digesting with EcoRI (Gibco/BRL), and running on a 1% agarose gel. Appropriately sized inserts were sequenced from both ends using M13 Forward and Reverse vector primers. The resulting sequence was aligned to the known mMEKK3 sequence, and determined to be hMEKK3 by homology. In order to sequence the 5' end of HMEKK, the sense strand primer 5'-GTAGTCGCCACCGCCGCCTCC-3' (SEQ ID NO: 31), which annealed to the 5' untranslated region of hMEKK3, was designed from the mMEKK3 cDNA sequence, and used in conjunction with the antisense primer 5'-CTGACAAGGAATTTTCGGCAC-3' (SEQ ID NO:32) which overlapped the previously sequenced portion of hMEKK3, in a RT-PCR of 30 cycles (1 min, 94° C.; 1 min, 50° C.; 3 min, 72° C.) in seven different buffers of varying pH and magnesium concentrations, followed by a 10-min incubation at 72° C. One microlitre of the resulting reaction mixture were used as a template for a second PCR under the same conditions with the nested sense strand oligo 5'-ACCGCCGCCTCCGCCATCGCC-3' (SEQ ID NO:33) and the nested antisense strand oligo 5'-CACTGTTCGCTGGTCTCTGGG-3' (SEQ ID NO:34). A band of approximately 700 bp was isolated from the reaction mixture buffered with 1 7.5mM MgCl$_2$ at pH 8.5 by purification from a 1% agarose gel, ligated, cloned, and sequenced as stated above. In order to sequence the 3' portion of hMEKK3, the sense primer 5'-AGACAAGCAAGGAGGTGAGTG-3' (SEQ ID NO:35), which annealed to a region that overlapped the previously sequenced region of hMEKK3, was used in conjunction with the antisense primer 5'-GCCTGACAGCAGCCCCTTGCC-3' (SEQ ID NO:36), which annealed to the 3' untranslated region of hMEKK3, in a RT-PCR of 30 cycles (1 min, 94° C.; 1 min, 50° C.; 2 min, 72° C.), followed by a 10-min incubation at 72° C. Subsequently, the nested sense primer 5'-TCCAGTTGCTAAAGAACTTGC-3' (SEQ ID NO:37) was used in conjunction with the nested antisense primer 5'-TGGCAGCTGGCAGCCTGATAG-3' (SEQ ID NO:38) in a secondary RT-PCR of 30 cycles (1 min, 94° C.; 1 min, 50° C.; 2 min, 72° C.), followed by a 10-min incubation at 72° C. A band of approximately 670 bp was isolated by purification from a 1% agarose gel, ligated, cloned, and sequenced as stated above. The overlapping sequence data was compiled into a single contig using Sequencher 2.0 (Gene Codes), and aligned to the mMEKK3 sequence (FIG. 11). The nucleotide and predicted amino acid sequences of human MEKK3 are shown in FIGS. 9 and 10, respectively. FIG. 12 depicts an alignment of the amino acid sequences of hMEKK3 and mMEKK3. Amino acid differences between the two proteins are evident, which differences are underlined and bolded.

A BLASTN search using the nucleic acid sequence of human MEKK3 reveals the following nucleic acid molecules having homology to SEQ ID NO:5: GenBank Accession Nos. U43187 and U78876, having 95% and 93% identity, respectively. A BLASTP search using the human MEKK3 amino acid sequence set forth in SEQ ID NO:6 reveals the following proteins having homology to human MEKK3: Swiss Prot Accession Nos. Q61084, Q99759, and Q61083, having 97%, 95%, and 62% identity to SEQ ID NO:6.

EXAMPLE 4
Antibodies to Human MEKK Proteins

Peptides corresponding to COOH-terminal sequence of a human MEKK protein (e.g., amino acids 1280–1300 of SEQ ID NO:2, amino acids 599–617 of SEQ ID NO:4, or amino acids 605–623 of SEQ ID NO:6) are conjugated to keyhole limpet hemocyanin and used to irnmunize rabbits. Antisera are characterized for specificity by immunoblotting of lysates prepared from appropriately transfected HEK293 cells.

EXAMPLE 5
Assays of Activity of MEKK and Downstream Signaling Molecules

Assay ofJNK Activity—JNK activity is measured using GST (glutathione S-transferase)-c-Jun$_{(1-79)}$ coupled to glutathione-Sepharose 4B (M. Hibi et al., *Genes & Dev.*; 7:2135–2148 (1993)). Cells transfected with MEEK3 and control transfected cells are lysed in 0.5% Nonidet P-40, 20 mM Tris-HCL, pH 7.6, 0.25 M NaCl, 3 mM EDTA, 3 mM EGTA, 1 mM dithiothreitol, 1 mM phenymethylsulfonyl fluoride, 2 mM sodium vanadate, 20 $\mu$/ml aprotinin, and 5 $\mu$g/ml leupeptin. Nuclei are removed by centrifugation at 15,000×g for 10 min., and the supernatants (25 $\mu$g of protein) are mixed with 10 $\mu$l of slurry of GST-c-Jun$_{(1-79)}$-Sepharose (3–5 $\mu$g of GST-c-Jun$_{(1-79)}$. The mixture is rotated at 4° C. for 1 h, washed trice in lysis buffer and once in kinase buffer (20 mM Hepes, pH 7.5, 10 mM MgCl$_2$, 20 mM β-glycerophosphate, 10 mM p-nitrophenyl phosphate, 1 mM dithiothreitol, 50 $\mu$M sodium vanadate). Beads are suspended in 40 $\mu$l of kinase assay buffer containing 10 $\mu$Ci of [$\gamma$-$^{32}$P]ATP and incubated at 30° C. for 20 minutes. Reactions mixtures are added to Laemmli sample buffer, boiled, and phosphorylated proteins are resolved on SDS-01% polyacrylamide gels. When JNK activity is assayed following fractionation by Mono Q ion exchange chromatography, 50 $\mu$l of each fraction is incubated with the GST-c-Jun$_{(1-79)}$ beads.

p42/44$^{MAPK}$ Assay—MAPK activity following Mono Q PPLC fractionation is measured as described in L. E. Heasley et al., Mol. Biol. Cell; 3:545–533 (1992) using the epidermal growth factor receptor 662–681 peptide as a selective p42/44$^{MAPK}$ substrate (M. Russell et al., *Biochemistry*; 34:6611–6615 (1995)). Alternatively, for cells transfected with varying amounts of MEKK plasmids MAPK activity is assayed after elution from DEAE-Sephacel columns (L. E. Heasley et al., *Am. J. Physiol.*; 267:F366–F373 (1994)).

Assay of MEKK Kinase Activity in Vitro—To assay MEKK activity in vitro, immune complexes are incubated with recombinant wild type or kinase-inactive MEK 1 (Lys$^{97}$→Met) or JNKK (Lys$^{116}$→Arg) as a substrate (A. Lin et al, *Science*; 268:286–290 (1995), C. A. Lange-Carter et al, *Science*; 265:1458–1461 (1994), M. Russell et al., *Biochemistry*; 34:6611–6615 (1995)). Transfected HEK293 cells are lysed in 1% Triton X-100, 0.5% Nonidet P-40, 20 mM Tris-HCl, pH 7.5, 150 mM NaCL, 20 mM NaF, 0.2 mM sodium vanadate, 1 mM EDTA, 1 mM EGTA, 5 mM phenylmethylsulfonyl fluoride. Nuclei are removed by centrifugation at 15,000×g for 5 min. HA epitope-tagged MEKK are immunoprecipitated with the 12CA5 antibody and protein A-Sepharose (B. E. Wadzinski et al., *J. Biol. Chem.*; 267:16883–16888 (1992), N.-X. Qian et al., *Proc. Natl. Acad. Sci. U.S.A.*; 90:40774081 (1993)). Immunoprecipitates are washed twice in lysis buffer, twice in 20 mM Pipes, 10 mM MnCl$_2$, 20 µg/ml aprotinin, and used in an in vitro kinase assay with 20–50 ng of recombinant MEK 1 or JNKK as substrates and 20 µCi of [γ-$^{32}$P]ATP (M. Russell et al., *Biochemistry*; 34:6611–6615 (1995)). Reactions are terminated by the addition of Laemmli sample buffer, boiled, and proteins are resolved by SDS-10% polyacrylamide gel electrophoresis.

To demonstrate MEKK activation of JNKK activity, the in vitro kinase reactions are performed with different combinations of recombinant wild type or kinase-inactive JNK. Kinase-inactive NJK is made by mutating the active site lysine 55 to methionine. Incubations are for 30 min, at 30° C. in the presence of 50 µM ATP. GST-c-Jun$_{(1-79)}$-Sepharose beads are then added, and the mixture is rotated at 4° C. for 30 minutes. The beads are washed, suspended in 40 µl of c-Jun kinase assay buffer containing 20 µCi of [γ-$^{32}$P]ATP, and incubated for 15 min, at 30° C. Reaction mixtures are added to Laemmli sample buffer, boiled, and phosphorylated proteins are resolved in SDS-10% polyacrylamide gels.

Assay of p38 Kinase Activity—Sorbitol-treated (0.4 M, 20 min.) or control HEK293 cells are lysed in the same buffer as that used for assay of MEKK. Supernatants (200 µg of protein) are used for COOH-terminal peptide sequence of p38 (J. Han et al, Science; 265:8-8–811 (1994)). Immunoprecipitates are washed once in lysis buffer, once in assay buffer (25 mM Hepes, pH 7.4, sodium vanadate), resuspended, and used in an in vitro kinase assay susbstrate and 20 µCi of [γ-$^{32}$P]ATP (H. Abdel-Hafez et al., *Mol. Endocrinology*; 6:2079–2089 (1992)). For analysis of p38 kinase activity from Mono Q FPLC fractions, 20 µl aliquots are mixed with kinase buffer containing 20–50 ng of recombinant ATF 2 and 10 µCi of [γ-$^{32}$P]ATP (M. Russell et al., *Biochemistry*; 34:6611–6615 (1995), H. Abdel-Hafez et al., *Mol. Endocrinology*; 6:2079–2089 (1992)). Reactions are quenched in Laemmli sample buffer, boiled, and proteins are resolved using SDS-10% polyacrylamide gels.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. An isolated nucleic acid molecule comprising a nucleotide sequence encoding a human MEKK protein, said MEKK protein having an amino acid sequence at least 98% identical to the amino acid sequence of SEQ ID NO:2, wherein % identity is determined according to the ALIGN algorithm using a PAM120 weight residue table, a gap length penalty of 12 and a gap penalty of 4.

2. An isolated nucleic acid molecule which comprises the nucleotide sequence of SEQ ID NO:1.

3. The nucleic acid molecule of claim 1, which encodes a MEKK protein having an amino acid sequence at least 99% identical to amino acid sequence of SEQ ID NO:2.

4. The nucleic acid molecule of claim 1, which encodes a MEKK protein having an amino acid sequence at least 99.5% identical to the amino acid sequence of SEQ ID NO:2.

5. An isolated human MEKK protein comprising an amino acid sequence at least 98% identical to the amino acid sequence of SEQ ID NO:2, wherein % identity is determined according to the ALIGN algorithm using a PAM120 weight residue table, a gap length penalty of 12 and a gap penalty of 4.

6. An isolated protein comprising the amino acid sequence of SEQ ID NO:2.

7. The protein of claim 5, which comprises an amino acid sequence at least 99% identical to the amino acid sequence of SEQ ID NO:2.

8. The protein of claim 5, which comprises an amino acid sequence at least 99.5% identical to the amino acid sequence of SEQ ID NO:2.

9. An isolated nucleic acid molecule which encodes a MEKK protein having the amino acid sequence of SEQ ID NO:2.

10. An isolated nucleic acid molecule comprising a nucleotide sequence encoding a human MEKK protein, said human MEKK protein having an amino acid sequence at least 99.5% identical to the amino acid sequence of SEQ ID NO:4, wherein % identity is determined according to the ALIGN algorithm using a PAM120 weight residue table, a gap length penalty of 12 and a gap penalty of 4.

11. An isolated nucleic acid molecule which comprises the nucleotide sequence of SEQ ID NO:3.

12. An isolated nucleic acid molecule which encodes a MEKK protein having the amino acid sequence of SEQ ID NO:4.

13. An isolated nucleic acid molecule comprising a nucleotide sequence encoding a human MEKK protein, said human MEKK protein having an amino acid sequence at least 98% identical to the amino acid sequence of SEQ ID NO:6, wherein % identity is determined according to the ALIGN algorithm using a PAM120 weight residue table, a gap length penalty of 12 and a gap penalty of 4.

14. An isolated nucleic acid molecule which comprises the nucleotide sequence of SEQ ID NO:5.

15. The nucleic acid molecule of claim 13, which encodes a MEKK protein having an amino acid sequence at least 99% identical to amino acid sequence of SEQ ID NO:6.

16. The nucleic acid molecule of claim 13, which encodes a MEKK protein having an amino acid sequence at least 99.5% identical to the amino acid sequence of SEQ ID NO:6.

17. An isolated nucleic acid molecule which encodes a MEKK protein having the amino acid sequence of SEQ ID NO:6.

18. An isolated human MEKK protein comprising an amino acid sequence at least 99.5% identical to the amino acid sequence of SEQ ID NO:4, wherein % identity is determined according to the ALIGN alogarithm using a PAM120 weight residue table, a gap length penalty of 12 and a gap penalty of 4.

19. An isolated protein comprising the amino acid sequence of SEQ ID NO:4.

20. An isolated human MEKK protein comprising an amino acid sequence at least 98% identical to the amino acid sequence of SEQ ID NO:6, wherein % identity is determined according to the ALIGN alogarithm using a PAM120 weight residue table, a gap length penalty of 12 and a gap penalty of 4.

21. An isolated protein comprising the amino acid sequence of SEQ ID NO:6.

22. The protein of claim 20, which comprises an amino acid sequence at least 99% identical to the amino acid sequence of SEQ ID NO:6.

23. The protein of claim 20, which comprises an amino acid sequence at least 99.5% identical to the amino acid sequence of SEQ ID NO:6.

24. A vector comprising the nucleic acid molecule of any one of claims 1–2, 3–4, 9–11 or 12–14.

25. The vector of claim 5, which is an expression vector.

26. A host cell containing the vector of claim 25.

27. A method for producing a human MEKK protein comprising culturing the host cell of claim 26 in a suitable medium until a human MEKK protein is produced.

28. The method of claim 27, further comprising isolating the human MEKK protein from the medium or the host cell.

29. A fusion protein comprising the MEKK protein of any one of claims 5–6, 12–13, 18–19 or 20–23 operatively linked to a polypeptide other than MEKK.

* * * * *

UNITED STATES PATENT AND TRADEMARK OFFICE
CERTIFICATE OF CORRECTION

PATENT NO.    : 6,312,934 B1
DATED         : November 6, 2001
INVENTOR(S)   : Gary L. Johnson Page 1 of 1

It is certified that error appears in the above-identified patent and that said Letters Patent is hereby corrected as shown below:

Column 128,
Line 10, the claim reference numerals "12-14" should read -- 12-17 --.
Line 11, the claim reference numeral "5" should read -- 24 --.
Line 19, the claim reference numerals "12-13" should read -- 7-8 --.

Signed and Sealed this

Third Day of September, 2002

Attest:

JAMES E. ROGAN
Attesting Officer    Director of the United States Patent and Trademark Office